United States Patent
Short, III et al.

(10) Patent No.: US 11,236,078 B2
(45) Date of Patent: Feb. 1, 2022

(54) HETEROCYCLIC INHIBITORS OF THE SODIUM CHANNEL

(71) Applicant: Mark G. DeGiacomo, Boston, MA (US)

(72) Inventors: Glenn F. Short, III, Scituate, MA (US); Donna L. Romero, Chesterfield, MO (US); Margaret S. Lee, Middleton, MA (US)

(73) Assignee: Mark G. DeGiacomo, Boston, MA (US)

( * ) Notice: Subject to any disclaimer, the term of this patent is extended or adjusted under 35 U.S.C. 154(b) by 0 days.

(21) Appl. No.: 16/579,803

(22) Filed: Sep. 23, 2019

(65) Prior Publication Data

US 2020/0017488 A1  Jan. 16, 2020

Related U.S. Application Data

(63) Continuation of application No. 15/122,085, filed as application No. PCT/US2015/017806 on Feb. 26, 2015, now abandoned.

(60) Provisional application No. 61/945,309, filed on Feb. 27, 2014.

(51) Int. Cl.
| | |
|---|---|
| *C07D 417/12* | (2006.01) |
| *C07C 311/51* | (2006.01) |
| *C07C 235/40* | (2006.01) |
| *C07C 237/24* | (2006.01) |
| *C07D 237/20* | (2006.01) |
| *C07D 239/42* | (2006.01) |
| *C07D 207/16* | (2006.01) |
| *C07D 285/08* | (2006.01) |
| *C07C 311/04* | (2006.01) |
| *C07C 233/66* | (2006.01) |
| *C07C 233/58* | (2006.01) |
| *C07C 311/10* | (2006.01) |
| *C07D 277/52* | (2006.01) |
| *C07D 307/24* | (2006.01) |

(52) U.S. Cl.
CPC .......... *C07D 417/12* (2013.01); *C07C 233/58* (2013.01); *C07C 233/66* (2013.01); *C07C 235/40* (2013.01); *C07C 237/24* (2013.01); *C07C 311/04* (2013.01); *C07C 311/10* (2013.01); *C07C 311/51* (2013.01); *C07D 207/16* (2013.01); *C07D 237/20* (2013.01); *C07D 239/42* (2013.01); *C07D 277/52* (2013.01); *C07D 285/08* (2013.01); *C07D 307/24* (2013.01); *C07C 2601/08* (2017.05); *C07C 2601/14* (2017.05)

(58) Field of Classification Search
CPC .. C07D 417/12; C07D 307/24; C07D 277/52; C07D 285/08; C07D 207/16
See application file for complete search history.

(56) References Cited

FOREIGN PATENT DOCUMENTS

WO  WO-2013131018 A1 * 9/2013 ........... C07D 413/06

* cited by examiner

*Primary Examiner* — Amanda L. Aguirre
(74) *Attorney, Agent, or Firm* — Entralta P.C.; James F. Fleming; Peter D. Weinstein

(57) ABSTRACT

The invention relates to compounds useful in treating conditions associated with voltage-gated ion channel function, particularly conditions associated with sodium channel activity. More specifically, the invention concerns heterocyclic compounds (e.g., compounds according to any of Formulas (I)-(III) or Compounds (1)-(65) of Table 1) that are that are useful in treatment of conditions such as epilepsy, cancer, pain, migraine, Parkinson's Disease, mood disorders, schizophrenia, psychosis, tinnitus, amyotropic lateral sclerosis, glaucoma, ischaemia, spasticity disorders, obsessive compulsive disorder, restless leg syndrome and Tourette syndrome.

2 Claims, No Drawings

HETEROCYCLIC INHIBITORS OF THE SODIUM CHANNEL

CROSS-REFERENCE TO RELATED APPLICATIONS

This application is a continuation of U.S. patent application Ser. No. 15/122,085 filed Aug. 26, 2016 which is a national phase application of PCT/US2015/017806 filed Feb. 26, 2014 which claims benefit to U.S. Provisional Patent Application No. 61/945,309 filed Feb. 27, 2014, and which is hereby incorporated by reference in its entirety.

FIELD OF THE INVENTION

The invention relates to compounds useful in treating conditions associated with voltage-gated ion channel function, particularly conditions associated with sodium channel activity. More specifically, the invention relates to heterocyclic compounds (e.g., compounds according to any of Formulas (I)-(III) or Compounds (1)-(65) of Table 1) that are that are useful in treatment of diseases and conditions such as epilepsy, cancer, pain, migraine, Parkinson's Disease, mood disorders, schizophrenia, psychosis, tinnitus, amyotropic lateral sclerosis, glaucoma, ischaemia, spasticity disorders, obsessive compulsive disorder, restless leg syndrome and Tourette syndrome.

BACKGROUND OF THE INVENTION

Voltage-gated sodium (Nav) channels are present in neurons and excitable tissues where they contribute to processes such as membrane excitability and muscle contraction (Ogata et al., *Jpn. J. Pharmacol.* 88:365-77, 2002). Nine different transmembrane 3-subunits (Nav1.1-1.9) from a single Nav1 family combine with auxiliary β-subunits that modify channel function to form functional Nav channels. Of the nine Nav1 β-subunit isoforms, five are expressed in the dorsal root ganglion where they are involved in setting the resting membrane potential and the threshold for generating action potentials, and also contribute to the upstroke as well as firing of action potentials during sustained depolarization. In particular, the tetrodotoxin (TTX) sensitive Nav1.7 and TTX-insensitive Nav1.8 channel subtypes act as major contributors to both inflammatory and neuropathic pain (Momin et al., *Curr. Opin. Neurobiol.* 18:383-8, 2008; Rush et al., *J. Physiol.* 579:1-14, 2007).

Pathological pain states induce neuronal hyper-excitability in the peripheral and central nervous systems and as a consequence modulate voltage-gated ion channel behavior (Coderre and Katz, *Behav. Brain Sci.* 20:404-19, 1997; Hildebrand et al., *Pain.* 152:833-843, 2011). In humans, gain-of-function mutations in the Nav1.7 gene, SNC9A, yield the condition of inherited erythromelalgia typified by extreme pain, redness and swelling in the extremities (Drenth and Waxman, *J. Clin. Invest.* 117:3603-3609, 2007). These mutations result in amino acid substitutions that alter channel function and induce hyper-excitability of the Nav1.7 channel by allowing the ion channel to open at lower membrane potentials (Cheng et al., *Mol. Pain.* 4:1-9, 2008). Across the various Nav1.7 mutations identified as contributing to erythromelalgia, select mutations result in a reduction of pain severity (Cheng et al., *Brain* 134:1972-1986, 2011). While these mutations still allow the channel to open at lower membrane potentials, this subset alters the manner in which the ion channel resets to its original closed state so that it can continue to participate in pain signaling. While unmutated Nav1.7 channels reset primarily through a kinetically rapid state on the millisecond timescale (fast-inactivation), erythromelalgia mutations resulting in less pain promote channel resetting through a kinetically slow state on the second time scale (slow-inactivation). By limiting channel availability and further participation in sodium ion gating, enhanced entry into the slow-inactivated state reduces pain signaling.

Novel allosteric modulators of voltage-gated ion channels, e.g., voltage gated sodium channels, are thus desired to promote therapeutic analgesia. Modulators may affect the kinetics and/or the voltage potentials of, e.g., Nav1.7 or Nav1.8, channels. In particular, modulators that affect the state-dependence of voltage gated sodium channels by enhancing entry in the slow-inactivated state may be of particular utility in limiting pain signaling by limiting channel availability.

SUMMARY OF THE INVENTION

The invention relates to compounds useful in conditions modulated by sodium channels.

In a first aspect, the invention features a compound having a structure according to the following formula,

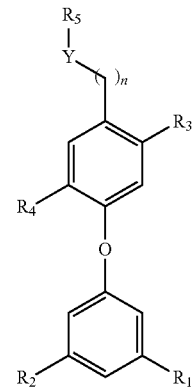

wherein $R_1$ and $R_2$ are independently H, a halogen, a nitrile, an optionally substituted C1-C3 alkyl, an optionally substituted 4-membered heterocyclic ring, an optionally substituted C1-C3 alkoxy, an optionally N-substituted amide wherein the N-substituents are independently chosen from H and C1-C4 alkyl, an optionally N-substituted amide wherein the two N-substituents may combine to form an unsubstituted 5-membered N-heterocyclic ring, or a —CO$_2$R group, wherein R is H, Me, or Et;

$R_3$ and $R_4$ are independently H, a halogen, or a nitrile;

$R_5$ is a sulfonyl methyl, or a monocyclic ring with two substituted positions, wherein the substituents are chosen from H, a halogen, C1-C3 alkyl, hydroxyl or C1-C3 alkoxy, wherein $R_5 \neq H$;

n is 0, 1, 2;

or a stereoisomer thereof; or a pharmaceutically acceptable salt thereof.

In some embodiments, $R_1$ and $R_2$ are both perfluoralkyl groups.

In certain embodiments, $R_1$ and $R_2$ are both CF$_3$ groups.

In other embodiments, $R_3$ and $R_4$ are both a halogen.

In further embodiments, $R_3$ and $R_4$ are both F.

In still further embodiments, at least one of $R_3$ and $R_4$ is H.

In some embodiments, at least one of $R_1$ and $R_2$ is H.

In other embodiments, at least one of $R_3$ and $R_4$ is a halogen.

In yet other embodiments, only one of $R_1$ and $R_2$ is $CF_3$.

In certain embodiments, only one of $R_1$ and $R_2$ is a halogen.

In some embodiments, Y is —CONH— and $R_5$ is sulfonyl methyl.

In some other embodiments, $R_5$ is an unsubstituted heterocyclic ring chosen from

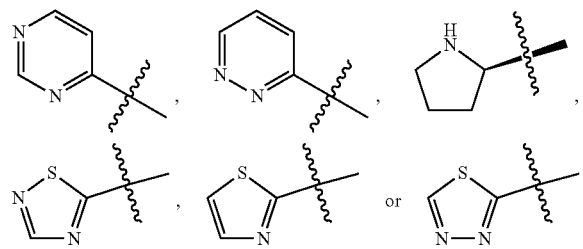

In a second aspect, the present invention features a compound having a structure according to the following formula,

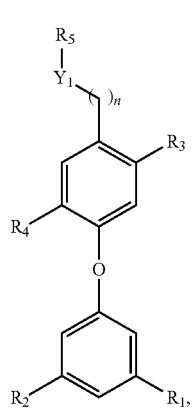

(II)

wherein $R_1$ and $R_2$ are independently H, a halogen, a nitrile group, an optionally substituted C1-C3 alkyl, an optionally substituted 4-membered heterocyclic ring, an optionally substituted C1-C3 alkoxy, an optionally N-substituted amide wherein the N-substituents are independently chosen from H and C1-C4 alkyl, an optionally N-substituted amide wherein the two N-substituents may combine to form an unsubstituted 5-membered N-heterocyclic ring, or a —$CO_2R$ group, wherein R is H, Me, or Et;

$R_3$ and $R_4$ are independently H, a halogen, or a nitrile group;

$R_5$ is a sulfonyl methyl, a methyl, or a monocyclic ring with two substituted positions, wherein the substituents are chosen from H, a halogen, C1-C3 alkyl, hydroxyl, C1-C3 alkoxy, benzyl, methylene methoxy, or methylene N-morpholine, such that $R_5 \neq H$ and when $R_5$ is methyl, $R_{1-4} \neq H$;

$R_6$ is independently H or $CH_3$;

$Y_1$ is independently —$NHSO_2$—, —$SO_2NR_6$—, or —$SO_2CH_2$—;

n is 0, 1 or 2;

or a stereoisomer thereof; or a pharmaceutically acceptable salt thereof.

In some embodiments, $R_1$ and $R_2$ are both perfluoralkyl groups.

In other embodiments, $R_1$ and $R_2$ are both $CF_3$ groups.

In certain embodiments, $R_3$ and $R_4$ are both halogen.

In specific embodiments, $R_3$ and $R_4$ are both F.

In some other embodiments, at least one of $R_3$ and $R_4$ is a halogen, nitrile, or H.

In further embodiments, Y is —$SO_2CH_2$—.

In yet further embodiments, only one of $R_1$ and $R_2$ is $CF_3$.

In still further embodiments, at least one of $R_1$ and $R_2$ is a halogen.

In other embodiments, one of $R_1$ or $R_2$ is chosen from —$CO_2H$, nitrile, halogen, C1-C3 alkoxy, C1-C3 ester, —$CONR_xR_y$, or an optionally substituted 4-membered heterocycle.

In some embodiments, $R_x$ and $R_y$ are independently H, Methyl, Ethyl, or $R_x$ combines with $R_y$ to form a 5-membered heterocycle.

In certain embodiments, $R_5$ is a mono-substituted monocyclic heterocycle.

In other embodiments, said substituent is chosen from methyl, benzyl, methylene methoxy, or methylene N-morpholine.

In yet other embodiments, $R_5$ is a methyl or an unsubstituted heterocyclic ring chosen from

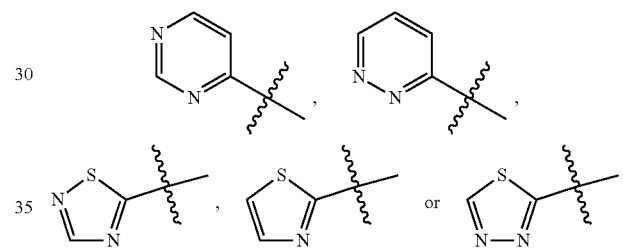

In a third aspect, the present invention features a compound having a structure according to the following formula,

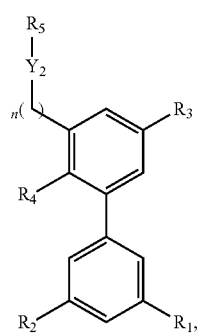

(III)

wherein $R_1$ and $R_2$ are independently H, a halogen, a nitrile group, an optionally substituted C1-3 alkyl, an optionally substituted 4-membered heterocyclic ring, an optionally substituted C1-C3 alkoxy, a carboxylic acid, C1-C2 ester group, an optionally N-substituted amide wherein the N-substituents are independently chosen from H and C1-C4 alkyl, an optionally N-substituted amide wherein the two N-substituents may combine to form an unsubstituted 5-membered N-heterocyclic ring;

$R_3$ and $R_4$ are independently H, a halogen, or a nitrile group;

$R_5$ is a sulfonyl methyl, a methyl, or a monocyclic ring with two substituted positions, wherein the substituents are chosen from H, a halogen, —$NH_2$, —$SO_2NHPh$, C1-C3 alkyl, hydroxyl, C1-C3 alkoxy, benzyl, methylene methoxy, or N-methylene morpholine, wherein $R_5$ a unsubstituted cyclohexyl or unsubstituted thiazole if $R_{1-4}$=H;

$R_6$ is H or $CH_3$;

$Y_2$ is independently —CONH—, —NMeCO—, —NHCO—, —$NHSO_2$— or —$SO_2NR_6$—;

n is independently 0, 1 or 2;

or a stereoisomer thereof; or a pharmaceutically acceptable salt thereof.

In some embodiments, $R_1$ and $R_2$ are both perfluoralkyl groups.

In other embodiments, $R_1$ and $R_2$ are both $CF_3$ groups.

In certain embodiments, at least one of $R_3$ and $R_4$ is a $CF_3$ group or H.

In a fourth aspect, the invention is a compound selected from compounds 1-65 in Table 1.

In a fifth aspect, the invention features a pharmaceutical composition that includes any of the compounds described herein (e.g., a compound according to any of Formulas (I)-(III) or any of Compounds (1)-(65) of Table 1) and a pharmaceutically acceptable carrier or excipient.

In some embodiments, the pharmaceutical composition is formulated in unit dosage form (e.g., a tablet, caplet, capsule, lozenge, film, strip, gelcap, or syrup).

In a sixth aspect, the invention features method to treat a disease or condition by administering to a subject in need of such treatment an effective amount of any of the compounds described herein (e.g., a compound according to any of Formulas (I)-(III) or any of Compounds (1)-(65) of Table 1), or a pharmaceutical composition thereof. In some embodiments, the condition is pain, epilepsy, Parkinson's disease, a mood disorder (e.g., a major depressive disorder (e.g., atypical depression, melancholic depression, psychotic major depression, catatonic depression, postpartum depression, seasonal affective disorder, dysthymia, and depressive disorder not otherwise specified (DD-NOS)), recurrent brief depression, minor depressive disorder, or a bipolar disorder), psychosis (e.g., schizophrenia), tinnitus, amyotropic lateral sclerosis, glaucoma, ischaemia, spasticity disorders, obsessive compulsive disorder, restless leg syndrome, and Tourette syndrome.

In particular embodiments, the condition is pain or epilepsy.

In some embodiments, the pain is inflammatory pain (e.g., inflammatory pain caused by rheumatoid arthritis, juvenile idiopathic arthritis, ankylosing spondylitis, psoriatic arthritis, inflammatory bowel disease, primary dysmenorrhea, or endometriosis) or neuropathic pain.

In certain embodiments, the pain is chronic pain.

In further embodiments, the chronic pain is peripheral neuropathic pain; central neuropathic pain, musculoskeletal pain, headache, visceral pain, or mixed pain.

In some embodiments, the peripheral neuropathic pain is post-herpetic neuralgia, diabetic neuropathic pain, neuropathic cancer pain, HIV-associated neuropathy, erythromelalgia, failed back-surgery syndrome, trigeminal neuralgia, or phantom limb pain; said central neuropathic pain is multiple sclerosis related pain, Parkinson disease related pain, post-stroke pain, post-traumatic spinal cord injury pain, lumbosacral radiculopathy, cervical radiculopathy, brachial radiculopathy, or pain in dementia; the musculoskeletal pain is osteoarthritic pain and fibromyalgia syndrome; inflammatory pain such as rheumatoid arthritis, or endometriosis; the headache is migraine, cluster headache, tension headache syndrome, facial pain, or headache caused by other diseases; the visceral pain is interstitial cystitis, irritable bowel syndrome, or chronic pelvic pain syndrome; or the mixed pain is lower back pain, neck and shoulder pain, burning mouth syndrome, or complex regional pain syndrome.

In a seventh aspect, the invention features a method of modulating a voltage-gated ion channel (e.g., a voltage-gated sodium channel), where the method includes contacting a cell with any of the compounds described herein (e.g., a compound according to any of Formulas (I)-(III) or any of Compounds (1)-(65) of Table 1).

In a further aspect, the invention features a pharmaceutical composition that includes any of the compounds described herein (e.g., a compound according to any of Formulas (I)-(III) or any of Compounds (1)-(65) of Table 1) and a pharmaceutically acceptable carrier or excipient.

In some embodiments, the pharmaceutical composition is formulated in unit dosage form (e.g., a tablet, caplet, capsule, lozenge, film, strip, gelcap, or syrup).

In yet another aspect, the invention features a method of modulating a voltage-gated ion channel (e.g., a voltage-gated sodium channel), where the method includes contacting a cell with any of the compounds described herein (e.g., a compound according to any of Formulas (I)-(III) or any of Compounds (1)-(65) of Table 1).

As used herein, the term "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. The term "cycloalkyl," as used herein, represents a monovalent saturated or unsaturated non-aromatic cyclic alkyl group having between three to nine carbons (e.g., a C3-C9 cycloalkyl), unless otherwise specified, and is exemplified by cyclopropyl, cyclobutyl, cyclopentyl, cyclohexyl, cycloheptyl, bicyclo[2.2.1.]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like.

Typically, the alkyl, alkenyl and alkynyl groups contain 1-12 carbons (e.g., C1-C12 alkyl) or 2-12 carbons (e.g., C2-C12 alkenyl or C2-C12 alkynyl). In some embodiments, the alkyl groups are C1-C8, C1-C6, C1-C4, C1-C3, or C1-C2 alkyl groups; or C2-C8, C2-C6, C2-C4, or C2-C3 alkenyl or alkynyl groups. Further, any hydrogen atom on one of these groups can be replaced with a substituent as described herein. For example, the term "aminoalkyl" refers to an alkyl group, as defined herein, comprising an optionally substituted amino group (e.g., $NH_2$).

Heteroalkyl, heteroalkenyl and heteroalkynyl are similarly defined and contain at least one carbon atom but also contain one or more O, S or N heteroatoms or combinations thereof within the backbone residue whereby each heteroatom in the heteroalkyl, heteroalkenyl or heteroalkynyl group replaces one carbon atom of the alkyl, alkenyl or alkynyl group to which the heteroform corresponds. In some embodiments, the heteroalkyl, heteroalkenyl and heteroalkynyl groups have C at each terminus to which the group is attached to other groups, and the heteroatom(s) present are not located at a terminal position. As is understood in the art, these heteroforms do not contain more than three contiguous heteroatoms. In some embodiments, the heteroatom is O or N. The term "heterocyclyl," as used herein represents cyclic heteroalkyl or heteroalkenyl that is, e.g., a 3-, 4-, 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like.

The designated number of carbons in heteroforms of alkyl, alkenyl and alkynyl includes the heteroatom count. For example, if heteroalkyl is defined as C1-C6, it will contain 1-6 C, N, O, or S atoms such that the heteroalkyl contains at least one C atom and at least one heteroatom, for example 1-5 carbons and 1 N atom, or 1-4 carbons and 2 N atoms. Similarly, when heteroalkyl is defined as C1-C6 or C1-C4, it would contain 1-5 carbons or 1-3 carbons respectively, i.e., at least one C is replaced by O, N or S. Accordingly, when heteroalkenyl or heteroalkynyl is defined as C2-C6 (or C2-C4), it would contain 2-6 or 2-4 C, N, O, or S atoms, since the heteroalkenyl or heteroalkynyl contains at least one carbon atom and at least one heteroatom, e.g. 2-5 carbons and 1 N atom, or 2-4 carbons, and 2 O atoms. Further, heteroalkyl, heteroalkenyl or heteroalkynyl substituents may also contain one or more carbonyl groups. Examples of heteroalkyl, heteroalkenyl and heteroalkynyl groups include $CH_2OCH_3$, $CH_2N(CH_3)_2$, $CH_2OH$, $(CH_2)_n NR_2$, OR, COOR, $CONR_2$, $(CH_2)_nOR$, $(CH_2)_nCOR$, $(CH_2)_n COOR$, $(CH_2)_nSR$, $(CH_2)_nSOR$, $(CH_2)_nSO_2R$, $(CH_2)_n CONR_2$, NRCOR, NRCOOR, $OCONR_2$, OCOR and the like wherein the R group contains at least one C and the size of the substituent is consistent with the definition of e.g., alkyl, alkenyl, and alkynyl, as described herein (e.g., n is 1, 2, 3, 4, 5, 6, 7, 8, 9, 10, 11, or 12).

As used herein, the terms "alkylene," "alkenylene," and "alkynylene," or the prefix "alk" refer to divalent or trivalent groups having a specified size, typically C1-C2, C1-C3, C1-C4, C1-C6, or C1-C8 for the saturated groups (e.g., alkylene or alk) and C2-C3, C2-C4, C2-C6, or C2-C8 for the unsaturated groups (e.g., alkenylene or alkynylene). They include straight-chain, branched-chain and cyclic forms as well as combinations of these, containing only C and H when unsubstituted. Because they are divalent, they can link together two parts of a molecule, as exemplified by X in the compounds described herein. Examples are methylene, ethylene, propylene, cyclopropan-1,1-diyl, ethylidene, 2-butene-1,4-diyl, and the like. These groups can be substituted by the groups typically suitable as substituents for alkyl, alkenyl and alkynyl groups as set forth herein. Thus C=O is a C1 alkylene that is substituted by =O, for example. For example, the term "alkaryl," as used herein, represents an aryl group, as defined herein, attached to the parent molecular group through an alkylene group, as defined herein, and the term "alkheteroaryl" refers to a heteroaryl group, as defined herein, attached to the parent molecular group through an alkylene group, as defined herein. The alkylene and the aryl or heteroaryl group are each optionally substituted as described herein.

Heteroalkylene, heteroalkenylene and heteroalkynylene are similarly defined as divalent groups having a specified size, typically C1-C3, C1-C4, C1-C6, or C1-C8 for the saturated groups and C2-C3, C2-C4, C2-C6, or C2-C8 for the unsaturated groups. They include straight chain, branched chain and cyclic groups as well as combinations of these, and they further contain at least one carbon atom but also contain one or more O, S or N heteroatoms or combinations thereof within the backbone residue, whereby each heteroatom in the heteroalkylene, heteroalkenylene or heteroalkynylene group replaces one carbon atom of the alkylene, alkenylene or alkynylene group to which the heteroform corresponds. As is understood in the art, these heteroforms do not contain more than three contiguous heteroatoms. The term "alkoxy" represents a chemical substituent of formula —OR, where R is an optionally substituted alkyl group (e.g., C1-C6 alkyl group), unless otherwise specified. In some embodiments, the alkyl group can be substituted, e.g., the alkoxy group can have 1, 2, 3, 4, 5 or 6 substituent groups as defined herein.

The term "alkoxyalkyl" represents a heteroalkyl group, as defined herein, that is described as an alkyl group that is substituted with an alkoxy group. Exemplary unsubstituted alkoxyalkyl groups include between 2 to 12 carbons. In some embodiments, the alkyl and the alkoxy each can be further substituted with 1, 2, 3, or 4 substituent groups as defined herein for the respective group.

The term "amino," as used herein, represents $-N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two $R^{N1}$ combine to form a heterocyclyl or an N-protecting group, and wherein each $R^{N2}$ is, independently, H, alkyl, or aryl. In a preferred embodiment, amino is $-NH_2$, or $-NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, or aryl, and each $R^{N2}$ can be H, alkyl, or aryl. The term "aminoalkyl," as used herein, represents a heteroalkyl group, as defined herein, that is described as an alkyl group, as defined herein, substituted by an amino group, as defined herein. The alkyl and amino each can be further substituted with 1, 2, 3, or 4 substituent groups as described herein for the respective group. For example, the alkyl moiety may comprise an oxo (=O) substituent.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, imidazolyl and the like. Because tautomers are theoretically possible, phthalimido is also considered aromatic. Typically, the ring systems contain 5-12 ring member atoms or 6-10 ring member atoms. In some embodiments, the aromatic or heteroaromatic moiety is a 6-membered aromatic rings system optionally containing 1-2 nitrogen atoms. More particularly, the moiety is an optionally substituted phenyl, pyridyl, indolyl, pyrimidyl, pyridazinyl, benzothiazolyl, benzimidazolyl, pyrazolyl, imidazolyl, isoxazolyl, thiazolyl, benzothiazolyl, indolyl, or imidazopyridinyl. Even more particularly, such moiety is phenyl, pyridyl, thiazolyl, imidazopyridinyl, or pyrimidyl and even more particularly, it is phenyl.

"O-aryl" or "O-heteroaryl" refers to aromatic or heteroaromatic systems which are coupled to another residue through an oxygen atom. A typical example of an O-aryl is phenoxy. Similarly, "arylalkyl" refers to aromatic and heteroaromatic systems which are coupled to another residue through a carbon chain, saturated or unsaturated, typically of C1-C8, C1-C6, or more particularly C1-C4 or C1-C3 when saturated or C2-C8, C2-C6, C2-C4, or C2-C3 when unsaturated, including the heteroforms thereof. For greater certainty, arylalkyl thus includes an aryl or heteroaryl group as defined above connected to an alkyl, heteroalkyl, alkenyl, heteroalkenyl, alkynyl or heteroalkynyl moiety also as defined above. Typical arylalkyls would be an aryl(C6-C12)alkyl(C1-C8), aryl(C6-C12)alkenyl(C2-C8), or aryl(C6-C12)alkynyl(C2-C8), plus the heteroforms. A typical example is phenylmethyl, commonly referred to as benzyl.

Halo may be any halogen atom, especially F, Cl, Br, or I, and more particularly it is fluoro or chloro.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls. In some embodiments, the haloalkyl group can be further substituted with 1, 2, 3, or 4 substituent groups as described herein for alkyl groups.

The term "hydroxy," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

An "oxo" group is a substituent having the structure C=O, where there is a double bond between a carbon and an oxygen atom.

Typical optional substituents on aromatic or heteroaromatic groups include independently halo, CN, $NO_2$, $CF_3$, $OCF_3$, COOR', CONR'$_2$, OR', SR', SOR', $SO_2$R', NR'$_2$, NR'(CO)R', NR'C(O)OR', NR'C(O)NR'$_2$, NR'$SO_2$NR'$_2$, or NR'$SO_2$R', wherein each R' is independently H or an optionally substituted group selected from alkyl, alkenyl, alkynyl, heteroalkyl, heteroalkenyl, heteroalkynyl, heteroaryl, and aryl or two R' groups may combine to form a heterocyclyl (all as defined above); or the substituent may be an optionally substituted group selected from alkyl, alkenyl, alkynyl, heterocyclyl, heteroalkyl, heteroalkenyl, heteroalkynyl, aryl, heteroaryl, O-aryl, O-heteroaryl, and arylalkyl.

Optional substituents on a non-aromatic group (e.g., alkyl, alkenyl, and alkynyl groups), are typically selected from the same list of substituents suitable for aromatic or heteroaromatic groups, except as noted otherwise herein. A non-aromatic group may also include a substituent selected from =O and =NOR' where R' is H or an optionally substituted group selected from alkyl, alkenyl, alkynyl, heteroalkyl, heteroalkenyl, heteralkynyl, heteroaryl, and aryl (all as defined above).

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. However, alkyl substituted by aryl, amino, halo and the like would be included. For example, where a group is substituted, the group may be substituted with 1, 2, 3, 4, 5, or 6 substituents. Optional substituents include, but are not limited to: C1-C6 alkyl or heteroaryl, C2-C6 alkenyl or heteroalkenyl, C2-C6 alkynyl or heteroalkynyl, halogen; aryl, heteroaryl, azido(—$N_3$), nitro (—$NO_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—$CO_2$H), carboxylic ester (—$CO_2$R'), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, C1-C6 alkyl or heteroaryl, C2-C6 alkenyl or heteroalkenyl, 2C-6C alkynyl or heteroalkynyl, aryl, or heteroaryl. A substituted group may have, for example, 1, 2, 3, 4, 5, 6, 7, 8, or 9 substituents.

In some embodiments, the invention features moieties that are amino acid residues. The amino acid residue may be of a naturally occurring amino acid (e.g., Ala, Arg, Asn, Asp, Cys, Gin, Glu, Gly, His, lie, Leu, Lys, Met, Phe, Pro, Ser, Thr, Trp, Tyr, or Val), or the amino acid residue may be of a non-naturally occurring amino acid. A "non-naturally occurring amino acid" is an amino acid which is not naturally produced or found in a mammal. Examples of non-naturally occurring amino acids include D-amino acids; an amino acid having an acetylaminomethyl group attached to a sulfur atom of a cysteine; a pegylated amino acid; the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine; phenylglycine; citrulline; methionine sulfoxide; cysteic acid; ornithine; and hydroxyproline.

The term an "effective amount" of an agent (e.g., a compound according to any of Formulas (I)-(III) or any of Compounds (1)-(65) of Table 1), as used herein, is that amount sufficient to effect beneficial or desired results, such as clinical results, and, as such, an "effective amount" depends upon the context in which it is being applied. For example, in the context of administering an agent that is a modulator of a sodium channel (e.g., Nav1.7 or Nav1.8), an effective amount of an agent is, for example, an amount sufficient to achieve a change in sodium channel activity as compared to the response obtained without administration of the agent.

The term "pharmaceutical composition," as used herein, represents a composition containing a compound described herein (e.g., a compound according to any of Formulas (I)-(III) or any of Compounds (1)-(65) in Table 1) formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. The term "pharmaceutically acceptable prodrugs" as used herein, represents those prodrugs of the compounds of the present invention that are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, represents those salts of the compounds described here (e.g., a compound according to any of Formulas (I)-(III) or any of Compounds (1)-(65) in Table 1) that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvate" as used herein means a compound as described herein (e.g., a compound according to any of Formulas (I)-(III) or any of Compounds (1)-(65) in Table 1) where molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

The term "prevent," as used herein, refers to prophylactic treatment or treatment that prevents one or more symptoms or conditions of a disease, disorder, or conditions described herein (for example, pain (e.g., chronic or acute pain), epilepsy, Alzheimer's disease, Parkinson's disease, cardiovascular disease, diabetes, cancer, sleep disorders, obesity, psychosis such as schizophrenia, overactive bladder, renal disease, neuroprotection, addiction, and male birth control). Preventative treatment can be initiated, for example, prior to ("pre-exposure prophylaxis") or following ("post-exposure prophylaxis") an event that precedes the onset of the disease, disorder, or conditions. Preventive treatment that includes administration of a compound described herein (e.g., a compound according to any of Formulas (I)-(III) or any of Compounds (1)-(65) in Table 1), or a pharmaceutically acceptable salt or solvate thereof, or a pharmaceutical composition thereof, can be acute, short-term, or chronic. The doses administered may be varied during the course of preventative treatment.

The term "prodrug," as used herein, represents compounds that are rapidly transformed in vivo to the parent compound of the above formula, for example, by hydrolysis in blood. Prodrugs of the compounds described herein may be conventional esters. Some common esters that have been utilized as prodrugs are phenyl esters, aliphatic (C1-C8 or C8-C24) esters, cholesterol esters, acyloxymethyl esters, carbamates, and amino acid esters. For example, a compound that contains an OH group may be acylated at this position in its prodrug form. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins et al., *Synthetic Communications* 26:4351-4367, 1996, each of which is incorporated herein by reference. Preferably, prodrugs of the compounds of the present invention are suitable for use in contact with the tissues of humans and animals with undue toxicity, irritation, allergic response, and the like, commensurate with a reasonable benefit/risk ratio, and effective for their intended use.

In addition, the compounds of the invention may be coupled through conjugation to substances designed to alter the pharmacokinetics, for targeting, or for other reasons. Thus, the invention further includes conjugates of these compounds. For example, polyethylene glycol is often coupled to substances to enhance half-life; the compounds may be coupled to liposomes covalently or noncovalently or to other particulate carriers. They may also be coupled to targeting agents such as antibodies or peptidomimetics, often through linker moieties. Thus, the invention is also directed to compounds (e.g., a compound according to any of Formulas (I)-(III) or any of Compounds (1)-(65) in Table 1) when modified so as to be included in a conjugate of this type.

As used herein, and as well understood in the art, "to treat" a condition or "treatment" of the condition (e.g., the conditions described herein such as pain (e.g., chronic or acute pain), epilepsy, Alzheimer's disease, Parkinson's disease, cardiovascular disease, diabetes, cancer, sleep disorders, obesity, psychosis such as schizophrenia, overactive bladder, renal disease, neuroprotection, addiction, and male birth control) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gelcap, and syrup.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers, enantiomers, and tautomers that can be formed.

Compounds useful in the invention may contain isotopes. Useful isotopes include hydrogen, carbon, nitrogen, oxygen, phosphorous, fluorine, and chlorine, (e.g., $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl). Compounds containing isotopes can be prepared by synthesizing a compound using a readily available isotopically labeled reagent in place of a non-isotopically labeled reagent. In some embodiments, the compound (e.g., a compound according to any of Formulas (I)-(III) or any of Compounds (1)-(65) in Table 1), or a composition that includes the compound, has the natural abundance of each element present in the compound. In other embodiments, the compound has one or more isotopes in non-natural abundance.

Other features and advantages of the invention will be apparent from the following Detailed Description and the claims.

The compounds described herein (e.g., a compound according to any of Formulas (I)-(III) or any of Compounds (1)-(65) of Table 1) are also useful for the manufacture of a medicament useful to treat conditions requiring modulation of voltage-gated ion channel, e.g., sodium channel activity, and in particular Nav1.7 or Nav1.8 channel activity, or any combination thereof.

Other features and advantages of the invention will be apparent from the following detailed description, the drawings, and the claims.

DETAILED DESCRIPTION OF THE INVENTION

Compounds

The invention features compounds that can inhibit voltage-gated ion channel activity (e.g., voltage-gated sodium channels) by state-dependent enhancement of slow-inactivation and other use-dependent mechanisms. Exemplary compounds described herein include compounds having a structure according to one of the following formulae (I)-(III) as described herein:

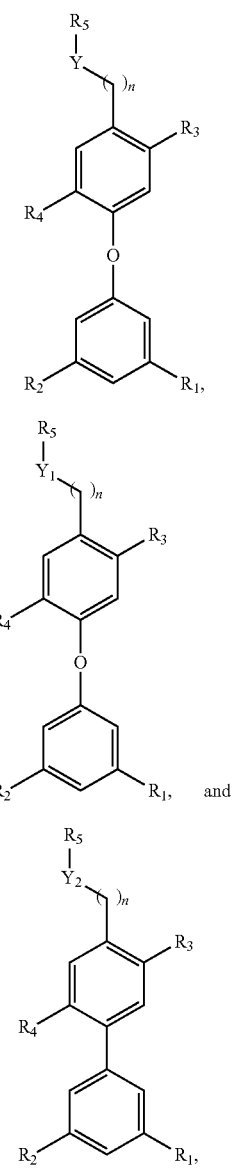

or a stereoisomer thereof, or a pharmaceutically acceptable salt thereof.

Other embodiments (e.g., Compounds (1)-(65) of Table 1), as well as exemplary methods for the synthesis of these compounds, are described herein.

Utility and Administrations

The compounds described herein (e.g., a compound according to any of Formulas (I)-(III) or any of Compounds (1)-(65) of Table 1) are useful in the methods of the invention and, while not bound by theory, are believed to exert their desirable effects through their ability to modulate the activity of voltage-gated ion channels, e.g., sodium channels such as the Nav1.7 and Nav1.8 channels. The compounds described herein (e.g., a compound according to any of Formulas (I)-(III) or any of Compounds (1)-(65) of Table 1) can also be used for the treatment of certain conditions such as pain, epilepsy, migraine, Parkinson's disease, mood disorders, schizophrenia, psychosis, tinnitus, amyotropic lateral sclerosis, glaucoma, ischaemia, spasticity disorders, obsessive compulsive disorder, restless leg syndrome, and Tourette syndrome.

Modulation of Sodium Channels

There are nine Nav1 β-subunit isoforms: Nav1.1-1.9 (see, e.g., Yu et al., *Genome Biolog.*, 4:207, 2003). In addition to pain, other conditions associated with voltage-dependent sodium channel activity include seizures (e.g., Nav1.1), epilepsy (e.g., Nav1.2), neurodegeneration (e.g., Nav1.1, Nav1.2), myotonia (e.g., Nav1.4), arrhythmia (e.g., Nav1.5), and movement disorders (e.g., Nav1.6) as described in PCT Publication No. WO 2008/118758, herein incorporated by reference. The expression of particular isoforms in particular tissues can influence the therapeutic effects of sodium channel modulators. For example, the Nav1.4 and Nav1.5 isoforms are largely found in skeletal and cardiac myocytes (see, e.g., Gold, *Exp. Neurol.* 210:1-6, 2008).

Sodium Channel Activity and Pain

Voltage-dependent ion channels in pain-sensing neurons are currently of great interest in developing drugs to treat pain. For example, blocking voltage-dependent sodium channels in pain-sensing neurons can block pain signals by interrupting initiation and transmission of the action potential. Studies also indicate that particular sodium channel isoforms are predominantly expressed in peripheral sensory neurons associated with pain sensation; for example, Nav1.7, Nav1.8 and Nav1.9 activity are thought to be involved in inflammatory, and possibly neuropathic, pain (see, e.g., Cummins et al., *Pain* 131:243-257, 2007). The Nav1.3 isoform has also been implicated in pain, e.g., pain associated with tissue injury (Gold, *Exp. Neurol.* 210:1-6, 2008).

The Nav1.7 and Nav1.8 channel subtypes act as major contributors to both inflammatory and neuropathic pain (vide infra). Recently, mutations have been identified in the Nav1.7 channel that lead either to a gain of channel function (Dib-Hajj et al., *Brain* 128:1847-1854, 2005) or more commonly to a loss of channel function (Chatelier et al., *J. Neurophisiol.* 99:2241-50, 2008). These mutations underlie human heritable disorders such as erythrormelalgia (Yang et al., *J Med Genet.* 41:171-4, 2004), paroxysmal extreme pain disorder (Fertleman et al., *Neuron.* 52:767-74, 2006), and congenital indifference to pain (Cox et al., *Nature* 444:894-8, 2006). Behavioral studies have shown in mice that inflammatory and acute mechanosensory pain is reduced when Nav1.7 is knocked out in Nav1.8-positive neurons (Nassar et al., *Proc. Natl. Acad. Sci. USA.* 101:12706-11, 2004). In addition, siRNA of Nav1.7 attenuates inflammatory hyperalgesia (Yeomans et al., *Hum. Gene Ther.* 16:271-7, 2005).

The Nav1.8 isoform is selectively expressed in sensory neurons and has been identified as a target for the treatment of pain, e.g., chronic pain (e.g., Swanwick et al., *Neurosci. Lett.* 486:78-83, 2010). The role of Nav1.8 in inflammatory (Khasar et al. *Neurosci. Lett.* 256:17-20, 1998), neuropathic and mechanical hyperalgesia (Joshi et al., *Pain* 123:75-82, 2006) has also emerged using molecular techniques to knockdown Nav1.8, which has been shown to reduce the maintenance of these different pain states.

Lacosamide is a functionalized amino acid that has shown effectiveness as an analgesic in several animal models of neuropathic pain and is currently in late stages of clinical development for epilepsy and diabetic neuropathic pain. One mode of action that has been validated for lacosamide is inhibition of voltage-gated sodium channel activity by selective inhibition with the slow-inactivated conformation of the channel (Sheets et al., *J. Pharmacol. Exper. Therapeut.*, 326:89-99 (2008)). Modulators of sodium channels, including clinically relevant compounds, can exhibit a pronounced state-dependent binding, where sodium channels that are rapidly and repeatedly activated and inactivated are more readily blocked. In a simplified scheme, voltage-gated sodium channels have four distinct states: open, closed, fast-inactivated and slow-inactivated. Classic sodium channel modulators, such as lidocaine, are believed to exhibit the highest affinity for the fast-inactivated state. However, alteration of the slow inactivated state is also clinically relevant. As demonstrated by gain-of-function mutations of the Nav1.7 gene, SCN9A, a subset of mutations that promote entry of the Nav1.7 channel into the slow inactivated state result in less severe forms of erythromelalgia (Cheng et al., *Brain* 134:1972-1986, 2011). Because repeated Nav1.7 channel activation results in greater proportions of the channel to be in the slow inactivated state and further stabilization of the channel in the slow-inactivated state limits pain, the identification of modulators that enhance ion channel entry into the slow inactivated state would be believed to produce a therapeutic analgesic effect (Blair and Bean, *J. Neurosci.* 23:10338-20350, 2003).

The modulation of ion channels by the compounds described herein (e.g., a compound according to any of Formulas (I)-(III) or any of Compounds (1)-(65) of Table 1) can be measured according to methods known in the art (e.g., in the references provided herein) to monitor both use- and state-dependence. This electrophysiological data can be used to further characterize the modulators as enhancers of slow inactivation (Table 2). Modulators of ion channels, e.g., voltage gated sodium ion channels, and the medicinal chemistry or methods by which such compounds can be identified, are also described in, for example: Birch et al., *Drug Discovery Today*, 9:410-418 (2004); Audesirk, "Chapter 6-Electrophysiological Analysis of Ion Channel Function," Neurotoxicology: Approaches and Methods, 137-156 (1995); Camerino et al., "Chapter 4: Therapeutic Approaches to Ion Channel Diseases," Advances in Genetics, 64:81-145 (2008); Petkov, "Chapter 16-Ion Channels," Pharmacology: Principles and Practice, 387-427 (2009); Standen et al., "Chapter 15—Patch Clamping Methods and Analysis of Ion Channels," Principles of Medical Biology, Vol. 7, Part 2, 355-375 (1997); Xu et al., Drug Discovery Today, 6:1278-1287 (2001); and Sullivan et al., *Methods Mol. Biol.* 114:125-133 (1999).

Diseases and Conditions

Conditions that can be treated using the compounds described herein include pain (e.g., chronic or acute pain), epilepsy, Alzheimer's disease, Parkinson's disease, diabetes; cancer; sleep disorders; obesity; psychosis such as schizophrenia; overactive bladder; renal disease, neuroprotection, and addiction. For example, the condition can be pain (e.g., neuropathic pain or post-surgery pain), epilepsy, migraine, Parkinson's disease, mood disorders, schizophrenia, psychosis, tinnitus, amyotropic lateral sclerosis, glaucoma, ischaemia, spasticity disorders, obsessive compulsive disorder, restless leg syndrome and Tourette syndrome.

Epilepsy as used herein includes but is not limited to partial seizures such as temporal lobe epilepsy, absence seizures, generalized seizures, and tonic/clonic seizures.

Cancer as used herein includes but is not limited to breast carcinoma, neuroblastoma, retinoblastoma, glioma, prostate carcinoma, esophageal carcinoma, fibrosarcoma, colorectal carcinoma, pheochromocytoma, adrenocarcinoma, insulinoma, lung carcinoma, melanoma, and ovarian cancer.

Acute pain as used herein includes but is not limited to nociceptive pain and post-operative pain. Chronic pain includes but is not limited by: peripheral neuropathic pain (e.g., post-herpetic neuralgia, diabetic neuropathic pain, neuropathic cancer pain, HIV-associated neuropathy, erythromelalgia, failed back-surgery syndrome, trigeminal neuralgia, or phantom limb pain); central neuropathic pain (e.g., multiple sclerosis related pain, Parkinson disease related pain, post-stroke pain, post-traumatic spinal cord injury pain, lumbosacral radiculopathy, cervical radiculopathy, brachial radiculopathy, or pain in dementia); musculoskeletal pain such as osteoarthritic pain and fibromyalgia syndrome; inflammatory pain (e.g., inflammatory pain caused by rheumatoid arthritis, juvenile idiopathic arthritis, ankylosing spondylitis, psoriatic arthritis, inflammatory bowel disease, primary dysmenorrhea, or endometriosis); headache such as migraine, cluster headache, tension headache syndrome, facial pain, headache caused by other diseases; visceral pain such as interstitial cystitis, irritable bowel syndrome and chronic pelvic pain syndrome; and mixed pain such as lower back pain, neck and shoulder pain, burning mouth syndrome and complex regional pain syndrome.

In treating osteoarthritic pain, joint mobility can also improve as the underlying chronic pain is reduced. Thus, use of compounds of the present invention to treat osteoarthritic pain inherently includes use of such compounds to improve joint mobility in patients suffering from osteoarthritis.

The compounds described herein can be tested for efficacy in any standard animal model of pain. Various models test the sensitivity of normal animals to intense or noxious stimuli (physiological or nociceptive pain). These tests include responses to thermal, mechanical, or chemical stimuli. Thermal stimuli usually involve the application of hot stimuli (typically varying between 42-55° C.) including, for example: radiant heat to the tail (the tail flick test), radiant heat to the plantar surface of the hindpaw (the Hargreaves test), the hotplate test, and immersion of the hindpaw or tail into hot water. Immersion in cold water, acetone evaporation, or cold plate tests may also be used to test cold pain responsiveness. Tests involving mechanical stimuli typically measure the threshold for eliciting a withdrawal reflex of the hindpaw to graded strength monofilament von Frey hairs or to a sustained pressure stimulus to a paw (e.g., the Ugo Basile analgesiometer). The duration of a response to a standard pinprick may also be measured. When using a chemical stimulus, the response to the application or injection of a chemical irritant (e.g., capsaicin, mustard oil, bradykinin, ATP, formalin, acetic acid) to the skin, muscle joints or internal organs (e.g., bladder or peritoneum) is measured.

In addition, various tests assess pain sensitization by measuring changes in the excitability of the peripheral or central components of the pain neural pathway. In this regard, peripheral sensitization (i.e., changes in the threshold and responsiveness of high threshold nociceptors) can be induced by repeated heat stimuli as well as the application or injection of sensitizing chemicals (e.g., prostaglandins, bradykinin, histamine, serotonin, capsaicin, or mustard oil). Central sensitization (i.e., changes in the excitability of neurons in the central nervous system induced by activity in peripheral pain fibers) can be induced by noxious stimuli (e.g., heat), chemical stimuli (e.g., injection or application of chemical irritants), or electrical activation of sensory fibers.

Various pain tests developed to measure the effect of peripheral inflammation on pain sensitivity can also be used to study the efficacy of the compounds (Stein et al., *Pharmacol. Biochem. Behav.* 31:445-451, 1988; Woolf et al., *Neurosci.* 62:327-331, 1994). Additionally, various tests assess peripheral neuropathic pain using lesions of the peripheral nervous system. One such example is the "axotomy pain model" (Watson, *J. Physiol.* 231:41, 1973). Other similar tests include the SNL test which involves the ligation of a spinal segmental nerve (Kim and Chung Pain 50:355, 1992), the Seltzer model involving partial nerve injury (Seltzer, *Pain* 43:205-18, 1990), the spared nerve injury (SNI) model (Decosterd and Woolf, Pain 87:149, 2000), chronic constriction injury (CCI) model (Bennett (1993) Muscle Nerve 16: 1040), tests involving toxic neuropathies such as diabetes (streptozocin model), pyridoxine neuropathy, taxol, vincristine, and other antineoplastic agent-induced neuropathies, tests involving ischaemia to a nerve, peripheral neuritis models (e.g., CFA applied perineurally), models of post-herpetic neuralgia using HSV infection, and compression models.

In all of the above tests, outcome measures may be assessed, for example, according to behavior, electrophysiology, neurochemistry, or imaging techniques to detect changes in neural activity.

Exemplary disease models include, but are not limited to, the following models described below.

Pain Models

L5/L6 Spinal Nerve Ligation (SNL)—Chung Pain Model

The Spinal Nerve Ligation is an animal model representing peripheral nerve injury generating a neuropathic pain syndrome. In this model experimental animals develop the clinical symptoms of tactile allodynia and hyperalgesia. L5/L6 Spinal nerve ligation (SNL) injury was induced using the procedure of Kim and Chung (Kim et al., Pain 50:355-363, 1992) in male Sprague-Dawley rats (Harlan; Indianapolis, Ind.). An exemplary protocol is provided below.

Animals can be anesthetized with isoflurane, and the left L6 transverse process can be removed, and the L5 and L6 spinal nerves can be tightly ligated with 6-0 silk suture. The wound can then be closed with internal sutures and external tissue adhesive. Rats that exhibit motor deficiency (such as paw-dragging) or failure to exhibit subsequent tactile allodynia can be excluded from further testing.

Sham control rats can undergo the same operation and handling as the experimental animals, but without SNL.

Assessment of Mechanical Hyperalgesia

Baseline and post-treatment values for mechanical hyperalgesia can be evaluated using a digital Randall-Selitto device (dRS; IITC Life Sciences, Woodland Hills, Calif.). Animals can be allowed to acclimate to the testing room for a minimum of 30 minutes before testing. Animals can be placed in a restraint sling that suspends the animal, leaving the hind limbs available for testing. Paw compression threshold was measured once at each time point for the ipsilateral and contralateral paws. The stimulus can be applied to the plantar surface of the hind paw by a dome-shaped tip placed between the 3rd and 4th metatarsus, and pressure can be applied gradually over approximately 10 seconds. Measurements can be taken from the first observed nocifensive behavior of vocalization, struggle or withdrawal. A cut-off value of 300 g can be used to prevent injury to the animal. The mean and standard error of the mean (SEM) can be determined for each paw for each treatment group. Fourteen days after surgery, mechanical hyperalgesia can be assessed, and rats can be assigned to treatment groups based on pre-treatment baseline values. Prior to initiating drug delivery, baseline behavioral testing data can be obtained. At selected times after infusion of the Test or Control Article behavioural data can then be collected again.

Assessment of Tactile Allodynia—Von Frey

The assessment of tactile allodynia can consist of measuring the withdrawal threshold of the paw ipsilateral to the site of nerve injury in response to probing with a series of calibrated von Frey filaments (innocuous stimuli). Animals can be acclimated to the suspended wire-mesh cages for 30 min before testing. Each von Frey filament can be applied perpendicularly to the plantar surface of the ligated paw of rats for 5 sec. A positive response can be indicated by a sharp withdrawal of the paw. For rats, the first testing filament is 4.31. Measurements can be taken before and after administration of test articles. The paw withdrawal threshold can be determined by the non-parametric method of Dixon (Dixon, *Ann. Rev. Pharmacol. Toxicol.* 20:441-462, 1980), in which the stimulus was incrementally increased until a positive response was obtained, and then decreased until a negative result was observed. The protocol can be repeated until three changes in behaviour were determined ("up and down" method; Chaplan et al., *J. Neurosci. Methods* 53:55-63, 1994). The 50% paw withdrawal threshold can be determined as $(10^{[Xf+k\delta]})/10{,}000$, where $X_f$=the value of the last von Frey filament employed, k=Dixon value for the positive/negative pattern, and $\delta$=the logarithmic difference between stimuli. The cut-off values for rats can be, for example, no less than 0.2 g and no higher than 15 g (5.18 filament); for mice no less than 0.03 g and no higher than 2.34 g (4.56 filament). A significant drop of the paw withdrawal threshold compared to the pre-treatment baseline is considered tactile allodynia. Rat SNL tactile allodynia can be tested for the compounds described herein at, e.g., 60 minutes compared to baseline and post-SNL.

Assessment of Thermal Hypersensitivity—Hargreaves

The method of Hargreaves and colleagues (Hargreaves et al., *Pain* 32:77-8, 1988) can be employed to assess paw-withdrawal latency to a noxious thermal stimulus.

Rats may be allowed to acclimate within a Plexiglas enclosure on a clear glass plate for 30 minutes. A radiant heat source (e.g., halogen bulb coupled to an infrared filter) can then be activated with a timer and focused onto the plantar surface of the affected paw of treated rats. Paw-withdrawal latency can be determined by a photocell that halts both lamp and timer when the paw is withdrawn. The latency to withdrawal of the paw from the radiant heat source can be determined prior to L5/L6 SNL, 7-14 days after L5/L6 SNL but before drug, as well as after drug administration. A maximal cut-off of 33 seconds is typically employed to prevent tissue damage. Paw withdrawal latency can be thus determined to the nearest 0.1 second. A significant drop of the paw withdrawal latency from the baseline indicates the status of thermal hyperalgesia. Antinociception is indicated by a reversal of thermal hyperalgesia to the pre-treatment baseline or a significant (p<0.05) increase in paw withdrawal latency above this baseline. Data is converted to % anti hyperalgesia or % anti nociception by the formula: (100×(test latency −baseline latency)/(cut-off−baseline latency) where cut-off is 21 seconds for determining anti hyperalgesia and 40 seconds for determining anti nociception.

Epilepsy Models

6 Hz Psychomotor Seizure Model of Partial Epilepsy

Compounds can be evaluated for the protection against seizures induced by a 6 Hz, 0.2 ms rectangular pulse width of 3 s duration, at a stimulus intensity of 32 mA (CC97) applied to the cornea of male CF1 mice (20-30 g) according to procedures described by Barton et al, "Pharmacological Characterization of the 6 Hz Psychomotor Seizure Model of Partial Epilepsy," *Epilepsy Res.* 47:217-27, 2001. Seizures are characterised by the expression of one or more of the following behaviours: stun, forelimb clonus, twitching of the vibrissae and Straub-tail immediately following electrical stimulation. Animals can be considered "protected" if, following pre-treatment with a compound, the 6 Hz stimulus failed to evoke a behavioural response as describe above.

Assessments of Neurological or Muscular Impairments

To assess a compound's undesirable side effects (toxicity), animals can be monitored for overt signs of impaired neurological or muscular function. In mice, the rotarod procedure (Dunham et al., *J. Am. Pharmacol. Assoc.* 46:208-209, 1957) is used to disclose minimal muscular or neurological impairment (MMI). When a mouse is placed on a rod that rotates at a speed of 6 rpm, the animal can maintain its equilibrium for long periods of time. The animal is considered toxic if it falls off this rotating rod three times during a 1-min period. In addition to MMI, animals may exhibit a circular or zigzag gait, abnormal body posture and spread of the legs, tremors, hyperactivity, lack of exploratory behavior, somnolence, stupor, catalepsy, loss of placing response and changes in muscle tone.

Recordings on Lamina I/II Spinal Cord Neurons

Male Wistar rats (P6 to P9 for voltage-clamp and P15 to P18 for current-clamp recordings) can be anaesthetized through intraperitoneal injection of Inactin (Sigma). The spinal cord can then be rapidly dissected out and placed in an ice-cold solution protective sucrose solution containing (in mM): 50 sucrose, 92 NaCl, 15 D-Glucose, 26 $NaHCO_3$, 5 KCl, 1.25 $NaH_2PO_4$, 0.5 $CaCl_2$, 7 $MgSO_4$, 1 kynurenic acid, and bubbled with 5% $CO_2$/95% $O_2$. The meninges, dura, and dorsal and ventral roots can then removed from the lumbar region of the spinal cord under a dissecting microscope. The "cleaned" lumbar region of the spinal cord may be glued to the vibratome stage and immediately immersed in ice cold, bubbled, sucrose solution. For current-clamp recordings, 300 to 350 μm parasagittal slices can be cut to preserve the dendritic arbour of lamina 1 neurons, while 350 to 400 μm transverse slices can be prepared for voltage-clamped Nav channel recordings. Slices may be allowed to recover for 1 hour at 35° C. in Ringer solution containing (in mM): 125 NaCl, 20 D-Glucose, 26 $NaHCO_3$, 3 KCl, 1.25 $NaH_2PO_4$, 2 $CaCl_2$, 1 $MgCl_2$, 1 kynurenic acid, 0.1 picrotoxin, bubbled with 5% $CO_2$/95% $O_2$. The slice recovery chamber can then returned to room temperature (20 to 22° C.) for recordings.

Neurons may be visualized using IR-DIC optics (Zeiss Axioskop 2 FS plus, Gottingen, Germany), and neurons from lamina 1 and the outer layer of lamina II can be selected based on their location relative to the substantia gelatinosa layer. Neurons can be patch-clamped using borosilicate glass patch pipettes with resistances of 3 to 6 MΩ. Current-clamp recordings of lamina I/II neurons in the intact slice, the external recording solution was the above Ringer solution, while the internal patch pipette solution contained (in mM): 140 KGluconate, 4 NaCl, 10 HEPES, 1 EGTA, 0.5 $MgCl_2$, 4 MgATP, 0.5 $Na_2GTP$, adjusted to pH 7.2 with 5 M KOH and to 290 mOsm with D-Mannitol (if necessary). Tonic firing neurons can be selected for current-clamp experiments, while phasic, delayed onset and single spike neurons may be discarded (22). Recordings can be digitized at 50 kHz and low-pass filtered at 2.4 kHz.

hERG $K^+$ Channel Activity

In addition to being able to modulate a particular voltage-gated ion channel, e.g. a sodium channel, it may be desirable that the compound has very low activity with respect to the hERG $K^+$ channel, which is expressed in the heart: compounds that block this channel with high potency may cause reactions which are fatal. See, e.g., Bowlby et al., "hERG (KCNH2 or $K_v11.1$ $K^+$ Channels: Screening for Cardiac Arrhythmia Risk," *Curr. Drug Metab.* 9:965-70, 2008). Thus, for a compound that modulates sodium channel activity, it may also be shown that the hERG $K^+$ channel is not inhibited or only minimally inhibited as compared to the inhibition of the primary channel targeted. Similarly, it may be desirable that the compound does not inhibit cytochrome p450, an enzyme that is required for drug detoxification. Such compounds may be particularly useful in the methods described herein.

Compounds can be tested using a standard electrophysiological assay (Kiss et al., *Assay & Drug Development Technologies,* 1:1-2, 2003; Bridgland-Taylor et al., *J Pharmacol Toxicol Methods,* 54:189-199, 2006). For example, compounds can be tested at 3 μM using IonWorks, and the percent inhibition of the peak of the slowly deactivating hERG tail current can be used to assess the affinity.

Pharmacokinetic Parameters

Preliminary exposure characteristics of the compounds can be evaluated using, e.g., an in vivo Rat Early Pharmacokinetic (EPK) study design to show bioavailability. For example, Male Sprague-Dawley rats can be dosed via oral (PO) gavage in a particular formulation. Blood samples can then be collected from the animals at 6 timepoints out to 4 hours post-dose. Pharmacokinetic analysis can then performed on the LC-MS/MS measured concentrations for each timepoint of each compound.

Pharmaceutical Compositions

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, or therapy—the compounds are formulated in ways consonant with these parameters. A summary of such techniques is found in Remington: The Science and Practice of Pharmacy, 21$^{st}$ Edition, Lippincott Williams & Wilkins, (2005); and Encyclopedia of Pharmaceutical Technology, eds. J. Swarbrick and J. C. Boylan, 1988-1999, Marcel Dekker, New York, each of which is incorporated herein by reference.

The compounds described herein (e.g., a compound according to any of Formulas (I)-(III) or any of Compounds (1)-(65) of Table 1) may be present in amounts totaling 1-95% by weight of the total weight of the composition. The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, gastrointesitnal, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

In general, for use in treatment, the compounds described herein (e.g., a compound according to any of Formulas (I)-(III) or any of Compounds (1)-(65) of Table 1) may be used alone, as mixtures of two or more compounds or in combination with other pharmaceuticals. An example of other pharmaceuticals to combine with the compounds described herein (e.g., a compound according to any of Formulas (I)-(III) or any of Compounds (1)-(65) of Table 1) would include pharmaceuticals for the treatment of the same indication. For example, in the treatment of pain, a compound may be combined with another pain relief treatment such as an NSAID, or a compound which selectively inhibits COX-2, or an opioid, or an adjuvant analgesic such as an antidepressant. Another example of a potential pharmaceutical to combine with the compounds described herein (e.g., a compound according to any of Formulas (I)-(III) or any of Compounds (1)-(65) of Table 1) would include pharmaceuticals for the treatment of different yet associated or related symptoms or indications. Depending on the mode of administration, the compounds will be formulated into suitable compositions to permit facile delivery. Each compound of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

The compounds of the invention may be prepared and used as pharmaceutical compositions comprising an effective amount of a compound described herein (e.g., a compound according to any of Formulas (I)-(III) or any of Compounds (1)-(65) of Table 1) and a pharmaceutically acceptable carrier or excipient, as is well known in the art. In some embodiments, the composition includes at least two different pharmaceutically acceptable excipients or carriers.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677, which is herein incorporated by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, and tablets, as is understood in the art.

For administration to animal or human subjects, the dosage of the compounds of the invention may be, for example, 0.01-50 mg/kg (e.g., 0.01-15 mg/kg or 0.1-10 mg/kg). For example, the dosage can be 10-30 mg/kg.

Each compound of a combination therapy, as described herein, may be formulated in a variety of ways that are known in the art. For example, the first and second agents of the combination therapy may be formulated together or separately.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Formulations for oral use include tablets containing the active ingredient(s) in a mixture with nontoxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in a combination therapy as described herein, can, independently, be one to four times daily for one day to one year, and may even be for the life of the patient. Chronic, long-term administration may be indicated.

EXAMPLES

Compounds of the invention include, but are not limited to, the following compounds listed in Table 1. Mass spectrometry can be employed with final compounds and at various stages throughout the synthesis as a confirmation of the identity of the product obtained (M+1). For mass spectrometric analysis, samples can be prepared at an approximate concentration of 1 μg/mL in acetonitrile with 0.05% trifluoroacetic acid. Samples can be manually infused into a Shimadzu LCMS-2020 single quadrupole mass spectrometer and scanned in the range of 100 to 900 m/z.

TABLE 1

| No. | Structure | MW | IUPAC Name |
| --- | --- | --- | --- |
| 1 | 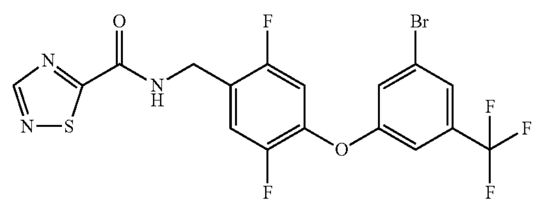 [SMILES: O=C(NCc1cc(F)c(Oc2cc(Br)cc(C(F)(F)F)c2)cc1F)c1ncns1] | 494.233 | N-(4-(3-bromo-5-(trifluoromethyl)phenoxy)-2,5-difluorobenzyl)-1,2,4-thiadiazole-5-carboxamide |
| 2 | 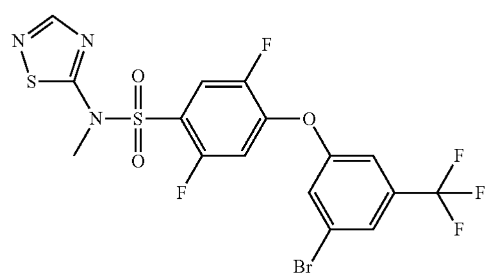 [SMILES: CN(c1ncns1)S(=O)(=O)c1cc(F)c(Oc2cc(Br)cc(C(F)(F)F)c2)cc1F] | 530.28 | 4-(3-bromo-5-(trifluoromethyl)phenoxy)-2,5-difluoro-N-methyl-N-(1,2,4-thiadiazol-5-yl)benzenesulfonamide |
| 3 | 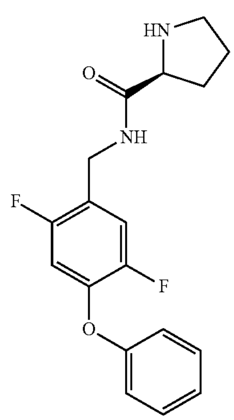 [SMILES: O=C(NCc1cc(F)c(Oc2ccccc2)cc1F)[C@@H]1CCCN1] | 332.344 | (2S)-N-[(2,5-difluoro-4-phenoxyphenyl)methyl]pyrrolidine-2-carboxamide |

TABLE 1-continued
| No. | Structure | MW | IUPAC Name |
|---|---|---|---|
| 4 | 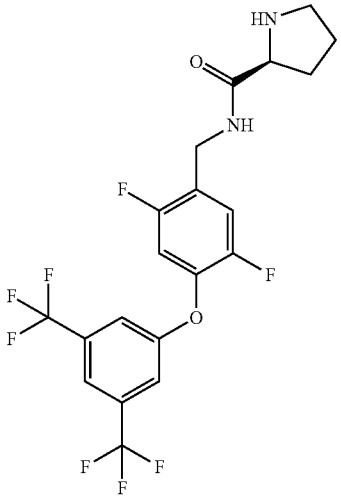 [SMILES: O=C(NCc1cc(F)c(Oc2cc(C(F)(F)F)cc(C(F)(F)F)c2)cc1F)[C@@H]1CCCN1] | 468.341 | (2S)-N-({4-[3,5-bis(trifluoromethyl)phenoxy]-2,5-difluorophenyl}methyl)pyrrolidine-2-carboxamide |
| 5 | 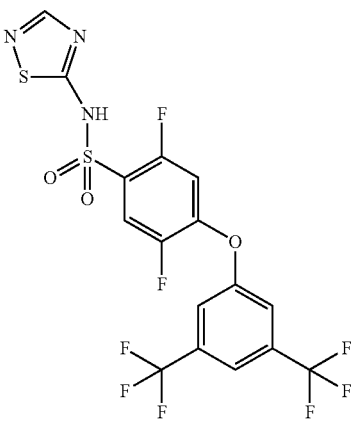 [SMILES: O=S(=O)(Nc1ncns1)c1cc(F)c(Oc2cc(C(F)(F)F)cc(C(F)(F)F)c2)cc1F] | 505.362 | 4-[3,5-bis(trifluoromethyl)phenoxy]-2,5-difluoro-N-(1,2,4-thiadiazol-5-yl)benzene-1-sulfonamide |
| 6 | 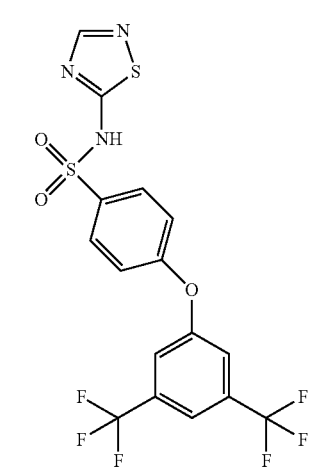 [SMILES: O=S(=O)(Nc1ncns1)c1ccc(Oc2cc(C(F)(F)F)cc(C(F)(F)F)c2)cc1] | 469.381 | 4-[3,5-bis(trifluoromethyl)phenoxy]-N-(1,2,4-thiadiazol-5-yl)benzene-1-sulfonamide |

TABLE 1-continued

| No. | Structure | MW | IUPAC Name |
|---|---|---|---|
| 7 | 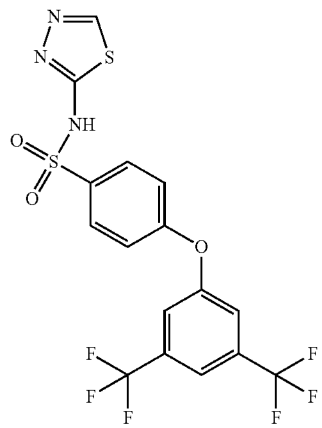 [SMILES: O=S(=O)(Nc1nncs1)c1ccc(Oc2cc(C(F)(F)F)cc(C(F)(F)F)c2)cc1] | 469.381 | 4-[3,5-bis(trifluoromethyl)phenoxy]-N-(1,3,4-thiadiazol-2-yl)benzene-1-sulfonamide |
| 8 | 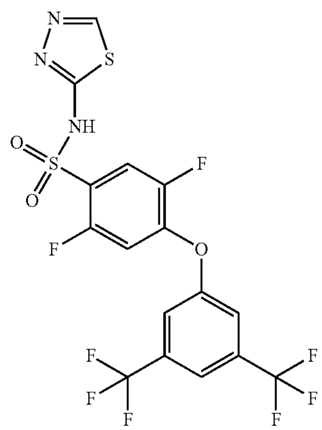 [SMILES: O=S(=O)(Nc1nncs1)c1cc(F)c(Oc2cc(C(F)(F)F)cc(C(F)(F)F)c2)cc1F] | 505.362 | 4-[3,5-bis(trifluoromethyl)phenoxy]-2,5-difluoro-N-(1,3,4-thiadiazol-2-yl)benzene-1-sulfonamide |
| 9 | 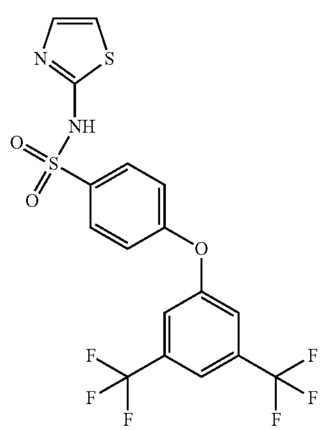 [SMILES: O=S(=O)(Nc1nccs1)c1ccc(Oc2cc(C(F)(F)F)cc(C(F)(F)F)c2)cc1] | 468.393 | 4-[3,5-bis(trifluoromethyl)phenoxy]-N-(1,3-thiazol-2-yl)benzene-1-sulfonamide |
| 10 | 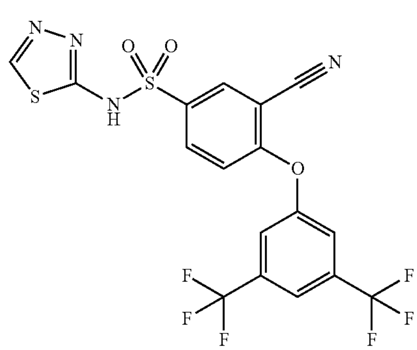 [SMILES: N#Cc1cc(S(=O)(=O)Nc2nncs2)ccc1Oc1cc(C(F)(F)F)cc(C(F)(F)F)c1] | 494.391 | 4-[3,5-bis(trifluoromethyl)phenoxy]-3-cyano-N-(1,3,4-thiadiazol-2-yl)benzene-1-sulfonamide |

TABLE 1-continued

| No. | Structure | MW | IUPAC Name |
|---|---|---|---|
| 11 | 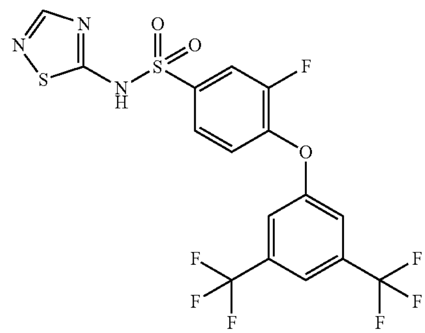 [SMILES: O=S(=O)(Nc1ncns1)c1ccc(Oc2cc(C(F)(F)F)cc(C(F)(F)F)c2)c(F)c1] | 487.372 | 4-[3,5-bis(trifluoromethyl)phenoxy]-3-fluoro-N-(1,2,4-thiadiazol-5-yl)benzene-1-sulfonamide |
| 12 | 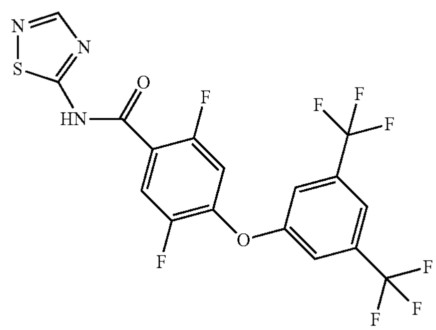 [SMILES: O=C(Nc1ncns1)c1cc(F)c(Oc2cc(C(F)(F)F)cc(C(F)(F)F)c2)cc1F] | 469.309 | 4-[3,5-bis(trifluoromethyl)phenoxy]-2,5-difluoro-N-(1,2,4-thiadiazol-5-yl)benzamide |
| 13 | 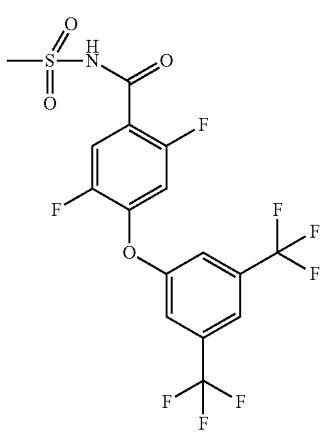 [SMILES: CS(=O)(=O)NC(=O)c1cc(F)c(Oc2cc(C(F)(F)F)cc(C(F)(F)F)c2)cc1F] | 463.299 | 4-[3,5-bis(trifluoromethyl)phenoxy]-2,5-difluoro-N-methanesulfonylbenzamide |
| 14 | 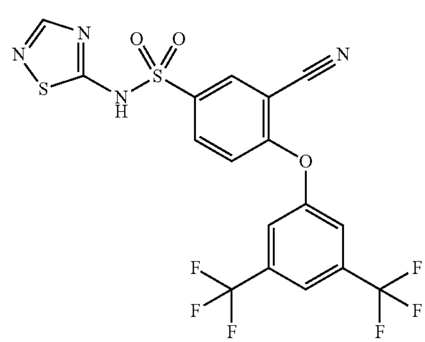 [SMILES: N#Cc1cc(S(=O)(=O)Nc2ncns2)ccc1Oc1cc(C(F)(F)F)cc(C(F)(F)F)c1] | 494.391 | 4-[3,5-bis(trifluoromethyl)phenoxy]-3-cyano-N-(1,2,4-thiadiazol-5-yl)benzene-1-sulfonamide |

TABLE 1-continued

| No. | Structure | MW | IUPAC Name |
|---|---|---|---|
| 15 | 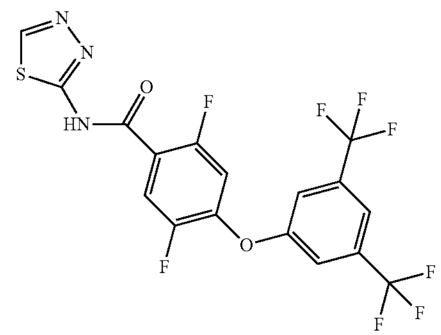 [SMILES: O=C(Nc1nncs1)c1cc(F)c(Oc2cc(C(F)(F)F)cc(C(F)(F)F)c2)cc1F] | 469.309 | 4-[3,5-bis(trifluoromethyl)phenoxy]-2,5-difluoro-N-(1,3,4-thiadiazol-2-yl)benzamide |
| 16 | 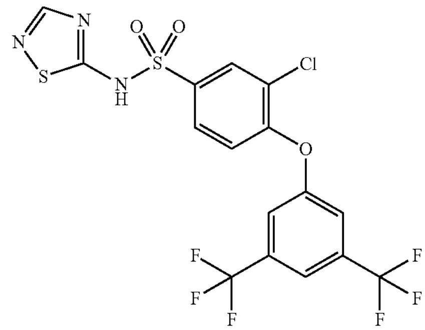 [SMILES: O=S(=O)(Nc1ncns1)c1ccc(Oc2cc(C(F)(F)F)cc(C(F)(F)F)c2)c(Cl)c1] | 503.826 | 4-[3,5-bis(trifluoromethyl)phenoxy]-3-chloro-N-(1,2,4-thiadiazol-5-yl)benzene-1-sulfonamide |
| 17 | 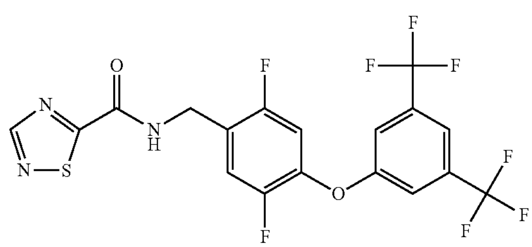 [SMILES: O=C(NCc1cc(F)c(Oc2cc(C(F)(F)F)cc(C(F)(F)F)c2)cc1F)c1ncns1] | 483.335 | N-({4-[3,5-bis(trifluoromethyl)phenoxy]-2,5-difluorophenyl}methyl)-1,2,4-thiadiazole-5-carboxamide |
| 18 | 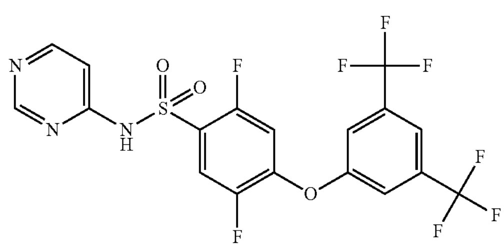 [SMILES: O=S(=O)(Nc1ccncn1)c1cc(F)c(Oc2cc(C(F)(F)F)cc(C(F)(F)F)c2)cc1F] | 499.335 | 4-[3,5-bis(trifluoromethyl)phenoxy]-2,5-difluoro-N-(pyrimidin-4-yl)benzene-1-sulfonamide |
| 19 | 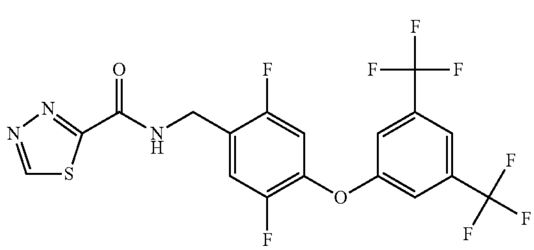 [SMILES: O=C(NCc1cc(F)c(Oc2cc(C(F)(F)F)cc(C(F)(F)F)c2)cc1F)c1nncs1] | 483.335 | N-({4-[3,5-bis(trifluoromethyl)phenoxy]-2,5-difluorophenyl}methyl)-1,3,4-thiadiazole-2-carboxamide |

TABLE 1-continued

| No. | Structure | MW | IUPAC Name |
|---|---|---|---|
| 20 | 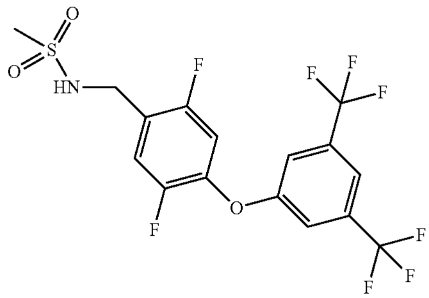 [SMILES: CS(=O)(=O)NCc1cc(F)c(Oc2cc(C(F)(F)F)cc(C(F)(F)F)c2)cc1F] | 449.316 | N-({4-[3,5-bis(trifluoromethyl)phenoxy]-2,5-difluorophenyl}methyl)methane-sulfonamide |
| 21 | 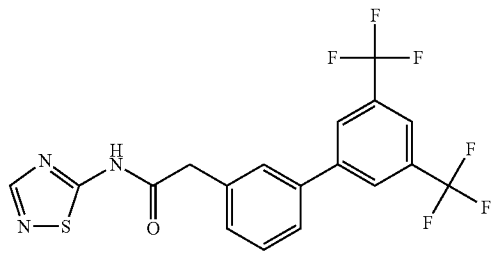 [SMILES: O=C(Cc1cccc(-c2cc(C(F)(F)F)cc(C(F)(F)F)c2)c1)Nc1ncns1] | 431.355 | 2-{3-[3,5-bis(trifluoromethyl)phenyl]phenyl}-N-(1,2,4-thiadiazol-5-yl)acetamide |
| 22 | 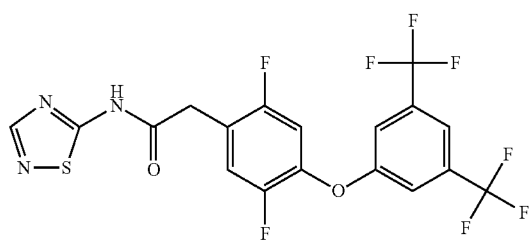 [SMILES: O=C(Cc1cc(F)c(Oc2cc(C(F)(F)F)cc(C(F)(F)F)c2)cc1F)Nc1ncns1] | 483.335 | 2-{4-[3,5-bis(trifluoromethyl)phenoxy]-2,5-difluorophenyl}-N-(1,2,4-thiadiazol-5-yl)acetamide |
| 23 | 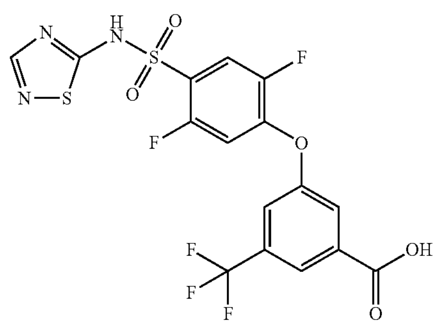 [SMILES: O=C(O)c1cc(Oc2cc(F)c(S(=O)(=O)Nc3ncns3)cc2F)cc(C(F)(F)F)c1] | 481.374 | 3-{2,5-difluoro-4-[(1,2,4-thiadiazol-5-yl)sulfamoyl]phenoxy}-5-(trifluoromethyl)benzoic |
| 24 | 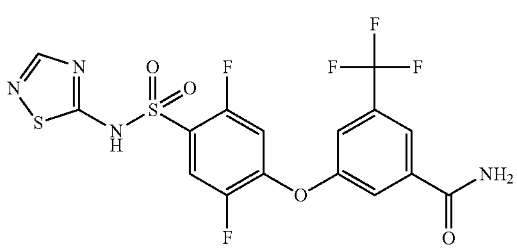 [SMILES: NC(=O)c1cc(Oc2cc(F)c(S(=O)(=O)Nc3ncns3)cc2F)cc(C(F)(F)F)c1] | 480.389 | 3-{2,5-difluoro-4-[(1,2,4-thiadiazol-5-yl)sulfamoyl]phenoxy}-5-(trifluoromethyl)benzamide |

TABLE 1-continued

| No. | Structure | MW | IUPAC Name |
|---|---|---|---|
| 25 | 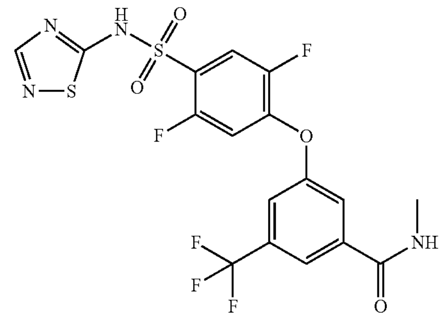 [SMILES: CNC(=O)c1cc(Oc2cc(F)c(S(=O)(=O)Nc3ncns3)cc2F)cc(C(F)(F)F)c1] | 494.416 | 3-{2,5-difluoro-4-[(1,2,4-thiadiazol-5-yl)sulfamoyl]phenoxy}-N-methyl-5-(trifluoromethyl)benzamide |
| 26 | 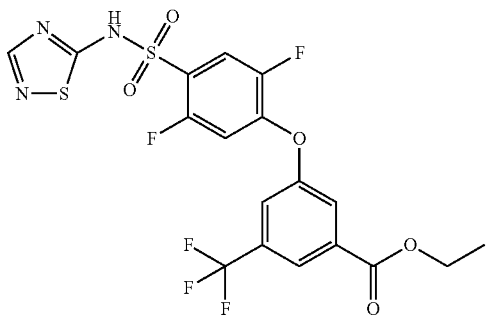 [SMILES: CCOC(=O)c1cc(Oc2cc(F)c(S(=O)(=O)Nc3ncns3)cc2F)cc(C(F)(F)F)c1] | 509.427 | ethyl 3-{2,5-difluoro-4-[(1,2,4-thiadiazol-5-yl)sulfamoyl]phenoxy}-5-(trifluoromethyl)benzoate |
| 27 | 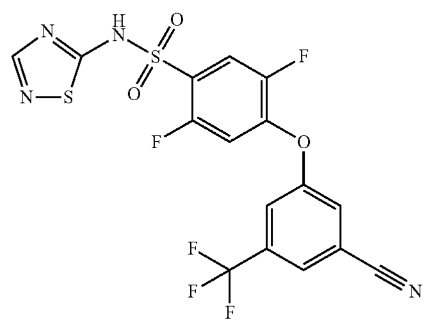 [SMILES: N#Cc1cc(Oc2cc(F)c(S(=O)(=O)Nc3ncns3)cc2F)cc(C(F)(F)F)c1] | 462.374 | 4-[3-cyano-5-(trifluoromethyl)phenoxy]-2,5-difluoro-N-(1,2,4-thiadiazol-5-yl)benzene-1-sulfonamide |
| 28 | 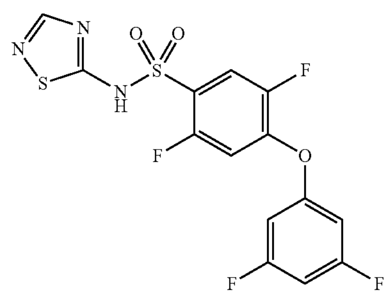 [SMILES: O=S(=O)(Nc1ncns1)c1cc(F)c(Oc2cc(F)cc(F)c2)cc1F] | 405.347 | 4-(3,5-difluorophenoxy)-2,5-difluoro-N-(1,2,4-thiadiazol-5-yl)benzene-1-sulfonamide |
| 29 | 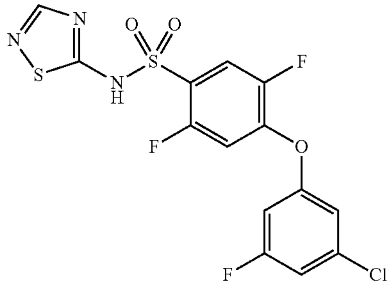 [SMILES: O=S(=O)(Nc1ncns1)c1cc(F)c(Oc2cc(F)cc(Cl)c2)cc1F] | 421.802 | 4-(3-chloro-5-fluorophenoxy)-2,5-difluoro-N-(1,2,4-thiadiazol-5-yl)benzene-1-sulfonamide |

TABLE 1-continued

| No. | Structure | MW | IUPAC Name |
|---|---|---|---|
| 30 | 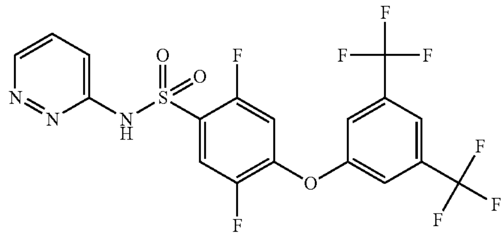 [SMILES: O=S(=O)(Nc1cccnn1)c1cc(F)c(Oc2cc(C(F)(F)F)cc(C(F)(F)F)c2)cc1F] | 499.335 | 4-[3,5-bis(trifluoromethyl)phenoxy]-2,5-difluoro-N-(pyridazin-3-yl)benzene-1-sulfonamide |
| 31 | 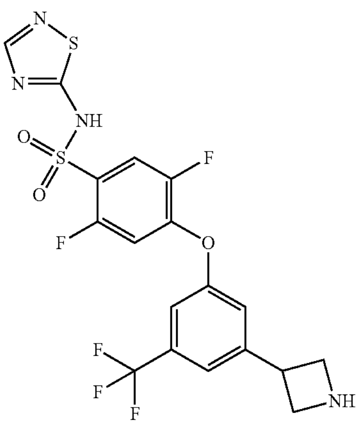 [SMILES: O=S(=O)(Nc1ncns1)c1cc(F)c(Oc2cc(C3CNC3)cc(C(F)(F)F)c2)cc1F] | 493.451. | 4-(3-(azetidin-3-yl)-5-(trifluoromethyl)phenoxy)-2,5-difluoro-N-(1,2,4-thiadiazol-5-yl)benzenesulfonamide |
| 32 | 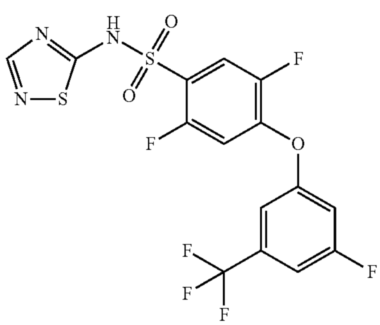 [SMILES: O=S(=O)(Nc1ncns1)c1cc(F)c(Oc2cc(F)cc(C(F)(F)F)c2)cc1F] | 455.355 | 2,5-difluoro-4-(3-fluoro-5-(trifluoromethyl)phenoxy)-N-(1,2,4-thiadiazol-5-yl)benzenesulfonamide |
| 33 | 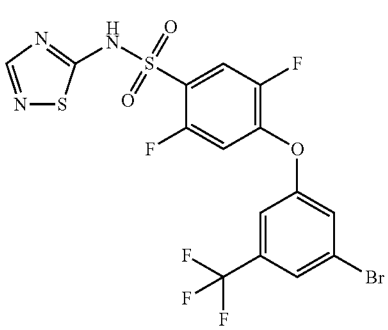 [SMILES: O=S(=O)(Nc1ncns1)c1cc(F)c(Oc2cc(Br)cc(C(F)(F)F)c2)cc1F] | 516.26 | 4-[3-bromo-5-(trifluoromethyl)phenoxy]-2,5-difluoro-N-(1,2,4-thiadiazol-5-yl)benzene-1-sulfonamide |

TABLE 1-continued

| No. | Structure | MW | IUPAC Name |
|---|---|---|---|
| 34 | 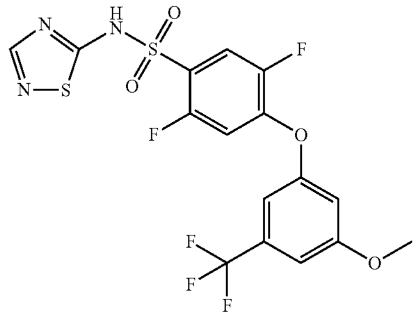 [SMILES: COc1cc(Oc2cc(F)c(S(=O)(=O)Nc3ncns3)cc2F)cc(C(F)(F)F)c1] | 467.39 | 2,5-difluoro-4-[3-methoxy-5-(trifluoromethyl)phenoxy]-N-(1,2,4-thiadiazol-5-yl)benzene-1-sulfonamide |
| 35 | 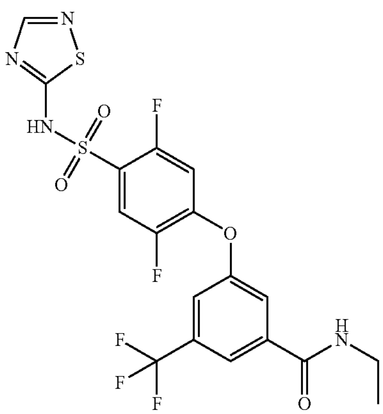 [SMILES: CCNC(=O)c1cc(Oc2cc(F)c(S(=O)(=O)Nc3ncns3)cc2F)cc(C(F)(F)F)c1] | 508.442 | 3-{2,5-difluoro-4-[(1,2,4-thiadiazol-5-yl)sulfamoyl]phenoxy}-N-ethyl-5-(trifluoromethyl)benzamide |
| 36 | 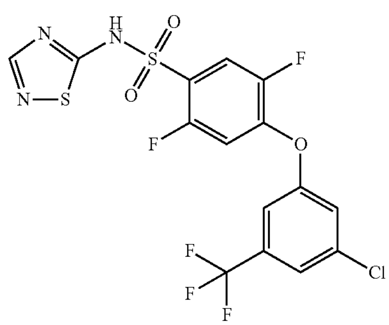 [SMILES: O=S(=O)(Nc1ncns1)c1cc(F)c(Oc2cc(Cl)cc(C(F)(F)F)c2)cc1F] | 471.809. | 4-[3-chloro-5-(trifluoromethyl)phenoxy]-2,5-difluoro-N-(1,2,4-thiadiazol-5-yl)benzene-1-sulfonamide |
| 37 | 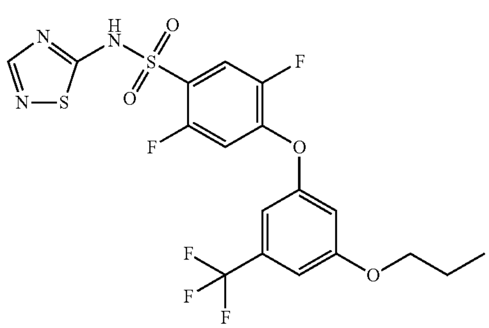 [SMILES: CCCOc1cc(Oc2cc(F)c(S(=O)(=O)Nc3ncns3)cc2F)cc(C(F)(F)F)c1] | 495.443 | 2,5-difluoro-4-[3-propoxy-5-(trifluoromethyl)phenoxy]-N-(1,2,4-thiadiazol-5-yl)benzene-1-sulfonamide |

TABLE 1-continued

| No. | Structure | MW | IUPAC Name |
|---|---|---|---|
| 38 | 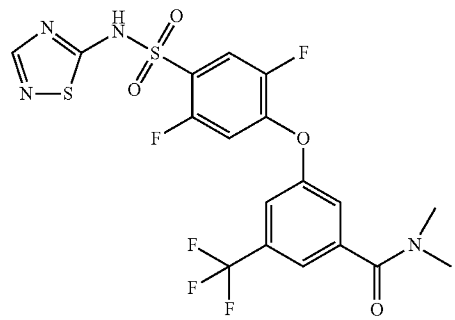 [SMILES: CN(C)C(=O)c1cc(Oc2cc(F)c(S(=O)(=O)Nc3ncns3)cc2F)cc(C(F)(F)F)c1] | 508.442 | 3-{2,5-difluoro-4-[(1,2,4-thiadiazol-5-yl)sulfamoyl]phenoxy}-N,N-dimethyl-5-(trifluoromethyl)benzamide |
| 39 | 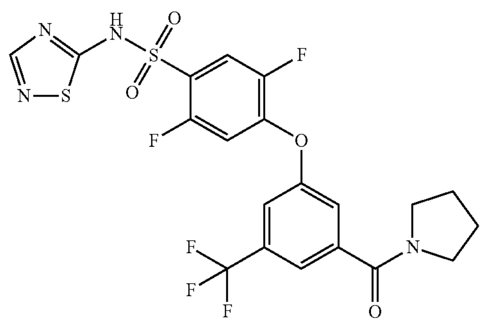 [SMILES: O=C(c1cc(Oc2cc(F)c(S(=O)(=O)Nc3ncns3)cc2F)cc(C(F)(F)F)c1)N1CCCC1] | 534.48 | 2,5-difluoro-4-{3-[(pyrrolidin-1-yl)carbonyl]-5-(trifluoromethyl)phenoxy}-N-(1,2,4-thiadiazol-5-yl)benzene-1-sulfonamide |
| 40 | 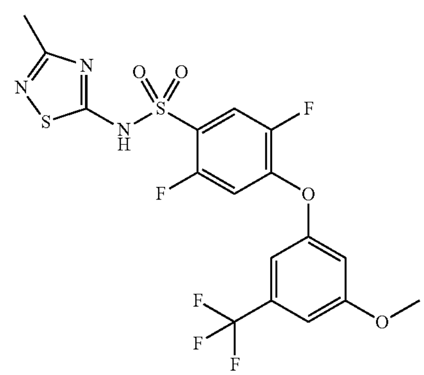 [SMILES: COc1cc(Oc2cc(F)c(S(=O)(=O)Nc3nc(C)ns3)cc2F)cc(C(F)(F)F)c1] | 481.417 | 2,5-difluoro-4-[3-methoxy-5-(trifluoromethyl)phenoxy]-N-(3-methyl-1,2,4-thiadiazol-5-yl)benzene-1-sulfonamide |
| 41 | 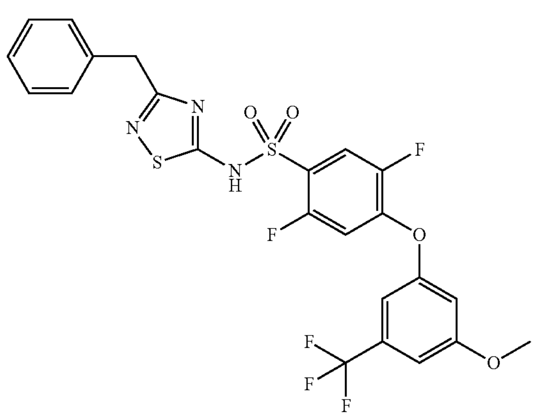 [SMILES: COc1cc(Oc2cc(F)c(S(=O)(=O)Nc3nc(Cc4ccccc4)ns3)cc2F)cc(C(F)(F)F)c1] | 557.513 | N-(3-benzyl-1,2,4-thiadiazol-5-yl)-2,5-difluoro-4-[3-methoxy-5-(trifluoromethyl)phenoxy]benzene-1-sulfonamide |

TABLE 1-continued

| No. | Structure | MW | IUPAC Name |
|---|---|---|---|
| 42 | 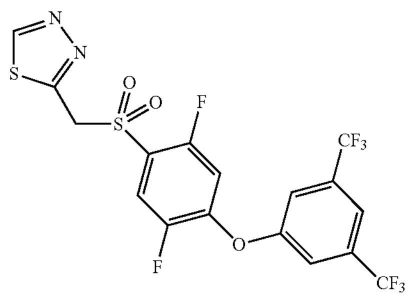 [SMILES: O=S(=O)(Cc1nncs1)c1cc(F)c(Oc2cc(C(F)(F)F)cc(C(F)(F)F)c2)cc1F] | 504.37 | 2-(((4-(3,5-bis(trifluoromethyl)phenoxy)-2,5-difluorophenyl)sulfonyl)methyl)-1,3,4-thiadiazole |
| 43 | 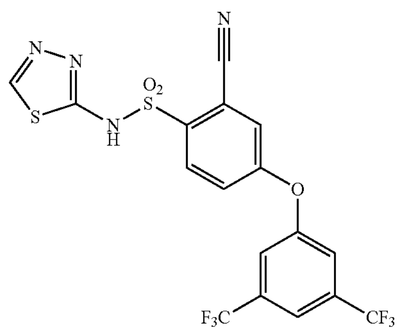 [SMILES: N#Cc1cc(Oc2cc(C(F)(F)F)cc(C(F)(F)F)c2)ccc1S(=O)(=O)Nc1nncs1] | 494.391 | 4-[3,5-bis(trifluoromethyl)phenoxy]-2-cyano-N-(1,3,4-thiadiazol-2-yl)benzene-1-sulfonamide |
| 44 | 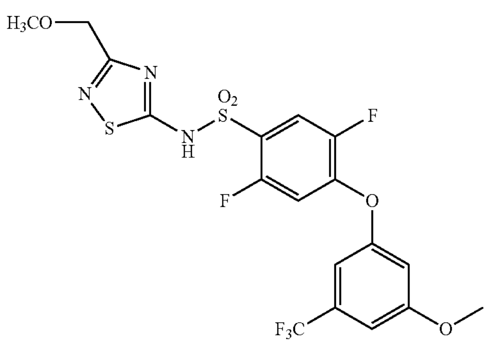 [SMILES: COCc1nsc(NS(=O)(=O)c2cc(F)c(Oc3cc(OC)cc(C(F)(F)F)c3)cc2F)n1] | 511.443 | 2,5-difluoro-4-[3-methoxy-5-(trifluoromethyl)phenoxy]-N-[3-(methoxymethyl)-1,2,4-thiadiazol-5-yl]benzene-1-sulfonamide |
| 45 | 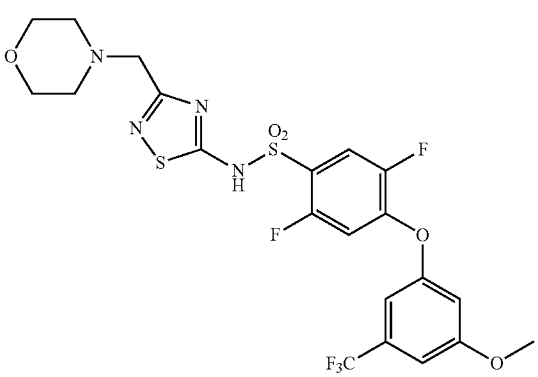 [SMILES: COc1cc(Oc2cc(F)c(S(=O)(=O)Nc3nc(CN4CCOCC4)ns3)cc2F)cc(C(F)(F)F)c1] | 566.521 | 2,5-difluoro-4-[3-methoxy-5-(trifluoromethyl)phenoxy]-N-[3-(morpholin-4-ylmethyl)-1,2,4-thiadiazol-5-yl]benzene-1-sulfonamide |

TABLE 1-continued

| No. | Structure | MW | IUPAC Name |
|---|---|---|---|
| 46 | 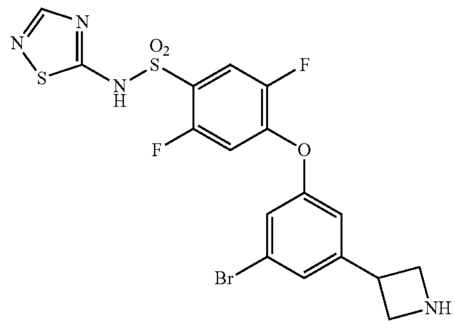 [SMILES: O=S(=O)(Nc1ncns1)c1cc(F)c(Oc2cc(Br)cc(C3CNC3)c2)cc1F] | 503.34 | 4-(3-(azetidin-3-yl)-5-bromophenoxy)-2,5-difluoro-N-(1,2,4-thiadiazol-5-yl)benzenesulfonamide |
| 47 | 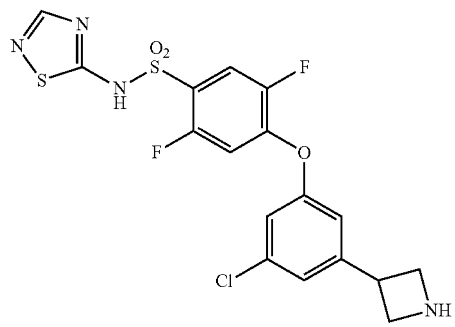 [SMILES: O=S(=O)(Nc1ncns1)c1cc(F)c(Oc2cc(Cl)cc(C3CNC3)c2)cc1F] | 458.88 | 4-(3-(azetidin-3-yl)-5-chlorophenoxy)-2,5-difluoro-N-(1,2,4-thiadiazol-5-yl)benzenesulfonamide |
| 48 | 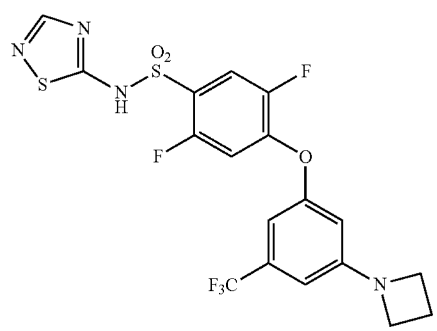 [SMILES: O=S(=O)(Nc1ncns1)c1cc(F)c(Oc2cc(N3CCC3)cc(C(F)(F)F)c2)cc1F] | 492.443 | 4-[3-(azetidin-1-yl)-5-(trifluoromethyl)phenoxy]-2,5-difluoro-N-(1,2,4-thiadiazol-5-yl)benzenesulfonamide |
| 49 | 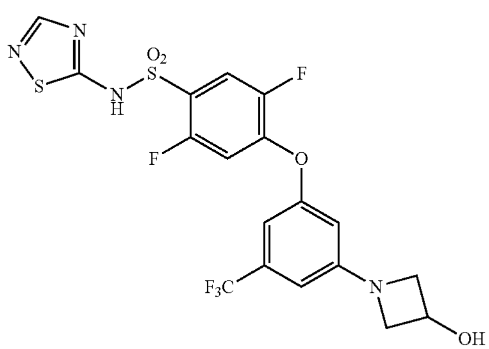 [SMILES: O=S(=O)(Nc1ncns1)c1cc(F)c(Oc2cc(N3CC(O)C3)cc(C(F)(F)F)c2)cc1F] | 508.442 | 2,5-difluoro-4-[3-(3-hydroxyazetidin-1-yl)-5-(trifluoromethyl)phenoxy]-N-(1,2,4-thiadiazol-5-yl)benzenesulfonamide |

TABLE 1-continued

| No. | Structure | MW | IUPAC Name |
|---|---|---|---|
| 50 | 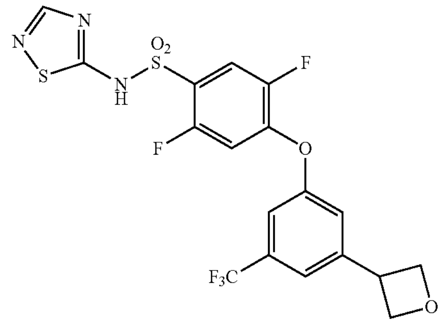 [SMILES: O=S(=O)(Nc1ncns1)c1cc(F)c(Oc2cc(C3COC3)cc(C(F)(F)F)c2)cc1F] | 493.42 | 2,5-difluoro-4-(3-(oxetan-3-yl)-5-(trifluoromethyl)phenoxy)-N-(1,2,4-thiadiazol-5-yl)benzenesulfonamide |
| 51 | 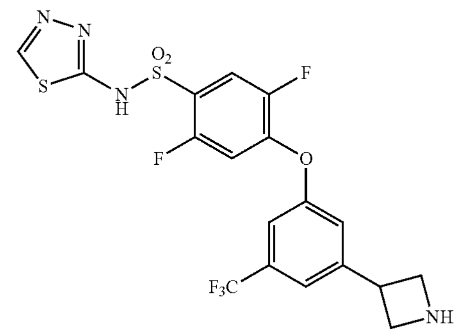 [SMILES: O=S(=O)(Nc1nncs1)c1cc(F)c(Oc2cc(C3CNC3)cc(C(F)(F)F)c2)cc1F] | 492.44 | 4-(3-(azetidin-3-yl)-5-(trifluoromethyl)phenoxy)-2,5-difluoro-N-(1,2,3-thiadiazol-5-yl)benzenesulfonamide |
| 52 | 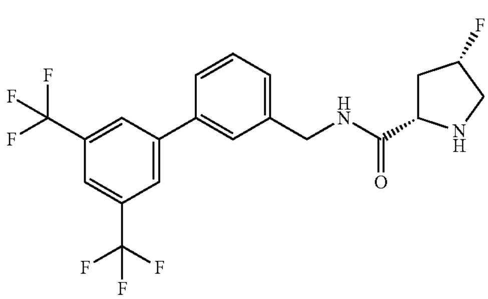 [SMILES: O=C(NCc1cccc(-c2cc(C(F)(F)F)cc(C(F)(F)F)c2)c1)[C@@H]1C[C@H](F)CN1] | 434.35 | (2S,4S)-N-((3',5'-bis(trifluoromethyl)-[1,1'-biphenyl]-3-yl)methyl)-4-fluoropyrrolidine-2-carboxamide |
| 53 | 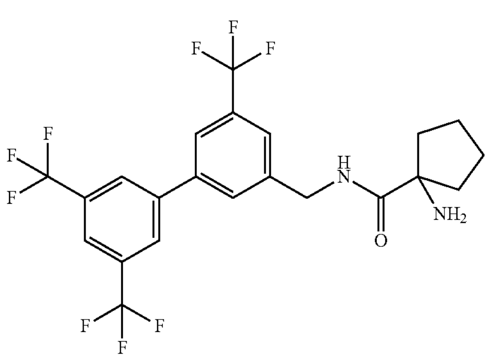 [SMILES: NC1(C(=O)NCc2cc(-c3cc(C(F)(F)F)cc(C(F)(F)F)c3)cc(C(F)(F)F)c2)CCCC1] | 498.38 | 1-amino-N-((3',5,5'-tris(trifluoromethyl)-[1,1'-biphenyl]-3-yl)methyl)cyclopentane-1-carboxamide |

TABLE 1-continued

| No. | Structure | MW | IUPAC Name |
|---|---|---|---|
| 54 | 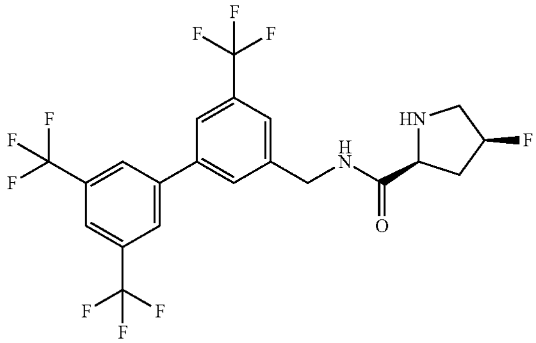 [SMILES: O=C(NCc1cc(-c2cc(C(F)(F)F)cc(C(F)(F)F)c2)cc(C(F)(F)F)c1)[C@@H]1C[C@H](F)CN1] | 502.35 | (2S,4S)-4-fluoro-N-((3',5,5'-tris(trifluoromethyl)-[1,1'-biphenyl]-3-yl)methyl)pyrrolidine-2-carboxamide |
| 55 | 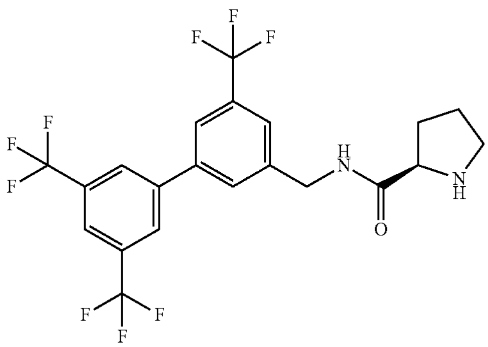 [SMILES: O=C(NCc1cc(-c2cc(C(F)(F)F)cc(C(F)(F)F)c2)cc(C(F)(F)F)c1)[C@H]1CCCN1] | 484.36 | (R)-N-((3',5,5'-tris(trifluoromethyl)-[1,1'-biphenyl]-3-yl)methyl)pyrrolidine-2-carboxamide |
| 56 | 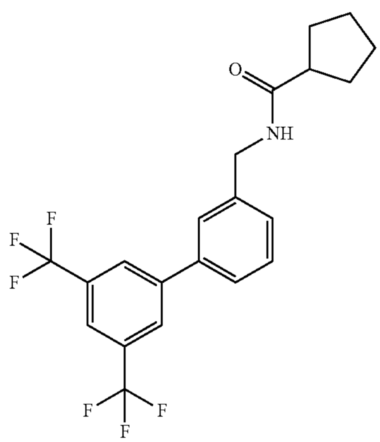 [SMILES: O=C(NCc1cccc(-c2cc(C(F)(F)F)cc(C(F)(F)F)c2)c1)C1CCCC1] | 415.372 | N-({3-[3,5-bis(trifluoromethyl)phenyl]phenyl}methyl)cyclopentanecarboxamide |
| 57 | 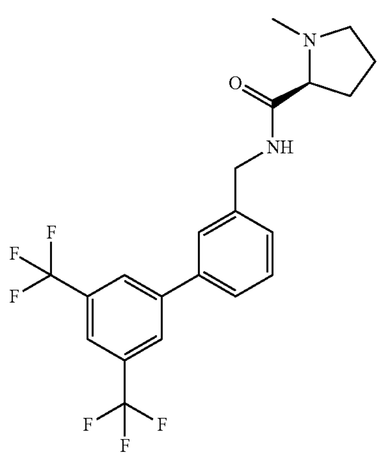 [SMILES: CN1CCC[C@H]1C(=O)NCc1cccc(-c2cc(C(F)(F)F)cc(C(F)(F)F)c2)c1] | 430.387 | (2S)-N-({3-[3,5-bis(trifluoromethyl)phenyl]phenyl}methyl)-1-methylpyrrolidine-2-carboxamide |

TABLE 1-continued

| No. | Structure | MW | IUPAC Name |
| --- | --- | --- | --- |
| 58 | 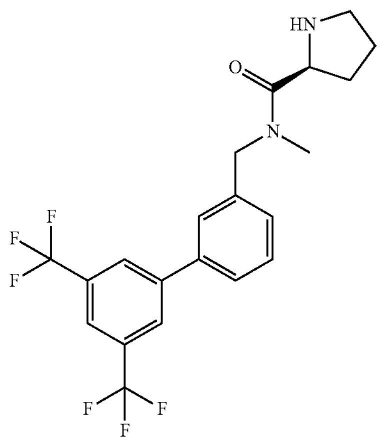 [SMILES: CN(Cc1cccc(-c2cc(C(F)(F)F)cc(C(F)(F)F)c2)c1)C(=O)[C@@H]1CCCN1] | 430.387 | (2S)-N-({3-[3,5-bis(trifluoromethyl)phenyl]phenyl}methyl)-N-methylpyrrolidine-2-carboxamide |
| 59 | 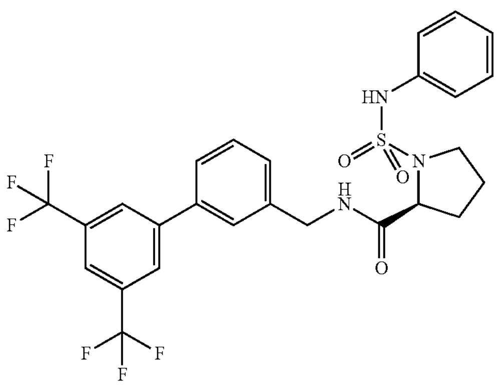 [SMILES: O=C(NCc1cccc(-c2cc(C(F)(F)F)cc(C(F)(F)F)c2)c1)[C@@H]1CCCN1S(=O)(=O)Nc1ccccc1] | 571.535 | (2S)-N-({3-[3,5-bis(trifluoromethyl)phenyl]phenyl}methyl)-1-(phenylsulfamoyl)pyrrolidine-2-carboxamide |
| 60 | 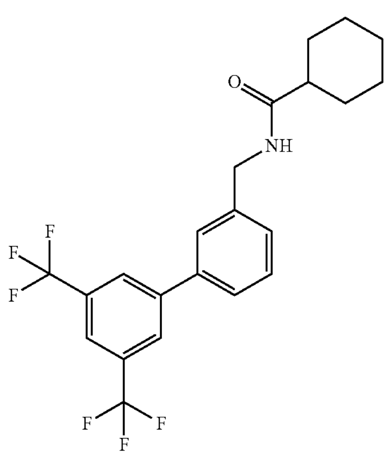 [SMILES: O=C(NCc1cccc(-c2cc(C(F)(F)F)cc(C(F)(F)F)c2)c1)C1CCCCC1] | 429.399 | N-({3-[3,5-bis(trifluoromethyl)phenyl]phenyl}methyl)cyclohexanecarboxamide |

TABLE 1-continued

| No. | Structure | MW | IUPAC Name |
|---|---|---|---|
| 61 | 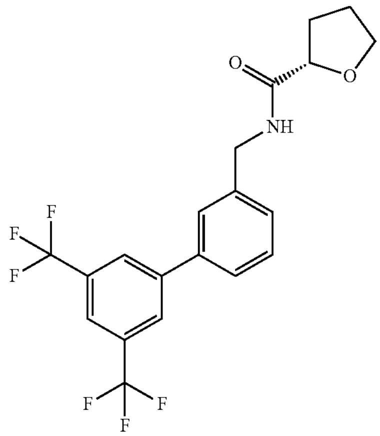 [SMILES: O=C(NCc1cccc(-c2cc(C(F)(F)F)cc(C(F)(F)F)c2)c1)[C@@H]1CCCO1] | 417.345 | (2S)-N-({3-[3,5-bis(trifluoromethyl)phenyl]phenyl}methyl)oxolane-2-carboxamide |
| 62 | 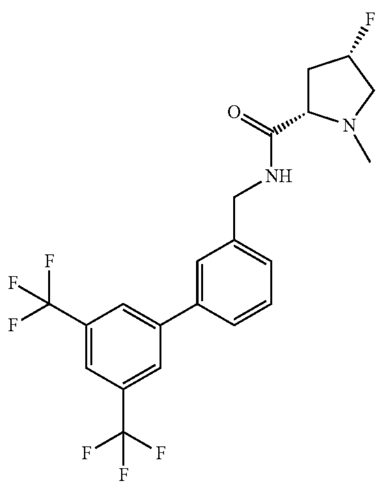 [SMILES: CN1C[C@@H](F)C[C@H]1C(=O)NCc1cccc(-c2cc(C(F)(F)F)cc(C(F)(F)F)c2)c1] | 448.377 | (2S,4S)-N-({3-[3,5-bis(trifluoromethyl)phenyl]phenyl}methyl)-4-fluoro-1-methylpyrrolidine-2-carboxamide |
| 63 | 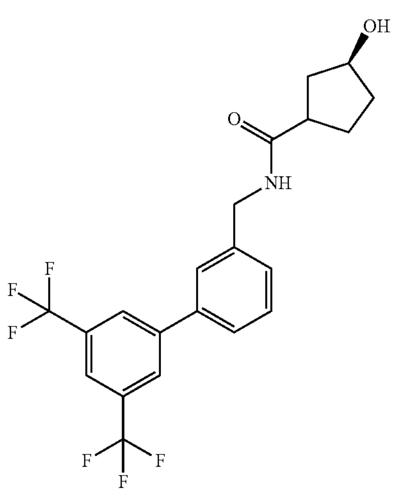 [SMILES: O=C(NCc1cccc(-c2cc(C(F)(F)F)cc(C(F)(F)F)c2)c1)C1CC[C@H](O)C1] | 431.372 | (3S)-N-({3-[3,5-bis(trifluoromethyl)phenyl]phenyl}methyl)-3-hydroxycyclopentane-1-carboxamide |

TABLE 1-continued

| No. | Structure | MW | IUPAC Name |
|---|---|---|---|
| 64 | 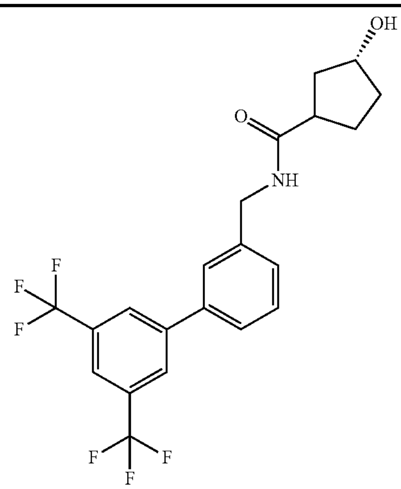 | 431.372 | (3R)-N-({3-[3,5-bis(trifluoromethyl)phenyl]phenyl}methyl)-3-hydroxycyclopentane-1-carboxamide |
| 65 | 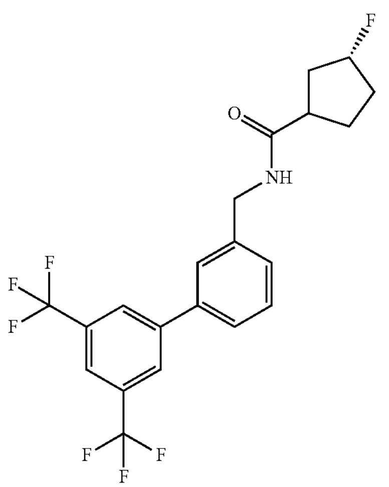 [SMILES: O=C(NCc1cccc(-c2cc(C(F)(F)F)cc(C(F)(F)F)c2)c1)C1CC[C@@H](F)C1] | 433.363 | (3R)-N-({3-[3,5-bis(trifluoromethyl)phenyl]phenyl}methyl)-3-fluorocyclopentane-1-carboxamide |

The following reaction schemes and examples are intended to illustrate the synthesis of a representative number of compounds. Accordingly, the following examples are intended to illustrate but not to limit the invention. Additional compounds not specifically exemplified may be synthesized using conventional methods in combination with the methods described herein below.

Example 1

Synthesis of N-(4-(3-bromo-5-(trifluoromethyl)phenoxy)-2,5-difluorobenzyl)-1,2,4-thiadiazole-5-carboxamide

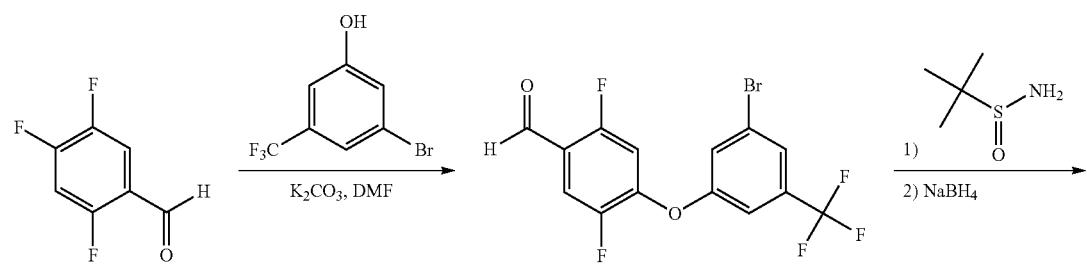

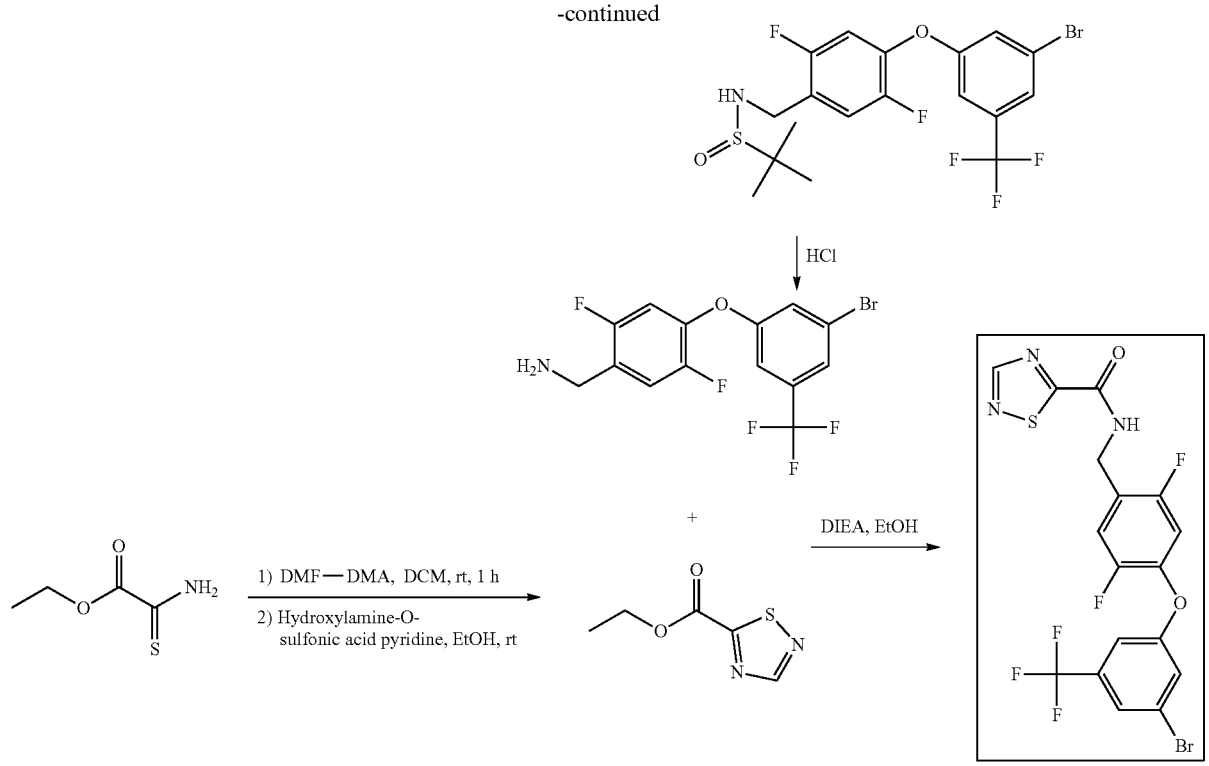

Step 1. Synthesis of 4-[3-bromo-5-(trifluoromethyl)phenoxy]-2,5-difluorobenzaldehyde Into a 25-mL round-bottom flask was placed a solution of 2,4,5-trifluorobenzaldehyde (500 mg, 3.12 mmol, 1.00 equiv) in N,N-dimethylformamide (10 mL). To the solution were added potassium carbonate (862 mg, 6.24 mmol, 2.00 equiv) and 3-bromo-5-(trifluoromethyl)phenol (753 mg, 3.12 mmol, 1.00 equiv). The solution was stirred for 1 hour at room temperature and then quenched by the addition of 10 mL of water. The resulting solution was extracted with 50 mL of ethyl acetate and the combined organic layers were washed with brine (4×20 mL), dried over anhydrous sodium sulfate and concentrated under vacuum. This resulted in 1.1 g (92%) of 4-[3-bromo-5-(trifluoromethyl)phenoxy]-2,5-difluorobenzaldehyde as a yellow solid.

Step 2. Synthesis of N-([4-[3-bromo-5-(trifluoromethyl)phenoxy]-2,5-difluorophenyl]methyl)-2-methylpropane-2-sulfinamide

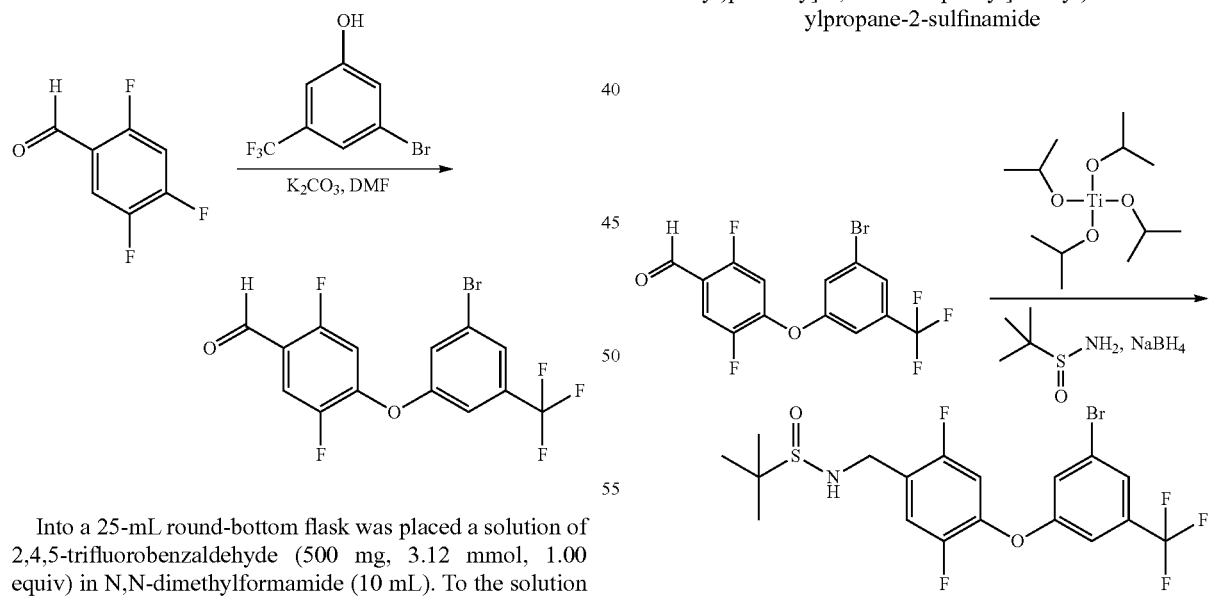

Into a 100-mL 3-necked round-bottom flask, purged and maintained with an inert atmosphere of nitrogen, was placed a solution of 1-[4-[3-bromo-5-(trifluoromethyl)phenoxy]-2,5-difluorophenyl]ethan-1-one (1.1 g, 2.78 mmol, 1.00 equiv) in tetrahydrofuran (40 mL). To the solution were added tetrakis(propan-2-yloxy)titanium (2.1 g, 7.44 mmol, 2.50 equiv) and 2-methylpropane-2-sulfinamide (345 mg, 3.25 mmol, 1.10 equiv). The mixture was stirred for 2 hours and then the resulting mixture was concentrated under vacuum. The residue was dissolved in 50 mL of methanol. This was followed by the addition of NaBH$_4$ (120 mg, 3.17 mmol, 1.10 equiv) in portions at 0° C. in 10 minutes. The resulting solution was stirred for 1 hour at room temperature and then quenched by the addition of 50 mL of NH$_4$Cl aqueous. The solution was extracted with ethyl acetate (2×50 mL) and the combined organic layers were then concentrated under vacuum. This resulted in 900 mg (66%) of N-([4-[3-bromo-5-(trifluoromethyl)phenoxy]-2,5-difluorophenyl]methyl)-2-methylpropane-2-sulfinamide as an off-white solid.

Step 3. Synthesis of [4-[3-bromo-5-(trifluoromethyl)phenoxy]-2,5-difluorophenyl]methanamine

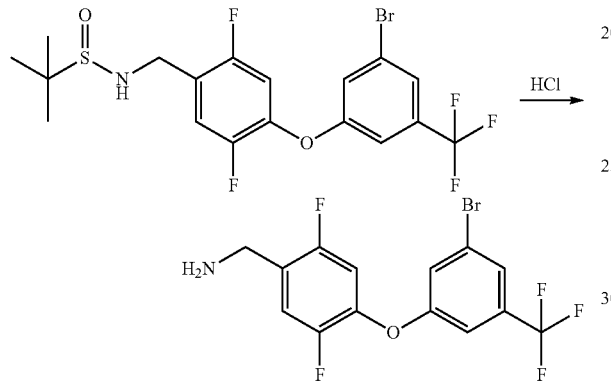

Into a 25-mL round-bottom flask was placed a solution of N-([4-[3-bromo-5-(trifluoromethyl)phenoxy]-2,5-difluorophenyl]methyl)-2-methylpropane-2-sulfinamide (900 mg, 1.85 mmol, 1.00 equiv) in dichloromethane (10 mL). To the solution was added concentrated aqueous hydrogen chloride (1.5 mL, 10.00 equiv). The resulting solution was stirred for 1 hour at room temperature and then concentrated under vacuum. This resulted in 700 mg (99%) of [4-[3-bromo-5-(trifluoromethyl)phenoxy]-2,5-difluorophenyl]methanamine as a yellow solid.

Step 4. Synthesis of ethyl 1,2,4-thiadiazole-5-carboxylate

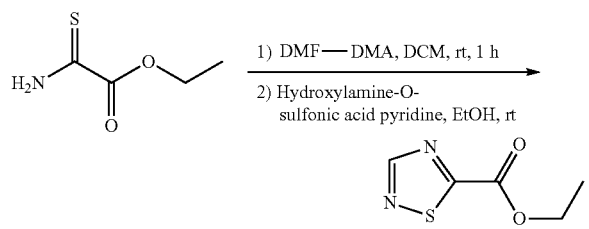

Into a 250-mL round-bottom flask was placed a solution of ethyl carbamothioylformate (10 g, 75.09 mmol, 1.00 equiv) and DMF-DMA (10.8 g) in dichloromethane (55 mL). The resulting solution was stirred for 1 hour at room temperature and then concentrated under vacuum. The residue was dissolved in 80 mL of ethanol and this was followed by the addition of hydroxylamine-O-sulfonic acid (10.27 g) and pyridine (11.9 g, 150.44 mmol). The resulting solution was allowed to react, with stirring, for an additional 12 hours at room temperature. The mixture was concentrated under vacuum and the residue was purified via column chromatography with an eluent of ethyl acetate/petroleum ether (1:10). This resulted in 1.5 g (13%) of ethyl 1,2,4-thiadiazole-5-carboxylate as a colorless oil.

Step 5. Synthesis of ([4-[3-bromo-5-(trifluoromethyl)phenoxy]-2,5-difluorophenyl]methyl)[1-(1,2,4-thiadiazol-5-yl)ethenyl]amine

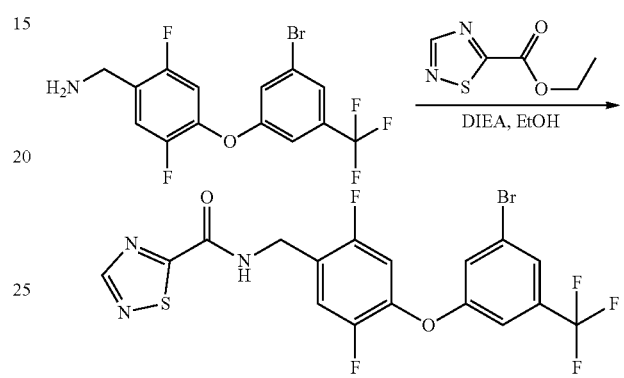

Into a 25-mL round-bottom flask was placed a solution of [4-[3-bromo-5-(trifluoromethyl)phenoxy]-2,5-difluorophenyl]methanamine (350 mg, 0.9 mmol, 1.00 equiv) in ethanol (10 mL). To the solution were added DIEA (0.7 g, 5.4 mmol, 6.00 equiv) and ethyl 1,2,4-thiadiazole-5-carboxylate (150 mg, 0.95 mmol, 1.00 equiv). The resulting solution was stirred overnight at 60° C. in an oil bath and then concentrated under vacuum. The residue was initially purified via column chromatography with an eluent of ethyl acetate/petroleum ether (1:5). The crude product (150 mg) was further purified by flash-prep-HPLC with the following conditions (IntelFlash-1): column, C18 silica gel; mobile phase, acetonitrile/water with NH$_4$HCO$_3$=40 increasing to acetonitrile/water with NH$_4$HCO$_3$=90 within 8 min; detector, UV 254 nm. This resulted in 43.9 mg (13%) of ([4-[3-bromo-5-(trifluoromethyl)phenoxy]-2,5-difluorophenyl]methyl)[1-(1,2,4-thiadiazol-5-yl)ethenyl]amine, the final product, as a white solid.

LC-MS (ES, m/z): [M+H]$^+$=494.

$^1$H-NMR: (400 MHz, DMSO-d$_6$, ppm): δ 9.81-9.77 (m, 1H), 9.14 (s, 1H), 7.77 (s, 1H), 7.57-7.47 (m, 2H), 7.43-7.36 (m, 2H), 4.55-4.53 (d, J=6.0 Hz, m, 2H).

Example 2

Synthesis of 4-(3-bromo-5-(trifluoromethyl)phenoxy)-2,5-difluoro-N-methyl-N-(1,2,4-thiadiazol-5-yl)benzenesulfonamide

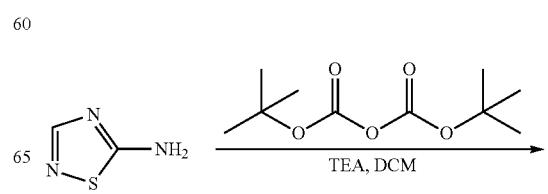

-continued

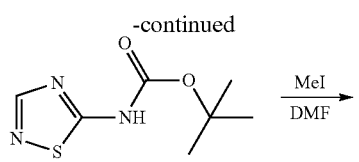

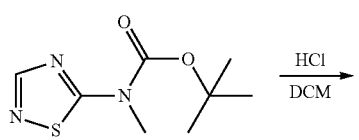

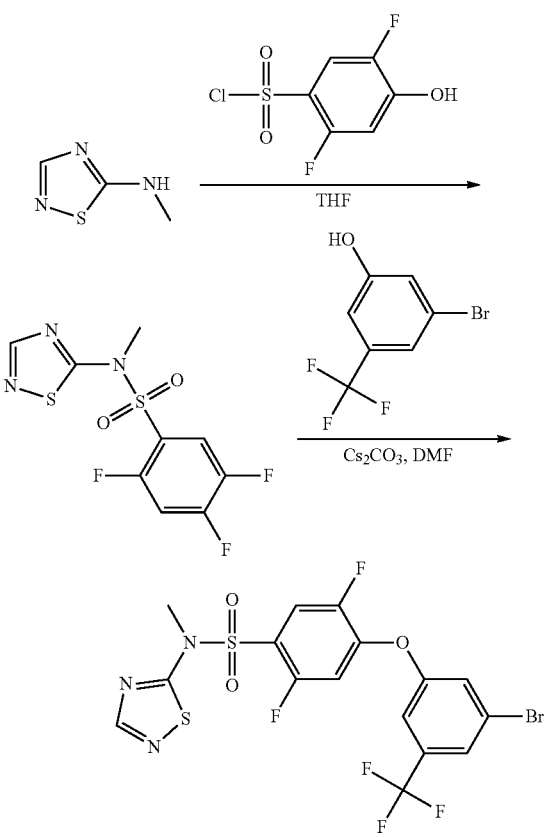

Step 1. Synthesis of tert-butyl
N-(1,2,4-thiadiazol-5-yl)carbamate

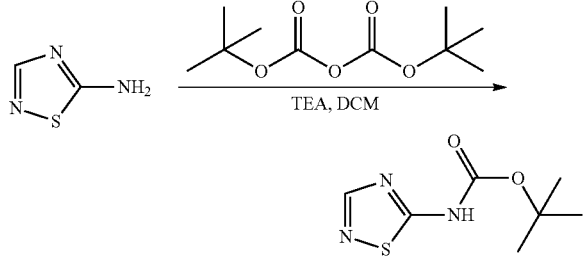

Into a 25-mL round-bottom flask, purged and maintained with an inert atmosphere of nitrogen, was placed a solution of 1,2,4-thiadiazol-5-amine (2 g, 19 mmol, 1.00 equiv) in dichloromethane (20 mL). To the mixture were added TEA (2.4 g, 23 mmol, 1.20 equiv) and di-tert-butyl dicarbonate (9.6 g, 43 mmol, 2.20 equiv) while stirring. The resulting solution was stirred for 12 hours at room temperature and then concentrated under vacuum. The residue was purified via column chromatography with an eluent of ethyl acetate/petroleum ether (2:1). This resulted in 1.8 g (45%) of tert-butyl N-(1,2,4-thiadiazol-5-yl)carbamate as a yellow solid.

Step 2. Synthesis of tert-butyl
N-methyl-N-(1,2,4-thiadiazol-5-yl)carbamate

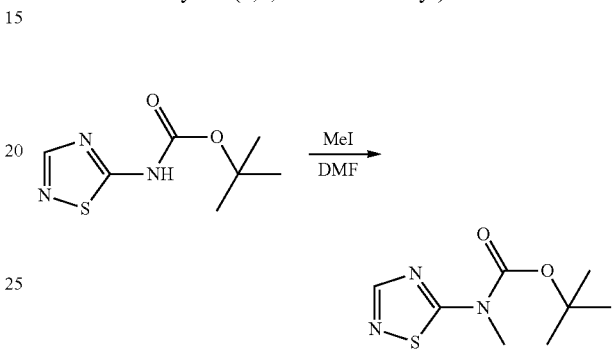

Into a 50-mL round-bottom flask, purged and maintained with an inert atmosphere of nitrogen, was placed a solution of tert-butyl N-(1,2,4-thiadiazol-5-yl)carbamate (1.8 g, 8.94 mmol, 1.00 equiv) in N,N-dimethylformamide (20 mL). To the solution were added potassium carbonate (2.47 g, 17.87 mmol, 2.00 equiv) and MeI (3.77 g, 26.74 mmol, 3.00 equiv). The resulting solution was stirred overnight at 40° C. in an oil bath and the reaction was then quenched by the addition of 20 mL of water. The mixture was extracted with ethyl acetate (50 mL×2) and the combined organic layers were washed with brine (4×20 mL) and concentrated under vacuum. This resulted in 1.5 g (78%) of tert-butyl N-methyl-N-(1,2,4-thiadiazol-5-yl)carbamate as yellow oil.

Step 3. Synthesis of
N-methyl-1,2,4-thiadiazol-5-amine hydrochloric acid salt

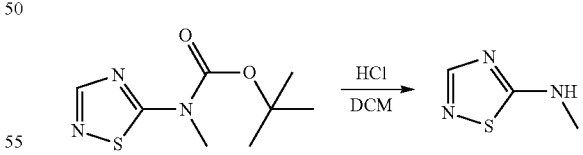

Into a 50-mL round-bottom flask was placed a solution of tert-butyl N-methyl-N-(1,2,4-thiadiazol-5-yl)carbamate (1.5 g, 6.97 mmol, 1.00 equiv) in dichloromethane (20 mL). To the solution was added concentrated aqueous hydrogen chloride (5.8 mL, 12 mol/L, 10.00 equiv). The resulting solution was stirred for 4 hours at 40° C. in an oil bath and then concentrated under vacuum. This resulted in 1.1 g (95%) of N-methyl-1,2,4-thiadiazol-5-amine hydrochloric acid salt as a off-white solid.

Step 4. Synthesis of 2,4,5-trifluoro-N-methyl-N-(1,2,4-thiadiazol-5-yl)benzene-1-sulfonamide

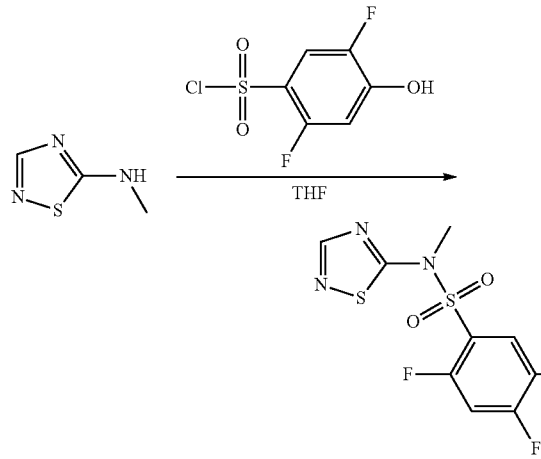

Into a 25-mL 3-necked round-bottom flask, purged and maintained with an inert atmosphere of nitrogen, was placed a solution of N-methyl-1,2,4-thiadiazol-5-amine (250 mg, 1.65 mmol, 1.00 equiv) in tetrahydrofuran (10 mL). This was followed by the addition of lithio bis(trimethylsilyl) amine (553 mg, 3.30 mmol, 2.00 equiv) dropwise while stirring at −78° C. in 30 minutes. The mixture was warmed to room temperature and stirred for 2 hours. Then the mixture was cooled to −78° C. and 2,4,5-trifluorobenzene-1-sulfonyl chloride (379 mg, 1.64 mmol, 1.00 equiv) was added. The resulting solution was stirred overnight at room temperature and then quenched by the addition of 10 mL of water. The resulting solution was extracted with ethyl acetate (50 mL×3) and the combined organic layers were washed with brine (2×20 mL), dried over anhydrous sodium sulfate and concentrated under vacuum. This resulted in 140 mg (27%) of 2,4,5-trifluoro-N-methyl-N-(1,2,4-thiadiazol-5-yl)benzene-1-sulfonamide as yellow oil.

Step 5. Synthesis of 4-[3-bromo-5-(trifluoromethyl)phenoxy]-2,5-difluoro-N-methyl-N-(1,2,4-thiadiazol-5-yl)benzene-1-sulfonamide

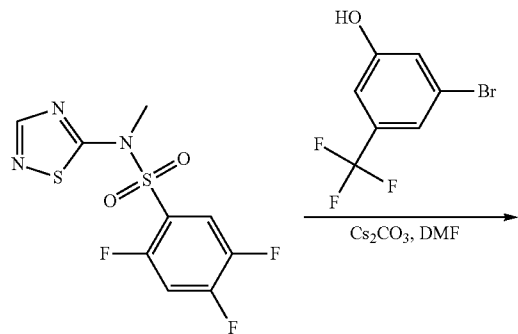

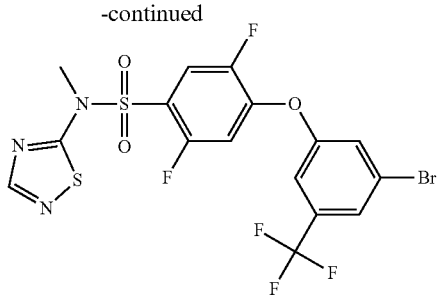

Into a 25-mL round-bottom flask was placed a solution of 2,4,5-trifluoro-N-methyl-N-(1,2,4-thiadiazol-5-yl)benzene-1-sulfonamide (140 mg, 0.45 mmol, 1.00 equiv) in N,N-dimethylformamide (10 mL). To the solution were added potassium carbonate (125 mg, 0.90 mmol, 2.00 equiv) and 3-bromo-5-(trifluoromethyl)phenol (109 mg, 0.45 mmol, 1.00 equiv). The solution was stirred for 2 hours at room temperature and the reaction was then quenched by the addition of 10 mL of water. The resulting solution was extracted with 50 mL of ethyl acetate and the combined organic layers were washed with brine (4×20 mL), dried over anhydrous sodium sulfate and concentrated under vacuum. The crude product (100 mg) was purified by flash-prep-HPLC with the following conditions (IntelFlash-1): column, C18 silica gel; mobile phase, acetonitrile/water with $NH_4HCO_3$=35:65 increasing to acetonitrile/water with $NH_4HCO_3$=85:15 within 8 min; detector, UV 254 nm. This resulted in 37.6 mg (16%) of 4-[3-bromo-5-(trifluoromethyl)phenoxy]-2,5-difluoro-N-methyl-N-(1,2,4-thiadiazol-5-yl)benzene-1-sulfonamide, the final product, as a white solid.

LC-MS (ES, m/z): $[M+H]^+$=531.

H-NMR: (400 MHz, DMSO-$d_6$, ppm): δ 8.44 (m, 1H), 8.12-8.06 (m, 1H), 7.85 (s, 2H), 7.69 (m, 1H), 7.52-7.46 (m, 1H), 3.49-3.46 (s, 3H).

Example 3

(2S)—N-[(2,5-difluoro-4-phenoxyphenyl)methyl]pyrrolidine-2-carboxamide

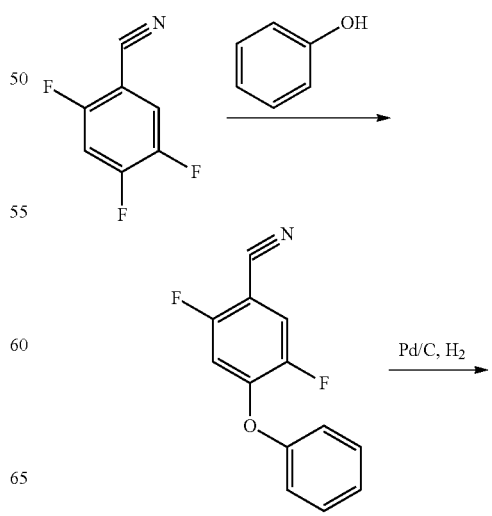

Step 1. Synthesis of 2,5-difluoro-4-phenoxybenzonitrile

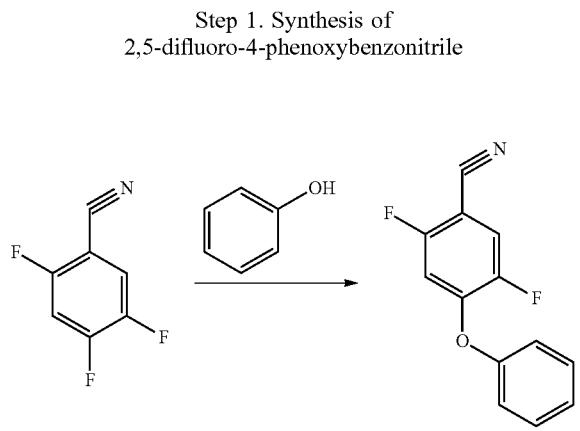

Into a 50-mL round-bottom flask purged and maintained with an inert atmosphere of nitrogen, was placed a solution of 2,4,5-trifluorobenzonitrile (500 mg, 3.18 mmol, 1.00 equiv) in N,N-dimethylformamide (10 mL), phenol (300 mg, 3.19 mmol, 1.00 equiv), $K_2CO_3$ (900 mg, 6.46 mmol, 2.00 equiv). The resulting solution was stirred overnight at room temperature and then the reaction was quenched by the addition of 200 mL of water. The resulting solution was extracted with ethyl acetate (3×100 mL) and the combined organic layers were washed with brine (4×300 mL), dried over sodium sulfate and concentrated under vacuum. The residue was purified via column chromatography with an eluent of ethyl acetate/petroleum ether (1:20). This resulted in 400 mg (54%) of 2,5-difluoro-4-phenoxybenzonitrile as a white solid.

Step 2. Synthesis of (2,5-difluoro-4-phenoxyphenyl)methanamine

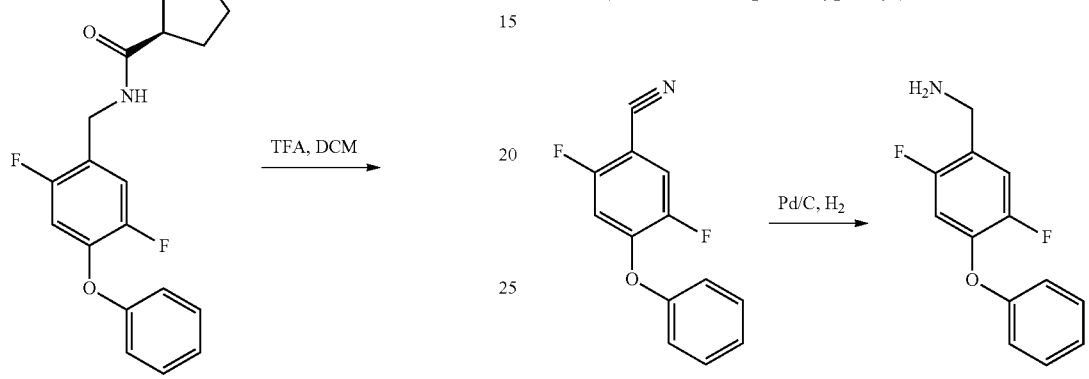

Into a 50-mL round-bottom flask, was placed a solution of 2,5-difluoro-4-phenoxybenzonitrile (400 mg, 1.73 mmol, 1.00 equiv) in methanol (10 mL). To the solution was added Palladium carbon (40 mg, 0.10 equiv). Following this, $H_2$ (gas) was introduced to the flask. The resulting solution was stirred for 1 hour at room temperature and then the solids were filtered out. The mixture that was left behind was concentrated then under vacuum. This resulted in 300 mg (74%) of (2,5-difluoro-4-phenoxyphenyl)methanamine as a white solid.

Step 3. Synthesis of tert-butyl (2S)-2-[[(2,5-difluoro-4-phenoxyphenyl)methyl]carbamoyl]pyrrolidine-1-carboxylate

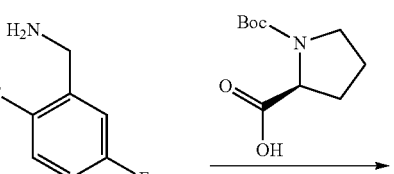

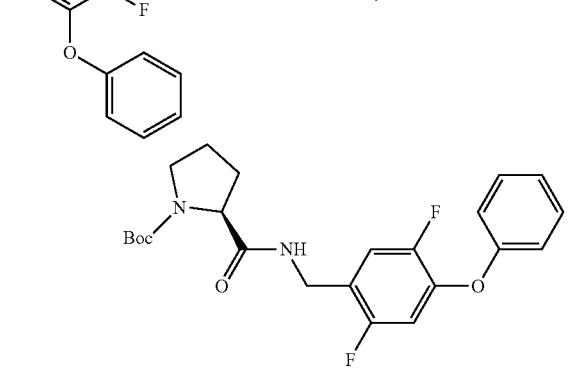

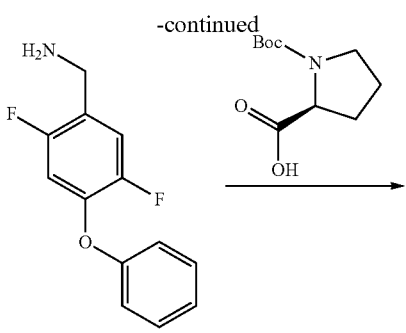

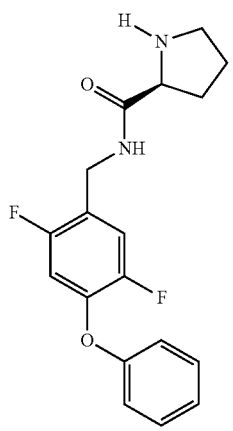

TFA, DCM

Into a 25-mL round-bottom flask purged and maintained with an inert atmosphere of nitrogen, was placed a solution of (2,5-difluoro-4-phenoxyphenyl)methanamine (200 mg, 0.85 mmol, 1.00 equiv) in N,N-dimethylformamide (5 mL). To the solution were added (2S)-1-[(tert-butoxy)carbonyl] pyrrolidine-2-carboxylic acid (185 mg, 0.86 mmol, 1.00 equiv), HATU (260 mg, 0.68 mmol, 1.20 equiv) and DIEA (250 mg, 1.93 mmol, 3.00 equiv). The resulting solution was stirred for 2 hours at room temperature and then the reaction was quenched by the addition of 100 mL of water. The resulting solution was extracted with ethyl acetate (3×50 mL) and then the combined organic layers were washed with brine (4×100 mL), dried over sodium sulfate and concentrated under vacuum. The residue was purified via column chromatography with an eluent of ethyl acetate/petroleum ether (1:2). This resulted in 250 mg (68%) of tert-butyl (2S)-2-[[(2,5-difluoro-4-phenoxyphenyl)methyl]carbamoyl]pyrrolidine-1-carboxylate as a white solid.

Step 4. Synthesis of (2S)—N-[(2,5-difluoro-4-phenoxyphenyl)methyl]pyrrolidine-2-carboxamide

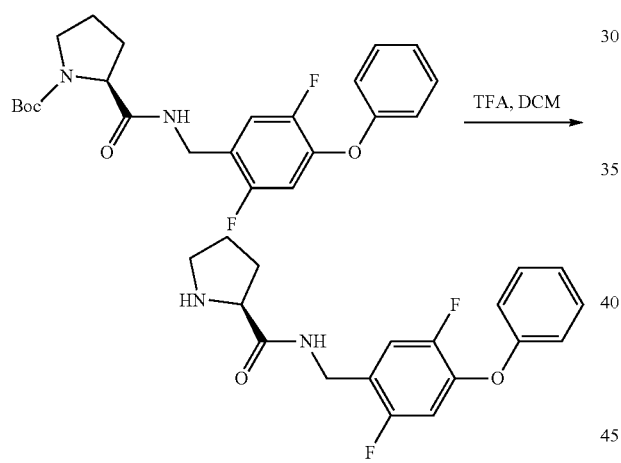

Into a 25-mL round-bottom flask, was placed a solution of tert-butyl (2S)-2-[[(2,5-difluoro-4-phenoxyphenyl)methyl]carbamoyl]pyrrolidine-1-carboxylate (150 mg, 0.35 mmol, 1.00 equiv) in dichloromethane (5 mL). To the solution was added trifluoroacetic acid (5 mL, 23.00 equiv). The resulting solution was stirred for 2 hours at room temperature and then concentrated under vacuum. The crude product was purified by Prep-HPLC with the following conditions (Column, Sunfire 15*190 mm; mobile phase, CH$_3$CN/H$_2$O (0.05% TFA)=30% increasing to CH$_3$CN/H$_2$O (0.05% TFA)=70% within 10 min; Detector, UV 254 nm. This resulted in 45 mg (39%) of (2S)—N-[(2,5-difluoro-4-phenoxyphenyl)methyl] pyrrolidine-2-carboxamide, the final product, as a light yellow oil.

LC-MS: (ES, m/z): [M+H]$^+$=333

$^1$H-NMR: (400 MHz, DMSO-d$_6$, ppm): δ 8.50-8.47 (m, 1H), 7.43-7.39 (m, 2H), 7.26-7.01 (m, 5H), 4.32-4.30 (m, 2H), 3.62-3.56 (m, 1H), 2.91-2.81 (m, 2H), 2.00-1.96 (m, 1H), 1.84-1.83 (m, 1H), 1.72-1.59 (m, 2H).

Example 4

Synthesis of (2S)—N-([4-[3,5-bis(trifluoromethyl) phenoxy]-2,5-difluorophenyl]methyl)pyrrolidine-2-carboxamide, trifluoroacetic acid

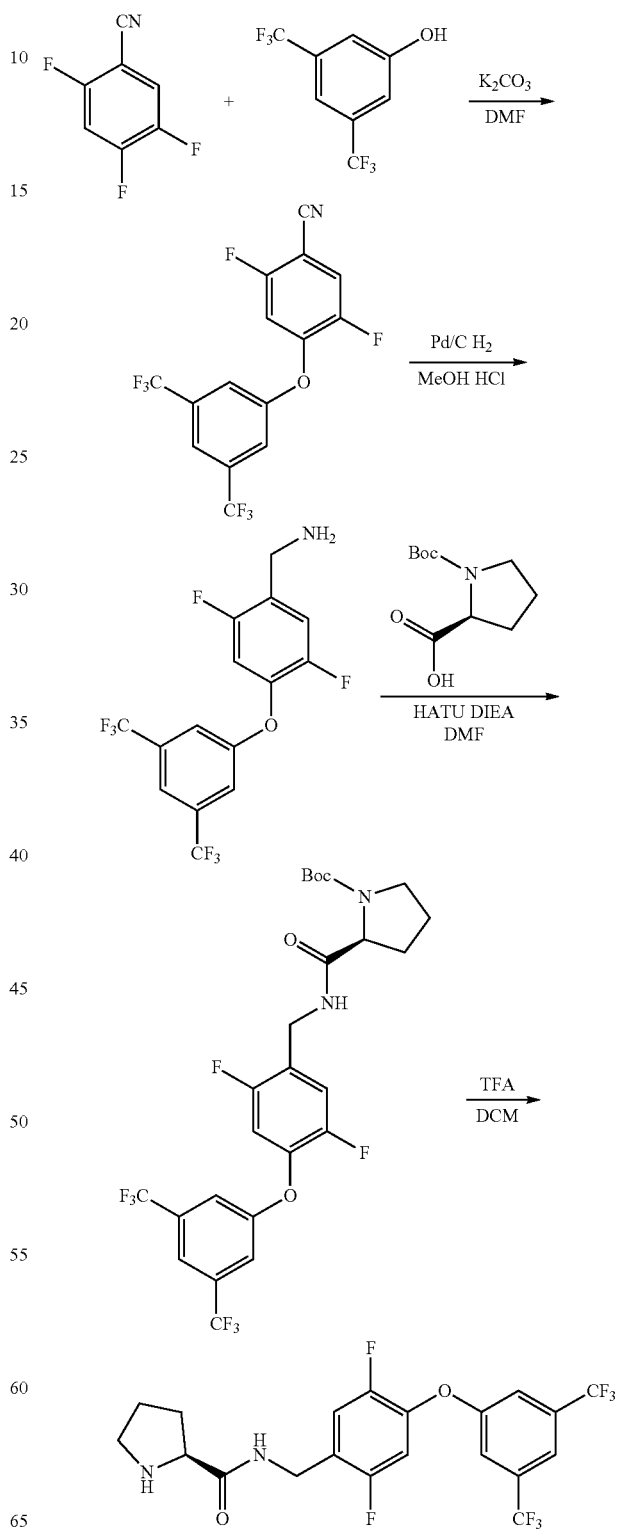

Step 1. Synthesis of 4-[3,5-bis(trifluoromethyl)phenoxy]-2,5-difluorobenzonitrile

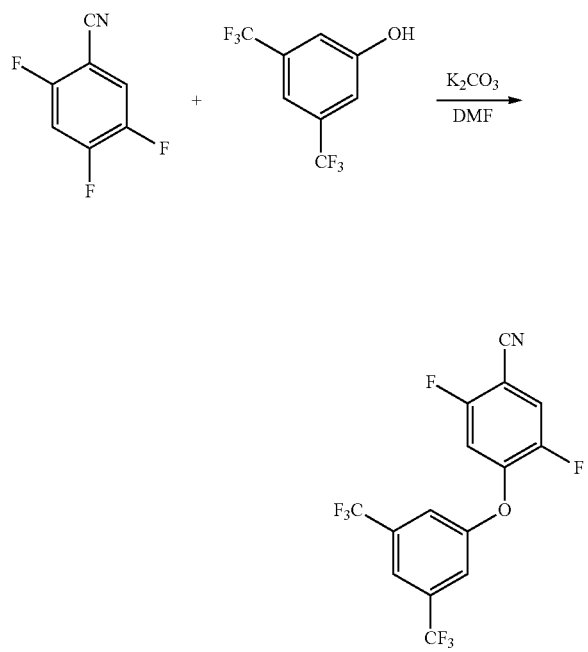

3,5-Bis(trifluoromethyl)phenol (300 mg, 1.30 mmol, 1.00 equiv), N,N-2,4,5-trifluorobenzonitrile (205 mg, 1.30 mmol, 1.00 equiv), and potassium carbonate (359 mg, 2.60 mmol, 1.99 equiv) were dissolved in 10 mL of DMF under an inert atmosphere of nitrogen. The mixture was then stirred overnight at room temperature and quenched by the addition of 100 mL of water. The resulting solution was extracted with 3×50 mL of ethyl acetate and the combined organic layers were concentrated in vacuo. The residue was purified by silica gel column chromatography with an eluent of ethyl acetate/petroleum ether (1:20). This resulted in 450 mg (94%) of 4-[3,5-bis(trifluoromethyl)phenoxy]-2,5-difluorobenzonitrile as a white solid.

Step 2. Synthesis of [4-[3,5-bis(trifluoromethyl)phenoxy]-2,5-difluorophenyl]methanamine

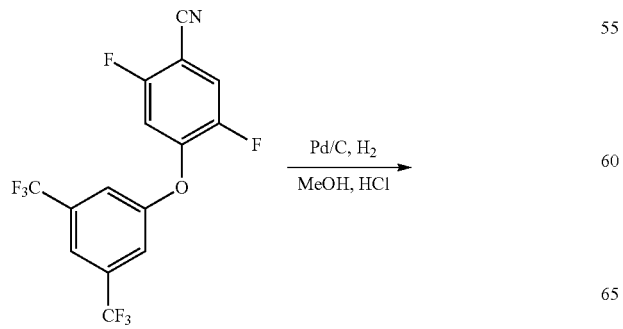

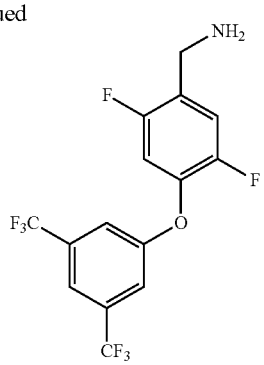

Into a 50-mL round-bottom flask purged and maintained under an atmosphere of nitrogen, was placed 4-[3,5-bis(trifluoromethyl)phenoxy]-2,5-difluorobenzonitrile (200 mg, 0.54 mmol, 1.00 equiv) and a solution of HCl in 20 mL of methanol. This was followed by the addition of Pd/C (100 mg). The flask was then evacuated and flushed three times with nitrogen, followed by flushing with hydrogen. The mixture was stirred for 1 hour at room temperature under an atmosphere of hydrogen, after which, the solids were filtered off, and the filtrate was concentrated in vacuo. This resulted in 200 mg (crude) of [4-[3,5-bis(trifluoromethyl)phenoxy]-2,5-difluorophenyl]methanamine as a white solid.

Step 3. Synthesis of tert-butyl (2S)-2-[([4-[3,5-bis(trifluoromethyl)phenoxy]-2,5-difluorophenyl]methyl)carbamoyl]pyrrolidine-1-carboxylate

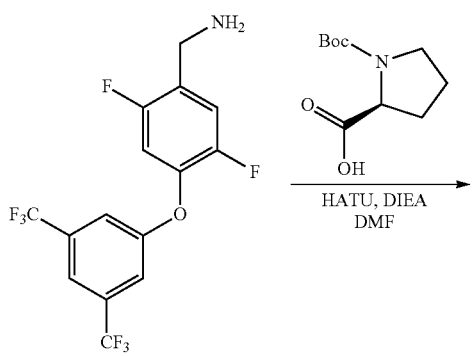

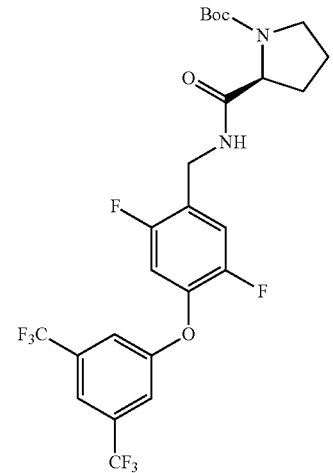

(2S)-1-[(tert-butoxy)carbonyl]pyrrolidine-2-carboxylic acid (116 mg, 0.54 mmol, 1.00 equiv), HATU (225 mg, 0.59 mmol, 1.10 equiv), DIEA (209 mg, 1.62 mmol, 3.00 equiv), and [4-[3,5-bis(trifluoromethyl)phenoxy]-2,5-difluorophenyl]methanamine (200 mg, 0.54 mmol, 1.00 equiv) were dissolved in 5 mL of DMF under nitrogen. The resulting solution was stirred for 2 hours at room temperature and then quenched by the addition of 100 mL of water. This mixture was then extracted with 3×50 mL of ethyl acetate and the combined organic layers concentrated in vacuo. The residue was purified by silica gel column chromatography with an eluent of ethyl acetate/petroleum ether (1:2). This resulted in 300 mg (98%) of tert-butyl (2S)-2-[([4-[3,5-bis(trifluoromethyl)phenoxy]-2,5-difluorophenyl]methyl)carbamoyl]pyrrolidine-1-carboxylate as a white solid.

Step 4. Synthesis of (2S)—N-([4-[3,5-bis(trifluoromethyl)phenoxy]-2,5-difluorophenyl]methyl)pyrrolidine-2-carboxamide trifluoroacetic acid

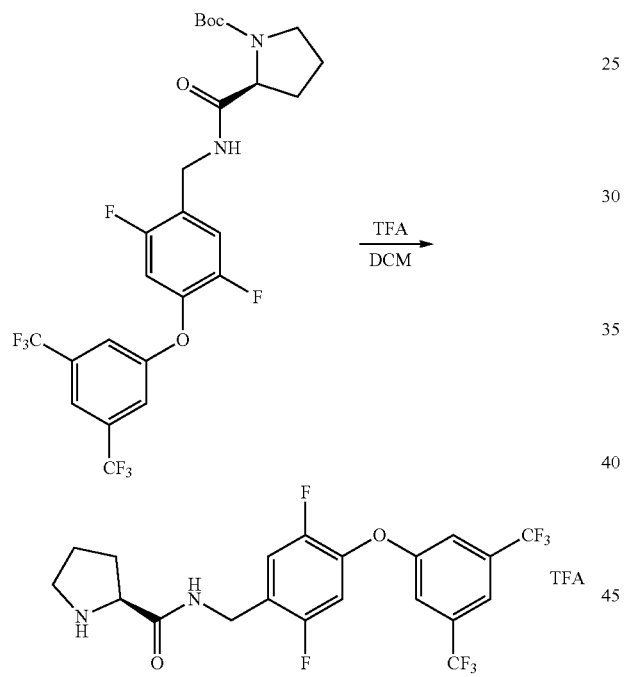

Tert-butyl (2S)-2-[([4-[3,5-bis(trifluoromethyl)phenoxy]-2,5-difluorophenyl]methyl) carbamoyl]pyrrolidine-1-carboxylate (300 mg, 0.53 mmol, 1.00 equiv) was dissolved in dichloromethane (9 mL) and trifluoroacetic acid (3 mL) under a nitrogen atmosphere. The resulting solution was stirred for 2 hours at room temperature and then concentrated in vacuo. The crude product was purified by Prep-HPLC under the following conditions: Column, XBridge Prep Shield RP18, 5 um, 19×150 mm; mobile phase, CH$_3$CN/H$_2$O (0.05% TFA)=30% increasing to CH$_3$CN/H$_2$O (0.05% TFA)=70% within 10 min; Detector, UV 254 nm. This resulted in 170 mg (69%) of (2S)—N-([4-[3,5-bis(trifluoromethyl)phenoxy]-2,5-difluorophenyl]methyl)pyrrolidine-2-carboxamide, trifluoroacetic acid as a white solid.

LC-MS (ES, m/z): [M−TFA+H]$^+$=469.

$^1$H-NMR (400 MHz, DMSO-d$_6$, ppm): δ 9.26 (s, 1H), 9.08-9.04 (m, 1H), 8.63 (s, 1H), 7.95 (s, 1H), 7.74 (s, 2H), 7.51-7.45 (m, 2H), 4.49-4.36 (m, 2H), 4.25 (s, 1H), 3.34 (s, 2H), 2.39-2.29 (m, 1H), 1.98-1.83 (m, 3H).

Example 5

Synthesis of 4-[3,5-bis(trifluoromethyl)phenoxy]-2,5-difluoro-N-(1,2,4-thiadiazol-5-yl)benzene-1-sulfonamide; trifluoroacetic acid

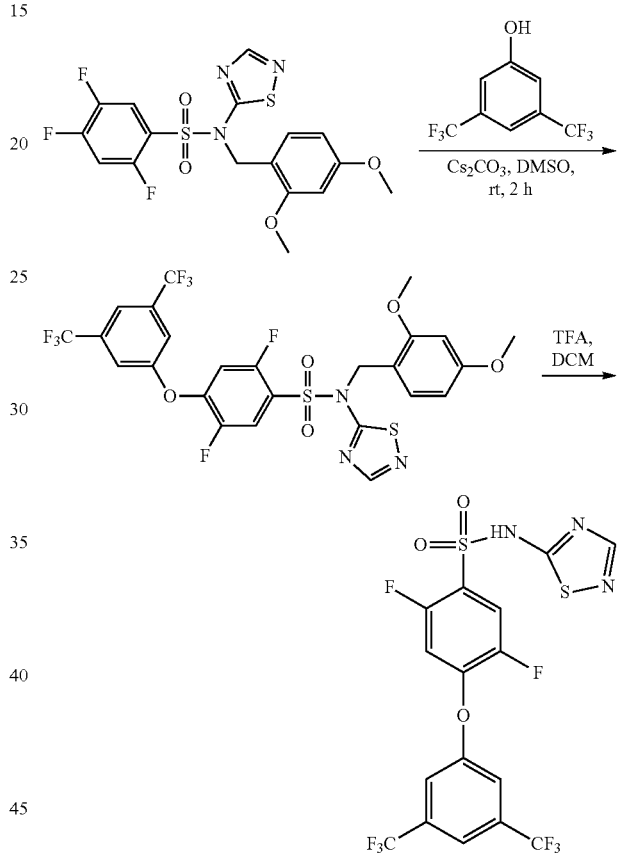

Step 1. Synthesis of 4-[3,5-bis(trifluoromethyl)phenoxy]-N-[(2,4-dimethoxyphenyl)methyl]-2,5-difluoro-N-(1,2,4-thiadiazol-5-yl)benzene-1-sulfonamide

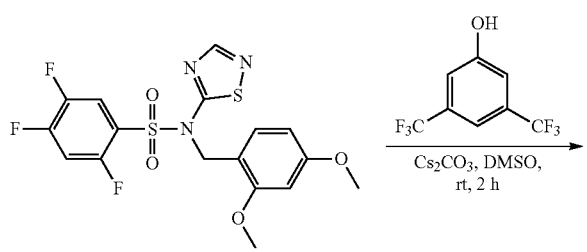

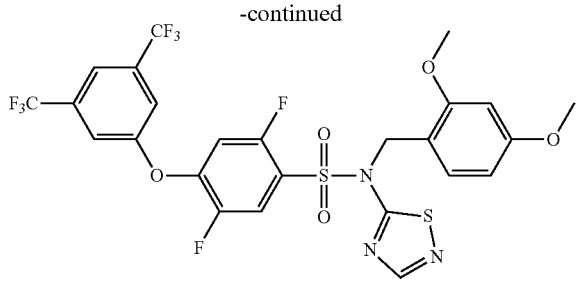

N-[(2,4-dimethoxyphenyl)methyl]-2,4,5-trifluoro-N-(1,2,4-thiadiazol-5-yl)benzene-1-sulfonamide (150 mg, 0.34 mmol, 1.00 equiv), 3,5-bis(trifluoromethyl)phenol (77.5 mg, 0.34 mmol, 1.00 equiv), and $Cs_2CO_3$ (164.8 mg, 0.51 mmol, 1.50 equiv) were dissolved in 3 mL of DMSO. The resulting reaction was stirred for 2 hours at 25° C. and then quenched by the addition of water. The mixture was then extracted with ethyl acetate and the combined organic layers were washed with brine, dried over anhydrous sodium sulfate and concentrated in vacuo. This resulted in 100 mg (45%) of 4-[3,5-bis(trifluoromethyl)phenoxy]-N-[(2,4-dimethoxyphenyl)methyl]-2,5-difluoro-N-(1,2,4-thiadiazol-5-yl)benzene-1-sulfonamide as a yellow oil.

Step 2. Synthesis of 4-[3,5-bis(trifluoromethyl)phenoxy]-2,5-difluoro-N-(1,2,4-thiadiazol-5-yl)benzene-1-sulfonamide, trifluoroacetic acid

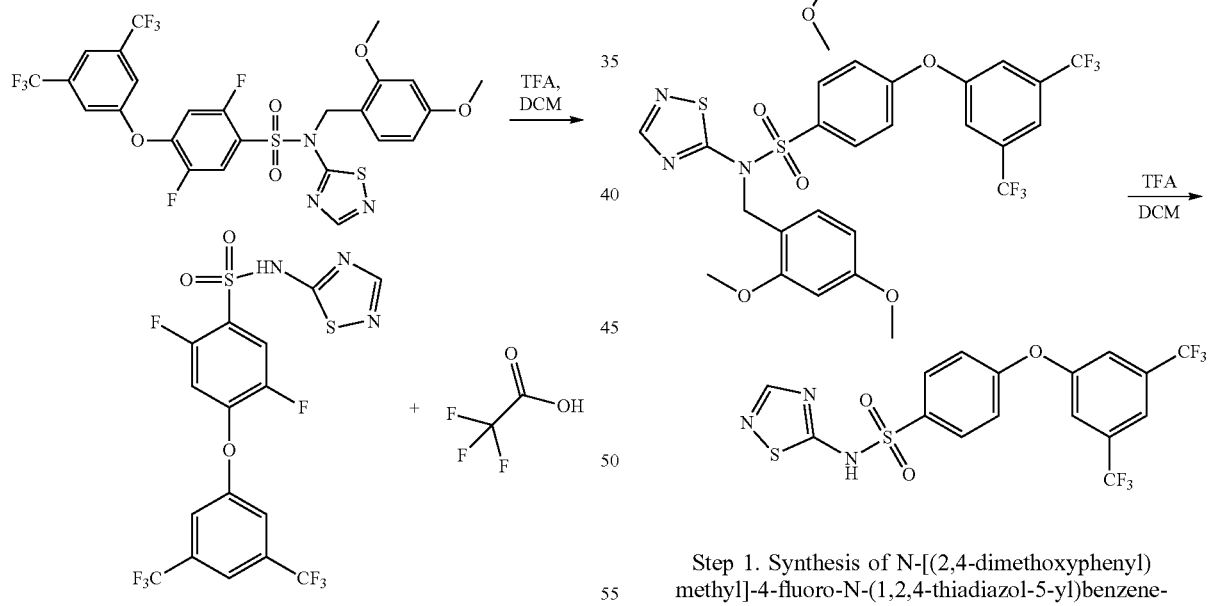

4-[3,5-Bis(trifluoromethyl)phenoxy]-N-[(2,5-dimethoxyphenyl)methyl]-2,5-difluoro-N-(1,2,4-thiadiazol-5-yl)benzene-1-sulfonamide (100 mg, 0.15 mmol, 1.00 equiv) was dissolved in dichloromethane (3.0 mL) and trifluoroacetic acid (1.5 mL). The resulting solution was stirred for 2 hours at 25° C. and then concentrated in vacuo. The crude product (93 mg) was purified by Prep-HPLC under the following conditions (1 #-Pre-HPLC-005(Waters)): Column, SunFire Prep C18, 19*150 mm 5 um; mobile phase, water with 0.05% TFA and $CH_3CN$ (20.0% $CH_3CN$ up to 80.0% in 10 min, up to 95.0% in 2 min, down to 20.0% in 1 min);

Detector, UV 254 nm. This resulted in 63.7 mg (67%) of 4-[3,5-bis(trifluoromethyl)phenoxy]-2,5-difluoro-N-(1,2,4-thiadiazol-5-yl)benzene-1-sulfonamide, trifluoroacetic acid as a white solid.

LC-MS: (ES, m/z): $[M-TFA+H]^+=506$.

$^1$H-NMR (400 MHz, DMSO-$d_6$, ppm): δ 8.55 (s, 1H), 8.02 (s, 3H), 7.89-7.85 (m, 1H), 7.51-7.47 (m, 1H).

Example 6

Synthesis of 4-[3,5-bis(trifluoromethyl)phenoxy]-N-(1,2,4-thiadiazol-5-yl)benzene-1-sulfonamide Step 1. Synthesis of N-[(2,4-dimethoxyphenyl)methyl]-4-fluoro-N-(1,2,4-thiadiazol-5-yl)benzene-1-sulfonamide -continued

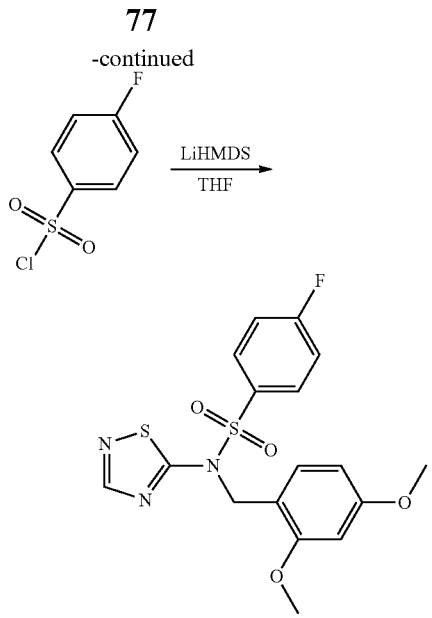

N-[(2,4-Dimethoxyphenyl)methyl]-1,2,4-thiadiazol-5-amine (500 mg, 1.99 mmol, 1.00 equiv) was dissolved in tetrahydrofuran (10 mL) under an inert atmosphere of nitrogen. Then a solution of LiHMDS (3 mL, 1.50 equiv) was added dropwise while stirring at −78° C. before the reaction mixture was gradually warmed to room temperature and stirred for a further 30 minutes. The reaction was then cooled back to −78° C. and a solution of 4-fluorobenzene-1-sulfonyl chloride (386 mg, 1.98 mmol, 1.00 equiv) in tetrahydrofuran (2 mL) was added dropwise. The temperature was once again gradually increased to room temperature and the reaction was stirred for a further 30 min. The reaction was then quenched by the addition of water, extracted with 3×20 mL of ethyl acetate and the combined organic layers were dried over anhydrous sodium sulfate and concentrated in vacuo. This resulted in 650 mg (80%) of N-[(2,4-dimethoxyphenyl)methyl]-4-fluoro-N-(1,2,4-thiadiazol-5-yl)benzene-1-sulfonamide as a light yellow solid.

Step 2. Synthesis of 4-[3,5-bis(trifluoromethyl)phenoxy]-N-[(2,4-dimethoxyphenyl)methyl]-N-(1,2,4-thiadiazol-5-yl)benzene-1-sulfonamide

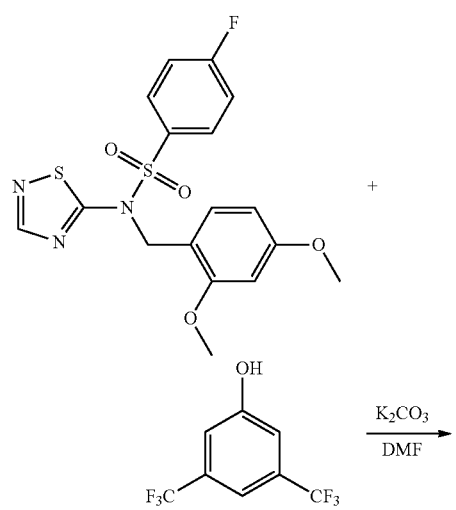

-continued

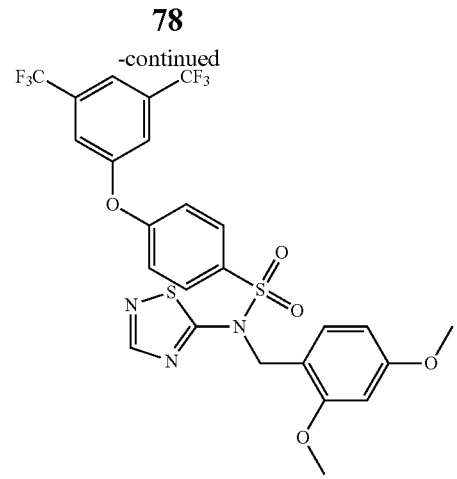

3,5-Bis(trifluoromethyl)phenol (85 mg, 0.37 mmol, 1.00 equiv) and K₂CO₃ (80 mg, 0.57 mmol, 1.50 equiv) were placed in 5 mL of DMF before N-[(2,4-dimethoxyphenyl)methyl]-4-fluoro-N-(1,2,4-thiadiazol-5-yl)benzene-1-sulfonamide (150 mg, 0.37 mmol, 1.00 equiv) was added. The reaction was stirred for 2 hours at 25° C. and then quenched by the addition of water. The mixture was extracted with 3×20 mL of ethyl acetate and the combined organic layers were dried over anhydrous sodium sulfate and concentrated in vacuo. The residue was purified by silica gel column chromatography eluting with ethyl acetate/petroleum ether (1:10). This resulted in 50 mg (22%) of 4-[3,5-bis(trifluoromethyl)phenoxy]-N-[(2,4-dimethoxyphenyl)methyl]-N-(1,2,4-thiadiazol-5-yl)benzene-1-sulfonamide as a light yellow solid.

Step 3. Synthesis of 4-[3,5-bis(trifluoromethyl)phenoxy]-N-(1,2,4-thiadiazol-5-yl)benzene-1-sulfonamide

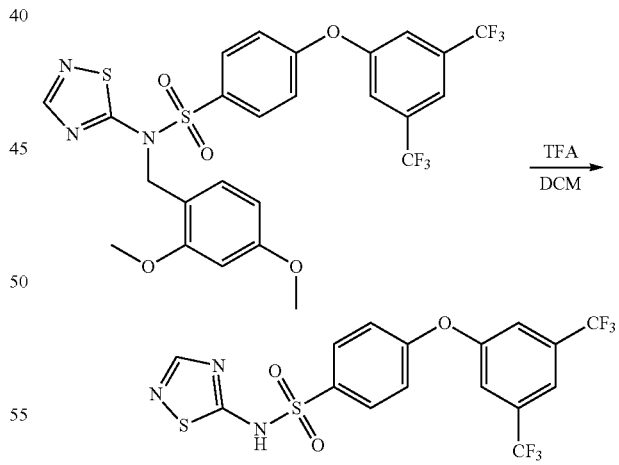

4-[3,5-Bis(trifluoromethyl)phenoxy]-N-[(2,4-dimethoxyphenyl)methyl]-N-(1,2,4-thiadiazol-5-yl)benzene-1-sulfonamide (50 mg, 0.08 mmol, 1.00 equiv) was dissolved in dichloromethane (8 mL). The reaction was cooled to 0° C. and trifluoroacetic acid (2 mL) was added dropwise. The resulting reaction was stirred for 2 hour at 25° C. and then concentrated in vacuo. The crude product was purified by Prep-HPLC under the following conditions: Column, Xbridge RP18, 19×150 mm; mobile phase: Water (0.05%

CF₃COOH) and acetonitrile (30% acetonitrile up to 75% in 10 min, hold 95% for 2 min, down to 30% in 2 min); Detector, UV 220 and 254 nm. This resulted in 27.6 mg (73%) of 4-[3,5-bis(trifluoromethyl)phenoxy]-N-(1,2,4-thiadiazol-5-yl)benzene-1-sulfonamide as a white solid.

LC-MS: (ES, m/z): [M+H]⁺470.0.

¹H-NMR (400 MHz, DMSO-d₆, ppm): δ 8.49 (s, 1H), 8.00 (s, 1H), 7.95-7.87 (m, 4H), 7.28-7.22 (m, 2H).

Example 7

Synthesis of 4-[3,5-bis(trifluoromethyl)phenoxy]-N-(1,3,4-thiadiazol-2-yl)benzene-1-sulfonamide Step 1. Synthesis of 4-[3,5-bis(trifluoromethyl)phenoxy]-N-[(2,4-dimethoxyphenyl)methyl]-N-(1,3,4-thiadiazol-2-yl)benzene-1-sulfonamide

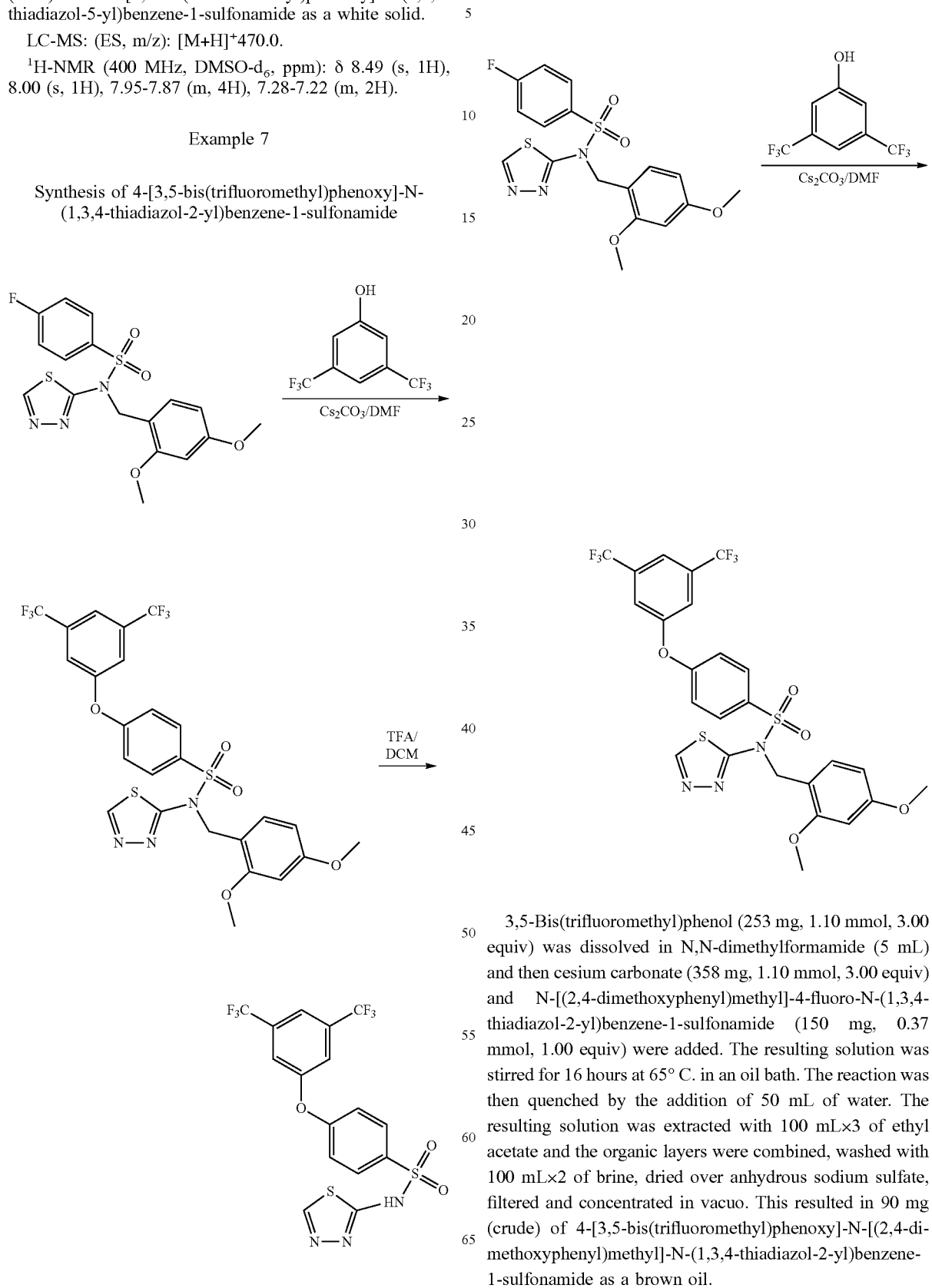

3,5-Bis(trifluoromethyl)phenol (253 mg, 1.10 mmol, 3.00 equiv) was dissolved in N,N-dimethylformamide (5 mL) and then cesium carbonate (358 mg, 1.10 mmol, 3.00 equiv) and N-[(2,4-dimethoxyphenyl)methyl]-4-fluoro-N-(1,3,4-thiadiazol-2-yl)benzene-1-sulfonamide (150 mg, 0.37 mmol, 1.00 equiv) were added. The resulting solution was stirred for 16 hours at 65° C. in an oil bath. The reaction was then quenched by the addition of 50 mL of water. The resulting solution was extracted with 100 mL×3 of ethyl acetate and the organic layers were combined, washed with 100 mL×2 of brine, dried over anhydrous sodium sulfate, filtered and concentrated in vacuo. This resulted in 90 mg (crude) of 4-[3,5-bis(trifluoromethyl)phenoxy]-N-[(2,4-dimethoxyphenyl)methyl]-N-(1,3,4-thiadiazol-2-yl)benzene-1-sulfonamide as a brown oil.

81

Step 2. Synthesis of 4-[3,5-bis(trifluoromethyl)phenoxy]-N-(1,3,4-thiadiazol-2-yl)benzene-1-sulfonamide

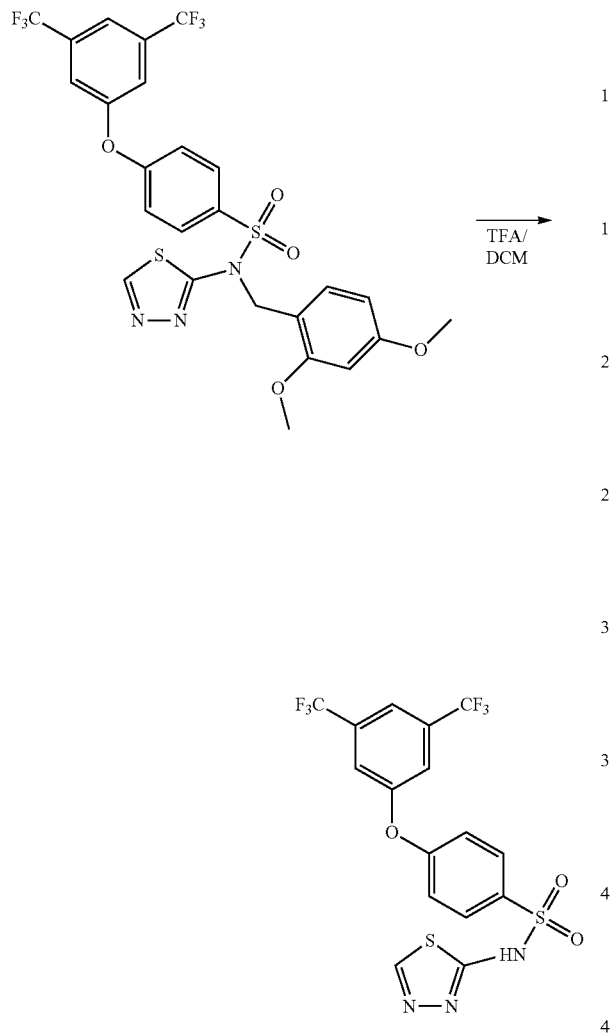

4-[3,5-Bis(trifluoromethyl)phenoxy]-N-[(2,4-dimethoxyphenyl)methyl]-N-(1,3,4-thiadiazol-2-yl)benzene-1-sulfonamide (90 mg, 0.15 mmol, 1.00 equiv) was dissolved in dichloromethane (4 mL) and trifluoroacetic acid (1 mL). The resulting solution was stirred for 1 h at room temperature and concentrated in vacuo. The crude product was purified by Prep-HPLC under the following conditions: Column, Xbridge RP18, 19×150 mm; mobile phase: Water (0.05% NH$_4$HCO$_3$) and acetonitrile (20% acetonitrile up to 60% in 10 min, hold 95% for 3 min, down to 20% in 1 min); Detector, UV 254 nm. This resulted in 45.9 mg (67%) of 4-[3,5-bis(trifluoromethyl)phenoxy]-N-(1,3,4-thiadiazol-2-yl)benzene-1-sulfonamide as a white solid.

LC-MS (ES, m/z): 470.2 (M+1)$^+$, 511.3 (M+1)$^+$.

$^1$H NMR (400 MHz, DMSO-d$_6$, ppm): δ 6.54 (s, 2H), 7.15-7.19 (m, 2H), 7.76-7.80 (m, 3H), 7.92 (s, 1H), 8.49 (s, 1H).

82

Example 8

Synthesis of 4-[3,5-bis(trifluoromethyl)phenoxy]-2,5-difluoro-N-(1,2,3-thiadiazol-5-yl)benzene-1-sulfonamide, trifluoroacetic acid

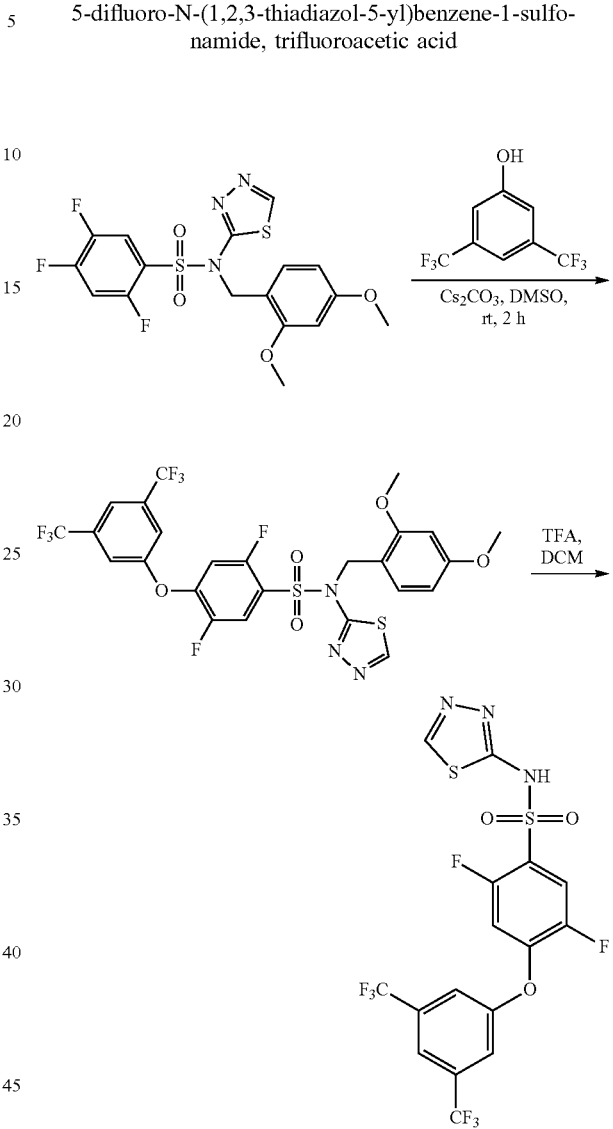

Step 1. Synthesis of 4-[3,5-bis(trifluoromethyl)phenoxy]-N-[(2,4-dimethoxyphenyl)methyl]-2,5-difluoro-N-(1,3,4-thiadiazol-2-yl)benzene-1-sulfonamide

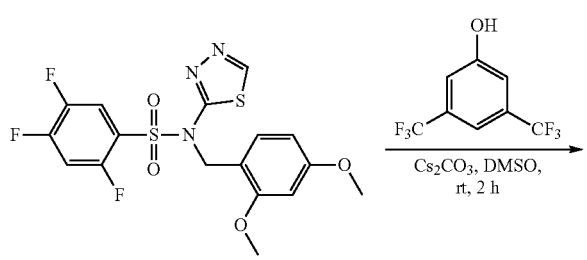

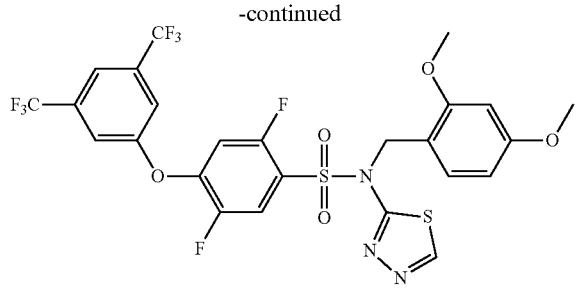

N-[(2,4-Dimethoxyphenyl)methyl]-2,4,5-trifluoro-N-(1,3,4-thiadiazol-2-yl)benzene-1-sulfonamide (150 mg, 0.34 mmol, 1.00 equiv), 3,5-bis(trifluoromethyl)phenol (77.5 mg, 0.34 mmol, 1.00 equiv), and Cs$_2$CO$_3$ (164.8 mg, 0.51 mmol, 1.50 equiv) were placed into DMSO (3 mL). The resulting reaction was stirred for 2 hours at 25° C. The reaction was then quenched by the addition of saturated aqueous ammonium chloride. The resulting solution was extracted with ethyl acetate and the combined organic layers were washed with brine, dried over anhydrous sodium sulfate and concentrated in vacuo. This resulted in 100 mg (45%) of 4-[3,5-bis(trifluoromethyl)phenoxy]-N-[(2,4-dimethoxyphenyl)methyl]-2,5-difluoro-N-(1,3,4-thiadiazol-2-yl)benzene-1-sulfonamide as a yellow oil.

Step 2. Synthesis of 4-[3,5-bis(trifluoromethyl)phenoxy]-2,5-difluoro-N-(1,2,3-thiadiazol-5-yl)benzene-1-sulfonamide, trifluoroacetic acid

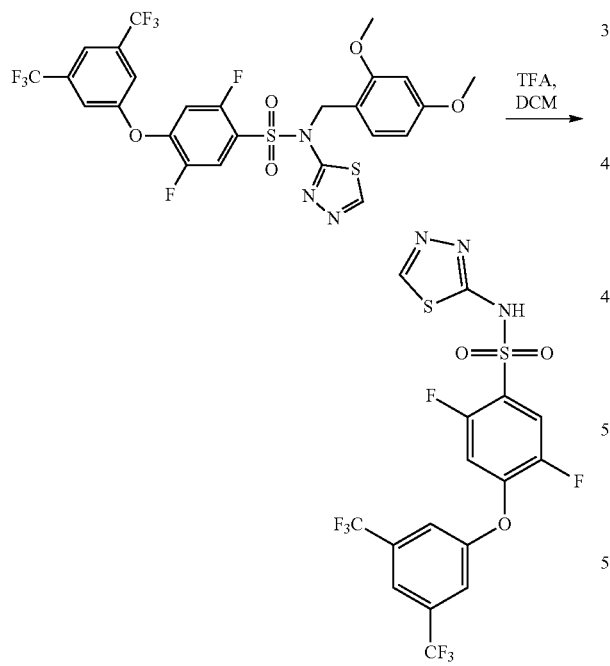

4-[3,5-Bis(trifluoromethyl)phenoxy]-N-[(2,5-dimethoxyphenyl)methyl]-2,5-difluoro-N-(1,3,4-thiadiazol-2-yl)benzene-1-sulfonamide (100 mg, 0.15 mmol, 1.00 equiv) was dissolved in dichloromethane (3.0 mL) and trifluoroacetic acid (1.5 mL). The resulting solution was stirred for 2 hours at 25° C. and then concentrated in vacuo. The crude product (93 mg) was purified by Prep-HPLC under the following conditions (1 #-Pre-HPLC-005(Waters)): Column, SunFire Prep C18, 19*150 mm 5 um; mobile phase, water with 0.05% TFA and CH$_3$CN (20.0% CH$_3$CN up to 80.0% in 10 min, up to 95.0% in 2 minutes, down to 20.0% in 1 min); Detector, UV 254 nm. This resulted in 45.8 mg (48%) of 4-[3,5-bis(trifluoromethyl)phenoxy]-2,5-difluoro-N-(1,2,3-thiadiazol-5-yl)benzene-1-sulfonamide, trifluoroacetic acid as a white solid.

LC-MS (ES, m/z): [M−TFA+H]$^+$=506.

$^1$H NMR (400 MHz, DMSO-d$_6$, ppm): δ 14.61-14.55 (s, 1H), 8.86 (s, 1H), 8.01 (s, 3H), 7.87-7.84 (m, 1H), 7.50-7.460 (m, 1H).

Example 9

Synthesis of 4-[3,5-bis(trifluoromethyl)phenoxy]-N-(1,3-thiazol-2-yl)benzene-1-sulfonamide

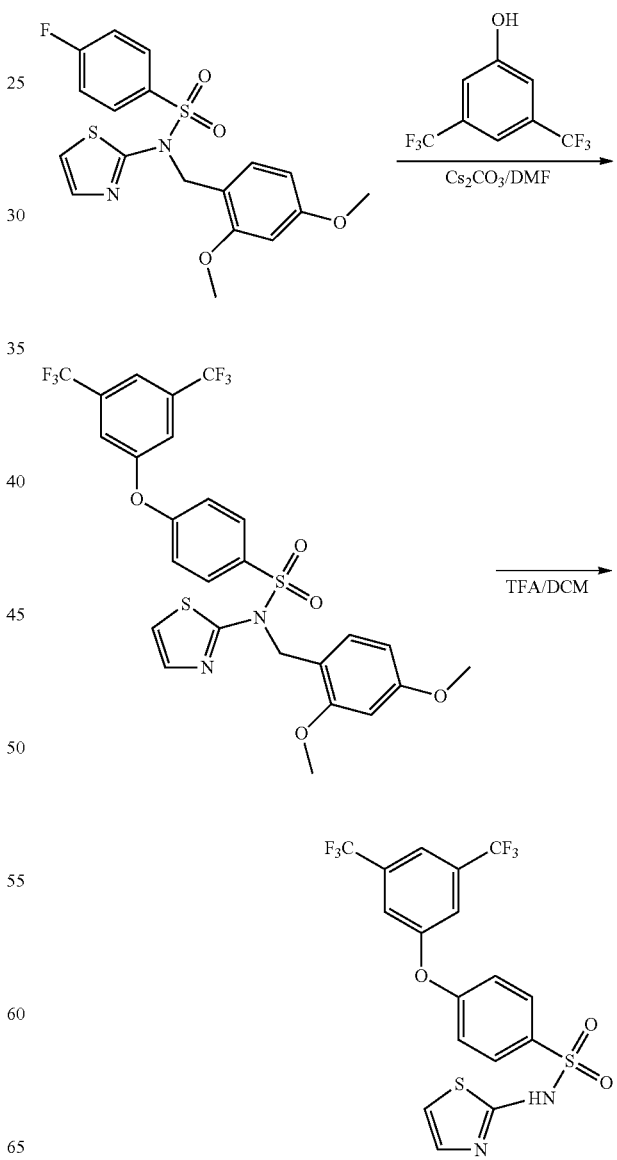

Step 1. Synthesis of 4-[3,5-bis(trifluoromethyl)phenoxy]-N-[(2,4-dimethoxyphenyl)methyl]-N-(1,3-thiazol-2-yl)benzene-1-sulfonamide

Step 2. Synthesis of 4-[3,5-bis(trifluoromethyl)phenoxy]-N-(1,3-thiazol-2-yl)benzene-1-sulfonamide

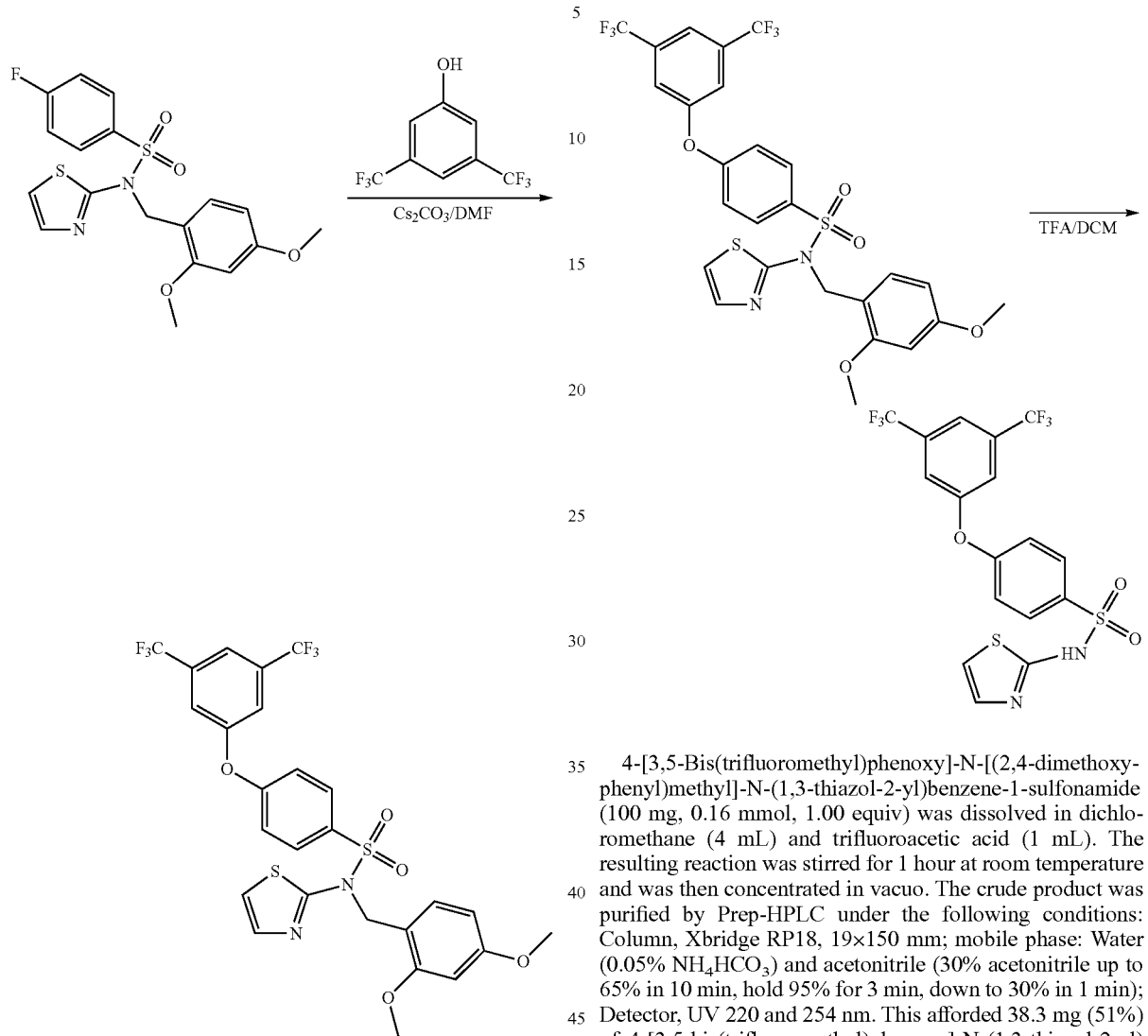

3,5-Bis(trifluoromethyl)phenol (253 mg, 1.10 mmol, 3.00 equiv) was dissolved in 5 mL of DMF before cesium carbonate (358 mg, 1.10 mmol, 3.00 equiv) and N-[(2,4-dimethoxyphenyl)methyl]-4-fluoro-N-(1,3-thiazol-2-yl)benzene-1-sulfonamide (150 mg, 0.37 mmol, 1.00 equiv) were added. The resulting reaction was stirred for 40 hours at 65° C. in an oil bath and then quenched by the addition of 50 mL of water. The mixture was extracted with 100 mL×3 of ethyl acetate and the combined organic layers were washed with 100 mL×2 of brine, dried over anhydrous sodium sulfate, filtered and concentrated in vacuo. The residue was purified by Prep-TLC with ethyl acetate/petroleum ether (1/1). This afforded 100 mg (crude) of 4-[3,5-bis(trifluoromethyl)phenoxy]-N-[(2,4-dimethoxyphenyl)methyl]-N-(1,3-thiazol-2-yl)benzene-1-sulfonamide as a brown oil.

4-[3,5-Bis(trifluoromethyl)phenoxy]-N-[(2,4-dimethoxyphenyl)methyl]-N-(1,3-thiazol-2-yl)benzene-1-sulfonamide (100 mg, 0.16 mmol, 1.00 equiv) was dissolved in dichloromethane (4 mL) and trifluoroacetic acid (1 mL). The resulting reaction was stirred for 1 hour at room temperature and was then concentrated in vacuo. The crude product was purified by Prep-HPLC under the following conditions: Column, Xbridge RP18, 19×150 mm; mobile phase: Water (0.05% NH$_4$HCO$_3$) and acetonitrile (30% acetonitrile up to 65% in 10 min, hold 95% for 3 min, down to 30% in 1 min); Detector, UV 220 and 254 nm. This afforded 38.3 mg (51%) of 4-[3,5-bis(trifluoromethyl)phenoxy]-N-(1,3-thiazol-2-yl)benzene-1-sulfonamide as a white solid.

LC-MS (ES, m/z): 469.2 (M+1)$^+$.

$^1$H NMR (400 MHz, DMSO): δ 6.74-6.75 (m, 1H), 7.18-7.23 (m, 3H), 7.83-7.86 (m, 4H), 7.96 (s, 1H);

Example 10

4-[3,5-bis(trifluoromethyl)phenoxy]-3-cyano-N-(1,3,4-thiadiazol-2-yl)benzene-1-sulfonamide

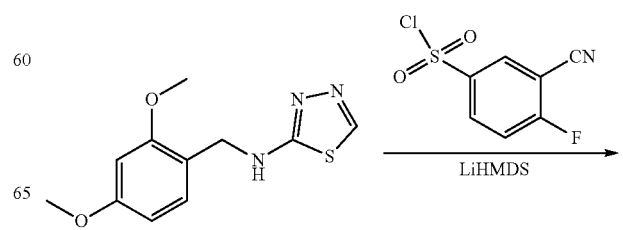

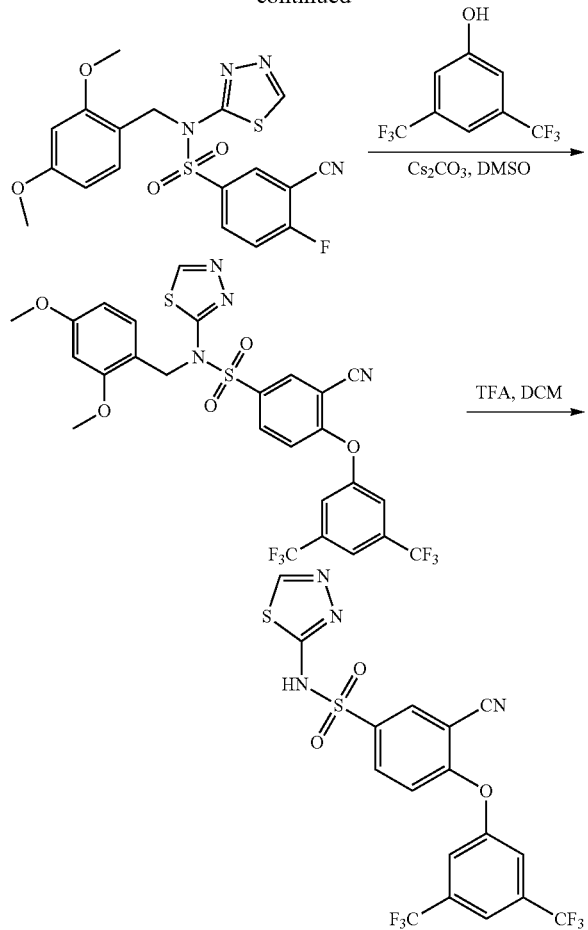

Step 1. Synthesis of 3-cyano-N-[(2,4-dimethoxyphenyl)methyl]-4-fluoro-N-(1,3,4-thiadiazol-2-yl)benzene-1-sulfonamide

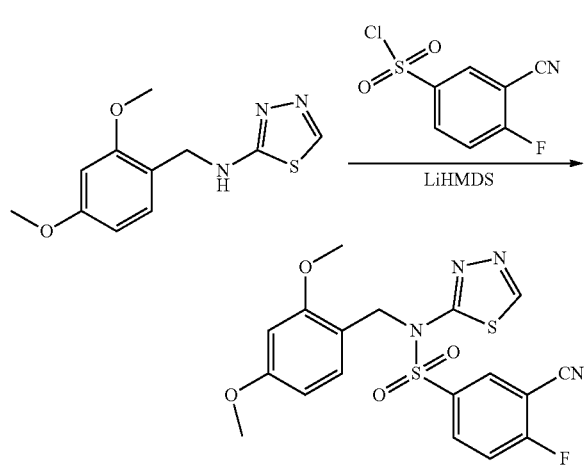

Into a 250-mL 3-necked round-bottom flask purged and maintained with an inert atmosphere of 1.00 equiv), tetrahydrofuran (90 mL). This was followed by the addition of LiHMDS (aq. 1 M) (7.2 mL, 2.00 equiv) at −78° C. The solution was stirred for 90 min at −78 to 2500. To this was added 3-cyano-4-fluorobenzene-1-sulfonyl chloride (786 mg, 3.58 mmol, 1.00 equiv) at −78° C. The resulting solution was stirred for 1 h at −78 to 0° C. The reaction was then quenched by the addition of water, extracted with ethyl acetate and the organic layers combined. The resulting mixture was washed with brine, dried over anhydrous sodium sulfate and concentrated under vacuum. This resulted in 1.13 g (73%) of 3-cyano-N-[(2,4-dimethoxyphenyl)methyl]-4-fluoro-N-(1,3,4-thiadiazol-2-yl)benzene-1-sulfonamide as a white solid.

Step 2. Synthesis of 4-[3,5-bis(trifluoromethyl)phenoxy]-3-cyano-N-[(2,4-dimethoxyphenyl)methyl]-N-(1,3,4-thiadiazol-2-yl)benzene-1-sulfonamide

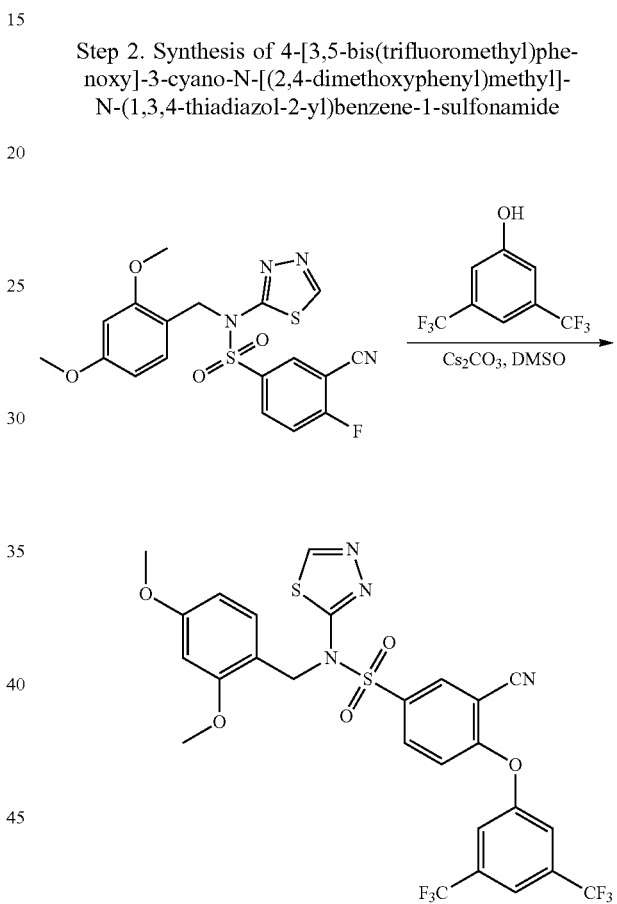

Into a 50-mL round-bottom flask, were placed 3,5-bis(trifluoromethyl)phenol (106 mg, 0.46 mmol, 1.00 equiv), Cs2CO3 (225 mg, 0.69 mmol, 1.50 equiv), DMSO (8 mL), 3-cyano-N-[(2,4-dimethoxyphenyl)methyl]-4-fluoro-N-(1,3,4-thiadiazol-2-yl)benzene-1-sulfonamide (200 mg, 0.46 mmol, 1.00 equiv). The resulting solution was stirred for 2.5 h at 25° C. The reaction was then quenched by the addition of water. The resulting solution was extracted with ethyl acetate and the organic layer combined. The resulting mixture was washed with brine, dried over anhydrous sodium sulfate and concentrated under vacuum. This resulted in 280 mg (94%) of 4-[3,5-bis(trifluoromethyl)phenoxy]-3-cyano-N-[(2,4-dimethoxyphenyl)methyl]-N-(1,3,4-thiadiazol-2-yl)benzene-1-sulfonamide as yellow oil.

Step 3. Synthesis of 4-[3,5-bis(trifluoromethyl)phenoxy]-3-cyano-N-(1,3,4-thiadiazol-2-yl)benzene-1-sulfonamide

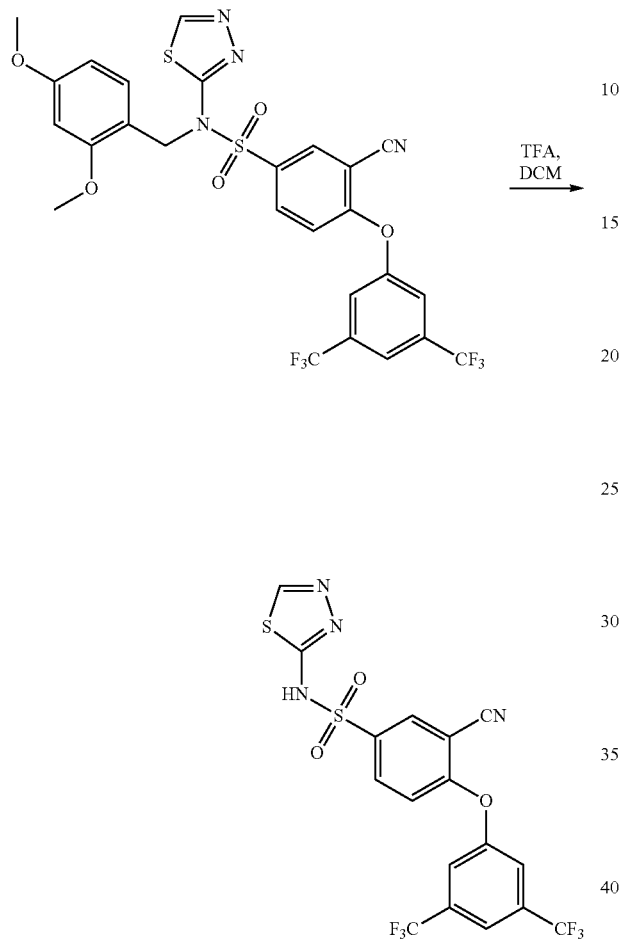

Into a 50-mL round-bottom flask, were placed 4-[3,5-bis(trifluoromethyl)phenoxy]-3-cyano-N-[(2,4-dimethoxyphenyl)methyl]-N-(1,3,4-thiadiazol-2-yl)benzene-1-sulfonamide (100 mg, 0.16 mmol, 1.00 equiv), dichloromethane (6 mL), trifluoroacetic acid (2 mL). The resulting solution was stirred for 1 h at 25° C. The resulting mixture was concentrated under vacuum. The crude product (80 mg) was purified by Prep-HPLC with the following conditions (1 #-Pre-HPLC-005(Waters)): Column, SunFire Prep C18, 19*150 mm 5 um; mobile phase, water with 0.05% TFA and CH$_3$CN (20.0% CH$_3$CN up to 80.0% in 10 min, up to 95.0% in 2 min, down to 20.0% in 1 min); Detector, UV 254 nm. This resulted in 31.8 mg (41%) of 4-[3,5-bis(trifluoromethyl)phenoxy]-3-cyano-N-(1,3,4-thiadiazol-2-yl)benzene-1-sulfonamide as white solid.

LC-MS: (ES, m/z): [M+H]$^+$ 495

H-NMR: (400 MHz, DMSO-d$_6$, ppm): δ 14.51 (m, 1H), 8.82 (s, 1H), 8.32 (s, 1H), 8.18 (s, 2H), 8.11 (s, 1H), 8.03-8.01 (m, 1H), 7.18-7.16 (d, 1H).

Example 11

4-[3,5-bis(trifluoromethyl)phenoxy]-3-fluoro-N-(1,2,4-thiadiazol-5-yl)benzene-1-sulfonamide

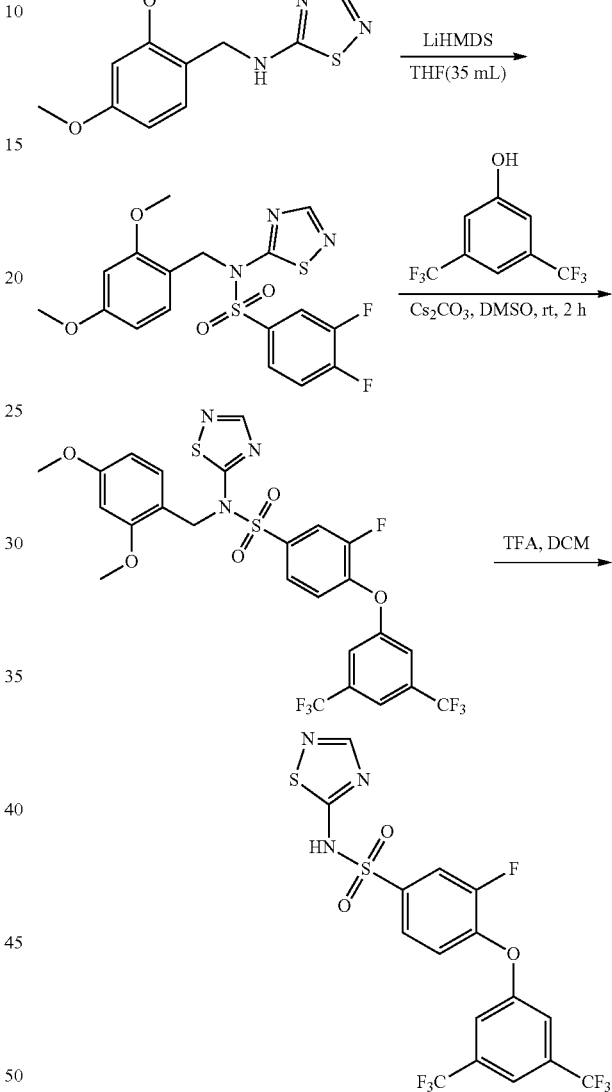

Step 1. Synthesis of N-[(2,4-dimethoxyphenyl)methyl]-3,4-difluoro-N-(1,2,4-thiadiazol-5-yl)benzene-1-sulfonamide

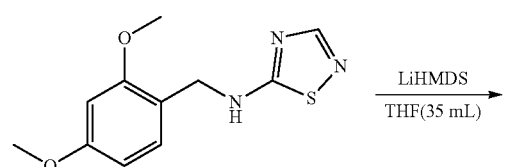

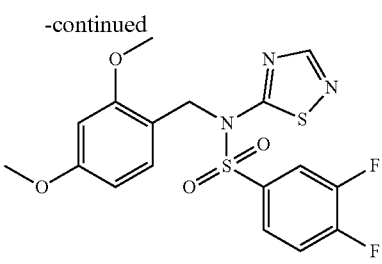

Into a 100-mL 3-necked round-bottom flask purged and maintained with an inert atmosphere of nitrogen, were placed N-[(2,4-dimethoxyphenyl) methyl]-1,2,4-thiadiazol-5-amine (200 mg, 0.80 mmol, 1.00 equiv), tetrahydrofuran (35 mL). This was followed by the addition of LiHMDS (aq., 1M) (16 mL, 2.00 equiv) dropwise with stirring at −5° C. The solution was stirred for 90 min at 25° C. To this was added 3,4-difluorobenzene-1-sulfonyl chloride (168 mg, 0.79 mmol, 1.00 equiv) dropwise with stirring at −78° C. The resulting solution was stirred for 50 min at −78 to 0° C. The reaction was then quenched by the addition of NH$_4$Cl (aq.). The resulting solution was extracted with ethyl acetate and the organic layers combined. The resulting mixture was washed with brine, dried over anhydrous sodium sulfate. The residue was applied onto a silica gel column with ethyl acetate/petroleum ether (1:10). This resulted in 110 mg (32%) of N-[(2,4-dimethoxyphenyl)methyl]-3,4-difluoro-N-(1,2,4-thiadiazol-5-yl)benzene-1-sulfonamide as a white solid.

Step 2. Synthesis of 4-[3,5-bis(trifluoromethyl)phenoxy]-N-[(2,4-dimethoxyphenyl)methyl]-3-fluoro-N-(1,2,4-thiadiazol-5-yl)benzene-1-sulfonamide

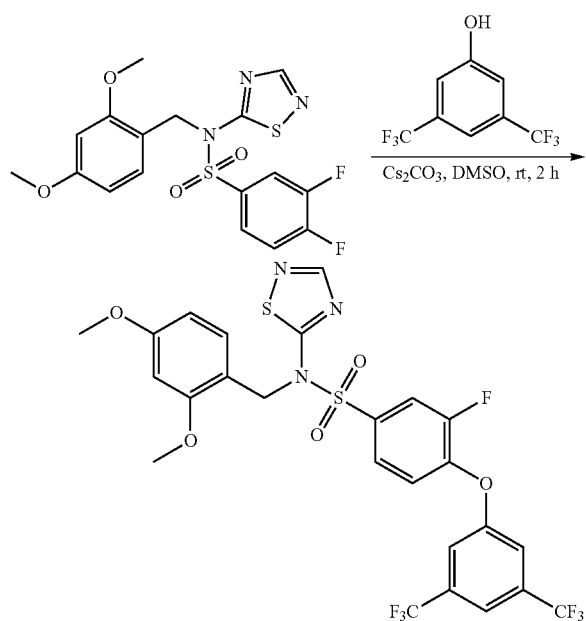

Into a 25-mL round-bottom flask, were placed 3,5-bis(trifluoromethyl)phenol (59.2 mg, 0.26 mmol, 1.00 equiv), Cs$_2$CO$_3$ (168 mg, 0.52 mmol, 2.00 equiv), DMSO (5 mL), N-[(2,4-dimethoxyphenyl)methyl]-3,4-difluoro-N-(1,2,4-thiadiazol-5-yl)benzene-1-sulfonamide (110 mg, 0.26 mmol, 1.00 equiv). The resulting solution was stirred for 2 h at 25° C. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 100 mg (61%) of 4-[3,5-bis(trifluoromethyl)phenoxy]-N-[(2,4-dimethoxyphenyl)methyl]-3-fluoro-N-(1,2,4-thiadiazol-5-yl)benzene-1-sulfonamide as yellow oil.

Step 3. Synthesis of 4-[3,5-bis(trifluoromethyl)phenoxy]-3-fluoro-N-(1,2,4-thiadiazol-5-yl)benzene-1-sulfonamide

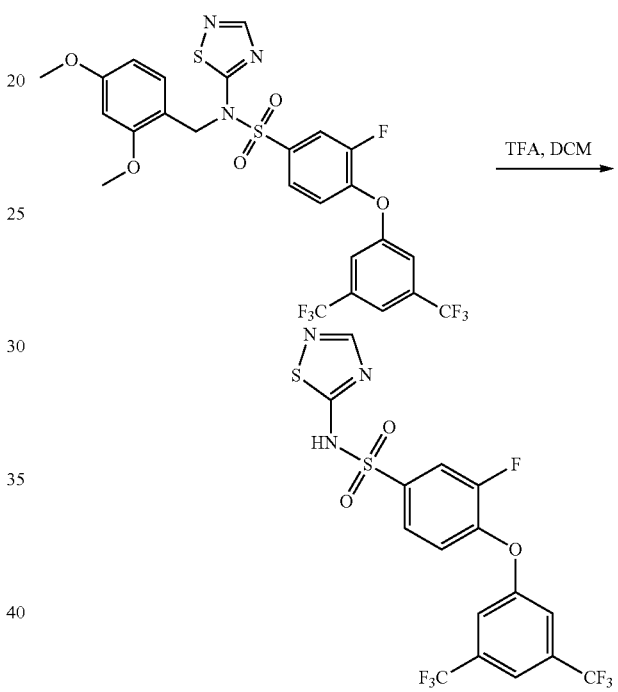

Into a 25-mL round-bottom flask, were placed 4-[3,5-bis(trifluoromethyl)phenoxy]-N-[(2,4-dimethoxyphenyl)methyl]-3-fluoro-N-(1,2,4-thiadiazol-5-yl)benzene-1-sulfonamide (100 mg, 0.16 mmol, 1.00 equiv), dichloromethane (2 mL), trifluoroacetic acid (1 mL). The resulting solution was stirred for 1 h at 25° C. The resulting mixture was concentrated under vacuum. The crude product (75 mg) was purified by Prep-HPLC with the following conditions (1 #-Pre-HPLC-005(Waters)): Column, SunFire Prep C18, 19*150 mm 5 um; mobile phase, water with 0.05% TFA and CH$_3$CN (20.0% CH$_3$CN up to 80.0% in 10 min, up to 95.0% in 2 min, down to 20.0% in 1 min); Detector, UV 254 nm. This resulted in 19.1 mg (25%) of 4-[3,5-bis(trifluoromethyl)phenoxy]-3-fluoro-N-(1,2,4-thiadiazol-5-yl)benzene-1-sulfonamide as a white solid.

LC-MS: (ES, m/z): [M+H]$^+$ 488

$^1$H-NMR: (400 MHz, DMSO-d$_6$, ppm): δ 7.93 (s, 1H), 7.88 (s, 1H), 7.8208 (s, 2H), 7.68-7.65 (d, 1H), 7.61-7.59 (d, 1H), 7.34-7.30 (t, 1H).

Example 12

Synthesis of 4-[3,5-bis(trifluoromethyl)phenoxy]-2,5-difluoro-N-(1,2,4-thiadiazol-5-yl)benzamide

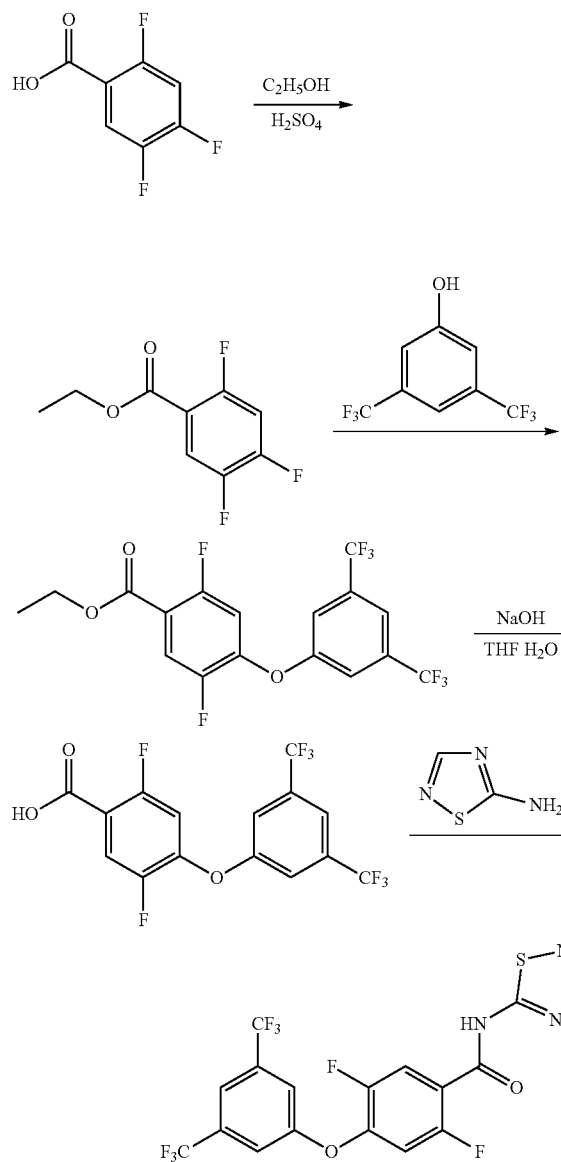

Step 1. Synthesis of ethyl 2,4,5-trifluorobenzoate

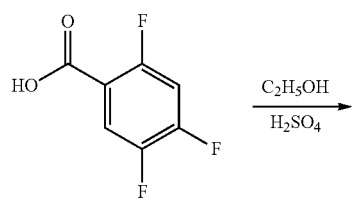

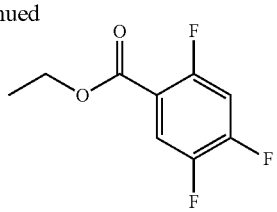

Into a 100-mL round-bottom flask purged and maintained with an inert atmosphere of nitrogen, was placed 2,4,5-trifluorobenzoic acid (5 g, 28.39 mmol, 1.00 equiv) in ethanol (25 mL). This was followed by the dropwise addition of sulfuroyl dichloride (6.8 g, 57.16 mmol, 2.01 equiv) with stirring at 0° C. The resulting solution was heated to reflux for 2 hr. The resulting mixture was concentrated in vacuo. The residue was diluted with water, then adjusted to pH 9~10 with sodium carbonate (aq.). The resulting solution was extracted with 2×100 mL of ether and the organic layers were combined and concentrated in vacuo. This resulted in 5.7 g (crude) of ethyl 2,4,5-trifluorobenzoate as a colorless oil.

Step 2. Synthesis of ethyl 4-[3,5-bis(trifluoromethyl)phenoxy]-2,5-difluorobenzoate

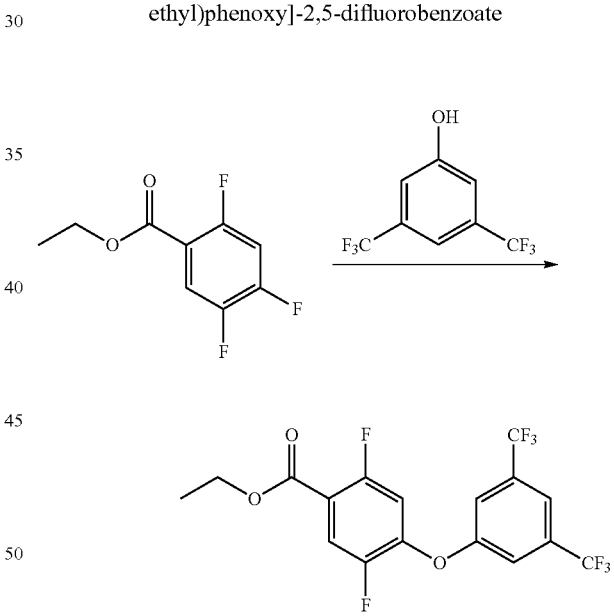

Into a 100-mL round-bottom flask, ethyl 2,4,5-trifluorobenzoate (1.19 g, 5.83 mmol, 1.00 equiv) was dissolved in DMSO (20 mL) and 3,5-bis(trifluoromethyl)phenol (1.4 g, 6.08 mmol, 1.04 equiv) and $Cs_2CO_3$ (2.5 g, 7.65 mmol, 1.31 equiv) were added. The reaction was stirred overnight at room temperature. Then it was quenched by the addition of 200 mL of $NH_4Cl$ (aq.). The resulting solution was extracted with 2×100 mL of ethyl acetate and the organic layers were combined and concentrated in vacuo. The residue was purified by silica gel column chromatography with ethyl acetate/petroleum ether (1:20). This resulted in 2.2 g (91%) of ethyl 4-[3,5-bis(trifluoromethyl)phenoxy]-2,5-difluorobenzoate as a colorless oil.

Step 3. Synthesis of 4-[3,5-bis(trifluoromethyl)phenoxy]-2,5-difluorobenzoic acid

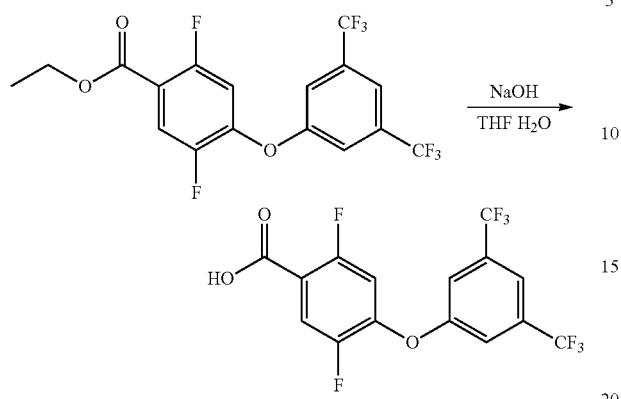

To a solution of 4-[3,5-bis(trifluoromethyl)phenoxy]-2,5-difluorobenzoate (2.2 g, 5.31 mmol, 1.00 equiv) in THF (30 mL), was added a solution of sodium hydroxide (638 mg, 15.95 mmol, 3.00 equiv) in water (10 mL). The resulting solution was stirred for 3 h at room temperature. Then the reaction was quenched by the addition of 100 mL of water. The resulting solution was extracted with 3×50 mL of ether and the aqueous layers were combined. The pH value of the solution was adjusted to pH 3 with aq. hydrogen chloride (5 mol/L). The solids were collected by filtration and air-dried. This resulted in 1.3 g (63%) of 4-[3,5-bis(trifluoromethyl)phenoxy]-2,5-difluorobenzoic acid as a white solid.

Step 4. Synthesis of 4-[3,5-bis(trifluoromethyl)phenoxy]-2,5-difluoro-N-(1,2,4-thiadiazol-5-yl)benzamide

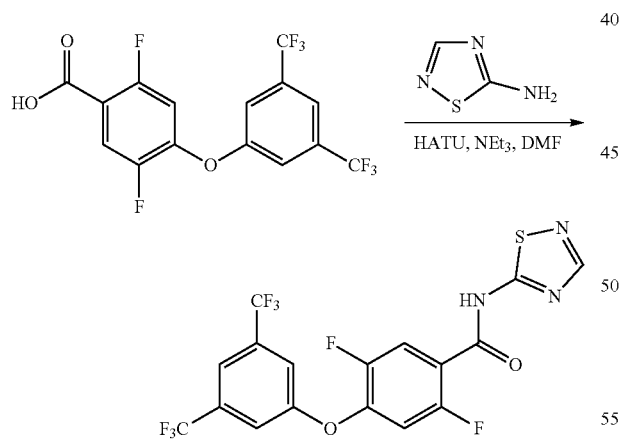

Into a 25-mL round-bottom flask purged and maintained with an inert atmosphere of nitrogen, was placed 4-[3,5-bis(trifluoromethyl)phenoxy]-2,5-difluorobenzoic acid (100 mg, 0.26 mmol, 1.00 equiv), NEt$_3$ (79 mg), HATU (148 mg, 0.39 mmol, 1.50 equiv), and 1,2,4-thiadiazol-5-amine (26 mg, 0.26 mmol, 0.99 equiv) in dichloromethane (5 mL). The resulting solution was stirred overnight at room temperature. Then the reaction was quenched by the addition of 100 mL of water. The resulting solution was extracted with 3×100 mL of dichloromethane and the organic layers were combined and concentrated in vacuo. The residue was purified by silica gel column chromatography with ethyl acetate/petroleum ether (1:2). This resulted in 43.5 mg (36%) of 4-[3,5-bis(trifluoromethyl)phenoxy]-2,5-difluoro-N-(1,2,4-thiadiazol-5-yl)benzamide as a light yellow solid.

LC-MS (ES, m/z): [M−H]⁻468.

$^1$H NMR (400 MHz, DMSO, ppm): δ 13.56 (s, 1H), 8.58 (s, 1H), 8.04-7.96 (m, 4H), 7.51 (t, 1H)

Example 13

4-[3,5-bis(trifluoromethyl)phenoxy]-2,5-difluoro-N-methanesulfonylbenzamide

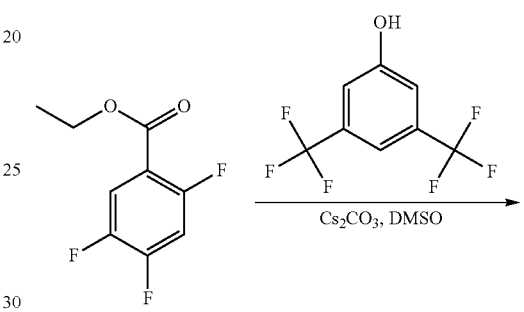

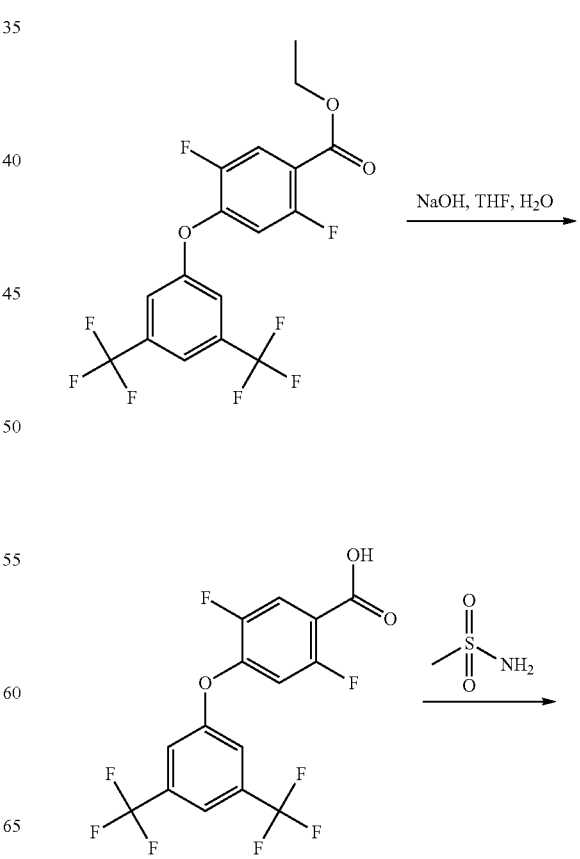

Step 1. Synthesis of 4-[3,5-bis(trifluoromethyl)phenoxy]-2,5-difluorobenzoate

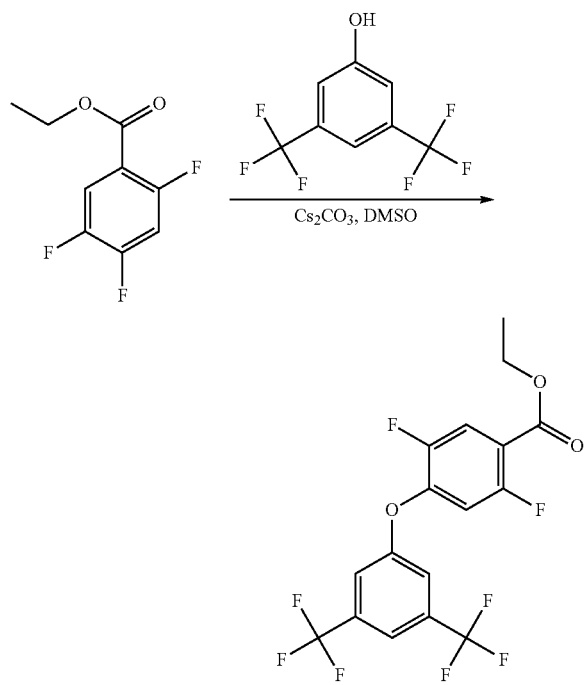

Into a 50-mL round-bottom flask, was placed a solution of ethyl 2,4,5-trifluorobenzoate (200 mg, 0.98 mmol, 1.00 equiv) in DMSO (15 mL). To the solution were added 3,5-bis(trifluoromethyl)phenol (225 mg, 0.98 mmol, 1.00 equiv) and $Cs_2CO_3$ (639 mg, 1.96 mmol, 2.00 equiv). The resulting solution was stirred for 16 h at room temperature. The resulting solution was extracted with of ethyl acetate and the organic layers combined and concentrated under vacuum. The residue was applied onto a silica gel column with ethyl acetate/petroleum ether (1:15). The collected fractions were combined and concentrated under vacuum. This resulted in 350 mg (86%) of ethyl 4-[3,5-bis(trifluoromethyl)phenoxy]-2,5-difluorobenzoate as a white solid.

Step 2. Synthesis of 4-[3,5-bis(trifluoromethyl)phenoxy]-2,5-difluorobenzoic acid

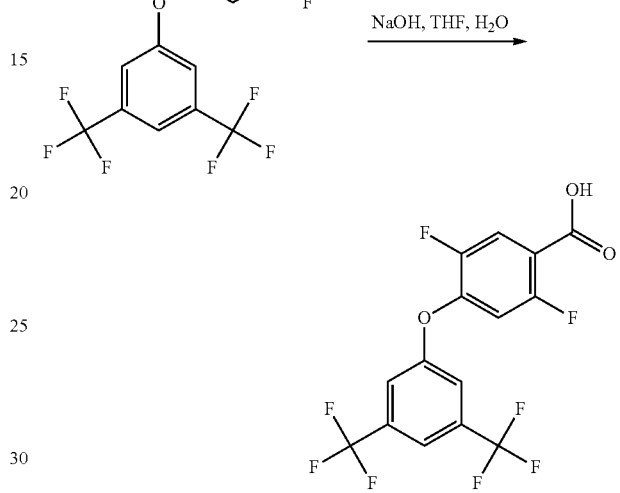

Into a 50-mL round-bottom flask, was placed a solution of ethyl 4-[3,5-bis(trifluoromethyl)phenoxy]-2,5-difluorobenzoate (350 mg, 0.84 mmol, 1.00 equiv) in tetrahydrofuran/$H_2O$ (10/1 mL). To the solution were added sodium hydroxide (169 mg, 4.22 mmol, 5.00 equiv). The resulting solution was stirred for 4 h at room temperature. The pH value of the solution was adjusted to 3-4 with hydrogen chloride aqueous (12 mol/L). The resulting solution was extracted with ethyl acetate (3×20 mL) and the organic layers combined and concentrated under vacuum. This resulted in 250 mg (77%) of 4-[3,5-bis(trifluoromethyl)phenoxy]-2,5-difluorobenzoic acid as a off-white solid.

Step 3. Synthesis of 4-[3,5-bis(trifluoromethyl)phenoxy]-2,5-difluoro-N-methanesulfonylbenzamide

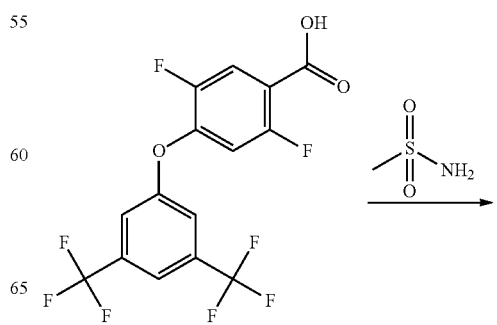

-continued

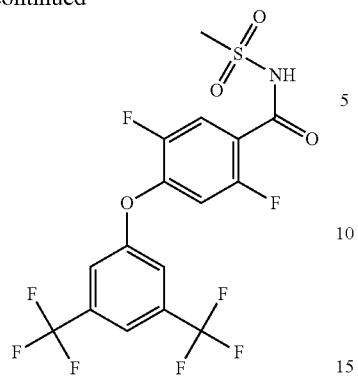

Into a 50-mL round-bottom flask, was placed a solution of 4-[3,5-bis(trifluoromethyl)phenoxy]-2,5-difluorobenzoic acid (250 mg, 0.65 mmol, 1.00 equiv) in N,N-dimethylformamide (15 mL). To the solution were added methanesulfonamide (74 mg, 0.78 mmol, 1.20 equiv), EDCI (124 mg, 0.65 mmol, 1.00 equiv), 4-dimethylaminopyridine (79 mg, 0.65 mmol, 1.00 equiv) and triethylamine (131 mg, 1.30 mmol, 2.00 equiv). The resulting solution was stirred for 16 h at room temperature. The resulting mixture was concentrated under vacuum. The crude product was purified by Prep-HPLC with conditions: Column, XBridge Prep Shield RP18, 5 um, 19×150 mm; Mobile phase, H$_2$O (0.05% TFA)/CH$_3$CN (30%~80% in 8 min); Detector, 254 nm, 220 nm; RT=6.2 min. This resulted in 65.1 mg (22%) of 4-[3,5-bis(trifluoromethyl)phenoxy]-2,5-difluoro-N-methanesulfonylbenzamide as a white solid.

LC-MS: (ES, m/z): [M+H]$^+$ 464

$^1$H NMR (300 MHz, DMSO, ppm) □ 3.34 (s, 3H), 7.43-7.49 (m, 1H), 7.81-7.99 (m, 4H), 12.41 (s, 1H).

Example 14

4-[3,5-bis(trifluoromethyl)phenoxy]-3-cyano-N-(1,2,4-thiadiazol-5-yl)benzene-1-sulfonamide

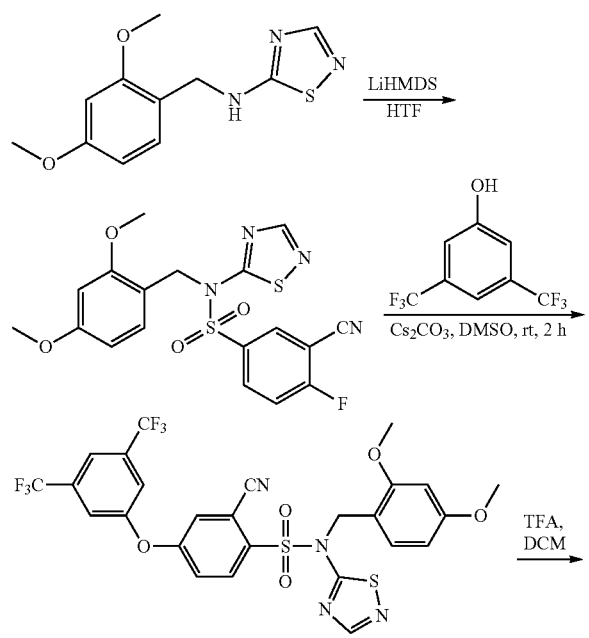

-continued

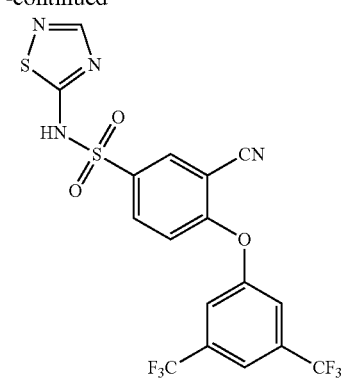

Step 1. Synthesis of 3-cyano-N-[(2,4-dimethoxyphenyl)methyl]-4-fluoro-N-(1,2,4-thiadiazol-5-yl)benzene-1-sulfonamide

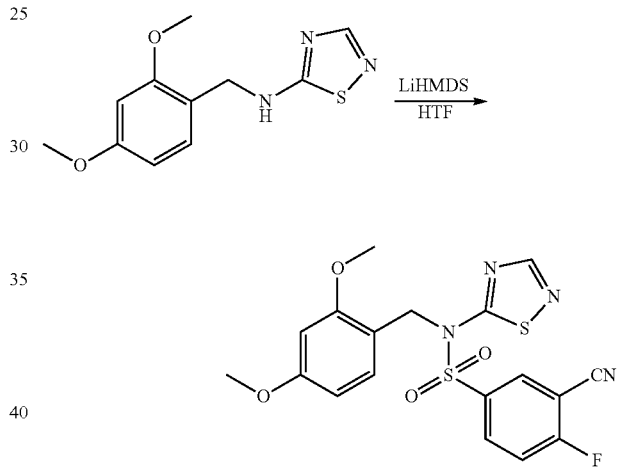

Into a 100-mL 3-necked round-bottom flask purged and maintained with an inert atmosphere of nitrogen, were placed N-[(2,4-dimethoxyphenyl) methyl]-1,2,4-thiadiazol-5-amine (200 mg, 0.80 mmol, 1.00 equiv), tetrahydrofuran (35 mL). This was followed by the addition of LiHMDS (1 M) (8 mL, 2.00 equiv) at −78° C. dropwise with stirring. The solution was stirred for 90 min at −78-25° C. To this was added 3-cyano-4-fluorobenzene-1-sulfonyl chloride (175 mg, 0.80 mmol, 1.00 equiv) dropwise at −78° C. with stirring. The resulting solution was stirred for 50 min at −78~0° C. The reaction was then quenched by the addition of NH$_4$Cl (aq.). The resulting solution was extracted with ethyl acetate and the organic layers combined. The resulting mixture was washed with brine. The mixture was dried over anhydrous sodium sulfate. The residue was applied onto a silica gel column with ethyl acetate/petroleum ether (1:10). This resulted in 120 mg (35%) of 3-cyano-N-[(2,4-dimethoxyphenyl)methyl]-4-fluoro-N-(1,2,4-thiadiazol-5-yl)benzene-1-sulfonamide as a white solid.

Step 2. Synthesis of 4-[3,5-bis(trifluoromethyl)phenoxy]-3-cyano-N-[(2,4-dimethoxyphenyl)methyl]-N-(1,2,4-thiadiazol-5-yl)benzene-1-sulfonamide

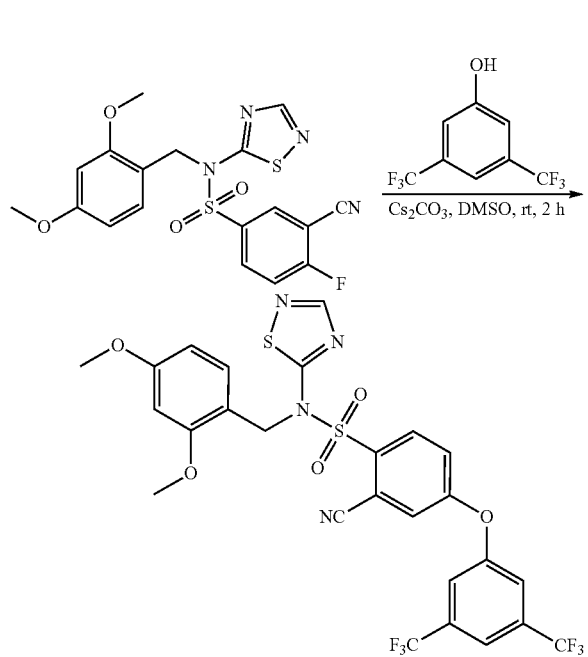

Into a 25-mL round-bottom flask, was placed 3,5-bis(trifluoromethyl)phenol (63.6 mg, 0.28 mmol, 1.00 equiv), Cs₂CO₃ (180 mg, 0.55 mmol, 2.00 equiv), DMSO (8 mL), 3-cyano-N-[(2,4-dimethoxyphenyl)methyl]-4-fluoro-N-(1,2,4-thiadiazol-5-yl)benzene-1-sulfonamide (120 mg, 0.28 mmol, 1.00 equiv). The resulting solution was stirred for 2 h at 25° C. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 150 mg (84%) of 4-[3,5-bis(trifluoromethyl)phenoxy]-3-cyano-N-[(2,4-dimethoxyphenyl)methyl]-N-(1,2,4-thiadiazol-5-yl)benzene-1-sulfonamide as yellow oil.

Step 3. Synthesis of 4-[3,5-bis(trifluoromethyl)phenoxy]-3-cyano-N-(1,2,4-thiadiazol-5-yl)benzene-1-sulfonamide

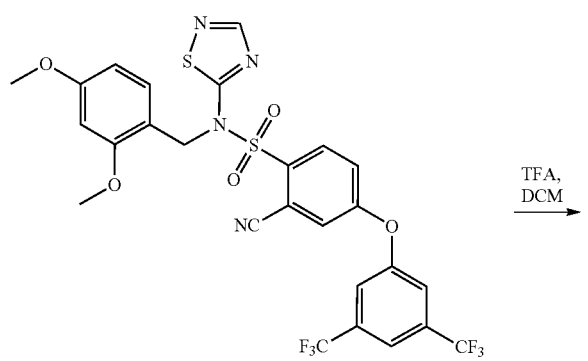

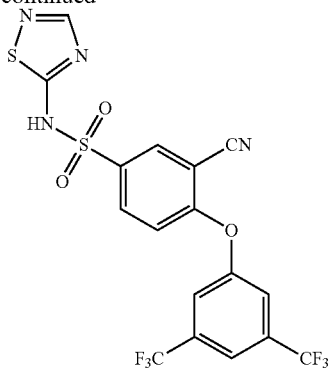

Into a 50-mL round-bottom flask, were placed 4-[3,5-bis(trifluoromethyl)phenoxy]-3-cyano-N-[(2,4-dimethoxyphenyl)methyl]-N-(1,2,4-thiadiazol-5-yl)benzene-1-sulfonamide (150 mg, 0.23 mmol, 1.00 equiv), dichloromethane (4 mL), trifluoroacetic acid (2 mL). The resulting solution was stirred for 1 h at 25° C. The resulting mixture was concentrated under vacuum. The crude product (100 mg) was purified by Prep-HPLC with the following conditions (1 #-Pre-HPLC-005(Waters)): Column, SunFire Prep C18, 19*150 mm 5 um; mobile phase, water with 0.05% TFA and CH₃CN (20.0% CH₃CN up to 80.0% in 10 min, up to 95.0% in 2 min, down to 20.0% in 1 min); Detector, UV 254 nm. This resulted in 28.6 mg (25%) of 4-[3,5-bis(trifluoromethyl)phenoxy]-3-cyano-N-(1,2,4-thiadiazol-5-yl)benzene-1-sulfonamide as a white solid.

LC-MS: (ES, m/z): [M+H]⁺ 495

¹H-NMR: (400 MHz, DMSO-d₆, ppm): δ 8.48-8.48 (m, 1H), 8.32 (s, 1H), 8.17 (s, 2H), 8.10 (s, 1H), 8.05-8.02 (m, 1H), 7.18-7.16 (m, 1H).

Example 15

Synthesis of 4-[3,5-bis(trifluoromethyl)phenoxy]-2,5-difluoro-N-(1,3,4-thiadiazol-2-yl)benzamide

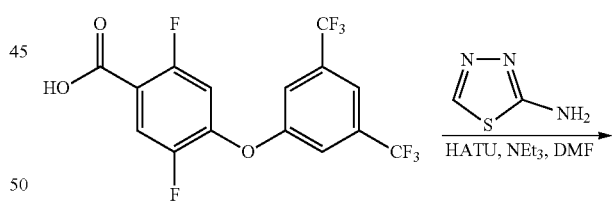

4-[3,5-Bis(trifluoromethyl)phenoxy]-2,5-difluorobenzoic acid (200 mg, 0.52 mmol, 1.00 equiv), HATU (297 mg, 0.78 mmol, 1.51 equiv), NEt₃ (158 mg), and 1,3,4-thiadiazol-2-amine (53 mg, 0.52 mmol, 1.01 equiv) were dissolved in dichloromethane (10 mL) under nitrogen atmosphere. The resulting solution was stirred for 2 days at room temperature. Then the reaction was quenched by the addition of 100 mL of water. The resulting solution was extracted with 3×100 mL of dichloromethane and the organic layers were combined and concentrated in vacuo. The residue was purified by silica gel column chromatography eluting with ethyl acetate/petroleum ether (1:1). This resulted in 21.5 mg (9%) of 4-[3,5-bis(trifluoromethyl)phenoxy]-2,5-difluoro-N-(1,3,4-thiadiazol-2-yl)benzamide as a white solid.

LC-MS (ES, m/z): [M+H]+470.

$^1$H NMR (400 MHz, DMSO, ppm): δ 13.16 (s, 1H), 9.28 (s, 1H), 8.00-7.93 (m, 4H), 7.53-7.48 (m, 1H).

Example 16

4-[3,5-bis(trifluoromethyl)phenoxy]-3-chloro-N-(1,2,4-thiadiazol-5-yl)benzene-1-sulfonamide

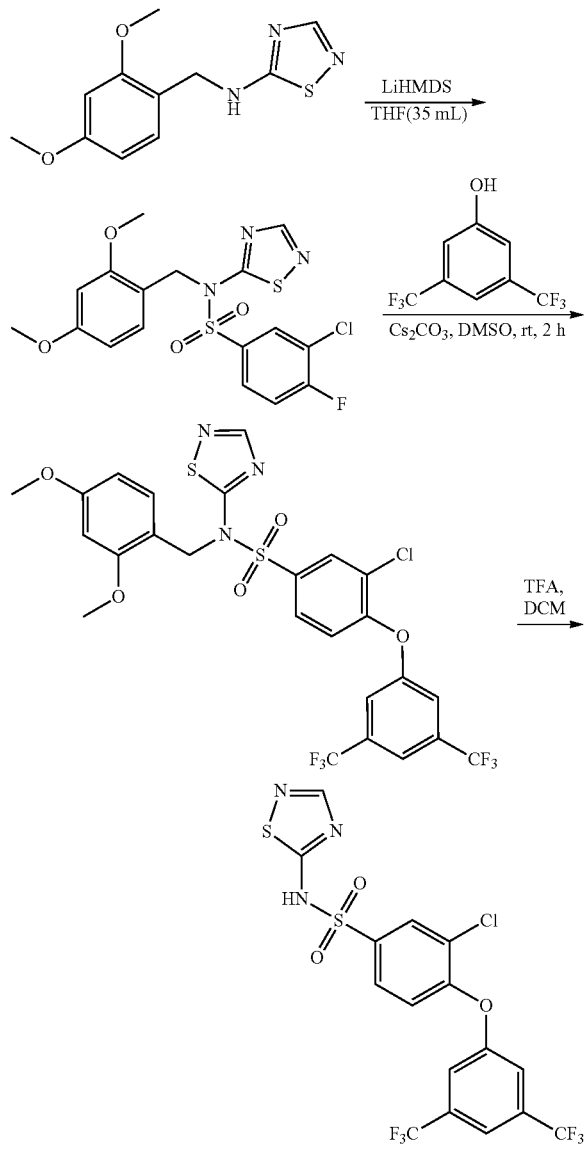

Step 1. Synthesis of 3-chloro-N-[(2,4-dimethoxyphenyl)methyl]-4-fluoro-N-(1,2,4-thiadiazol-5-yl)benzene-1-sulfonamide

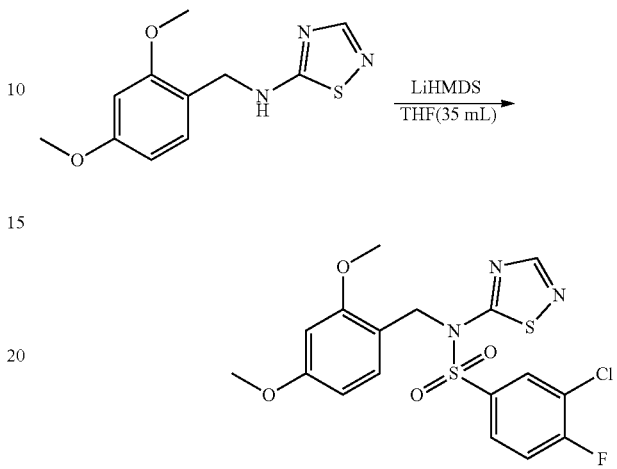

Into a 100-mL 3-necked round-bottom flask purged and maintained with an inert atmosphere of nitrogen, were placed N-[(2,4-dimethoxyphenyl) methyl]-1,2,4-thiadiazol-5-amine (200 mg, 0.80 mmol, 1.00 equiv), tetrahydrofuran (35 mL). This was followed by the addition of LiHMDS (1 M) (1.6 mL, 2.00 equiv) dropwise at −5° C. with stirring. The solution was stirred for 90 min at −5 to 25° C. To this was added 3-chloro-4-fluorobenzene-1-sulfonyl chloride (181 mg, 0.79 mmol, 1.00 equiv) dropwise at −78° C. with stirring. The resulting solution was stirred for 50 min at −78 to 0° C. The reaction was then quenched by the addition of NH$_4$Cl (aq.). The resulting solution was extracted with ethyl acetate and the organic layers combined. The resulting mixture was washed with brine, dried over anhydrous sodium sulfate and concentrated. The residue was applied onto a silica gel column with ethyl acetate/petroleum ether (1:10). This resulted in 120 mg (34%) of 3-chloro-N-[(2,4-dimethoxyphenyl)methyl]-4-fluoro-N-(1,2,4-thiadiazol-5-yl)benzene-1-sulfonamide as a white solid.

Step 2. Synthesis of 4-[3,5-bis(trifluoromethyl)phenoxy]-3-chloro-N-[(2,4-dimethoxyphenyl)methyl]-N-(1,2,4-thiadiazol-5-yl)benzene-1-sulfonamide

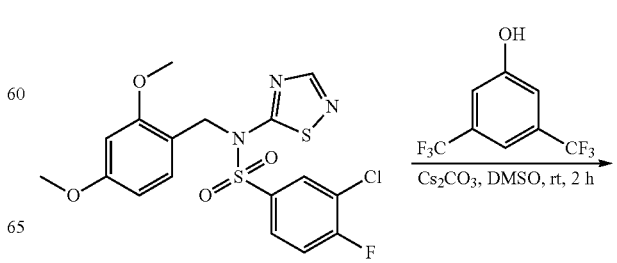

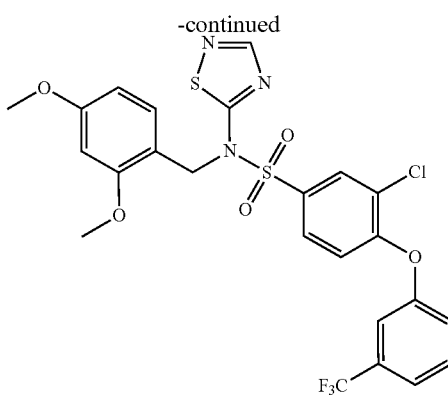

Into a 25-mL round-bottom flask, were placed 3,5-bis(trifluoromethyl)phenol (57.1 mg, 0.25 mmol, 1.00 equiv), Cs₂CO₃ (162 mg, 0.50 mmol, 2.00 equiv), DMSO (5 mL), 3-chloro-N-[(2,4-dimethoxyphenyl)methyl]-4-fluoro-N-(1,2,4-thiadiazol-5-yl)benzene-1-sulfonamide (120 mg, 0.27 mmol, 1.00 equiv). The resulting solution was stirred for 5 h at 25° C. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 100 mg (57%) of 4-[3,5-bis(trifluoromethyl)phenoxy]-3-chloro-N-[(2,4-dimethoxyphenyl)methyl]-N-(1,2,4-thiadiazol-5-yl)benzene-1-sulfonamide as yellow oil.

Step 3. Synthesis of 4-[3,5-bis(trifluoromethyl)phenoxy]-3-chloro-N-(1,2,4-thiadiazol-5-yl)benzene-1-sulfonamide

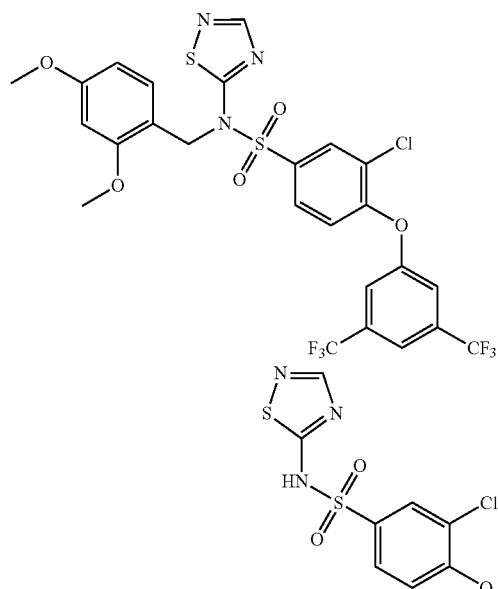

Into a 25-mL round-bottom flask, were placed 4-[3,5-bis(trifluoromethyl)phenoxy]-3-chloro-N-[(2,4-dimethoxyphenyl)methyl]-N-(1,2,4-thiadiazol-5-yl)benzene-1-sulfonamide (100 mg, 0.15 mmol, 1.00 equiv), dichloromethane (3 mL), trifluoroacetic acid (1 mL). The resulting solution was stirred for 1 h at 25° C. The resulting mixture was concentrated under vacuum. The residue was applied onto a silica gel column with dichloromethane/methanol (25:1). This resulted in 20.7 mg (27%) of 4-[3,5-bis(trifluoromethyl)phenoxy]-3-chloro-N-(1,2,4-thiadiazol-5-yl)benzene-1-sulfonamide as a white solid.

LC-MS: (ES, m/z): [M+H]⁺ 504

¹H-NMR: (300 MHz, DMSO-d₆, ppm): δ7.94 (s, 2H), 7.86-7.88 (m, 1H), 7.81 (s, 2H), 7.74-7.71 (m, 1H), 7.28-7.25 (m, 1H).

Example 17

Synthesis of N-([4-[3,5-bis(trifluoromethyl)phenoxy]-2,5-difluorophenyl]methyl)-1,2,4-thiadiazole-5-carboxamide

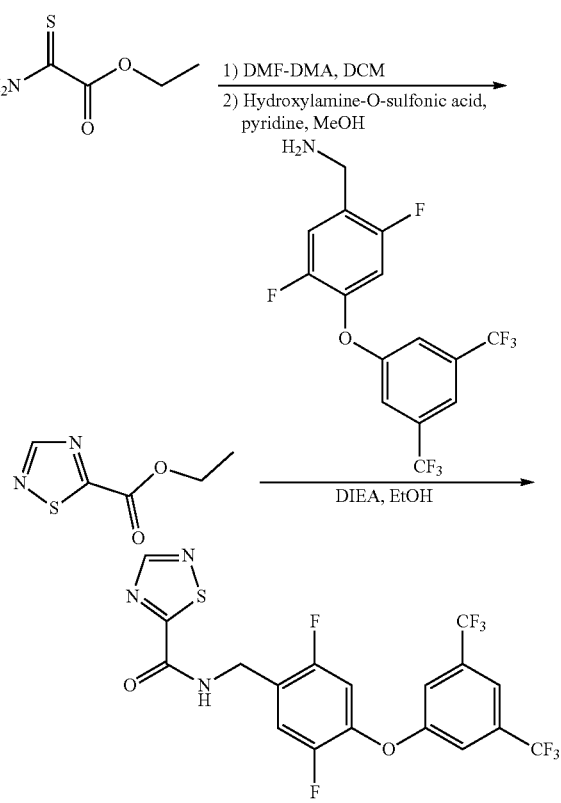

Step 1. Synthesis of ethyl 1,2,4-thiadiazole-5-carboxylate

107

-continued

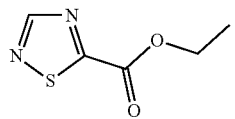

Ethyl carbamothioylformate (7.3 g, 54.82 mmol, 1.00 equiv) was dissolved in dichloromethane (40 mL), and DMF-DMA (7.9 g) was added. The resulting solution was stirred for 1 h at room temperature and concentrated in vacuo. The residue was dissolved in methanol (150 mL), then pyridine (8.7 g, 109.99 mmol, 2.01 equiv) and hydroxylamine-O-sulfonic acid (7.5 g) were added. The resulting reaction was stirred overnight at room temperature. Then the reaction was quenched by the addition of 200 mL of water. The resulting solution was extracted with 3×100 mL of ethyl acetate and the organic layers were combined and concentrated in vacuo. The residue was purified by silica gel column chromatography with ethyl acetate/petroleum ether (1:10). This resulted in 700 mg (8%) of ethyl 1,2,4-thiadiazole-5-carboxylate as a red oil.

Step 2. Synthesis of N-([4-[3,5-bis(trifluoromethyl)phenoxy]-2,5-difluorophenyl]methyl)-1,2,4-thiadiazole-5-carboxamide

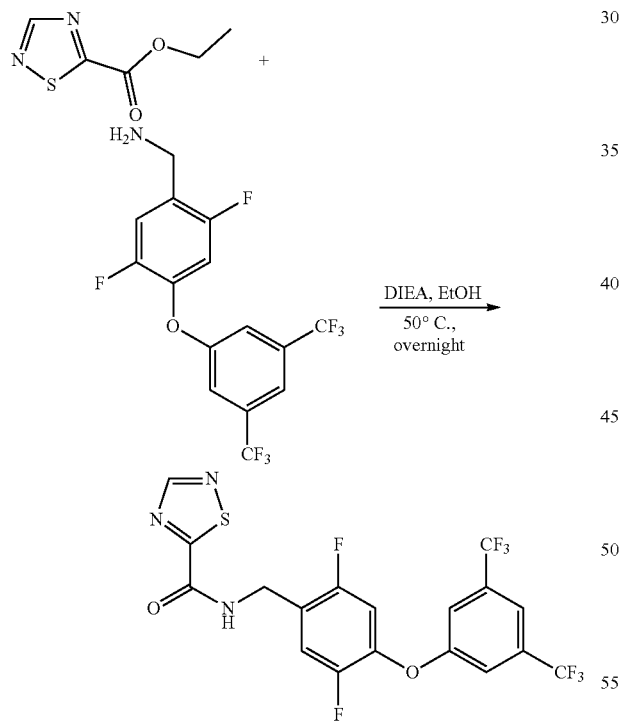

Ethyl 1,2,4-thiadiazole-5-carboxylate (70 mg, 0.44 mmol, 1.00 equiv), [4-[3,5-bis(trifluoromethyl)phenoxy]-2,5-difluorophenyl]methanamine (164 mg, 0.44 mmol, 1.00 equiv), and DIEA (172 mg, 1.33 mmol, 3.01 equiv) were dissolved in 3 mL of ethanol. The resulting reaction was stirred overnight at 50° C. Then it was concentrated in vacuo. The residue was purified by silica gel column chromatography with ethyl acetate/petroleum ether (1:2). This resulted in 64.5 mg (30%) of N-([4-[3,5-bis(trifluoromethyl)phenoxy]-2,5-difluorophenyl]methyl)-1,2,4-thiadiazole-5-carboxamide as an off-white solid.

LC-MS (ES, m/z): [M+H]$^+$ 484.

$^1$H NMR (400 MHz, DMSO, ppm): δ 9.79 (s, 1H), 9.14 (s, 1H), 7.89 (s, 1H), 7.73 (s, 2H), 7.53-7.48 (m, 1H), 7.44-7.39 (m, 1H), 4.54 (s, 2H).

Example 18

4-[3,5-bis(trifluoromethyl)phenoxy]-2,5-difluoro-N-(pyrimidin-4-yl)benzene-1-sulfonamide

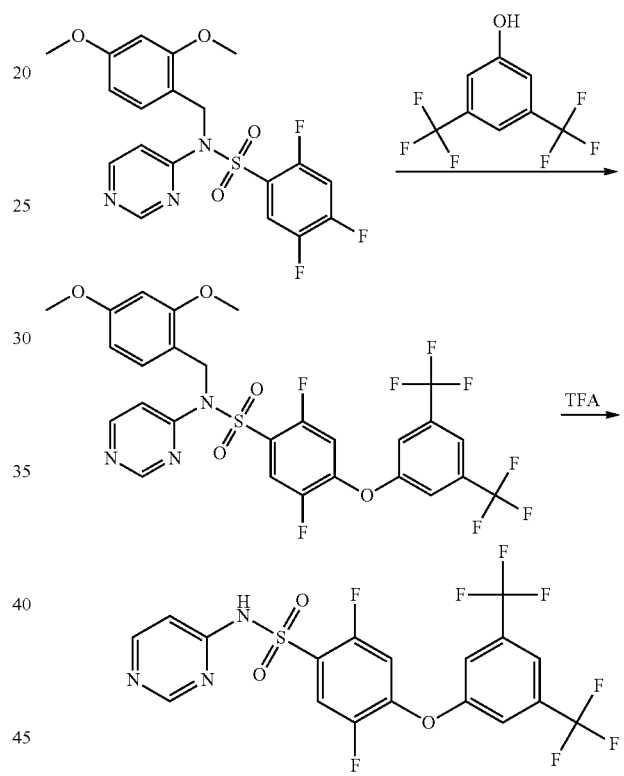

Step 1. Synthesis of 4-[3,5-bis(trifluoromethyl)phenoxy]-N-[(2,4-dimethoxyphenyl)methyl]-2,5-difluoro-N-(pyrimidin-4-yl)benzene-1-sulfonamide

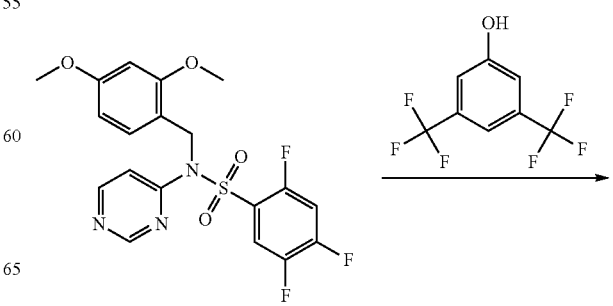

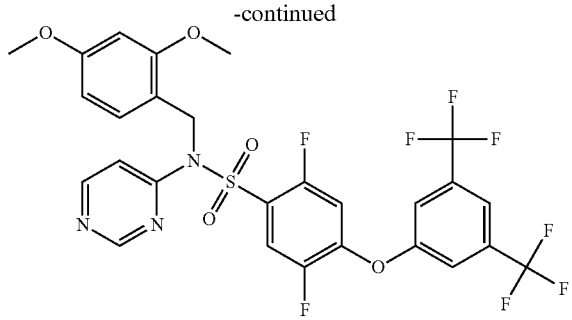

Into a 100-mL round-bottom flask, was placed a solution of N-[(2,4-dimethoxyphenyl)methyl]-2,4,5-trifluoro-N-(pyrimidin-4-yl)benzene-1-sulfonamide (250 mg, 0.57 mmol, 1.00 equiv) in N,N-dimethylformamide (30 mL). To the solution were added 3,5-bis(trifluoromethyl)phenol (131 mg, 0.57 mmol, 1.00 equiv) and $Cs_2CO_3$ (370 mg, 1.13 mmol, 2.00 equiv). The resulting solution was stirred for 16 h at room temperature. The resulting solution was extracted with ethyl acetate (3×30 mL) and the organic layers combined and concentrated under vacuum. This resulted in 250 mg (68%) of 4-[3,5-bis(trifluoromethyl)phenoxy]-N-[(2,4-dimethoxyphenyl)methyl]-2,5-difluoro-N-(pyrimidin-4-yl)benzene-1-sulfonamide as a white solid.

Step 2. Synthesis of 4-[3,5-bis(trifluoromethyl)phenoxy]-2,5-difluoro-N-(pyrimidin-4-yl)benzene-1-sulfonamide

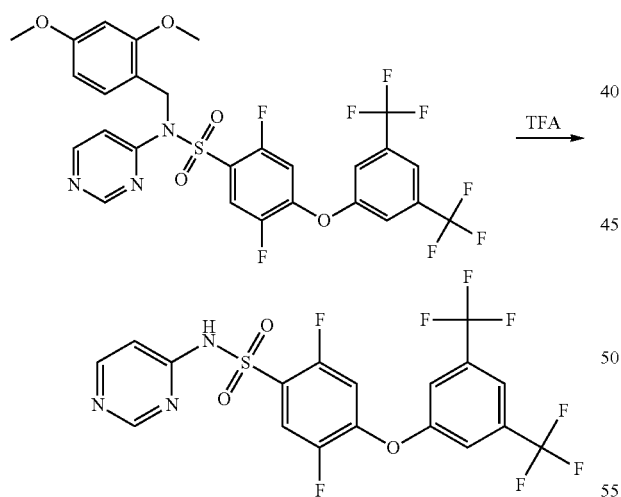

Into a 50-mL round-bottom flask, was placed a solution of 4-[3,5-bis(trifluoromethyl)phenoxy]-N-[(2,4-dimethoxyphenyl)methyl]-2,5-difluoro-N-(pyrimidin-4-yl)benzene-1-sulfonamide (250 mg, 0.38 mmol, 1.00 equiv) in dichloromethane (20 mL). To the solution was added trifluoroacetic acid (2 mL). The resulting solution was stirred for 16 h at room temperature. The resulting mixture was concentrated under vacuum. The crude product was purified by Prep-HPLC with conditions: Column, XBridge Prep Shield RP18, 5 um, 19×150 mm; Mobile phase, $H_2O$ (0.05% TFA)/$CH_3CN$ (10%-80% in 8 min); Detector, 254 nm, 220 nm; RT=6.0 min. This resulted in 16.7 mg (9%) of 4-[3,5-bis(trifluoromethyl)phenoxy]-2,5-difluoro-N-(pyrimidin-4-yl)benzene-1-sulfonamide as a white solid.

LC-MS: (ES, m/z): [M+H]$^+$ 500

$^1$H NMR (300 MHz, DMSO, ppm) δ 6.91 (s, 1H), 7.37-7.42 (m, 1H), 7.91-7.98 (m, 4H), 8.23 (s, 1H), 8.68 (s, 1H), 13.68 (s, 1H).

Example 19

Synthesis of N-([4-[3,5-bis(trifluoromethyl)phenoxy]-2,5-difluorophenyl]methyl)-1,3,4-thiadiazole-2-carboxamide (A Synthetic Intermediate)

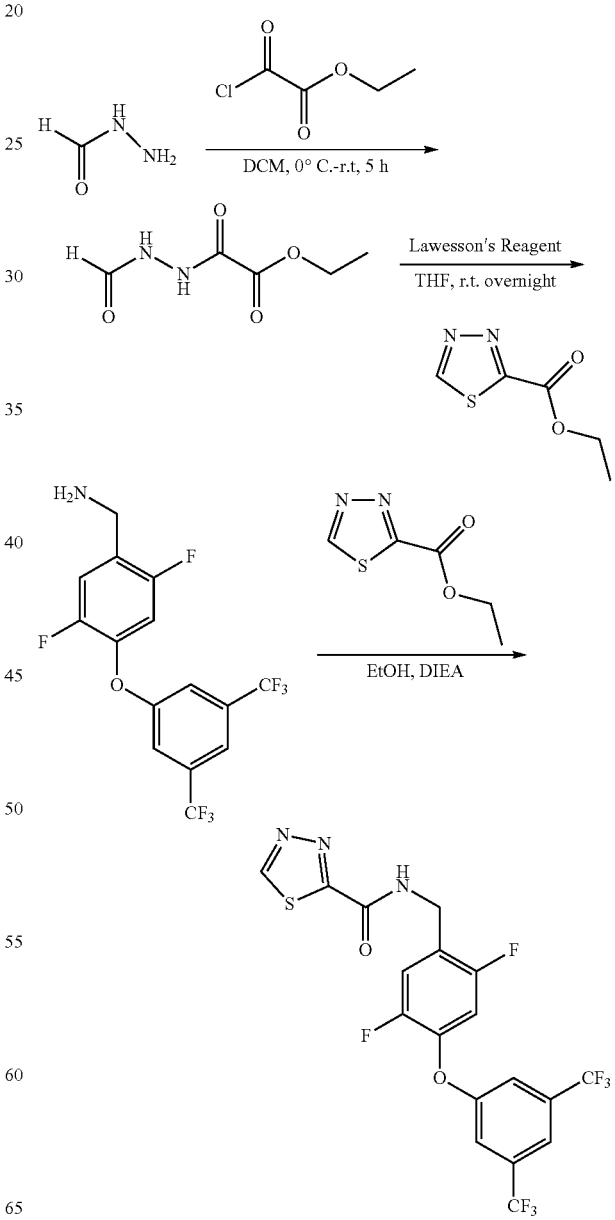

111

Step 1. Synthesis of Ethyl 2-formohydrazido-2-oxoacetate

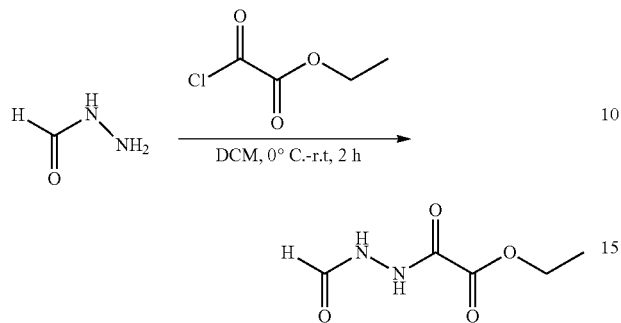

Formohydrazide (6.0 g, 99.91 mmol, 1.00 equiv) was dissolved in dichloromethane (200 mL) under an inert atmosphere of nitrogen. This was followed by the dropwise addition of ethyl 2-chloro-2-oxoacetate (4.5 g, 32.96 mmol, 0.33 equiv) with stirring at 0° C. The resulting solution was stirred for 2 h at 0° C. The solids were filtered off. The resulting mixture was concentrated in vacuo. This resulted in 6.5 g (crude) of ethyl 2-formohydrazido-2-oxoacetate as a yellow oil.

Step 2. Synthesis of ethyl 1,3,4-thiadiazole-2-carboxylate

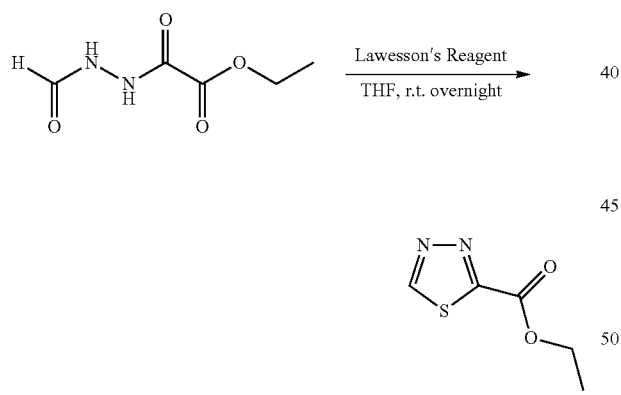

Ethyl 2-formohydrazido-2-oxoacetate (3.0 g, 18.74 mmol, 1.00 equiv) was dissolved in tetrahydrofuran (50 mL), and Lawesson's Reagent (7.6 g) was added. The resulting reaction was stirred overnight at room temperature. Then it was diluted with 100 mL of water. The resulting solution was extracted with 3×100 mL of ethyl acetate and the organic layers were combined, dried over anhydrous sodium sulfate, and concentrated in vacuo. The residue was purified by silica gel column chromatography with ethyl acetate/petroleum ether (1:2). This resulted in 1.3 g (44%) of ethyl 1,3,4-thiadiazole-2-carboxylate as a white solid.

112

Step 3. Synthesis of N-([4-[3,5-bis(trifluoromethyl)phenoxy]-2,5-difluorophenyl]methyl)-1,3,4-thiadiazole-2-carboxamide

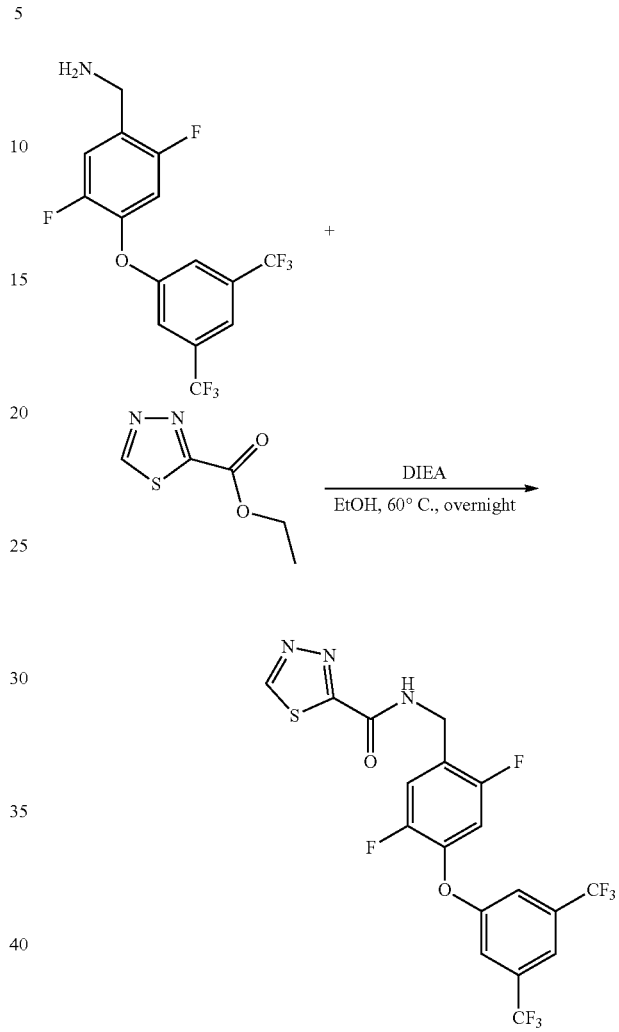

[4-[3,5-Bis(trifluoromethyl)phenoxy]-2,5-difluorophenyl]methanamine (141 mg, 0.38 mmol, 1.00 equiv) was dissolved in ethanol (5 mL) under nitrogen, and DIEA (148 mg, 1.15 mmol, 3.01 equiv) and ethyl 1,3,4-thiadiazole-2-carboxylate (60 mg, 0.38 mmol, 1.00 equiv) were added. The resulting reaction was stirred overnight at 60° C. Then it was concentrated in vacuo. The crude product was purified by Prep-HPLC under the following conditions: Column, XBridge Prep Shield RP18, 5 um, 19*150 mm; mobile phase, $CH_3CN/H_2O$ (0.05% TFA)=40% increasing to $CH_3CN/H_2O$ (0.05% TFA)=70% within 10 min; Detector, UV 254 nm. This resulted in 60.3 mg (33%) of N-([4-[3,5-bis(trifluoromethyl)phenoxy]-2,5-difluorophenyl]methyl)-1,3,4-thiadiazole-2-carboxamide as a white solid.

LC-MS (ES, m/z): [M+H]+ 484.

$^1$H NMR (400 MHz, DMSO, ppm): δ 9.87-9.82 (m, 2H), 7.92 (s, 1H), 7.75 (s, 2H), 7.54-7.49 (m, 1H), 7.45-7.41 (m, 1H), 4.55 (d, 2H).

Example 20

Synthesis of N-([4-[3,5-bis(trifluoromethyl)phenoxy]-2,5-difluorophenyl]methyl)methanesulfonamide

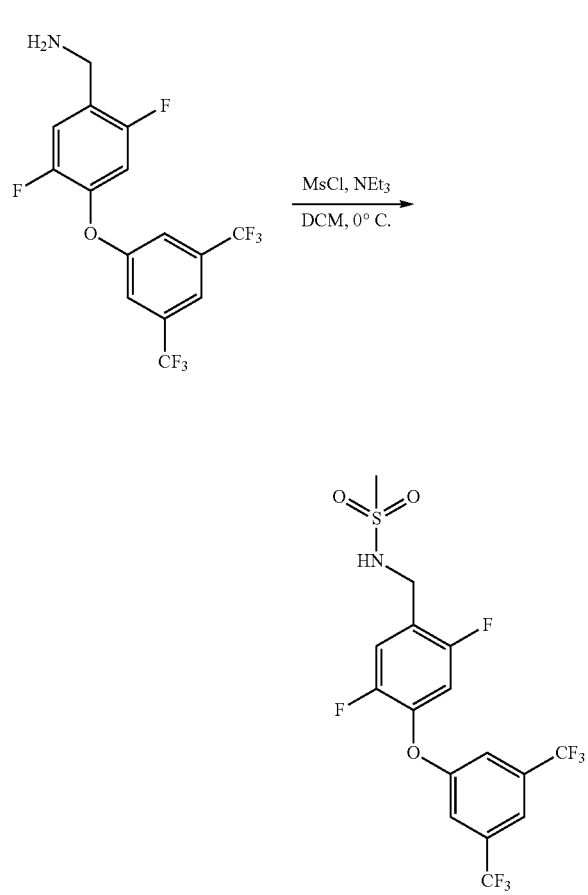

Into a 50-mL round-bottom flask, was placed [4-[3,5-bis(trifluoromethyl)phenoxy]-2,5-difluorophenyl]methanamine (100 mg, 0.27 mmol, 1.00 equiv), dichloromethane (5 mL), NEt$_3$ (127 mg). This was followed by the dropwise addition of MsCl (144 mg) at 0° C. The resulting reaction was stirred for 1 h at 0° C. The reaction was then quenched by the addition of 80 mL of water, extracted with 3×50 mL of ethyl acetate, and the organic layers were combined and concentrated in vacuo. The crude product was purified by Prep-HPLC with the following conditions: Column, XBridge Prep Shield RP18, 5 um, 19*150 mm; mobile phase, CH$_3$CN/H$_2$O (0.05% NH$_4$HCO$_3$)=40% increasing to CH$_3$CN/H$_2$O (0.05% NH$_4$HCO$_3$)=80% within 10 min; Detector, UV 254 nm. This resulted in 57.3 mg (47%) of N-([4-[3,5-bis(trifluoromethyl)phenoxy]-2,5-difluorophenyl]methyl)methanesulfonamide as a white solid.

LC-MS (ES, m/z): [M−H]$^-$448

$^1$H-NMR (300 MHz, DMSO, ppm): δ 7.91 (s, 1H), δ7.73 (s, 2H), 7.63 (s, 1H), 7.55-7.49 (m, 1H), 7.45-7.40 (m, 1H), δ4.23 (s, 2H), 2.96 (s, 3H).

Example 21

2-{3-[3,5-bis(trifluoromethyl)phenyl]phenyl}-N-(1,2,4-thiadiazol-5-yl)acetamide

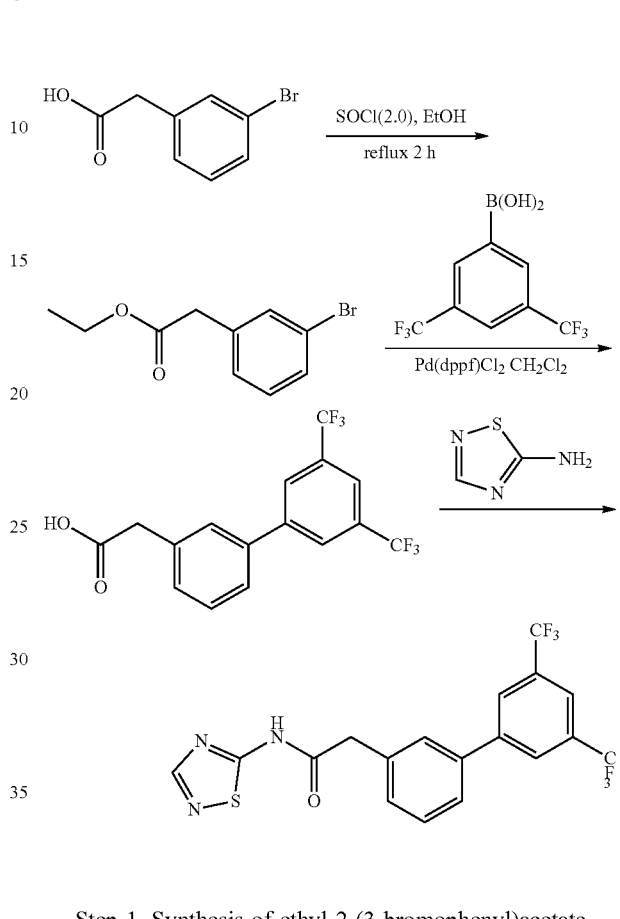

Step 1. Synthesis of ethyl 2-(3-bromophenyl)acetate

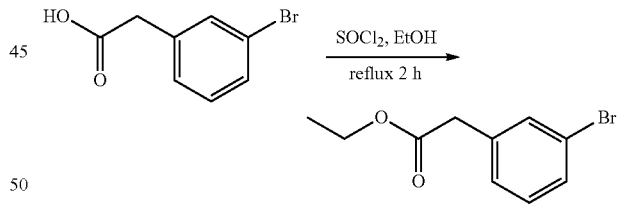

Into a 250-mL round-bottom flask, were placed 2-(3-bromophenyl)acetic acid (5 g, 23.25 mmol, 1.00 equiv), ethanol (80 mL). This was followed by the addition of thionyl chloride (5.6 g, 46.28 mmol, 2.00 equiv) dropwise with stirring at 0° C. The resulting solution was heated to reflux for 2 h. The resulting mixture was concentrated under vacuum. The reaction was then quenched by the addition of water. The resulting solution was extracted with ethyl acetate and the organic layers combined. The resulting mixture was washed with brine, dried over anhydrous sodium sulfate and concentrated. This resulted in 5.5 g (97%) of ethyl 2-(3-bromophenyl)acetate as colorless oil.

Step 2. Synthesis of 2-[3-[3,5-bis(trifluoromethyl)phenyl]phenyl]acetic acid

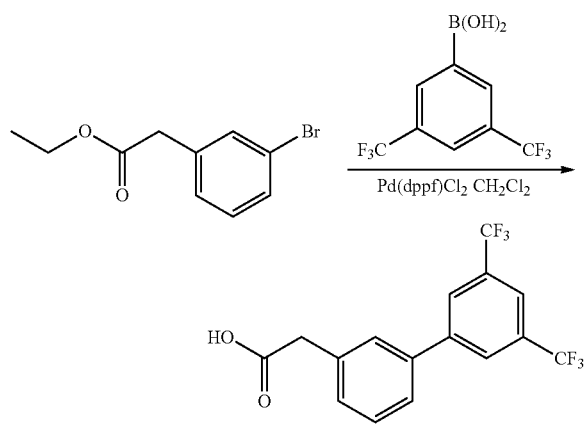

Into a 500-mL round-bottom flask purged and maintained with an inert atmosphere of nitrogen, were placed ethyl 2-(3-bromophenyl)acetate (5.7 g, 23.45 mmol, 1.00 equiv), [3,5-bis(trifluoromethyl)phenyl]boronic acid (6.0 g, 23.26 mmol, 1.00 equiv), sodium carbonate (5.0 g, 47.17 mmol, 2.00 equiv), Pd(dppf)Cl$_2$·CH$_2$Cl$_2$ (1.9 g, 0.10 equiv), toluene (80 mL), ethanol (40 mL), water (20 mL). The resulting solution was stirred for 16 h at 80° C. The reaction was then quenched by the addition of water. The resulting solution was extracted with ethyl acetate and the organic layers combined. The resulting mixture was washed with brine, dried over anhydrous sodium sulfate and concentrated. The residue was applied onto a silica gel column with ethyl acetate/petroleum ether (1:50). This resulted in 3.5 g (43%) of 2-[3-[3,5-bis(trifluoromethyl)phenyl]phenyl]acetic acid as a light yellow solid.

Step 3. Synthesis of 2-[3-[3,5-bis(trifluoromethyl)phenyl]phenyl]-N-(1,2,4-thiadiazol-5-yl)acetamide

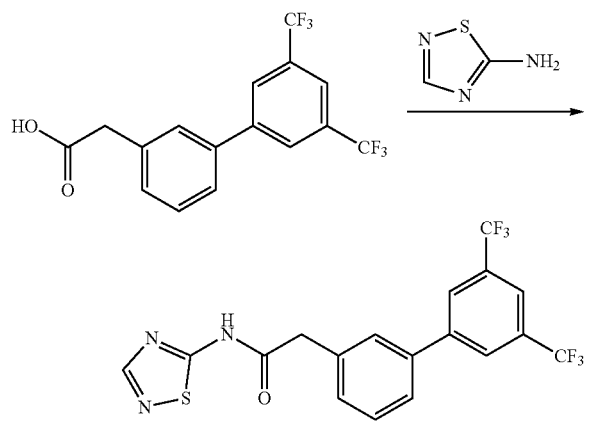

Into a 25-mL round-bottom flask, were placed 2-[3-[3,5-bis(trifluoromethyl)phenyl]phenyl]acetic acid (175 mg, 0.50 mmol, 1.00 equiv), 1,2,4-thiadiazol-5-amine (51 mg, 0.50 mmol, 1.00 equiv), DCC (124 mg, 0.60 mmol, 1.20 equiv), toluene (5 mL). The resulting solution was stirred for 16 h at 25° C. The reaction was then quenched by the addition of water. The resulting solution was extracted with ethyl acetate and the organic layers combined. The resulting mixture was washed with brine, over anhydrous sodium sulfate and concentrated. The crude product (100 mg) was purified by Prep-HPLC with the following conditions (1 #-Pre-HPLC-005(Waters)): Column, SunFire Prep C18, 19*150 mm 5 um; mobile phase, water with 0.05% TFA and CH$_3$CN (20.0% CH$_3$CN up to 80.0% in 10 min, up to 95.0% in 2 min, down to 20.0% in 1 min); Detector, UV 254 nm. This resulted in 56.5 mg (26%) of 2-[3-[3,5-bis(trifluoromethyl)phenyl]phenyl]-N-(1,2,4-thiadiazol-5-yl)acetamide as a white solid.

LC-MS: (ES, m/z): [M+H]$^+$ 432

$^1$H-NMR: (400 MHz, DMSO-d$_6$, ppm): δ8.47 (s, 1H), 8.34 (s, 2H), 8.12 (s, 1H), 7.87 (s, 1H), 7.82-7.80 (m, 1H), 7.54-7.50 (m, 1H), 7.46-7.45 (m, 1H).

Example 22

Synthesis of 2-[4-[3,5-bis(trifluoromethyl)phenoxy]-2,5-difluorophenyl]-N-(1,2,4-thiadiazol-5-yl)acetamide

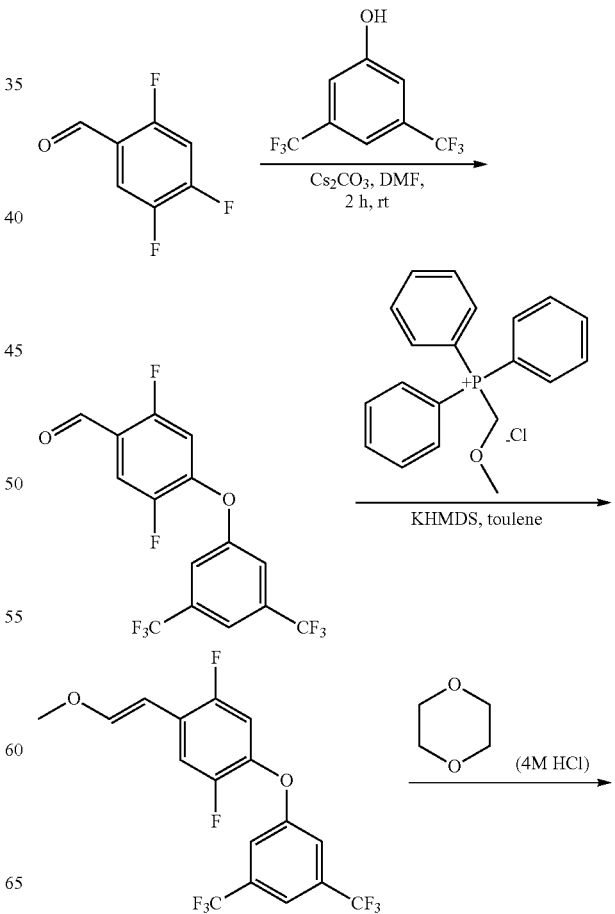

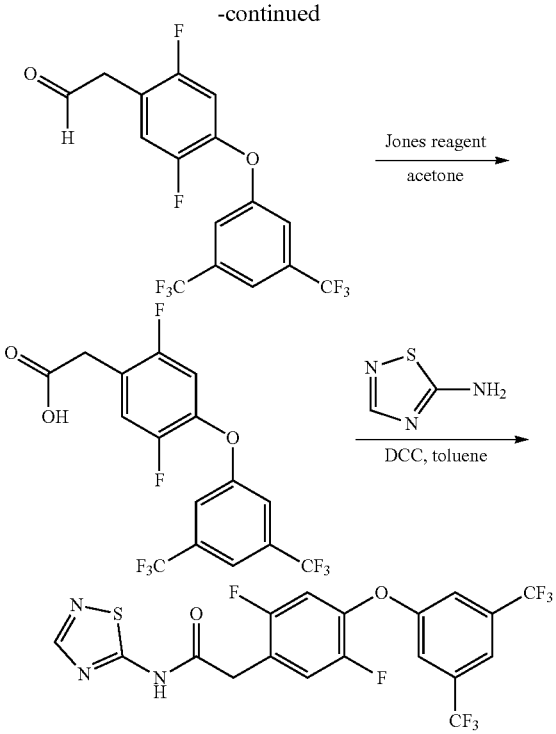

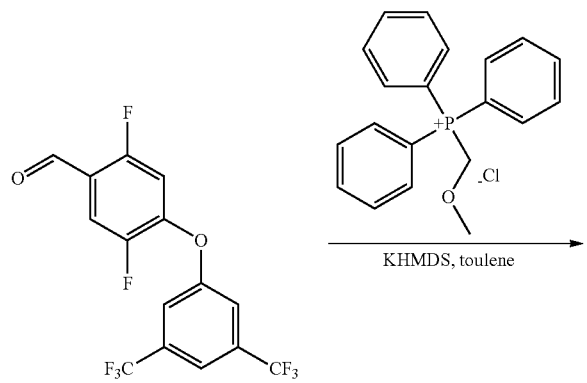

Step 1. Synthesis of 4-[3,5-bis(trifluoromethyl)phenoxy]-2,5-difluorobenzaldehyde 3,5-bis(trifluoromethyl)phenol (2.5 g, 10.86 mmol, 1.10 equiv) and Cs₂CO₃ (6.5 g, 19.95 mmol, 2.00 equiv) were dissolved in DMF (30 g, 410.45 mmol, 41.07 equiv) and 2,4,5-trifluorobenzaldehyde (1.6 g, 9.99 mmol, 1.00 equiv) was added. The resulting reaction was stirred for 2 h at 25° C. Then the reaction was quenched by the addition of water, extracted with ethyl acetate, and the organic layers were combined. The resulting mixture was washed with brine, dried over anhydrous sodium sulfate and concentrated in vacuo. The residue was purified by silica gel column chromatography with petroleum ether. This resulted in 2 g (54%) of 4-[3,5-bis(trifluoromethyl)phenoxy]-2,5-difluorobenzaldehyde as a white solid.

Step 2. Synthesis of 1-[3,5-bis(trifluoromethyl)phenoxy]-2,5-difluoro-4-[(Z)-2-methoxyethenyl]benzene

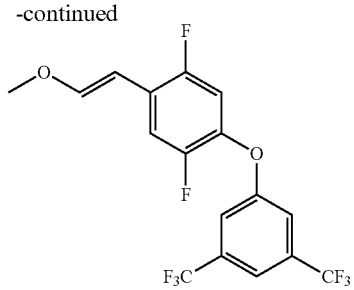

Into a 100-mL 3-necked round-bottom flask purged and maintained with an inert atmosphere of nitrogen was placed (methoxymethyl)triphenylphosphanium chloride (1.85 g, 5.40 mmol, 2.00 equiv) in 20 mL of toluene. This was followed by the dropwise addition of a solution of KHMDS (0.5 N in toluene) (13.5 mL) at 0° C. The resulting reaction was stirred for 0.5 h at 0° C. To this was added 4-[3,5-bis(trifluoromethyl)phenoxy]-2,5-difluorobenzaldehyde (1.0 g, 2.70 mmol, 1.00 equiv). The resulting reaction was stirred for 2 h at room temperature. Then the reaction was quenched by the addition of 100 mL of NH₄Cl (aq.) and extracted with 3×100 mL of ethyl acetate. The organic layers were combined and concentrated in vacuo. The residue was purified by silica gel column chromatography with ethyl acetate/petroleum ether (1:100). This resulted in 890 mg (83%) of 1-[3,5-bis(trifluoromethyl)phenoxy]-2,5-difluoro-4-[(Z)-2-methoxyethenyl]benzene as a white solid.

Step 3. Synthesis of 2-[4-[3,5-bis(trifluoromethyl)phenoxy]-2,5-difluorophenyl]acetaldehyde

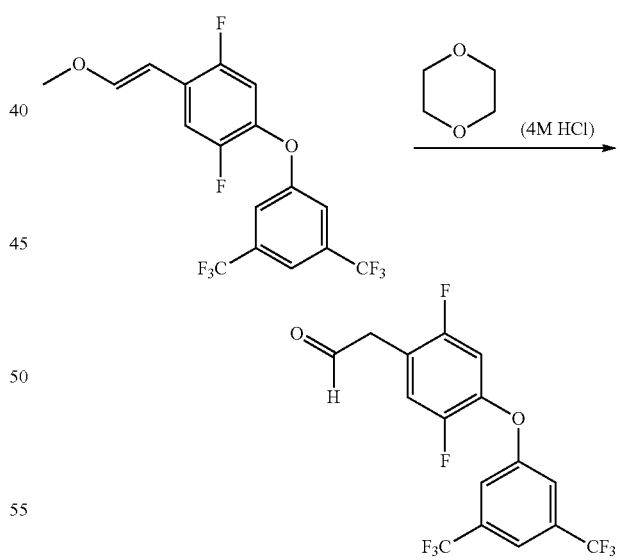

Into a 100-mL round-bottom flask, was placed 1-[3,5-bis(trifluoromethyl)phenoxy]-2,5-difluoro-4-[(Z)-2-methoxyethenyl]benzene (890 mg, 2.23 mmol, 1.00 equiv), a solution of hydrogen chloride in 1,4-dioxane (4 N, 30 mL). The resulting reaction was stirred overnight at room temperature. The pH value of the solution was adjusted to pH 7 with sodium carbonate (aq.). Then it was extracted with 3×50 mL of ethyl acetate and the organic layers were combined and concentrated in vacuo. This resulted in 800 mg (crude) of 2-[4-[3,5-bis(trifluoromethyl)phenoxy]-2,5-difluorophenyl]acetaldehyde as a colorless oil.

Step 4. Synthesis of 2-[4-[3,5-bis(trifluoromethyl)phenoxy]-2,5-difluorophenyl]acetic acid

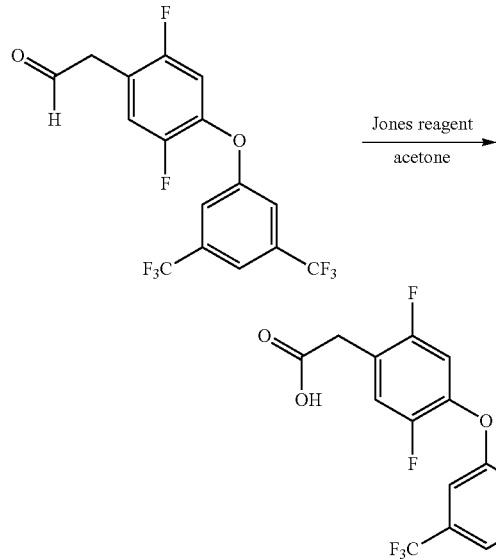

Into a 100-mL round-bottom flask, was placed 2-[4-[3,5-bis(trifluoromethyl)phenoxy]-2,5-difluorophenyl]acetaldehyde (800 mg, 2.08 mmol, 1.00 equiv), acetone (20 mL). This was followed by the dropwise addition of a solution of Jones reagent in water (10 mL) at 0° C. The resulting reaction was stirred for 2 h at room temperature. The reaction was then quenched by the addition of 10 mL of isopropanol. Then it was diluted with 50 mL of water, extracted with 3×30 mL of ethyl acetate, and the organic layers were combined and concentrated in vacuo. The residue was purified by silica gel column chromatography with dichloromethane/methanol (30:1). This resulted in 150 mg (18%) of 2-[4-[3,5-bis(trifluoromethyl)phenoxy]-2,5-difluorophenyl]acetic acid as an off-white solid.

Step 5. Synthesis of 2-[4-[3,5-bis(trifluoromethyl)phenoxy]-2,5-difluorophenyl]-N-(1,2,4-thiadiazol-5-yl)acetamide

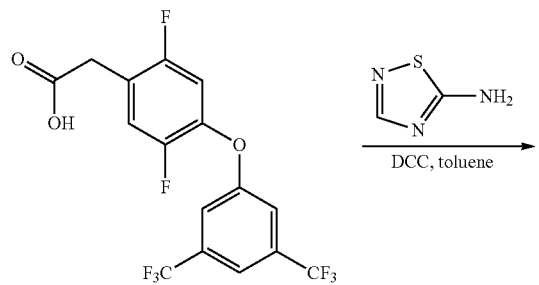

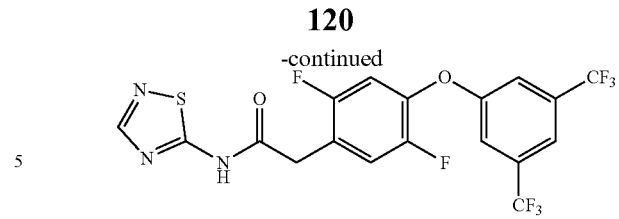

Into a 50-mL round-bottom flask purged and maintained with an inert atmosphere of nitrogen, was placed 1,2,4-thiadiazol-5-amine (56.8 mg, 0.56 mmol, 1.00 equiv), 2-[4-[3,5-bis(trifluoromethyl)phenoxy]-2,5-difluorophenyl]acetic acid (150 mg, 0.37 mmol, 0.67 equiv), toluene (5 mL), DCC (93 mg). The resulting reaction was stirred overnight at room temperature. The resulting mixture was concentrated in vacuo. The residue was purified by silica gel column chromatography with ethyl acetate/petroleum ether (1:2). The crude product was purified by Prep-HPLC with the following conditions: Column: XBridge Prep Shield RP18, 5 um, 19*150 mm; mobile phase, $CH_3CN/H_2O$ (0.05% $NH_4HCO_3$)=40% increasing to $CH_3CN/H_2O$ (0.05% $NH_4HCO_3$)=70% within 10 min; Detector, UV 254 nm. This resulted in 37.4 mg (14%) of 2-[4-[3,5-bis(trifluoromethyl)phenoxy]-2,5-difluorophenyl]-N-(1,2,4-thiadiazol-5-yl)acetamide as a white solid.

LC-MS (ES, m/z): [M+H]$^+$ 484

$^1$H-NMR (400 MHz, DMSO, ppm): δ 13.20 (s, 1H), 8.49 (s, 1H), 7.93 (s, 1H), 7.76 (s, 2H), 7.63-7.58 (m, 1H), 7.45-7.35 (m, 1H), 4.03 (s, 2H).

Example 23

3-{2,5-difluoro-4-[(1,2,4-thiadiazol-5-yl)sulfamoyl]phenoxy}-5-(trifluoromethyl)benzoic

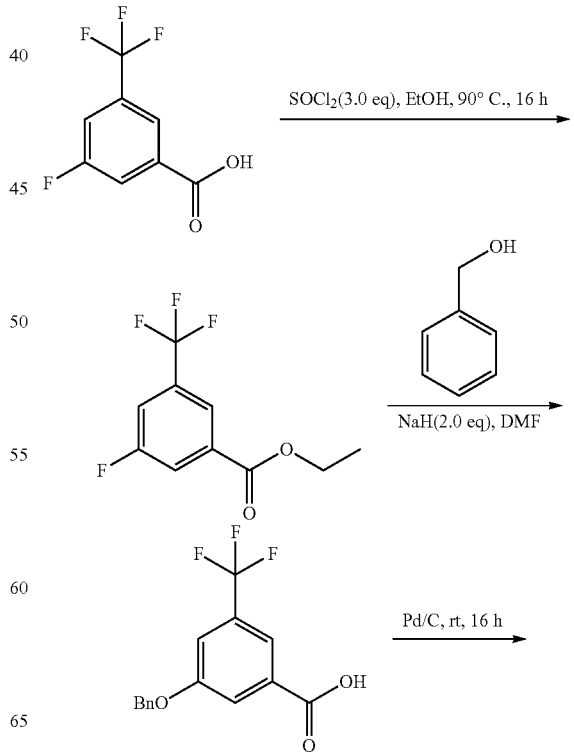

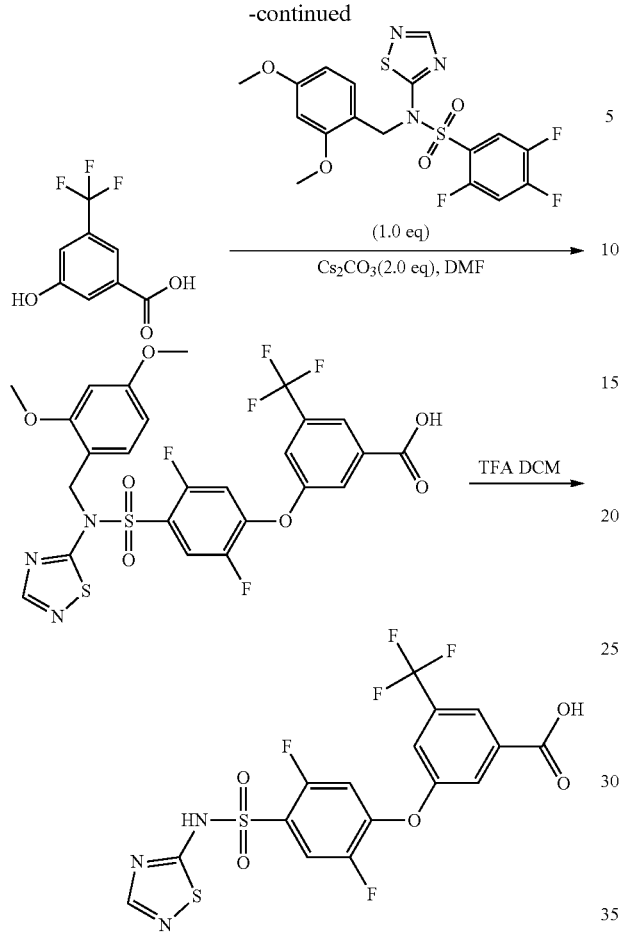

Step 1. Synthesis of ethyl 3-fluoro-5-(trifluoromethyl)benzoate

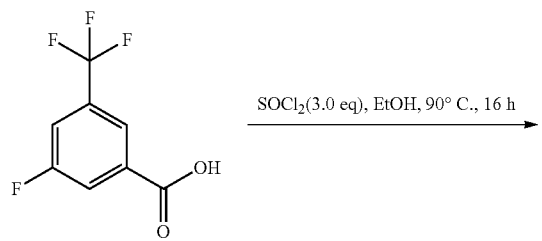

Into a 500-mL round-bottom flask, was placed a solution of 3-fluoro-5-(trifluoromethyl)benzoic acid (10 g, 48.05 mmol, 1.00 equiv) in ethanol (200 mL). To the solution was added thionyl chloride (20 mL). The resulting solution was stirred for 16 h at 90° C. in an oil bath. The resulting mixture was concentrated under vacuum. This resulted in 7.1 g (crude) of ethyl 3-fluoro-5-(trifluoromethyl)benzoate as colorless oil.

Step 2. Synthesis of 3-(benzyloxy)-5-(trifluoromethyl)benzoic acid

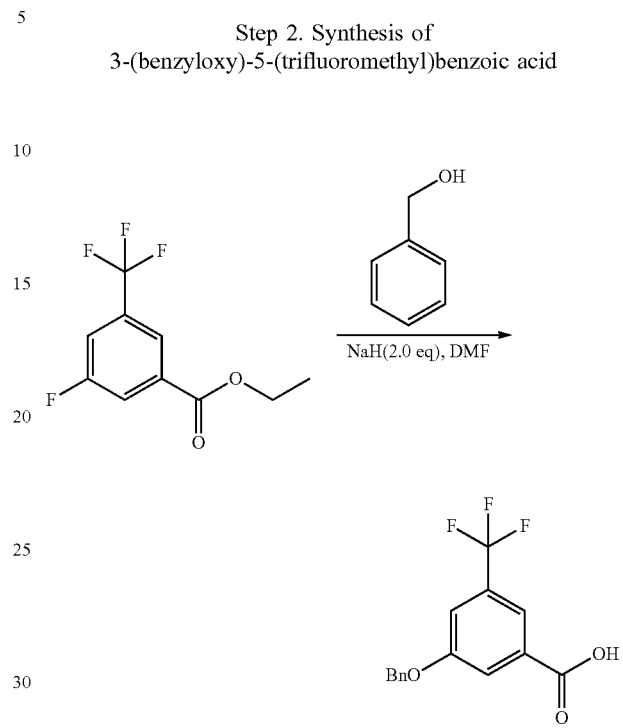

Into a 250-mL round-bottom flask, was placed a solution of ethyl 3-fluoro-5-(trifluoromethyl)benzoate (7.1 g, 30.06 mmol, 1.00 equiv) in N,N-dimethylformamide (120 mL). To the solution were added phenylmethanol (3.9 g, 36.07 mmol, 1.20 equiv) and sodium hydride (1.8 g, 75.00 mmol, 1.50 equiv). The resulting solution was stirred for 16 h at room temperature. The reaction was then quenched by the addition of 50 mL of water. The resulting solution was extracted with ethyl acetate (3×100 mL) and the organic layers combined and concentrated under vacuum. The residue was applied onto a silica gel column with ethyl acetate/petroleum ether (1:5). The collected fractions were combined and concentrated under vacuum. This resulted in 4 g (45%) of 3-(benzyloxy)-5-(trifluoromethyl)benzoic acid as light yellow oil.

Step 3. Synthesis of 3-hydroxy-5-(trifluoromethyl)benzoic acid

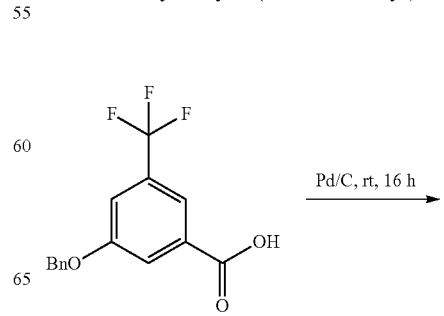

123
-continued

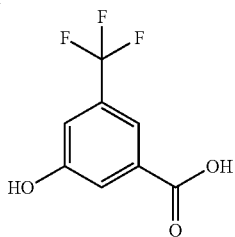

Into a 250-mL round-bottom flask, was placed a solution of 3-(benzyloxy)-5-(trifluoromethyl)benzoic acid (4 g, 13.50 mmol, 1.00 equiv) in methanol (80 mL). To the solution was added Palladium carbon (400 mg). To the above hydrogen was introduced in. The resulting solution was stirred for 16 h at room temperature. The solids were filtered out. The resulting mixture was concentrated under vacuum. This resulted in 2.8 g (crude) of 3-hydroxy-5-(trifluoromethyl) benzoic acid as light yellow oil.

Step 4. Synthesis of 3-(4-[[(2,4-dimethoxyphenyl) methyl](1,2,4-thiadiazol-5-yl)sulfamoyl]-2,5-difluorophenoxy)-5-(trifluoromethyl)benzoic acid

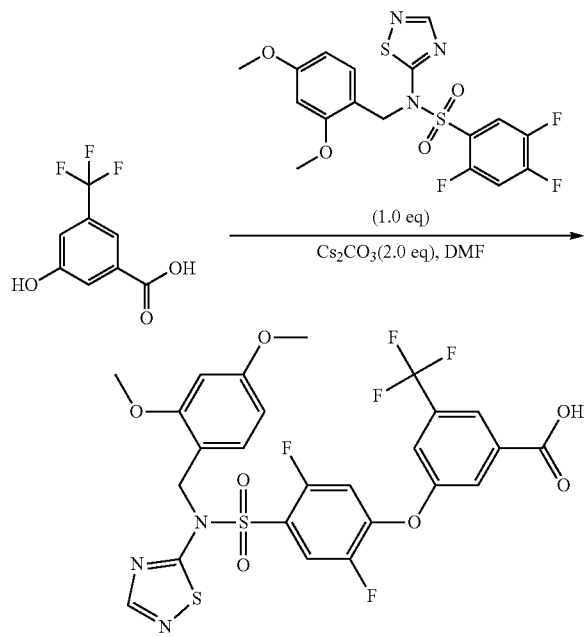

Into a 100-mL round-bottom flask, was placed a solution of 3-hydroxy-5-(trifluoromethyl)benzoic acid (500 mg, 2.43 mmol, 1.00 equiv) in N,N-dimethylformamide (30 mL). To the solution were added N-[(2,4-dimethoxyphenyl)methyl]-2,4,5-trifluoro-N-(1,2,4-thiadiazol-5-yl)benzene-1-sulfonamide (1.08 g, 2.42 mmol, 1.00 equiv) and Cs$_2$CO$_3$ (1.58 g, 4.85 mmol, 2.00 equiv). The resulting solution was stirred for 16 h at room temperature. The resulting solution was extracted with ethyl acetate (3×30 mL) and the organic layers combined and concentrated under vacuum. This resulted in 250 mg (16%) of 3-(4-[[(2,4-dimethoxyphenyl) methyl](1,2,4-thiadiazol-5-yl)sulfamoyl]-2,5-difluorophenoxy)-5-(trifluoromethyl)benzoic acid as a white solid.

124

Step 5. Synthesis of 3-[2,5-difluoro-4-[(1,2,4-thiadiazol-5-yl)sulfamoyl]phenoxy]-5-(trifluoromethyl) benzoic acid

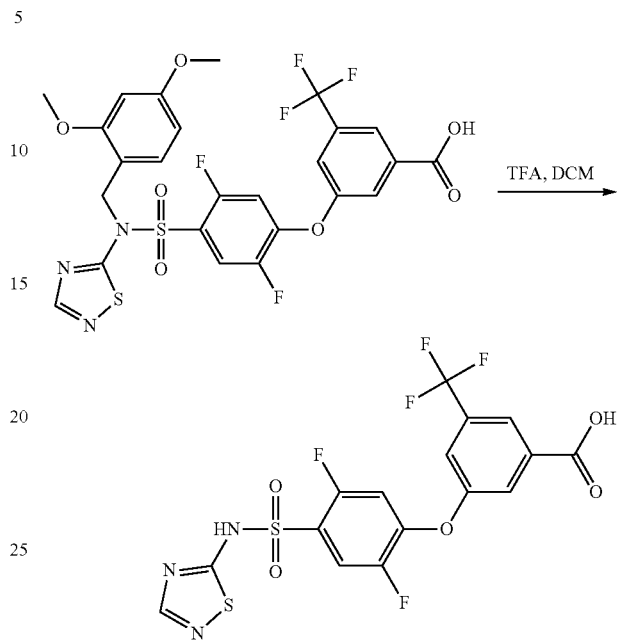

Into a 50-mL round-bottom flask, was placed a solution of 3-(4-[[(2,4-dimethoxyphenyl)methyl](1,2,4-thiadiazol-5-yl) sulfamoyl]-2,5-difluorophenoxy)-5-(trifluoromethyl)benzoic acid (250 mg, 0.40 mmol, 1.00 equiv) in dichloromethane (20 mL) and trifluoroacetic acid (2 mL). The resulting solution was stirred for 16 h at room temperature. The resulting mixture was concentrated under vacuum. The crude product was purified by Prep-HPLC with conditions: Column, XBridge Prep Shield RP18, 5 um, 19×150 mm; Mobile phase, H$_2$O (0.05% TFA)/CH$_3$CN (30%-65% in 8 min); Detector, 254 nm, 220 nm; RT=6.5 min. This resulted in 35.1 mg (18%) of 3-[2,5-difluoro-4-[(1,2,4-thiadiazol-5-yl)sulfamoyl]phenoxy]-5-(trifluoromethyl)benzoic acid as a white solid.

LC-MS: (ES, m/z): [M+H]$^+$ 482

$^1$H NMR (300 MHz, DMSO, ppm): δ 7.41-7.47 (m, 1H), 7.84-8.08 (m, 4H), 8.53 (s, 1H), 13.85 (s, 1H).

Example 24

3-{2,5-difluoro-4-[(1,2,4-thiadiazol-5-yl)sulfamoyl] phenoxy}-5-(trifluoromethyl)benzamide

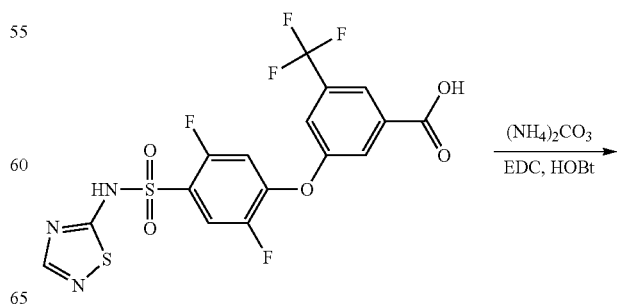

Example 23

-continued

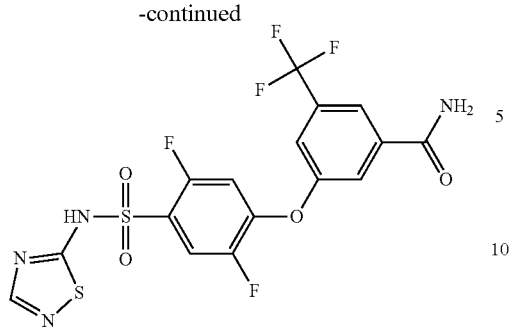

Example 24

Step 1. Synthesis of 3-[2,5-difluoro-4-[(1,2,4-thiadiazol-5-yl)sulfamoyl]phenoxy]-5-(trifluoromethyl)benzamide Into a 100-mL round-bottom flask, was placed a solution of 3-[2,5-difluoro-4-[(1,2,4-thiadiazol-5-yl)sulfamoyl]phenoxy]-5-(trifluoromethyl)benzoic acid (500 mg, 1.04 mmol, 1.00 equiv) in N,N-dimethylformamide (30 mL). To the solution were added $(NH_4)_2CO_3$ (499 mg, 5.20 mmol, 5.00 equiv), HOBT (168 mg, 1.24 mmol, 1.20 equiv) and EDCI (240 mg, 1.25 mmol, 1.20 equiv). The resulting solution was stirred for 16 h at room temperature. The resulting solution was extracted with ethyl acetate (3×30 mL) and the organic layers combined and concentrated under vacuum. The crude product was purified by Prep-HPLC with conditions: Column, XBridge Prep Shield RP18, 5 um, 19×150 mm; Mobile phase, $H_2O$ (0.05% $NH_4HCO_3$)/$CH_3CN$ (30%-80% in 10 min); Detector, 254 nm, 220 nm; RT=8.3 min. This resulted in 24.1 mg (5%) of 3-[2,5-difluoro-4-[(1,2,4-thiadiazol-5-yl)sulfamoyl]phenoxy]-5-(trifluoromethyl)benzamide as a white solid.

LC-MS: (ES, m/z): [M+H]$^+$ 480

$^1$H-NMR: (300 MHz, DMSO, ppm) δ 7.40-7.46 (m, 1H), 7.72-7.88 (m, 4H), 8.07 (s, 1H), 8.26 (s, 1H), 8.52 (s, 1H)

Example 25

3-{2,5-difluoro-4-[(1,2,4-thiadiazol-5-yl)sulfamoyl]phenoxy}-N-methyl-5-(trifluoromethyl)benzamide

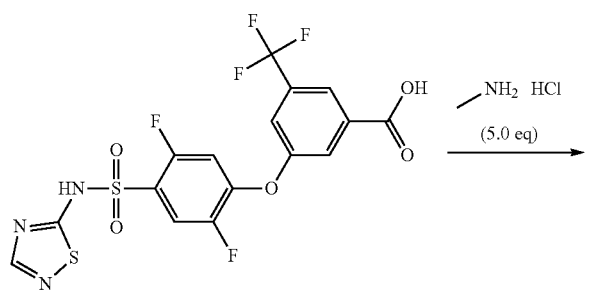

Example 23

-continued

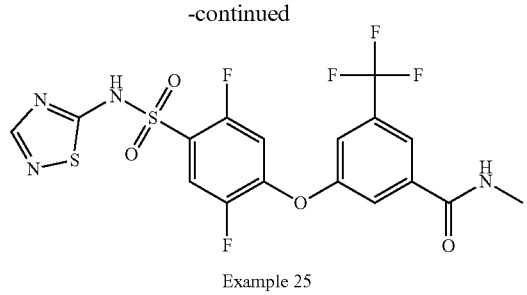

Example 25

Step 1. Synthesis of 3-[2,5-difluoro-4-[(1,2,4-thiadiazol-5-yl)sulfamoyl]phenoxy]-N-methyl-5-(trifluoromethyl)benzamide Into a 50-mL round-bottom flask, was placed a solution of 3-[2,5-difluoro-4-[(1,2,4-thiadiazol-5-yl)sulfamoyl]phenoxy]-5-(trifluoromethyl)benzoic acid (200 mg, 0.42 mmol, 1.00 equiv) in N,N-dimethylformamide (20 mL). To the mixture were added methanamine hydrochloride (141 mg, 2.09 mmol, 5.00 equiv), HOBT (67 mg, 0.50 mmol, 1.20 equiv) and EDCI (96 mg, 0.50 mmol, 1.20 equiv). The resulting solution was stirred for 16 h at room temperature. The resulting solution was extracted with ethyl acetate (3×20 mL) and the organic layers combined and concentrated under vacuum. The crude product was purified by Prep-HPLC with conditions: Column, XBridge Prep Shield RP18, 5 um, 19×150 mm; Mobile phase, $H_2O$ (0.05% $NH_4HCO_3$)/$CH_3CN$ (30%-80% in 10 min); Detector, 254 nm, 220 nm; RT=8.5 min. This resulted in 22.2 mg (11%) of 3-[2,5-difluoro-4-[(1,2,4-thiadiazol-5-yl)sulfamoyl]phenoxy]-N-methyl-5-(trifluoromethyl)benzamide as a white solid.

LC-MS: (ES, m/z): [M+H]$^+$ 495

$^1$H-NMR: (300 MHz, DMSO, ppm) δ 2.79-2.90 (m, 3H), 7.42-7.49 (m, 1H), 7.74-7.85 (m, 3H), 8.03 (s, 1H), 8.51 (s, 1H), 8.75 (s, 1H)

Example 26

Synthesis of ethyl 3-{2,5-difluoro-4-[(1,2,4-thiadiazol-5-yl)sulfamoyl]phenoxy}-5-(trifluoromethyl)benzoate

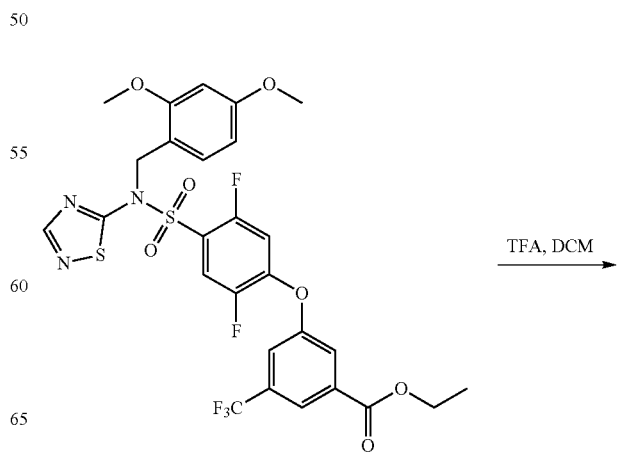

Step 1. Synthesis of ethyl 3-[2,5-difluoro-4-[(1,2,4-thiadiazol-5-yl)sulfamoyl]phenoxy]-5-(trifluoromethyl)benzoate

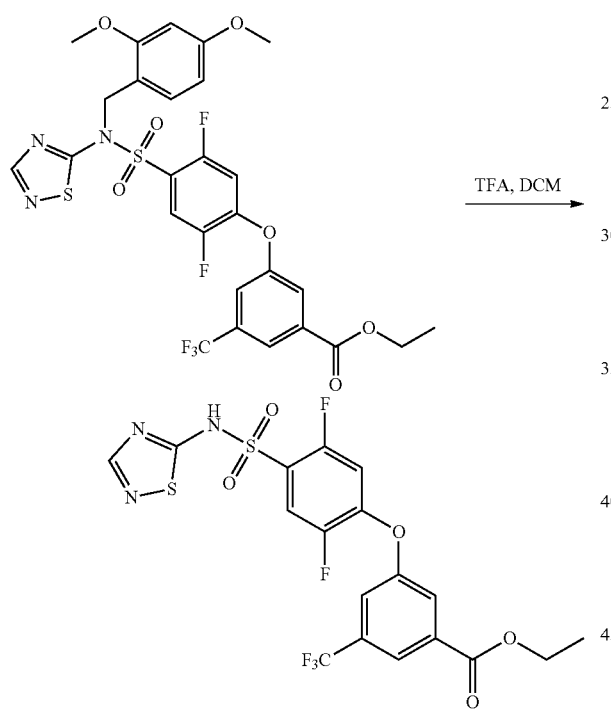

Into a 25-mL round-bottom flask, were placed ethyl 3-(4-[[(2,4-dimethoxyphenyl)methyl](1,2,4-thiadiazol-5-yl)sulfamoyl]-2,5-difluorophenoxy)-5-(trifluoromethyl)benzoate (80 mg, 0.12 mmol, 1.00 equiv), dichloromethane (3 mL), trifluoroacetic acid (1 mL). The resulting solution was stirred for 1 h at room temperature. The resulting mixture was concentrated under vacuum. The crude product (55 mg) was purified by Prep-HPLC with the following conditions (TFA): Column, C18; mobile phase, water with 0.05% TFA and CH$_3$CN (20.0% CH$_3$CN up to 80.0% in 7 min, up to 95.0% in 1 min, down to 20.0% in 1 min); Detector, UV 254 nm. This resulted in 30 mg (49%) of ethyl 3-[2,5-difluoro-4-[(1,2,4-thiadiazol-5-yl)sulfamoyl]phenoxy]-5-(trifluoromethyl)benzoate as a white solid.

LC-MS: (ES, m/z): [M+H]$^+$ 510

$^1$H-NMR: (300 MHz, DMSO-d, ppm): δ 8.52 (s, 1H), 8.03 (s, 1H), 7.97 (s, 1H), 7.91-7.83 (m, 2H), 7.44-7.37 (dd, 1H), 4.39-4.32 (m, 2H), 1.35-1.30 (m, 3H).

Example 27

Synthesis of 3-cyano-4-[2-methoxy-5-(trifluoromethyl)phenoxy]-N-(1,3,4-thiadiazol-2-yl)benzene-1-sulfonamide

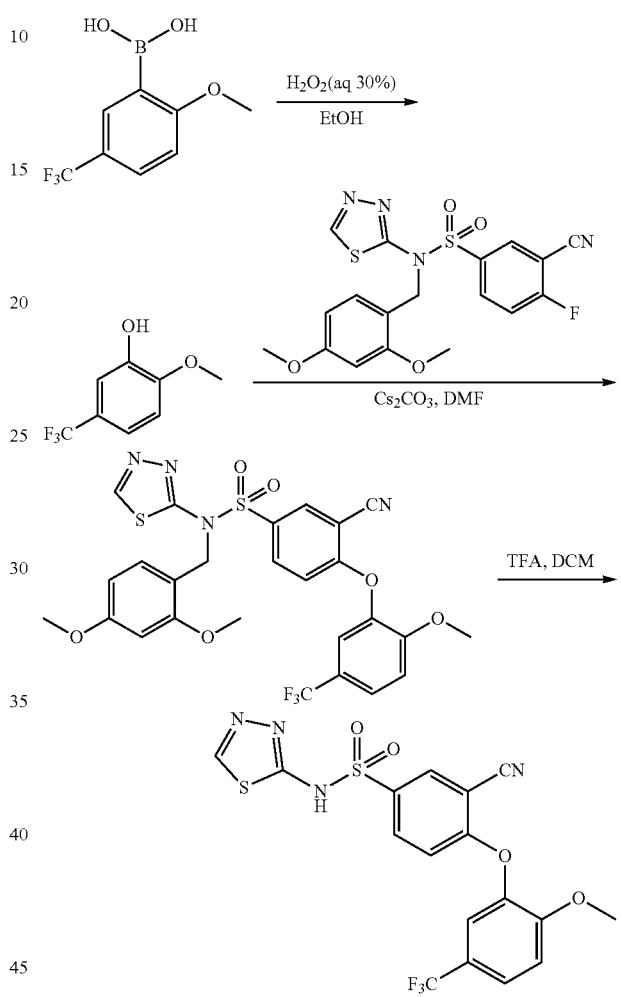

Step 1. Synthesis of 2-methoxy-5-(trifluoromethyl)phenol

Into a 100-mL round-bottom flask, were placed [2-methoxy-5-(trifluoromethyl) phenyl] boronic acid (300 mg, 1.36 mmol, 1.00 equiv), ethanol (15 mL), H$_2$O$_2$ (aq 30%) (2 mL). The resulting reaction was stirred for 2 h at 80° C. The resulting mixture was concentrated in vacuo. The reaction was then diluted by the addition of water. The resulting mixture was washed with Na$_2$SO$_3$ (aq). The aqueous layer was extracted with ethyl acetate and the organic layers combined. The resulting mixture was washed with brine, dried over anhydrous sodium sulfate and concentrated in vacuo. This resulted in 250 mg (95%) of 2-methoxy-5-(trifluoromethyl)phenol as a colorless oil.

Step 2. Synthesis of 3-cyano-N-[(2,4-dimethoxyphenyl)methyl]-4-[2-methoxy-5-(trifluoromethyl)phenoxy]-N-(1,3,4-thiadiazol-2-yl)benzene-1-sulfonamide

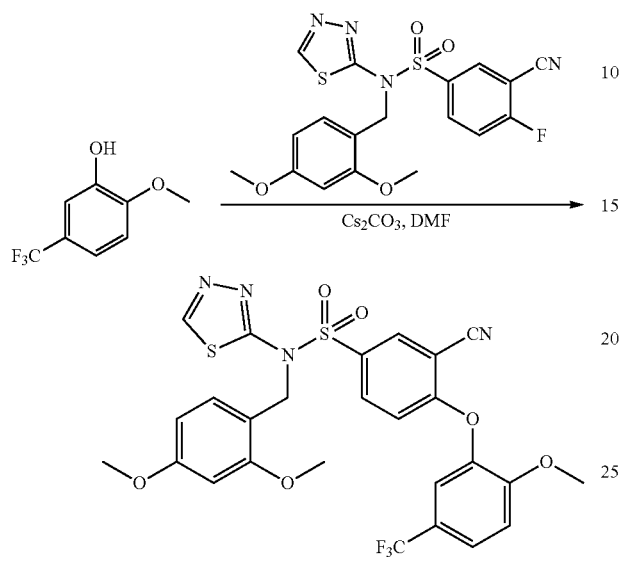

Into a 50-mL round-bottom flask, were placed a solution of 2-methoxy-5-(trifluoromethyl)phenol (100 mg, 0.52 mmol, 1.00 equiv), Cs₂CO₃ (340 mg, 1.04 mmol, 2.00 equiv), 3-cyano-N-[(2,4-dimethoxyphenyl)methyl]-4-fluoro-N-(1,3,4-thiadiazol-2-yl)benzene-1-sulfonamide (226 mg, 0.52 mmol, 1.00 equiv) in N,N-dimethylformamide (15 mL). The resulting reaction was stirred for 2 h at room temperature. The reaction was then quenched by the addition of water, extracted with ethyl acetate and the organic layers were combined. The resulting mixture was washed with brine, was dried over anhydrous sodium sulfate and concentrated in vacuo. This resulted in 200 mg (63%) of 3-cyano-N-[(2,4-dimethoxyphenyl)methyl]-4-[2-methoxy-5-(trifluoromethyl)phenoxy]-N-(1,3,4-thiadiazol-2-yl)benzene-1-sulfonamide as a yellow oil.

Step 3. Synthesis of 3-cyano-4-[2-methoxy-5-(trifluoromethyl)phenoxy]-N-(1,3,4-thiadiazol-2-yl)benzene-1-sulfonamide

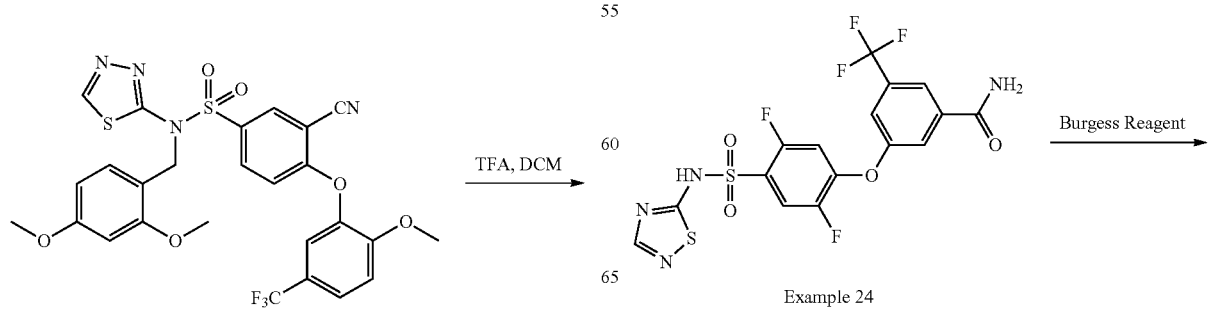

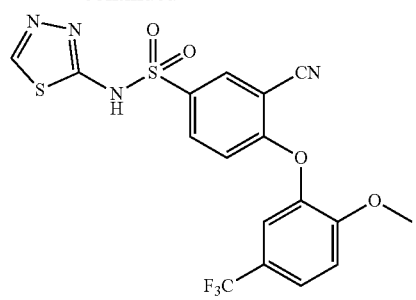

Into a 25-mL round-bottom flask, were placed a solution of 3-cyano-N-[(2,4-dimethoxyphenyl)methyl]-4-[2-methoxy-5-(trifluoromethyl)phenoxy]-N-(1,3,4-thiadiazol-2-yl)benzene-1-sulfonamide (200 mg, 0.33 mmol, 1.00 equiv), trifluoroacetic acid (2 mL) in dichloromethane (5 mL). The resulting reaction was stirred for 1 h at room temperature. The resulting mixture was concentrated in vacuo. The crude product (150 mg) was purified by Prep-HPLC with the following conditions (2 #-Pre-HPLC-007 (Waters)): Column, XBridge Shield RP18 OBD Column, 5 um, 19*150 mm; mobile phase, water with 0.05% TFA and CH₃CN (20.0% CH₃CN up to 80.0% in 7 min, up to 95.0% in 1 min, down to 20.0% in 1 min); Detector, UV 254 nm. This resulted in 65 mg (43%) of 3-cyano-4-[2-methoxy-5-(trifluoromethyl)phenoxy]-N-(1,3,4-thiadiazol-2-yl)benzene-1-sulfonamide as a white solid.

LC-MS (ES, m/z): [M+H]⁺ 457

¹H NMR (400 MHz, DMSO-d₆, ppm): δ 14.56-14.34 (m, 1H), 8.78 (s, 1H), 8.83-8.25 (d, 1H), 7.98-7.94 (m, 1H), 7.85-7.75 (m, 2H), 7.47-7.45 (m, 1H), 6.85-6.82 (d, 1H), 3.83 (s, 3H).

Example 28

4-[3-cyano-5-(trifluoromethyl)phenoxy]-2,5-difluoro-N-(1,2,4-thiadiazol-5-yl)benzene-1-sulfonamide

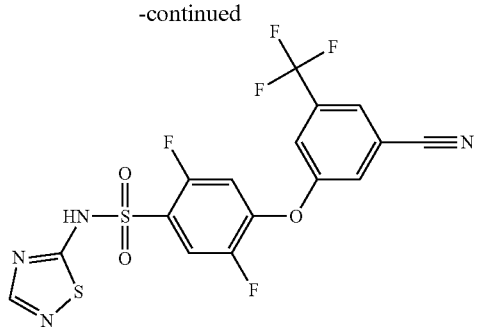

Example 28

Step 1. Synthesis of 4-[3-cyano-5-(trifluoromethyl) phenoxy]-2,5-difluoro-N-(1,2,4-thiadiazol-5-yl)benzene-1-sulfonamide Into a 25-mL round-bottom flask, was placed a solution of 3-[2,5-difluoro-4-[(1,2,4-thiadiazol-5-yl)sulfamoyl]phenoxy]-5-(trifluoromethyl)benzamide (150 mg, 0.31 mmol, 1.00 equiv) in dichloromethane (10 mL). To the solution was added Burgess Reagent (149 mg, 0.63 mmol, 2.00 equiv). The resulting solution was stirred for 16 h at room temperature. The reaction was then quenched by the addition of 10 mL of water. The resulting solution was extracted with dichloromethane (3×20 mL) and the organic layers combined and concentrated under vacuum. The crude product was purified by Prep-HPLC with conditions: Column, XBridge Prep Shield RP18, 5 um, 19×150 mm; Mobile phase, H$_2$O (0.05% NH$_4$HCO$_3$)/CH$_3$CN (30%-70% in 10 min); Detector, 254 nm, 220 nm; RT=7.7 min. This resulted in 12.3 mg (9%) of 4-[3-cyano-5-(trifluoromethyl)phenoxy]-2,5-difluoro-N-(1,2,4-thiadiazol-5-yl)benzene-1-sulfonamide as a white solid.

LC-MS: (ES, m/z): [M+H]$^+$ 463

$^1$H-NMR: (300 MHz, DMSO, ppm) δ 7.51-7.55 (m, 1H), 7.82-7.93 (m, 1H), 8.13 (s, 1H), 8.19 (s, 1H), 8.22 (s, 1H), 8.40 (s, 1H).

Example 29

Synthesis of 4-(3,5-difluorophenoxy)-2,5-difluoro-N-(1,2,4-thiadiazol-5-yl)benzene-1-sulfonamide

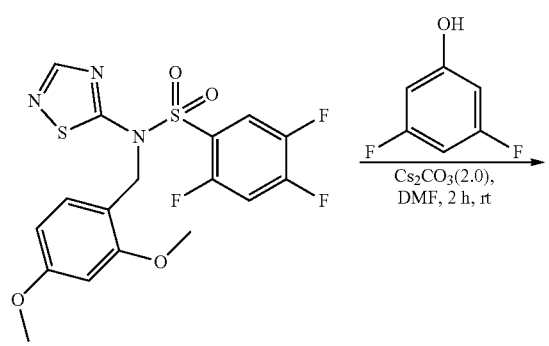

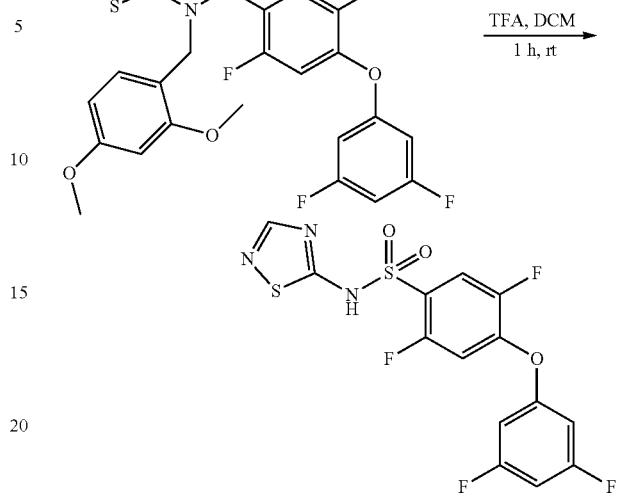

Step 1. Synthesis of 4-(3,5-difluorophenoxy)-N-[(2, 4-dimethoxyphenyl)methyl]-2,5-difluoro-N-(1,2,4-thiadiazol-5-yl)benzene-1-sulfonamide

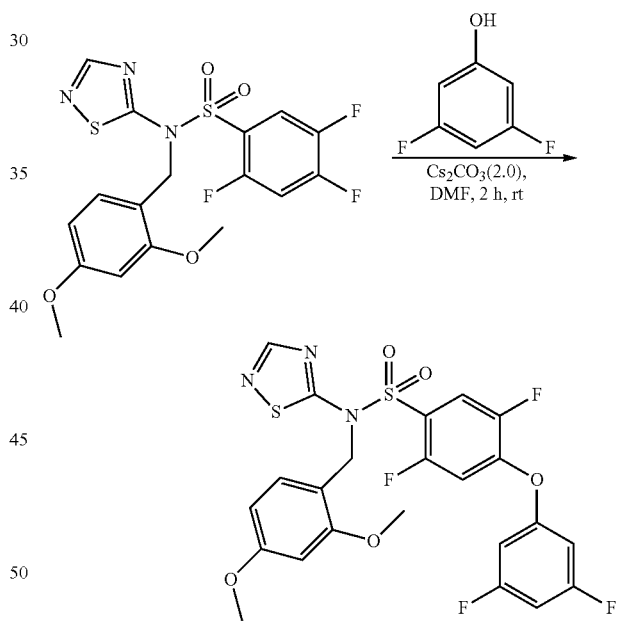

Into a 50-mL round-bottom flask, were placed a solution of N-[(2,4-dimethoxyphenyl)methyl]-2,4,5-trifluoro-N-(1,2,4-thiadiazol-5-yl)benzene-1-sulfonamide (150 mg, 0.34 mmol, 1.00 equiv), 3,5-difluorophenol (43.8 mg, 0.34 mmol, 1.00 equiv), Cs$_2$CO$_3$ (220 mg, 0.68 mmol, 2.00 equiv) in N,N-dimethylformamide (8 mL). The resulting reaction was stirred for 2 h at room temperature. The reaction was then quenched by the addition of water, extracted with ethyl acetate, and the organic layers were combined. The resulting mixture was washed with brine, dried over anhydrous sodium sulfate and concentrated in vacuo. This resulted in 120 mg (64%) of 4-(3,5-difluorophenoxy)-N-[(2,4-dimethoxyphenyl)methyl]-2,5-difluoro-N-(1,2,4-thiadiazol-5-yl) benzene-1-sulfonamide as a yellow oil.

Step 2. Synthesis of 4-(3,5-difluorophenoxy)-2,5-difluoro-N-(1,2,4-thiadiazol-5-yl)benzene-1-sulfonamide

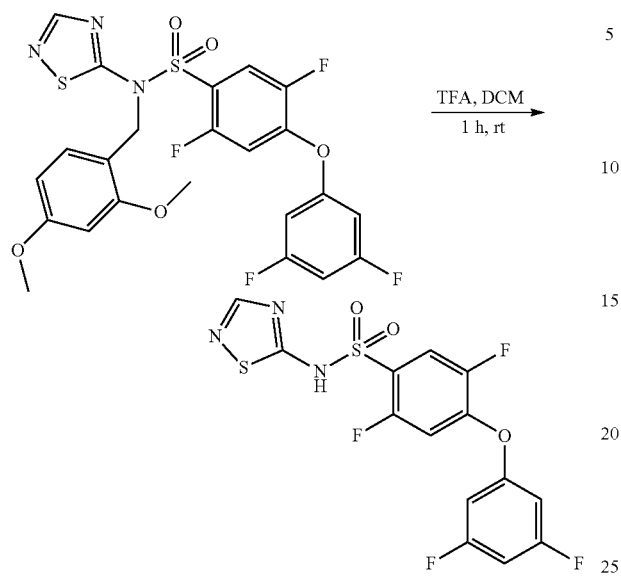

Into a 25-mL round-bottom flask, were placed a solution of 4-(3,5-difluorophenoxy)-N-[(2,4-dimethoxyphenyl)methyl]-2,5-difluoro-N-(1,2,4-thiadiazol-5-yl)benzene-1-sulfonamide (120 mg, 0.22 mmol, 1.00 equiv), trifluoroacetic acid (2 mL) in dichloromethane (4 mL). The resulting reaction was stirred for 1 h at room temperature. The resulting mixture was concentrated in vacuo. The crude product (100 mg) was purified by Prep-HPLC with the following conditions (1 #-Pre-HPLC-005(Waters)): Column, SunFire Prep C18, 19*150 mm 5 um; mobile phase, water with 0.05% TFA and CH$_3$CN (10.0% CH$_3$CN up to 90.0% in 7 min, up to 95.0% in 1 min, down to 10.0% in 1 min); Detector, UV 254 nm. This resulted in 53 mg (61%) of 4-(3,5-difluorophenoxy)-2,5-difluoro-N-(1,2,4-thiadiazol-5-yl)benzene-1-sulfonamide as a white solid.

LC-MS (ES, m/z): [M+H]$^+$ 406

$^1$H-NMR (300 MHz, DMSO-d$_6$, ppm): δ 8.51-8.51 (m, 1H), 7.85-7.80 (m, 1H), 7.45-7.40 (m, 1H), 7.16-7.09 (t, 1H), 7.05-7.02 (d, 2H).

Example 30

4-(3-chloro-5-fluorophenoxy)-2,5-difluoro-N-(1,2,4-thiadiazol-5-yl)benzene-1-sulfonamide

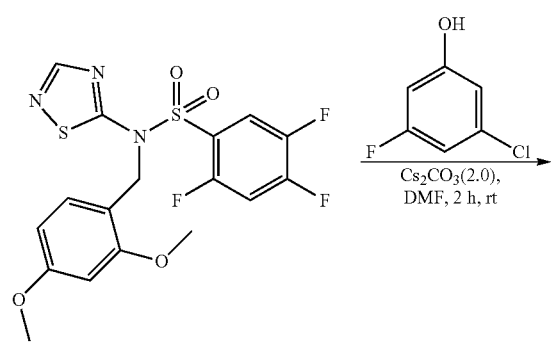

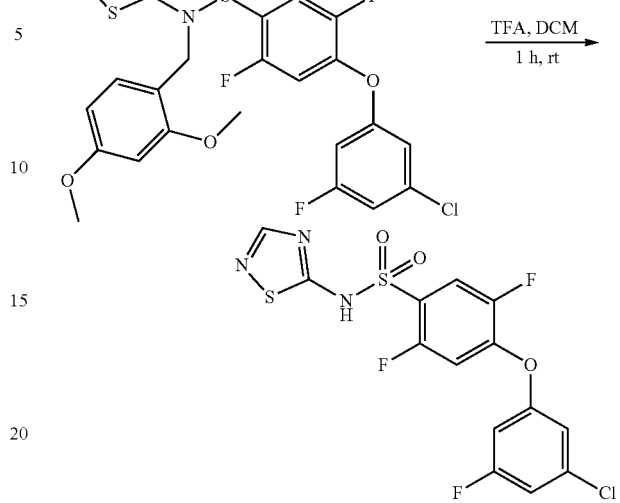

Step 1. Synthesis of 4-(3-chloro-5-fluorophenoxy)-N-[(2,4-dimethoxyphenyl)methyl]-2,5-difluoro-N-(1,2,4-thiadiazol-5-yl)benzene-1-sulfonamide

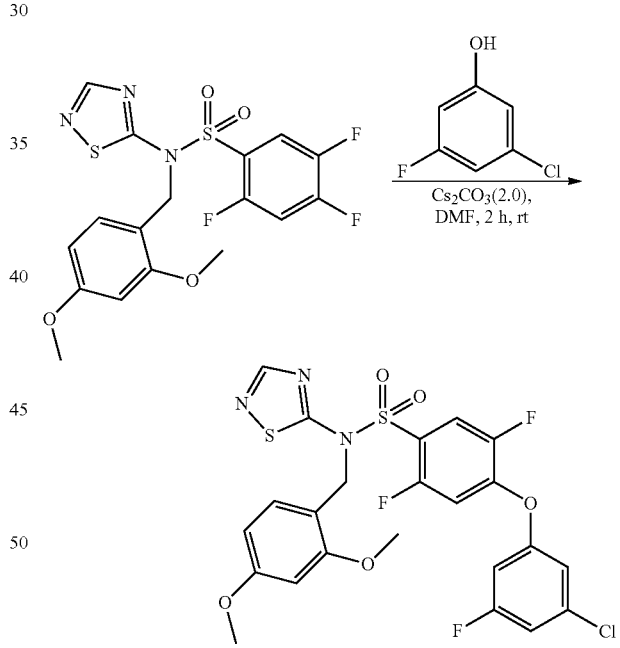

Into a 50-mL round-bottom flask, were placed a solution of N-[(2,4-dimethoxyphenyl)methyl]-2,4,5-trifluoro-N-(1,2,4-thiadiazol-5-yl)benzene-1-sulfonamide (150 mg, 0.34 mmol, 1.00 equiv), 3-chloro-5-fluorophenol (49.5 mg, 0.34 mmol, 1.00 equiv), Cs$_2$CO$_3$ (220 mg, 0.68 mmol, 2.00 equiv) in N,N-dimethylformamide (8 mL). The resulting solution was stirred for 2 hours at room temperature. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 120 mg (62%) of 4-(3-chloro-5-fluorophenoxy)-N-[(2,4-dimethoxyphenyl)methyl]-2,5-difluoro-N-(1,2,4-thiadiazol-5-yl)benzene-1-sulfonamide as yellow oil.

Step 2. Synthesis of 4-(3-chloro-5-fluorophenoxy)-2,5-difluoro-N-(1,2,4-thiadiazol-5-yl)benzene-1-sulfonate

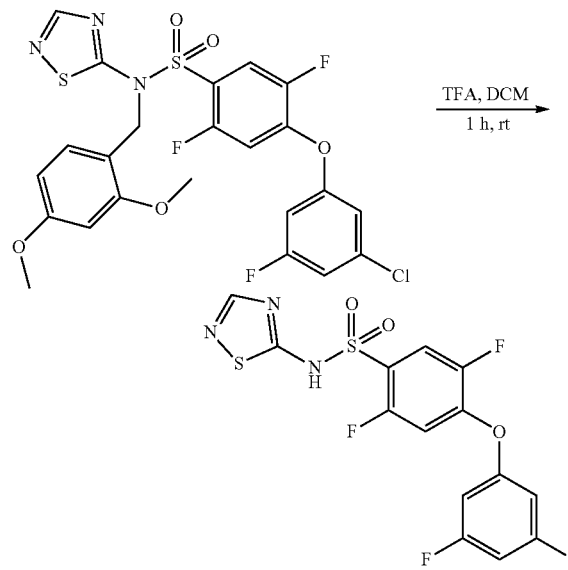

Into a 25-mL round-bottom flask, were placed a solution of 4-(3-chloro-5-fluorophenoxy)-N-[(2,4-dimethoxyphenyl)methyl]-2,5-difluoro-N-(1,2,4-thiadiazol-5-yl)benzene-1-sulfonamide (120 mg, 0.21 mmol, 1.00 equiv), trifluoroacetic acid (1 mL) in dichloromethane (3 mL). The resulting solution was stirred for 1 hour at room temperature. The resulting mixture was concentrated under vacuum. The crude product (100 mg) was purified by Prep-HPLC with the following conditions (1 #-Pre-HPLC-005(Waters)): Column, SunFire Prep C18, 19*150 mm 5 um; mobile phase, water with 0.05% TFA and CH$_3$CN (10.0% CH$_3$CN up to 90.0% in 7 min, up to 95.0% in 1 min, down to 10.0% in 1 min); Detector, UV 254 nm. This resulted in 50 mg (57%) of 4-(3-chloro-5-fluorophenoxy)-2,5-difluoro-N-(1,2,4-thiadiazol-5-yl)benzene-1-sulfonamide as a white solid.

LC-MS: (ES, m/z): [M+H]$^+$=422

$^1$H-NMR: (300 MHz, DMSO-d$_6$, ppm): δ 8.53 (s, 1H), 7.86-7.80 (m, 1H), 7.45-7.40 (m, 1H), 7.34-7.31 (d, 1H), 7.21-7.17 (m, 2H).

Example 31

4-[3,5-bis(trifluoromethyl)phenoxy]-2,5-difluoro-N-(pyridazin-3-yl)benzene-1-sulfonamide Step 1. Synthesis of 2,4,5-trifluoro-N-(pyridazin-3-yl)benzene-1-sulfonamide

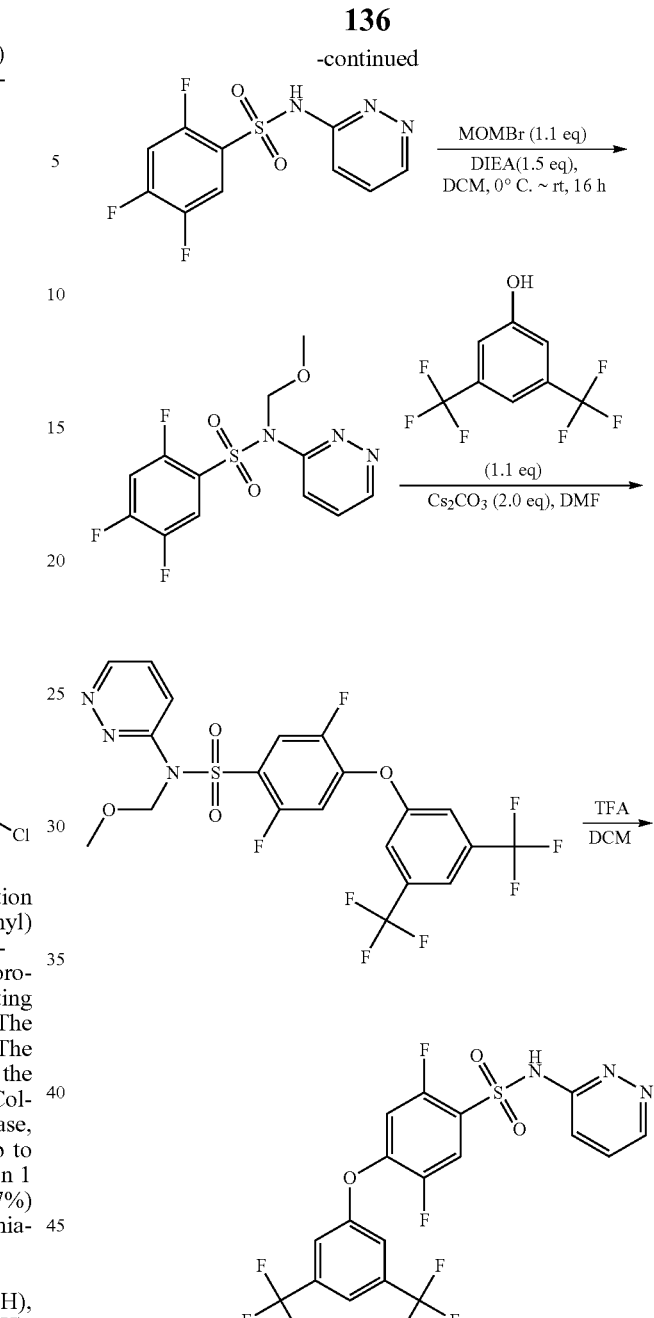

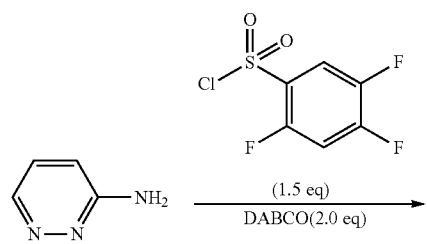

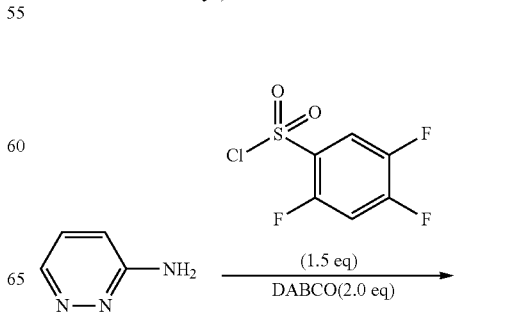

-continued

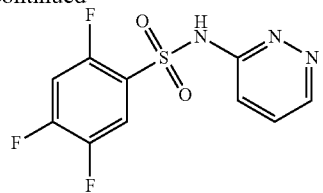

Into a 100-mL round-bottom flask, was placed a solution of pyridazin-3-amine (1 g, 10.51 mmol, 1.00 equiv) in CH3CN (30 mL). To the solution were added 2,4,5-trifluorobenzene-1-sulfonyl chloride (2.43 g, 10.54 mmol, 1.00 equiv) and DBU (3.2 g, 21.05 mmol, 2.00 equiv). The resulting solution was stirred for 16 hours at room temperature. The solution was concentrated and the residue was purified via silica gel column chromatography with ethyl acetate/petroleum ether (1:3). The collected fractions were combined and concentrated under vacuum. This resulted in 200 mg (7%) of 2,4,5-trifluoro-N-(pyridazin-3-yl)benzene-1-sulfonamide as a light yellow solid.

Step 2. Synthesis of 2,4,5-trifluoro-N-(methoxymethyl)-N-(pyridazin-3-yl)benzene-1-sulfonamide

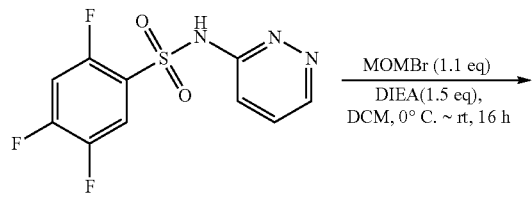

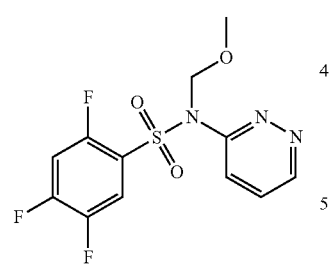

Into a 100-mL round-bottom flask, was placed a solution of 2,4,5-trifluoro-N-(pyridazin-3-yl)benzene-1-sulfonamide (200 mg, 0.69 mmol, 1.00 equiv) in dichloromethane (30 mL). To the solution were added MOMBr (94 mg, 0.76 mmol, 1.10 equiv) and DIEA (134 mg, 1.04 mmol, 1.50 equiv). The resulting solution was stirred for 16 hours at room temperature. The resulting solution was extracted with dichloromethane (3×30 mL) and the organic layers combined and concentrated under vacuum. This resulted in 190 mg (82%) of 2,4,5-trifluoro-N-(methoxymethyl)-N-(pyridazin-3-yl)benzene-1-sulfonamide as a off-white solid.

Step 3. Synthesis of 4-[3,5-bis(trifluoromethyl)phenoxy]-2,5-difluoro-N-(methoxymethyl)-N-(pyridazin-3-yl)benzene-1-sulfonamide

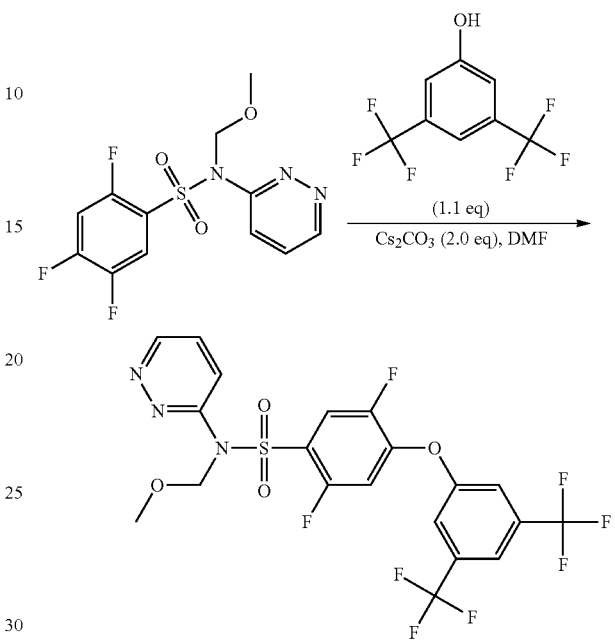

Into a 100-mL round-bottom flask, was placed a solution of 2,4,5-trifluoro-N-(methoxymethyl)-N-(pyridazin-3-yl) benzene-1-sulfonamide (190 mg, 0.57 mmol, 1.00 equiv) in N,N-dimethylformamide (30 mL). To the solution were added 3,5-bis(trifluoromethyl)phenol (131 mg, 0.57 mmol, 1.00 equiv) and Cs$_2$CO$_3$ (372 mg, 1.14 mmol, 2.00 equiv). The resulting solution was stirred for 16 hours at room temperature. The resulting mixture was concentrated under vacuum. The residue was purified via silica gel column chromatography with an eluent of ethyl acetate/petroleum ether (1:7). This resulted in 100 mg (32%) of 4-[3,5-bis (trifluoromethyl)phenoxy]-2,5-difluoro-N-(methoxymethyl)-N-(pyridazin-3-yl)benzene-1-sulfonamide as a white solid.

Step 4. Synthesis of 4-[3,5-bis(trifluoromethyl)phenoxy]-2,5-difluoro-N-(pyridazin-3-yl)benzene-1-sulfonamide

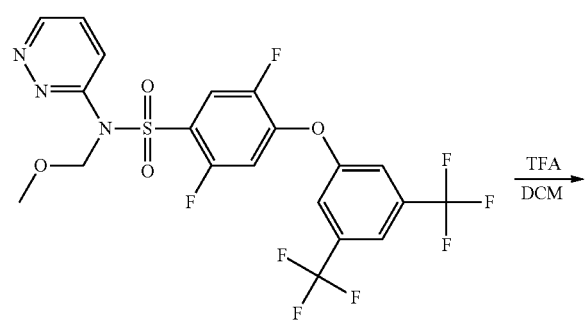

-continued

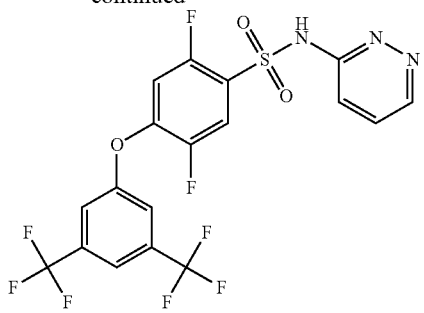

Into a 50-mL round-bottom flask, was placed a solution of 4-[3,5-bis(trifluoromethyl)phenoxy]-2,5-difluoro-N-(methoxymethyl)-N-(pyridazin-3-yl)benzene-1-sulfonamide (100 mg, 0.18 mmol, 1.00 equiv) in dichloromethane (15 mL). To the solution was added trifluoroacetic acid (1 mL). The resulting solution was stirred for 48 hours at room temperature. The resulting mixture was concentrated under vacuum. The crude product was purified by Prep-HPLC with conditions: Column, XBridge Prep Shield RP18, 5 um, 19×150 mm; Mobile phase, $H_2O$ (0.05% TFA)/$CH_3CN$ (20%~65% in 10 min); Detector, 254 nm, 220 nm; RT=6.2 min. This resulted in 11.3 mg (12%) of 4-[3,5-bis(trifluoromethyl)phenoxy]-2,5-difluoro-N-(pyridazin-3-yl)benzene-1-sulfonamide as a white solid.

LC-MS: (ES, m/z): $[M+H]^+$=500

$^1$H NMR (300 MHz, DMSO, ppm): δ 7.44 (s, 1H), 7.96-8.20 (m, 6H), 8.46 (s, 1H), 14.88 (s, 1H).

Example 32

Synthesis of 4-[3-(azetidin-3-yl)-5-(trifluoromethyl) phenoxy]-2,5-difluoro-N-(1,2,4-thiadiazol-5-yl)benzene-1-sulfonamide; trifluoroacetic acid

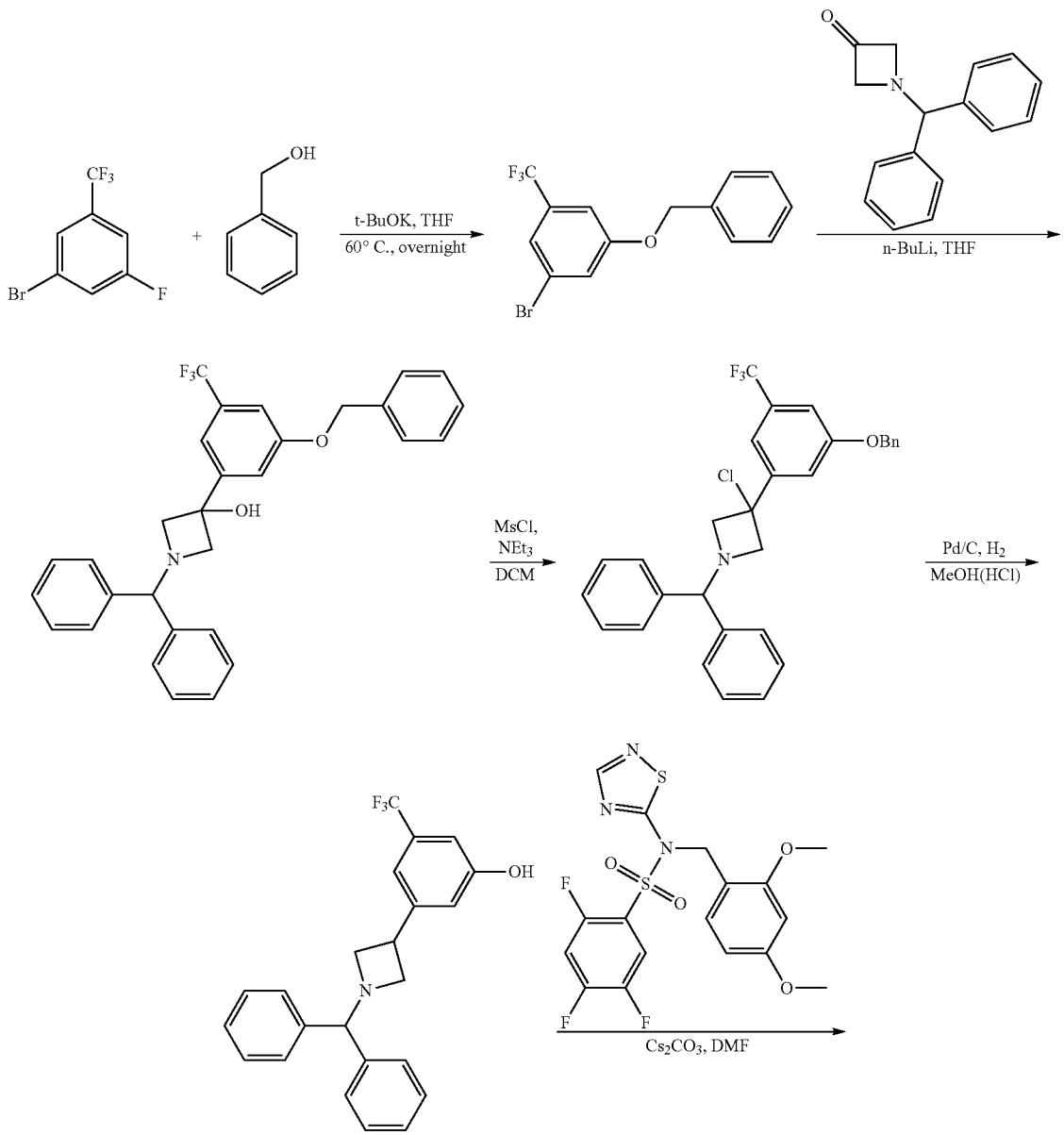

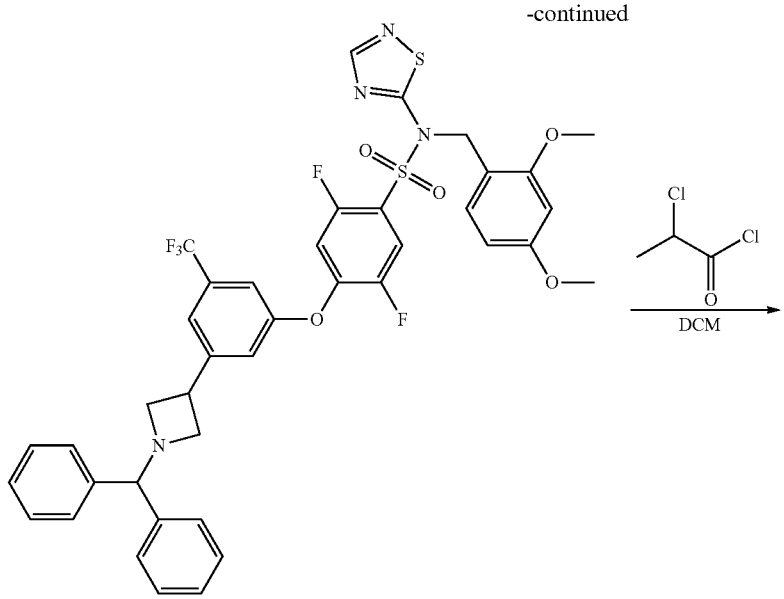

Step 1. Synthesis of 1-(benzyloxy)-3-bromo-5-(trifluoromethyl)benzene

Into a 500-mL round-bottom flask purged and maintained with an inert atmosphere of nitrogen, was placed 1-bromo-3-fluoro-5-(trifluoromethyl)benzene (6.0 g, 24.69 mmol, 1.00 equiv), tetrahydrofuran (200 mL), phenylmethanol (3.0 g, 27.74 mmol, 1.12 equiv), t-BuOK (5.55 g, 49.46 mmol, 2.00 equiv). The resulting reaction was stirred overnight at 60° C. The reaction was then quenched by the addition of 200 mL of NH$_4$Cl(aq.), extracted with 3×200 mL of ethyl acetate, and the organic layers were combined and concentrated in vacuo. The residue was purified by silica gel column chromatography with ethyl acetate/petroleum ether (1:200). This resulted in 5.6 g (68%) of 1-(benzyloxy)-3-bromo-5-(trifluoromethyl)benzene as a colorless oil.

Step 2. Synthesis of 3-[3-(benzyloxy)-5-(trifluoromethyl)phenyl]-1-(diphenylmethyl)azetidin-3-ol

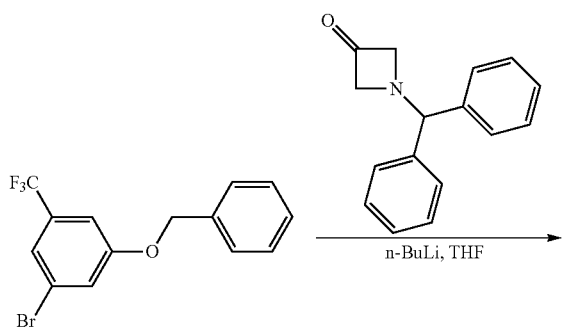

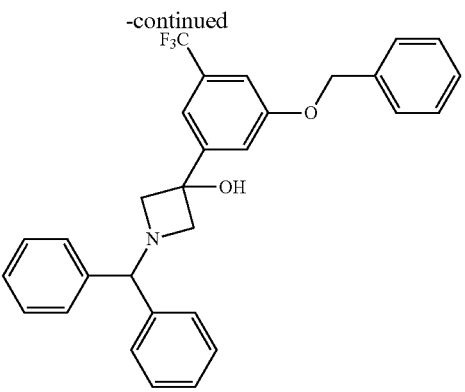

Into a 500-mL 3-necked round-bottom flask purged and maintained with an inert atmosphere of nitrogen, was placed 1-(benzyloxy)-3-bromo-5-(trifluoromethyl)benzene (4.0 g, 12.08 mmol, 1.00 equiv), THF (150 mL). This was followed by the dropwise addition of a solution of n-BuLi in hexane (7.2 mL) at −78° C. The resulting reaction was stirred for 1 h at −78° C. Then a solution of 1-(diphenylmethyl)azetidin-3-one (3.2 g, 13.49 mmol, 1.12 equiv) in THF (20 mL) was added dropwise with stirring at −78° C. The resulting reaction was stirred for 2 hours at room temperature. The reaction was then quenched by the addition of 200 mL of NH$_4$Cl (aq.), extracted with 3×200 mL of ethyl acetate and the organic layers were combined and concentrated in vacuo. The residue was purified by silica gel column chromatography with ethyl acetate/petroleum ether (1:5). This resulted in 2.2 g (37%) of 3-[3-(benzyloxy)-5-(trifluoromethyl)phenyl]-1-(diphenylmethyl)azetidin-3-ol as a colorless oil.

Step 3. Synthesis of 3-[3-(benzyloxy)-5-(trifluoromethyl)phenyl]-3-chloro-1-(diphenylmethyl)azetidine

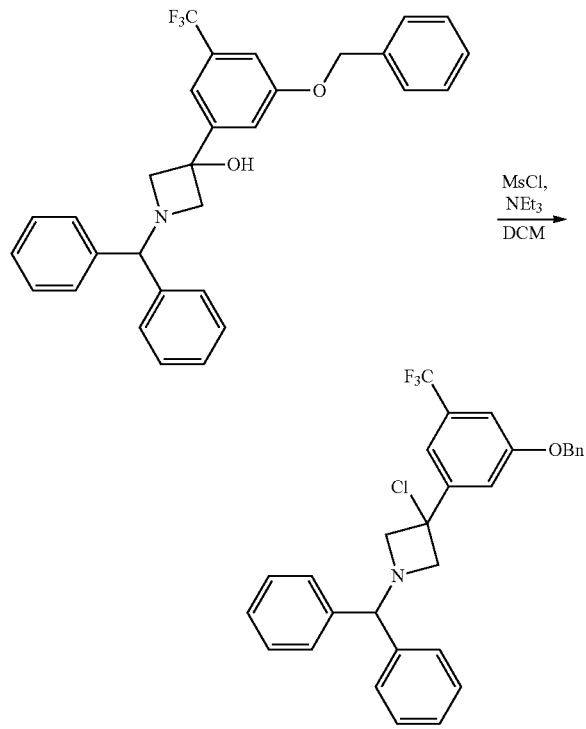

Into a 100-mL round-bottom flask purged and maintained with an inert atmosphere of nitrogen, was placed 3-[3-(benzyloxy)-5-(trifluoromethyl)phenyl]-1-(diphenylmethyl)azetidin-3-ol (2 g, 4.09 mmol, 1.00 equiv), dichloromethane (50 mL), NEt$_3$ (1.8 g). This was followed by the dropwise addition of MsCl (2 g) at 0° C. The resulting reaction was stirred overnight at room temperature. The reaction was then quenched by the addition of 200 mL of water, extracted with 3×100 mL of ethyl acetate and the organic layers were combined and concentrated in vacuo. The residue was purified by silica gel column chromatography with ethyl acetate/petroleum ether (1:5). This resulted in 1.8 g (69%) of 3-[3-(benzyloxy)-5-(trifluoromethyl)phenyl]-3-chloro-1-(diphenylmethyl)azetidine as a yellow oil.

Step 4. Synthesis of 3-[1-(diphenylmethyl)azetidin-3-yl]-5-(trifluoromethyl)phenol

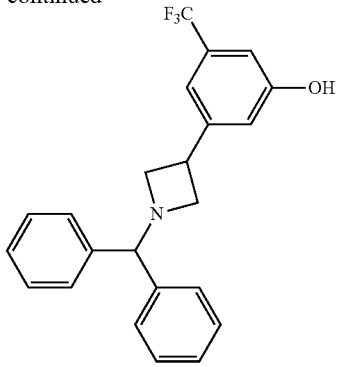

Into a 100-mL round-bottom flask, was placed 3-[3-(benzyloxy)-5-(trifluoromethyl)phenyl]-3-chloro-1-(diphenylmethyl)azetidine (1.8 g, 3.54 mmol, 1.00 equiv), methanol hydrochloride (60 mL), Palladium carbon (1 g). To the above, H$_2$ gas was introduced in. The resulting reaction was stirred overnight at room temperature. The solids were filtered out. The resulting mixture was concentrated in vacuo. The residue was purified by silica gel column chromatography with ethyl acetate/petroleum ether (1:2). This resulted in 270 mg (20%) of 3-[1-(diphenylmethyl)azetidin-3-yl]-5-(trifluoromethyl)phenol as a light yellow solid.

Step 5. Synthesis of N-[(2,4-dimethoxyphenyl)methyl]-4-[3-[1-(diphenylmethyl)azetidin-3-yl]-5-(trifluoromethyl)phenoxy]-2,5-difluoro-N-(1,2,4-thiadiazol-5-yl)benzene-1-sulfonamide

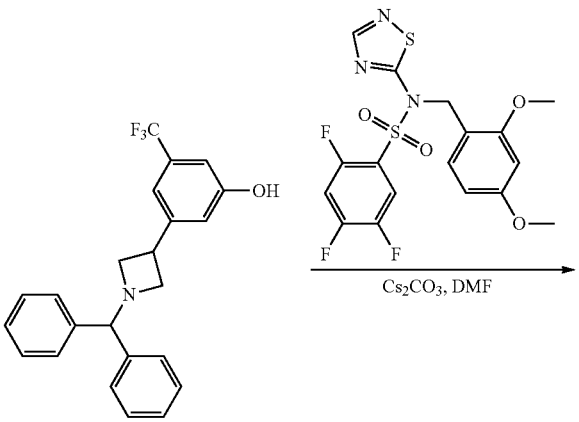

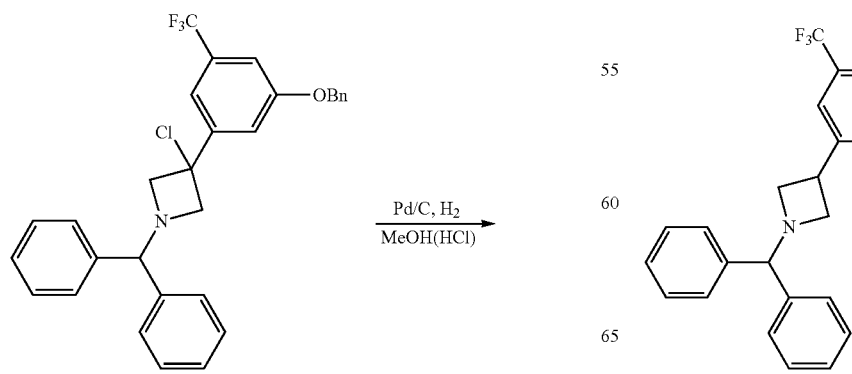

Into a 100-mL round-bottom flask, was placed 3-[1-(diphenylmethyl)azetidin-3-yl]-5-(trifluoromethyl)phenol (270 mg, 0.70 mmol, 1.00 equiv), N,N-dimethylformamide (10 mL), N-[(2,4-dimethoxyphenyl)methyl]-2,4,5-trifluoro-N-(1,2,4-thiadiazol-5-yl)benzene-1-sulfonamide (314 mg, 0.70 mmol, 1.00 equiv), Cs₂CO₃ (345 mg, 1.06 mmol, 1.50 equiv). The resulting reaction was stirred overnight at room temperature. The reaction was then quenched by the addition of 100 mL of water, extracted with 3×50 mL of ethyl acetate, and the organic layers were combined and concentrated in vacuo. The residue was purified by silica gel column chromatography with ethyl acetate/petroleum ether (1:2). This resulted in 540 mg (95%) of N-[(2,4-dimethoxyphenyl)methyl]-4-[3-[1-(diphenylmethyl)azetidin-3-yl]-5-(trifluoromethyl)phenoxy]-2,5-difluoro-N-(1,2,4-thiadiazol-5-yl)benzene-1-sulfonamide as a light yellow solid.

Step 6. Synthesis of 4-[3-(azetidin-3-yl)-5-(trifluoromethyl)phenoxy]-2,5-difluoro-N-(1,2,4-thiadiazol-5-yl)benzene-1-sulfonamide; trifluoroacetic acid Into a 50-mL round-bottom flask, was placed N-[(2,4-dimethoxyphenyl)methyl]-4-[3-[1-(diphenylmethyl)azetidin-3-yl]-5-(trifluoromethyl)phenoxy]-2,5-difluoro-N-(1,2,4-thiadiazol-5-yl)benzene-1-sulfonamide (540 mg, 0.67 mmol, 1.00 equiv), dichloromethane (10 mL), 1-chloroethyl chloroformate (421 mg, 2.94 mmol, 4.41 equiv). The resulting reaction was stirred for 2 days at room temperature. The reaction was then quenched by the addition of 50 mL of methanol. The resulting mixture was concentrated in vacuo. The crude product was purified by Prep-HPLC with the following conditions (1 #-Pre-HPLC-014(Waters)): Column, XBridge Prep Shield RP18, 5 um, 19*150 mm; mobile phase, CH₃CN/H₂O (0.05% TFA)=10% increasing to CH₃CN/H₂O (0.05% TFA)=50% within 10 min; Detector, UV 254 nm. This resulted in 10.4 mg (3%) of 4-[3-(azetidin-3-yl)-5-(trifluoromethyl)phenoxy]-2,5-difluoro-N-(1,2,4-thiadiazol-5-yl)benzene-1-sulfonamide; trifluoroacetic acid as a white solid.

LC-MS (ES, m/z): [M−TFA+H]⁺=493

¹H NMR (400 MHz, DMSO, ppm): δ 8.85 (s, 1H), 8.41 (s, 1H), 8.35 (s, 1H), 7.83-7.78 (m, 1H), 7.70 (s, 1H), 7.58-7.55 (m, 2H), 7.29-7.21 (m, 1H), 4.41-4.06 (m, 5H).

Example 33

Synthesis of 2,5-difluoro-4-[3-fluoro-5-(trifluoromethyl)phenoxy]-N-(1,2,4-thiadiazol-5-yl)benzene-1-sulfonamide

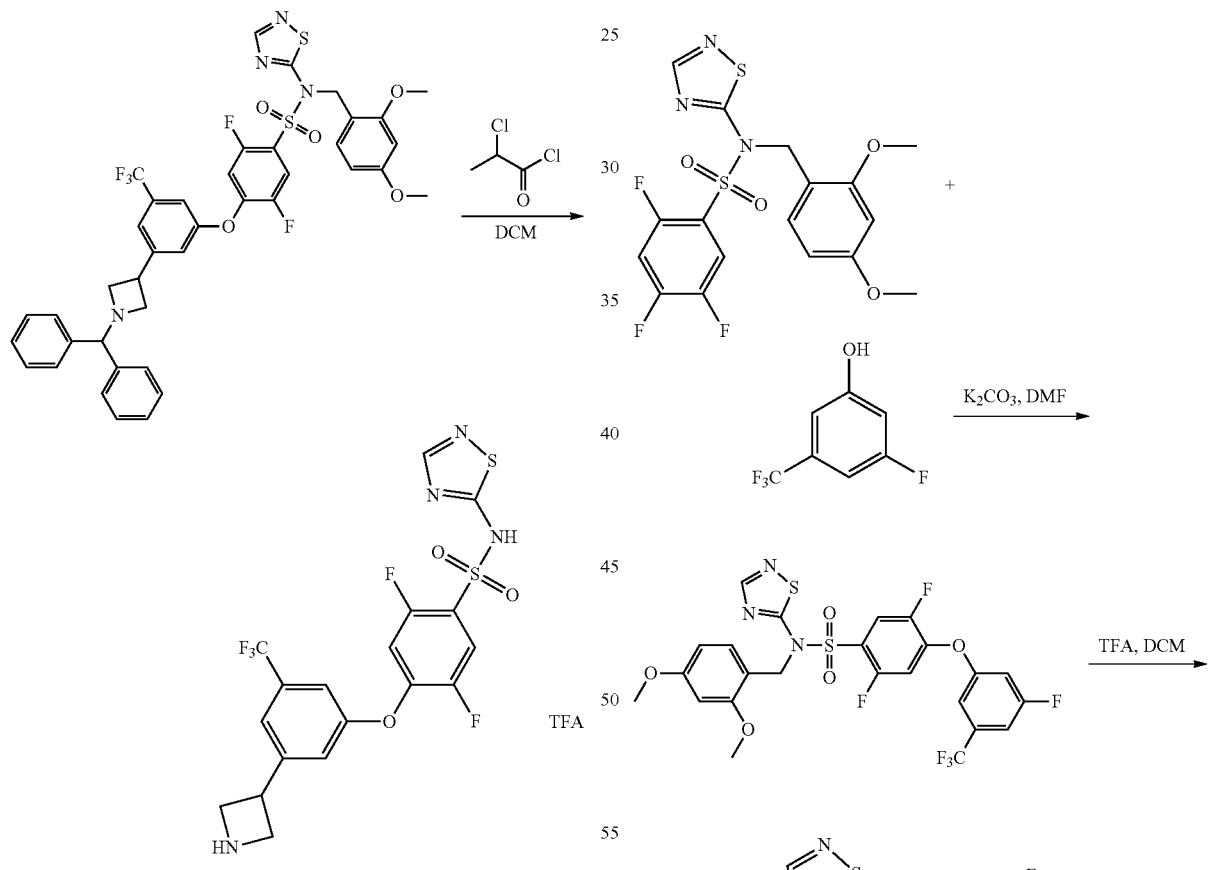

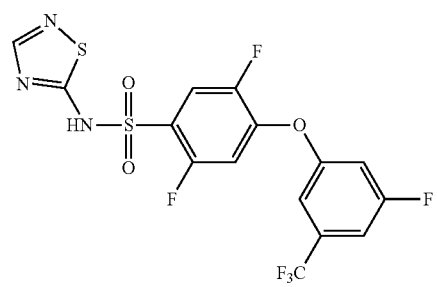

Step 1. Synthesis of N-[(2,4-dimethoxyphenyl)methyl]-2,5-difluoro-4-[3-fluoro-5-(trifluoromethyl)phenoxy]-N-(1,2,4-thiadiazol-5-yl)benzene-1-sulfonamide

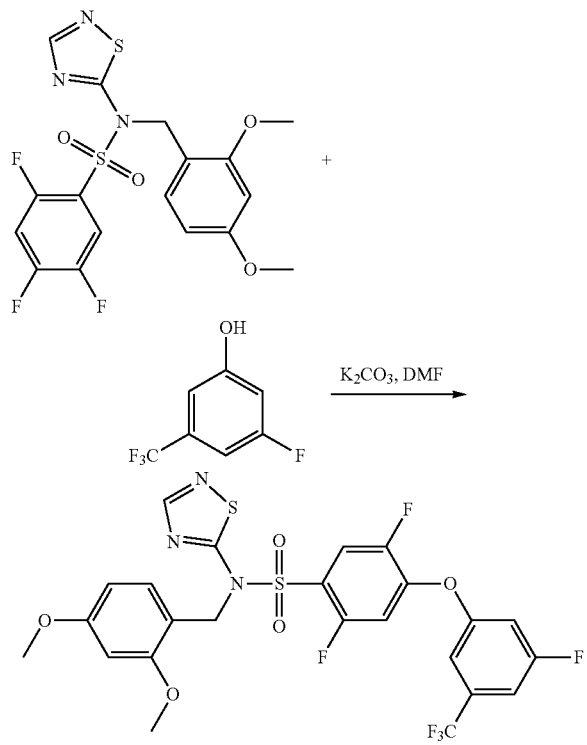

Into a 50-mL round-bottom flask, was placed N-[(2,4-dimethoxyphenyl)methyl]-2,4,5-trifluoro-N-(1,2,4-thiadiazol-5-yl)benzene-1-sulfonamide (150 mg, 0.34 mmol, 1.00 equiv), N,N-dimethylformamide (5 mL), potassium carbonate (70 mg, 0.51 mmol, 1.50 equiv), 3-fluoro-5-(trifluoromethyl)phenol (61 mg, 0.34 mmol, 1.01 equiv). The resulting reaction was stirred overnight at room temperature. The reaction was then quenched by the addition of 100 mL of water, extracted with 3×50 mL of ethyl acetate and the organic layers were combined and concentrated in vacuo. The residue was purified by silica gel column chromatography with ethyl acetate/petroleum ether (1:3). This resulted in 150 mg (74%) of N-[(2,4-dimethoxyphenyl)methyl]-2,5-difluoro-4-[3-fluoro-5-(trifluoromethyl)phenoxy]-N-(1,2,4-thiadiazol-5-yl)benzene-1-sulfonamide as an off-white solid.

Step 2. Synthesis of 2,5-difluoro-4-[3-fluoro-5-(trifluoromethyl)phenoxy]-N-(1,2,4-thiadiazol-5-yl)benzene-1-sulfonamide

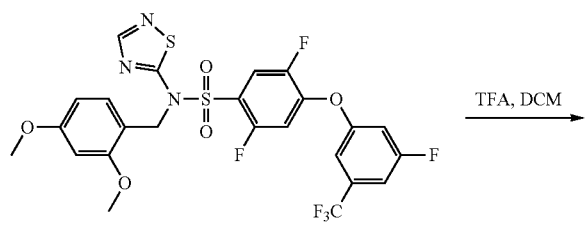

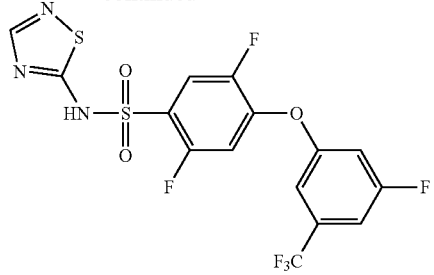

Into a 50-mL round-bottom flask, was placed N-[(2,4-dimethoxyphenyl)methyl]-2,5-difluoro-4-[3-fluoro-5-(trifluoromethyl)phenoxy]-N-(1,2,4-thiadiazol-5-yl)benzene-1-sulfonamide (150 mg, 0.25 mmol, 1.00 equiv), dichloromethane (3 mL), trifluoroacetic acid (1 mL). The resulting reaction was stirred for 2 h at room temperature. The resulting mixture was concentrated in vacuo. The crude product was purified by Prep-HPLC with the following conditions: Column, XBridge Prep Shield RP18, 5 um, 19*150 mm; mobile phase, CH$_3$CN/H$_2$O (0.05% TFA) =40% increasing to CH$_3$CN/H$_2$O (0.05% TFA)=75% within 10 min; Detector, UV 254 nm. This resulted in 79.6 mg (71%) of 2,5-difluoro-4-[3-fluoro-5-(trifluoromethyl)phenoxy]-N-(1,2,4-thiadiazol-5-yl)benzene-1-sulfonamide as a white solid.

LC-MS (ES, m/z): [M+H]$^+$=456.
$^1$H-NMR (300 MHz, DMSO, ppm): δ 8.91 (s, 1H), 7.88-7.82 (m, 1H), 7.59-7.24 (m, 4H).

Example 34

4-[3-bromo-5-(trifluoromethyl)phenoxy]-2,5-difluoro-N-(1,2,4-thiadiazol-5-yl)benzene-1-sulfonamide

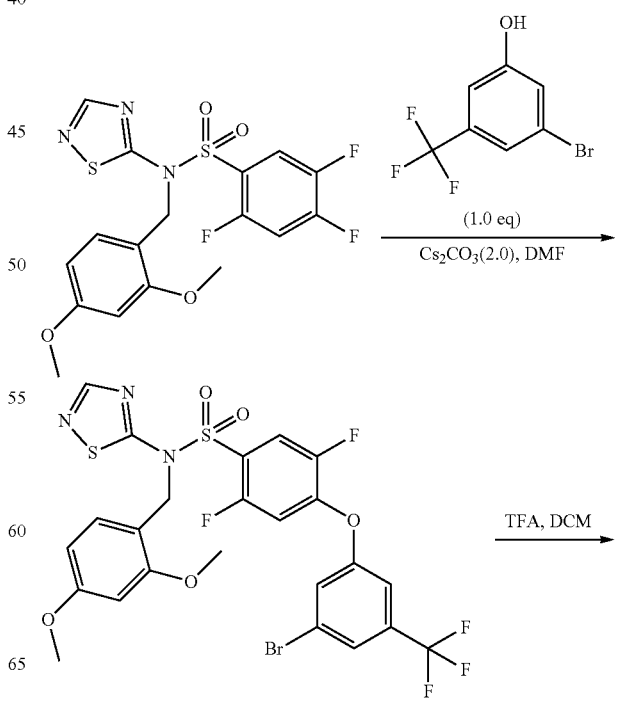

-continued

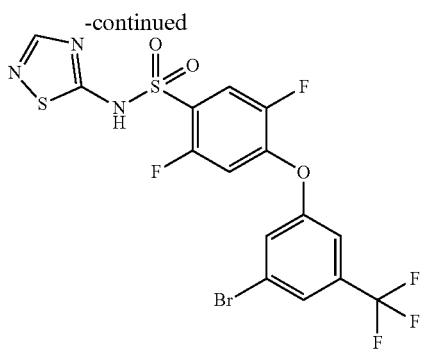

Step 1. Synthesis of 4-[3-bromo-5-(trifluoromethyl)phenoxy]-N-[(2,4-dimethoxyphenyl)methyl]-2,5-difluoro-N-(1,2,4-thiadiazol-5-yl)benzene-1-sulfonamide

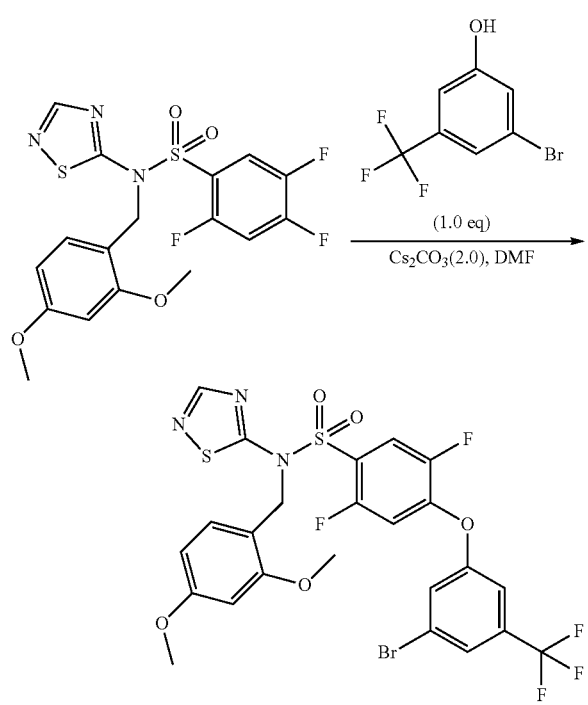

Into a 50-mL round-bottom flask, was placed a solution of N-[(2,4-dimethoxyphenyl)methyl]-2,4,5-trifluoro-N-(1,2,4-thiadiazol-5-yl)benzene-1-sulfonamide (150 mg, 0.34 mmol, 1.00 equiv) in N,N-dimethylformamide (20 mL). To the solution were added 3-bromo-5-(trifluoromethyl)phenol (81 mg, 0.34 mmol, 1.00 equiv) and Cs₂CO₃ (220 mg, 0.67 mmol, 2.00 equiv). The resulting solution was stirred for 16 h at room temperature. The resulting solution was extracted with ethyl acetate (3×20 mL) and the organic layers combined and concentrated under vacuum. The residue was applied onto a silica gel column with ethyl acetate/petroleum ether (1:5). This resulted in 170 mg (76%) of 4-[3-bromo-5-(trifluoromethyl)phenoxy]-N-[(2,4-dimethoxyphenyl)methyl]-2,5-difluoro-N-(1,2,4-thiadiazol-5-yl)benzene-1-sulfonamide as a white solid.

Step 2. Synthesis of 4-[3-bromo-5-(trifluoromethyl)phenoxy]-2,5-difluoro-N-(1,2,4-thiadiazol-5-yl)benzene-1-sulfonamide

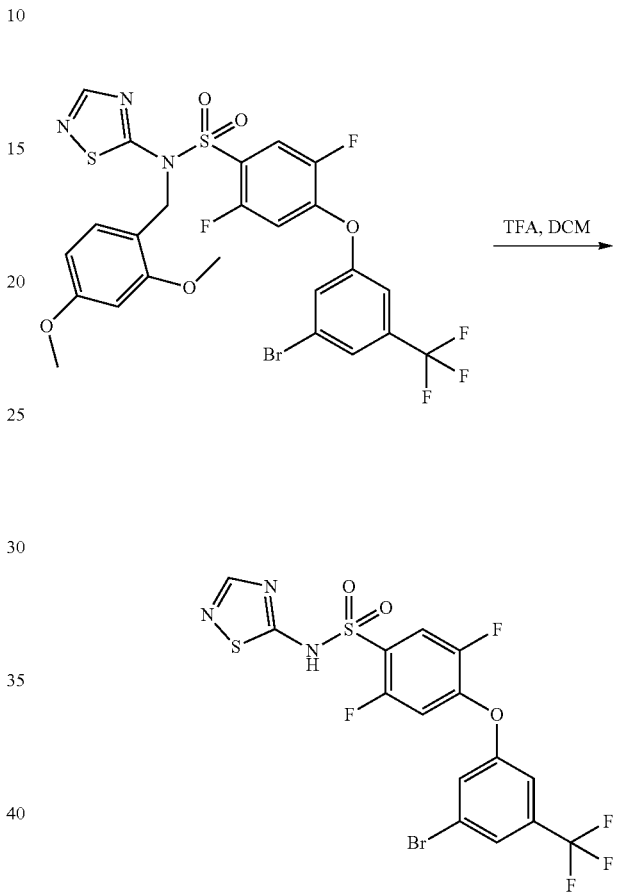

Into a 25-mL round-bottom flask, was placed a solution of 4-[3-bromo-5-(trifluoromethyl)phenoxy]-N-[(2,4-dimethoxyphenyl)methyl]-2,5-difluoro-N-(1,2,4-thiadiazol-5-yl)benzene-1-sulfonamide (170 mg, 0.26 mmol, 1.00 equiv) in dichloromethane (10 mL). To the solution was added trifluoroacetic acid (1 mL). The resulting solution was stirred for 16 h at room temperature. The crude product was purified by Prep-HPLC with conditions: Column, XBridge Prep Shield RP18, 5 um, 19×150 mm; Mobile phase, H₂O (0.05% TFA)/CH₃CN (10%-80% in 8 min); Detector, 254 nm, 220 nm; RT=6.5 min. This resulted in 58.8 mg (45%) of 4-[3-bromo-5-(trifluoromethyl)phenoxy]-2,5-difluoro-N-(1,2,4-thiadiazol-5-yl)benzene-1-sulfonamide as a white solid.

LC-MS: (ES, m/z): [M+H]⁺ 516

¹H-NMR: (300 MHz, DMSO, ppm) δ 7.41-7.47 (m, 1H), 7.66 (s, 1H), 7.82-7.91 (m, 3H), 8.63 (s, 1H).

Example 35

Synthesis of 2,5-difluoro-4-[3-methoxy-5-(trifluoromethyl)phenoxy]-N-(1,2,4-thiadiazol-5-yl)benzene-1-sulfonamide

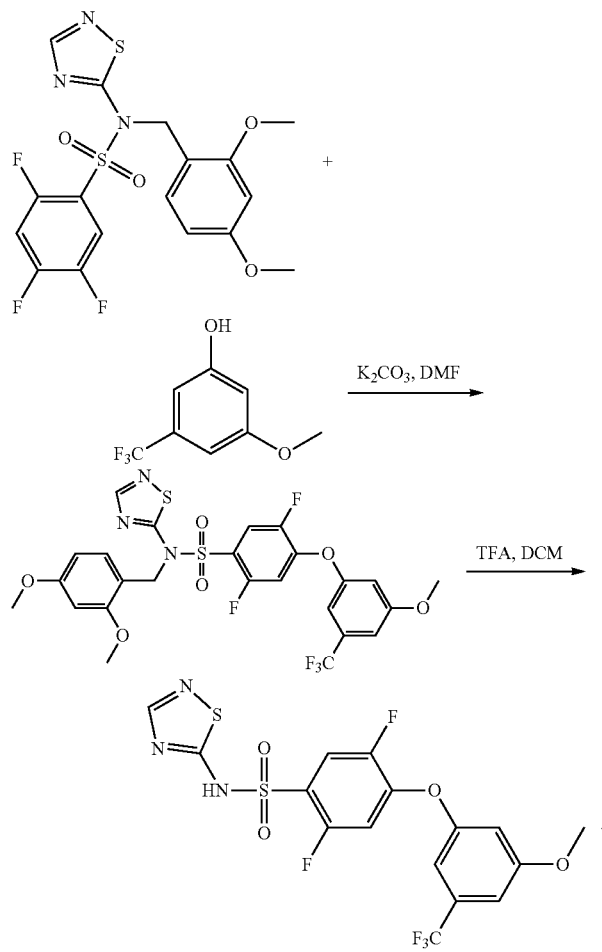

Step 1. Synthesis of N-[(2,4-dimethoxyphenyl)methyl]-2,5-difluoro-4-[3-methoxy-5-(trifluoromethyl)phenoxy]-N-(1,2,4-thiadiazol-5-yl)benzene-1-sulfonamide

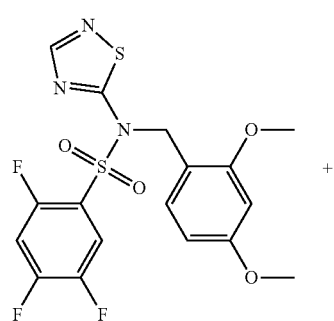

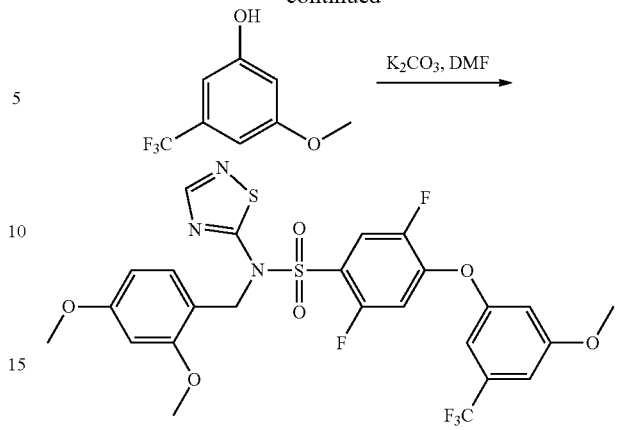

Into a 50-mL round-bottom flask, was placed N-[(2,4-dimethoxyphenyl)methyl]-2,4,5-trifluoro-N-(1,2,4-thiadiazol-5-yl)benzene-1-sulfonamide (150 mg, 0.34 mmol, 1.00 equiv), N,N-dimethylformamide (5 mL), potassium carbonate (93 mg, 0.67 mmol, 2.00 equiv), 3-methoxy-5-(trifluoromethyl)phenol (65 mg, 0.34 mmol, 1.00 equiv). The resulting reaction was stirred overnight at room temperature. The reaction was then quenched by the addition of 100 mL of water, extracted with 3×50 mL of ethyl acetate, and the organic layers were combined and concentrated in vacuo. The residue was purified by silica gel column chromatography with ethyl acetate/petroleum ether (1:3). This resulted in 180 mg (87%) of N-[(2,4-dimethoxyphenyl)methyl]-2,5-difluoro-4-[3-methoxy-5-(trifluoromethyl)phenoxy]-N-(1,2,4-thiadiazol-5-yl)benzene-1-sulfonamide as an off-white solid.

Step 2. Synthesis of 2,5-difluoro-4-[3-methoxy-5-(trifluoromethyl)phenoxy]-N-(1,2,4-thiadiazol-5-yl)benzene-1-sulfonamide

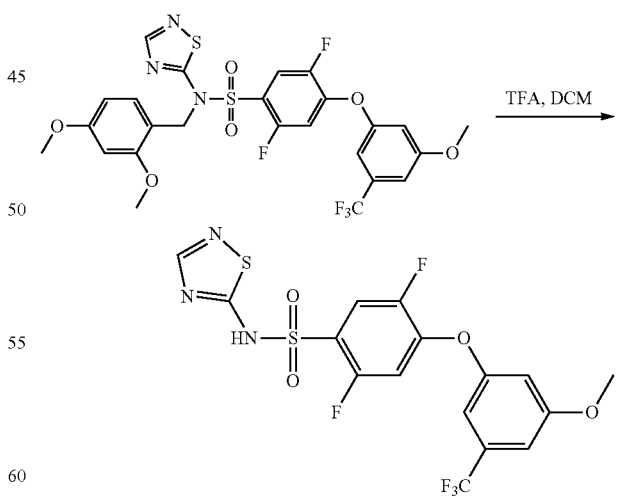

Into a 50-mL round-bottom flask, was placed N-[(2,4-dimethoxyphenyl)methyl]-2,5-difluoro-4-[3-methoxy-5-(trifluoromethyl)phenoxy]-N-(1,2,4-thiadiazol-5-yl)benzene-1-sulfonamide (180 mg, 0.29 mmol, 1.00 equiv), dichloromethane (3 mL), trifluoroacetic acid (1 mL). The resulting reaction was stirred for 2 h at room temperature. The resulting mixture was concentrated in vacuo. The crude product was purified by Prep-HPLC with the following conditions: Column, XBridge Prep Shield RP18, 5 um, 19*150 mm; mobile phase, $CH_3CN/H_2O$ (0.05% TFA) =40% increasing to $CH_3CN/H_2O$ (0.05% TFA)=75% within 10 min; Detector, UV 254 nm. This resulted in 56.8 mg (42%) of 2,5-difluoro-4-[3-methoxy-5-(trifluoromethyl) phenoxy]-N-(1,2,4-thiadiazol-5-yl)benzene-1-sulfonamide as a white solid.

LC-MS (ES, m/z): [M+H]$^+$ 468.

$^1$H NMR (300 MHz, DMSO, ppm): δ 8.54 (s, 1H), 7.97-7.76 (m, 1H), 7.38-7.31 (m, 1H), 7.28-7.11 (m, 3H), 3.84 (s, 3H).

Example 36

3-{2,5-difluoro-4-[(1,2,4-thiadiazol-5-yl)sulfamoyl] phenoxy}-N-ethyl-5 (trifluoromethyl)benzamide (Waters)): Column, SunFire Prep C18, 19*150 mm 5 um mobile phase, water with 0.05% TFA and $CH_3CN$ (10.0% $CH_3CN$ up to 90.0% in 7 min, up to 95.0% in 1 min, down to 10.0% in 1 min); Detector, UV 254 nm. This resulted in 16 mg (19%) of 3-[2,5-difluoro-4-[(1,2,4-thiadiazol-5-yl) sulfamoyl]phenoxy]-N-ethyl-5-(trifluoromethyl)benzamide as a white solid.

LC-MS: (ES, m/z): [M+H]$^+$ 509

$^1$H-NMR: (400 MHz, $D_2O$+DMSO-$d_6$, ppm): δ8.79-8.76 (m, 1H), 8.17 (s, 1H), 8.02 (s, 1H), 7.80-7.71 (m, 3H), 7.34-7.30 (m, 1H), 3.32-3.25 (m, 2H), 1.13-1.09 (t, 3H).

Example 37

Synthesis of 4-[3-chloro-5-(trifluoromethyl)phenoxy]-2,5-difluoro-N-(1,2,4-thiadiazol-5-yl)benzene-1-sulfonamide

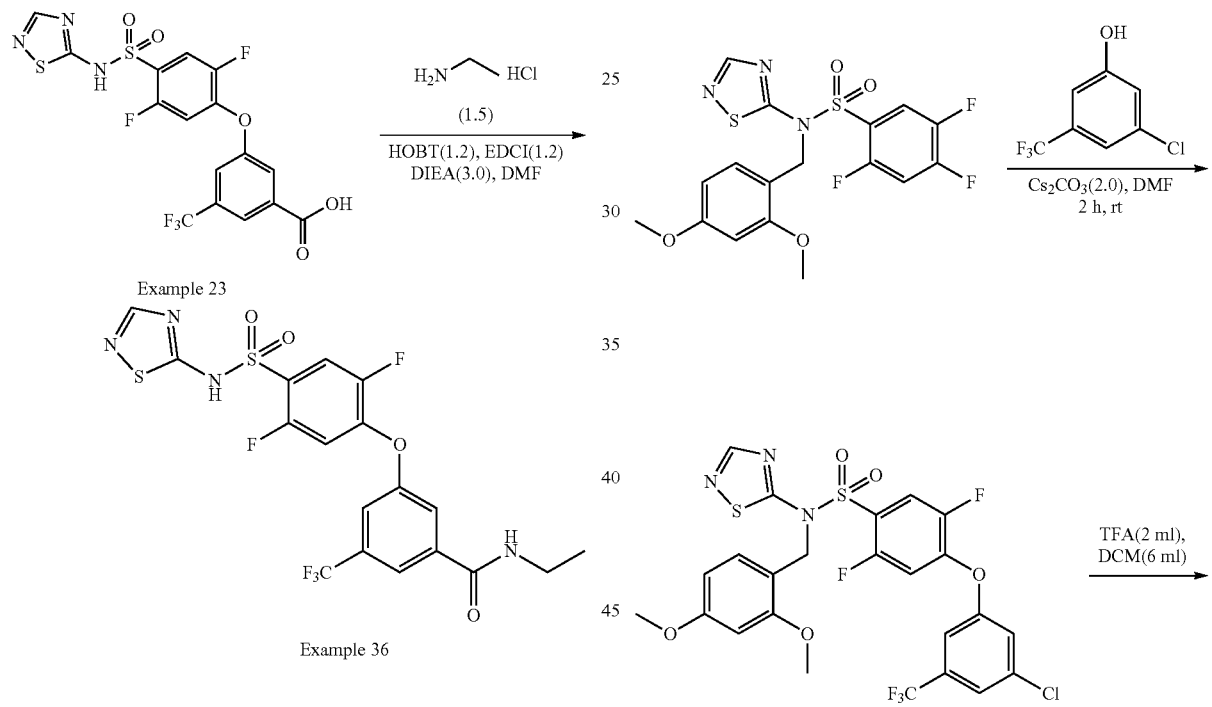
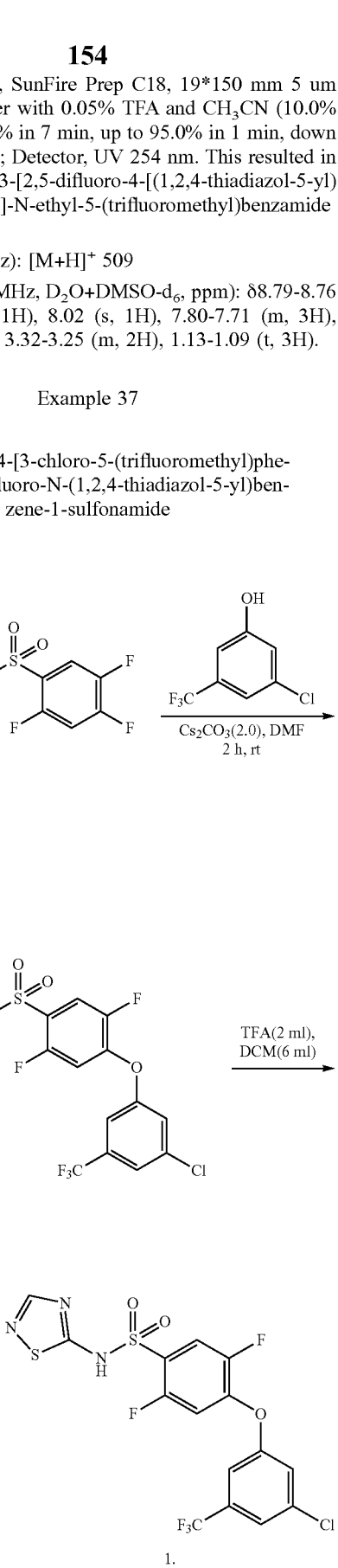

Step 1. Synthesis of 3-[2,5-difluoro-4-[(1,2,4-thiadiazol-5-yl)sulfamoyl]phenoxy]-N-ethyl-5-(trifluoromethyl)benzamide Into a 25-mL round-bottom flask, were placed a solution 3-[2,5-difluoro-4-[(1,2,4-thiadiazol-5-yl)sulfamoyl]phenoxy]-5-(trifluoromethyl)benzoic acid (80 mg, 0.17 mmol, 1.00 equiv), HOBT (27 mg, 0.20 mmol, 1.20 equiv), EDCI (38 mg, 0.20 mmol, 1.20 equiv), DIEA (64 mg, 0.50 mmol, 3.00 equiv), ethylamine hydrochloride (20 mg, 1.50 equiv) in N,N-dimethylformamide (5 mL). The resulting solution was stirred for 16 h at 50° C. The reaction was then quenched by the addition of water. The resulting solution was extracted with ethyl acetate and the organic layers combined. The resulting mixture was washed with brine, dried over anhydrous sodium sulfate and concentrated under vacuum. The crude product (45 mg) was purified by Prep-HPLC with the following conditions (1 #-Pre-HPLC-005

Step 1. Synthesis of 4-[3-chloro-5-(trifluoromethyl)phenoxy]-N-[(2,4-dimethoxyphenyl)methyl]-2,5-difluoro-N-(1,2,4-thiadiazol-5-yl)benzene-1-sulfonamide

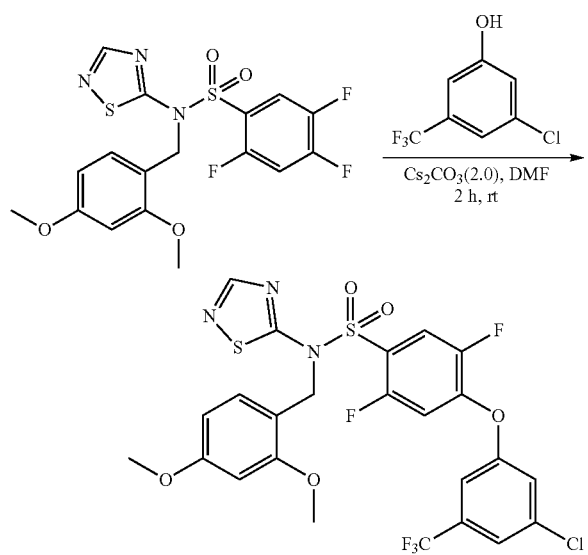

Into a 50-mL round-bottom flask, were placed a solution of N-[(2,4-dimethoxyphenyl)methyl]-2,4,5-trifluoro-N-(1,2,4-thiadiazol-5-yl)benzene-1-sulfonamide (150 mg, 0.34 mmol, 1.00 equiv), Cs₂CO₃ (220 mg, 0.68 mmol, 2.00 equiv), 3-chloro-5-(trifluoromethyl)phenol (66 mg, 0.34 mmol, 1.00 equiv) in N,N-dimethylformamide (8 mL). The resulting reaction was stirred for 2 h at room temperature. The reaction was then quenched by the addition of water, extracted with ethyl acetate, and the organic layers were combined. The resulting mixture was washed with brine, dried over anhydrous sodium sulfate and concentrated in vacuo. This resulted in 170 mg (81%) of 4-[3-chloro-5-(trifluoromethyl)phenoxy]-N-[(2,4-dimethoxyphenyl)methyl]-2,5-difluoro-N-(1,2,4-thiadiazol-5-yl)benzene-1-sulfonamide as a yellow oil.

Step 2. Synthesis of 4-[3-chloro-5-(trifluoromethyl)phenoxy]-2,5-difluoro-N-(1,2,4-thiadiazol-5-yl)benzene-1-sulfonamide

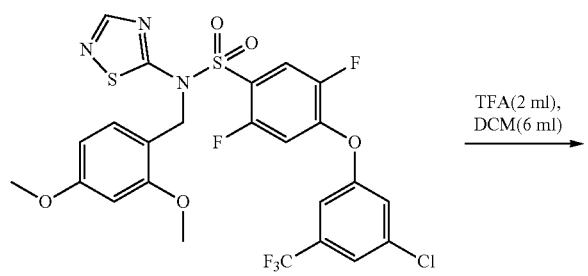

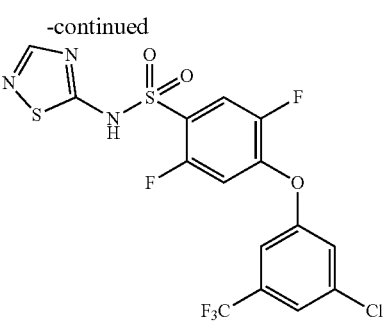

Into a 25-mL round-bottom flask, was placed 4-[3-chloro-5-(trifluoromethyl)phenoxy]-N-[(2,4-dimethoxyphenyl)methyl]-2,5-difluoro-N-(1,2,4-thiadiazol-5-yl)benzene-1-sulfonamide (100 mg, 0.16 mmol, 1.00 equiv), dichloromethane (3 mL), trifluoroacetic acid (1 mL). The resulting reaction was stirred for 1 h at room temperature. The resulting mixture was concentrated in vacuo. The crude product (75 mg) was purified by Prep-HPLC with the following conditions (1 #-Pre-HPLC-005(Waters)): Column, SunFire Prep C18, 19*150 mm 5 um; mobile phase, water with 0.05% TFA and CH₃CN (10.0% CH₃CN up to 90.0% in 7 min, up to 95.0% in 1 min, down to 10.0% in 1 min); Detector, UV 254 nm. This resulted in 35 mg (46%) of 4-[3-chloro-5-(trifluoromethyl)phenoxy]-2,5-difluoro-N-(1,2,4-thiadiazol-5-yl)benzene-1-sulfonamide as a white solid.

LC-MS (ES, m/z): [M+H]⁺ 472.

¹H-NMR (400 MHz, DMSO-d₆, ppm): δ 7.91 (s, 1H), 7.69-7.64 (m, 2H), 7.59 (s, 1H), 7.52 (s, 1H), 7.32-7.28 (m, 1H).

Example 38

2,5-difluoro-4-[3-propoxy-5-(trifluoromethyl)phenoxy]-N-(1,2,4-thiadiazol-5-yl)benzene-1-sulfonamide

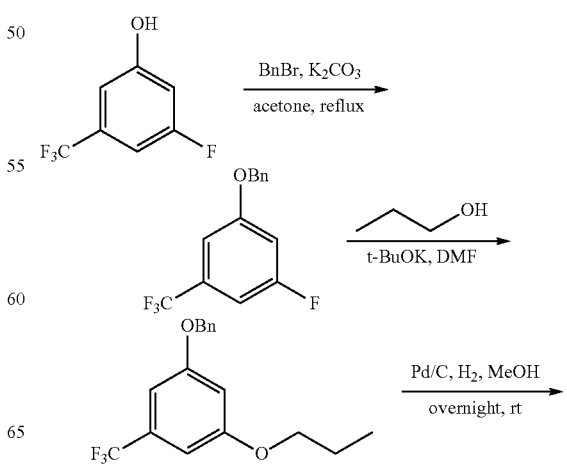

-continued

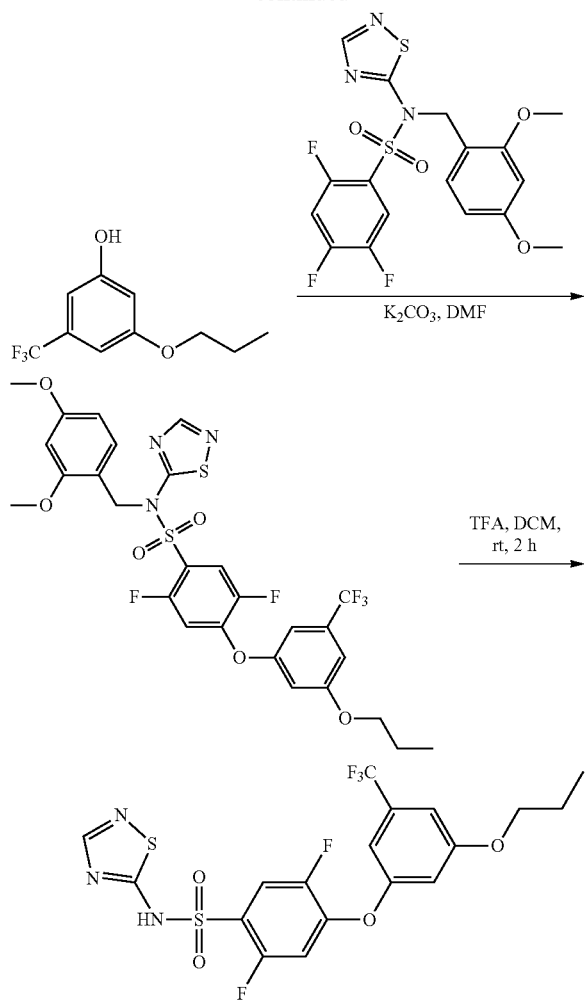

Step 1. Synthesis of 1-(benzyloxy)-3-fluoro-5-(trifluoromethyl)benzene

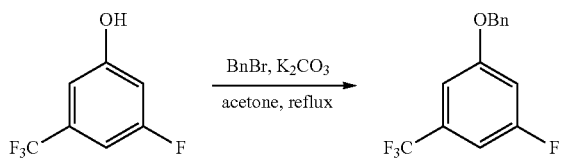

Into a 100-mL round-bottom flask, was placed 3-fluoro-5-(trifluoromethyl)phenol (500 mg, 2.78 mmol, 1.00 equiv), acetone (10 mL), BnBr (475 mg, 2.78 mmol, 1.00 equiv), potassium carbonate (575 mg, 4.16 mmol, 1.50 equiv). The resulting solution was heated to reflux overnight. The reaction was then quenched by the addition of 100 mL of water. The resulting solution was extracted with 3×50 mL of ethyl acetate and the organic layers combined and concentrated under vacuum. The residue was applied onto a silica gel column with petroleum ether. This resulted in 780 mg (crude) of 1-(benzyloxy)-3-fluoro-5-(trifluoromethyl)benzene as colorless oil.

Step 2. Synthesis of 1-(benzyloxy)-3-propoxy-5-(trifluoromethyl)benzene

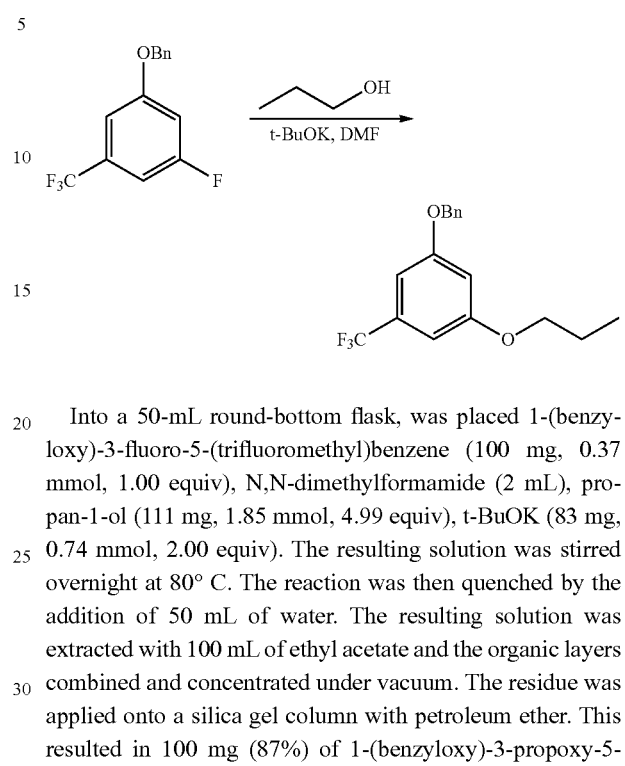

Into a 50-mL round-bottom flask, was placed 1-(benzyloxy)-3-fluoro-5-(trifluoromethyl)benzene (100 mg, 0.37 mmol, 1.00 equiv), N,N-dimethylformamide (2 mL), propan-1-ol (111 mg, 1.85 mmol, 4.99 equiv), t-BuOK (83 mg, 0.74 mmol, 2.00 equiv). The resulting solution was stirred overnight at 80° C. The reaction was then quenched by the addition of 50 mL of water. The resulting solution was extracted with 100 mL of ethyl acetate and the organic layers combined and concentrated under vacuum. The residue was applied onto a silica gel column with petroleum ether. This resulted in 100 mg (87%) of 1-(benzyloxy)-3-propoxy-5-(trifluoromethyl)benzene as colorless oil.

Step 3. Synthesis of 3-propoxy-5-(trifluoromethyl)phenol

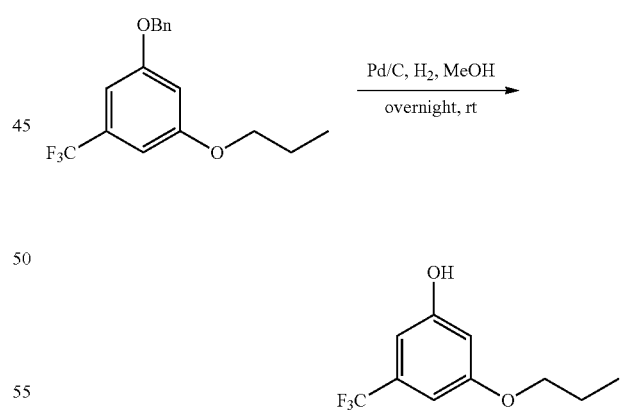

Into a 50-mL round-bottom flask, was placed 1-(benzyloxy)-3-propoxy-5-(trifluoromethyl)benzene (100 mg, 0.32 mmol, 1.00 equiv), methanol (3 mL), Palladium carbon (50 mg). To the above $H_2$ was introduced in. The resulting solution was stirred overnight at room temperature. The solids were filtrate out. The resulting mixture was concentrated under vacuum. This resulted in 60 mg (85%) of 3-propoxy-5-(trifluoromethyl)phenol as colorless oil.

Step 4. Synthesis of N-[(2,4-dimethoxyphenyl)methyl]-2,5-difluoro-4-[3-propoxy-5-(trifluoromethyl)phenoxy]-N-(1,2,4-thiadiazol-5-yl)benzene-1-sulfonamide

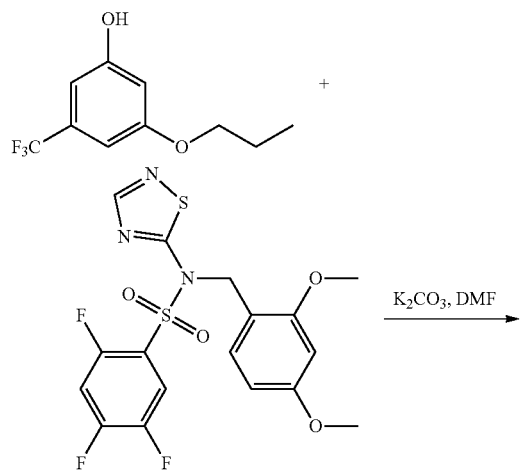

Step 5. Synthesis of 2,5-difluoro-4-[3-propoxy-5-(trifluoromethyl)phenoxy]-N-(1,2,4-thiadiazol-5-yl)benzene-1-sulfonamide

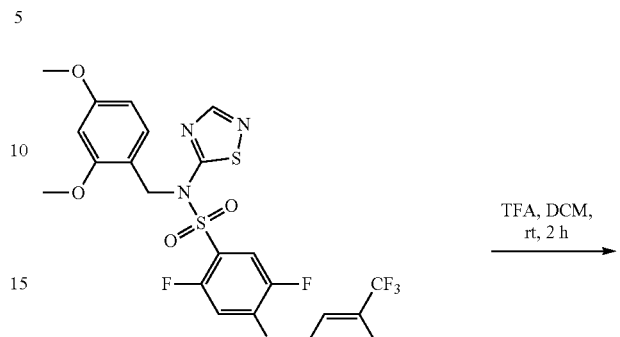

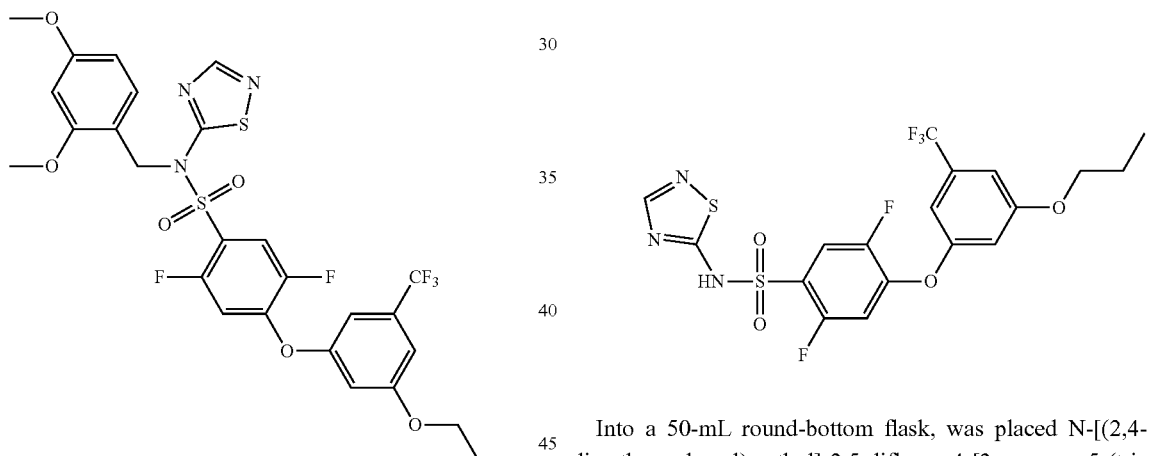

Into a 50-mL round-bottom flask, was placed 3-propoxy-5-(trifluoromethyl)phenol (60 mg, 0.27 mmol, 1.00 equiv), N,N-dimethylformamide (3 mL), N-[(2,4-dimethoxyphenyl)methyl]-2,4,5-trifluoro-N-(1,2,4-thiadiazol-5-yl)benzene-1-sulfonamide (122 mg, 0.27 mmol, 1.01 equiv), potassium carbonate (75 mg, 0.54 mmol, 1.99 equiv). The resulting solution was stirred overnight at room temperature. The reaction was then quenched by the addition of 50 mL of water. The resulting solution was extracted with 3×20 mL of ethyl acetate and the organic layers combined and concentrated under vacuum. The residue was applied onto a silica gel column with ethyl acetate/petroleum ether (1:3). This resulted in 120 mg (68%) of N-[(2,4-dimethoxyphenyl)methyl]-2,5-difluoro-4-[3-propoxy-5-(trifluoromethyl)phenoxy]-N-(1,2,4-thiadiazol-5-yl)benzene-1-sulfonamide as a white solid.

Into a 50-mL round-bottom flask, was placed N-[(2,4-dimethoxyphenyl)methyl]-2,5-difluoro-4-[3-propoxy-5-(trifluoromethyl)phenoxy]-N-(1,2,4-thiadiazol-5-yl)benzene-1-sulfonamide (120 mg, 0.19 mmol, 1.00 equiv), dichloromethane (3 mL), trifluoroacetic acid (1 mL). The resulting solution was stirred for 2 h at room temperature. The resulting mixture was concentrated under vacuum. The crude product was purified by Prep-HPLC with the following conditions: Column, XBridge Prep Shield RP18, 5 um, 19*150 mm; mobile phase, $CH_3CN/H_2O$ (0.05% TFA) =40% increasing to $CH_3CN/H_2O$ (0.05% TFA)=75% within 10 min; Detector, UV 254 nm. This resulted in 57.6 mg (63%) of 2,5-difluoro-4-[3-propoxy-5-(trifluoromethyl)phenoxy]-N-(1,2,4-thiadiazol-5-yl)benzene-1-sulfonamide as a off-white solid.

LC-MS: (ES, m/z): $[M+H]^+$ 496

$^1$H-NMR (400 MHz, DMSO, ppm): δ8.53 (s, 1H), δ7.83 (dd, 1H), δ7.31 (dd, 1H), δ7.13-7.07 (m, 3H), δ4.01 (t, 2H), δ1.77-1.68 (m, 2H), δ0.97 (t, 3H).

Example 39

3-{2,5-difluoro-4-[(1,2,4-thiadiazol-5-yl)sulfamoyl]phenoxy}-N,N-dimethyl-5-(trifluoromethyl)benzamide

Example 40

2,5-difluoro-4-{3-[(pyrrolidin-1-yl)carbonyl]-5-(trifluoromethyl)phenoxy}-N-(1,2,4-thiadiazol-5-yl)benzene-1-sulfonamide

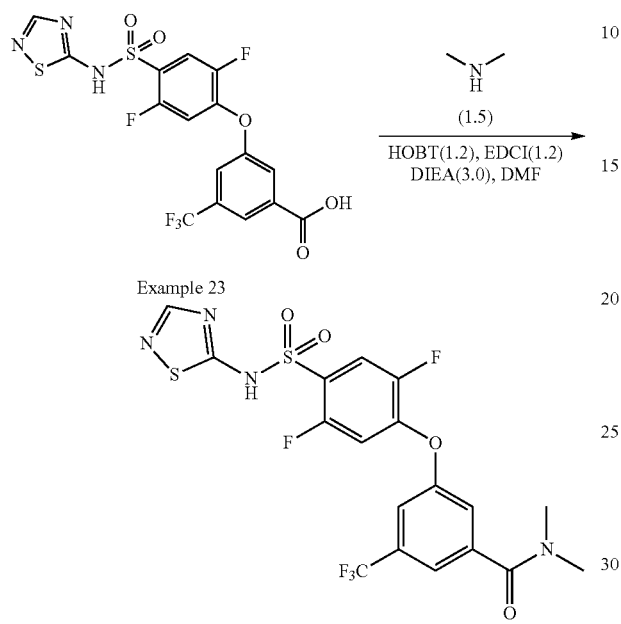

Step 1. Synthesis of 3-[2,5-difluoro-4-[(1,2,4-thiadiazol-5-yl)sulfamoyl]phenoxy]-N,N-dimethyl-5-(trifluoromethyl)benzamide Into a 25-mL round-bottom flask, were placed a solution of 3-[2,5-difluoro-4-[(1,2,4-thiadiazol-5-yl)sulfamoyl]phenoxy]-5-(trifluoromethyl)benzoic acid (80 mg, 0.17 mmol, 1.00 equiv), HOBT (27 mg, 0.20 mmol, 1.20 equiv), EDCI (38 mg, 0.20 mmol, 1.20 equiv), DIEA (64 mg, 0.50 mmol, 3.00 equiv), dimethylamine (20 mg, 0.44 mmol, 1.50 equiv) in N,N-dimethylformamide (5 mL). The resulting solution was stirred for 2 h at 50° C. The reaction was then quenched by the addition of water. The resulting solution was extracted with ethyl acetate and the organic layers combined. The resulting mixture was washed with brine, dried over anhydrous sodium sulfate and concentrated under vacuum. The crude product (45 mg) was purified by Prep-HPLC with the following conditions (1 #-Pre-HPLC-005 (Waters)): Column, SunFire Prep C18, 19*150 mm 5 um; mobile phase, water with 0.05% TFA and CH$_3$CN (10.0% CH$_3$CN up to 90.0% in 7 min, up to 95.0% in 1 min, down to 10.0% in 1 min); Detector, UV 254 nm. This resulted in 15 mg (18%) of 3-[2,5-difluoro-4-[(1,2,4-thiadiazol-5-yl)sulfamoyl]phenoxy]-N,N-dimethyl-5-(trifluoromethyl)benzamide as a white solid.

LC-MS: (ES, m/z): [M+H]$^+$ 509

$^1$H-NMR: (300 MHz, DMSO-d$_6$, ppm): 8.52 (s, 1H), 7.86-7.81 (m, 1H), 7.68 (s, 3H), 7.60 (s, 1H), 7.52 (s, 1H), 7.46-7.40 (m, 1H), 2.97-2.88 (d, 6H).

Step 1. Synthesis of 2,5-difluoro-4-[3-[(pyrrolidin-1-yl)carbonyl]-5-(trifluoromethyl)phenoxy]-N-(1,2,4-thiadiazol-5-yl)benzene-1-sulfonamide Into a 25-mL round-bottom flask, were placed a solution of 3-[2,5-difluoro-4-[(1,2,4-thiadiazol-5-yl)sulfamoyl]phenoxy]-5-(trifluoromethyl)benzoic acid (80 mg, 0.17 mmol, 1.00 equiv), BOP (110 mg, 0.25 mmol, 1.50 equiv), DIEA (64 mg, 0.50 mmol, 3.00 equiv), pyrrolidine (118 mg, 1.66 mmol, 10.00 equiv) in N,N-dimethylformamide (5 mL). The resulting solution was stirred for 16 h at 80° C. The reaction was then quenched by the addition of water. The resulting solution was extracted with ethyl acetate and the organic layers combined. The resulting mixture was washed with brine, dried over anhydrous sodium sulfate and concentrated under vacuum. The crude product (40 mg) was purified by Prep-HPLC with the following conditions (1 #-Pre-HPLC-005(Waters)): Column, SunFire Prep C18, 19*150 mm 5 um; mobile phase, water with 0.05% TFA and CH$_3$CN (10.0% CH$_3$CN up to 90.0% in 7 min, up to 95.0% in 1 min, down to 10.0% in 1 min); Detector, UV 254 nm. This resulted in 13 mg (15%) of 2,5-difluoro-4-[3-[(pyrrolidin-1-yl)carbonyl]-5-(trifluoromethyl)phenoxy]-N-(1,2,4-thiadiazol-5-yl)benzene-1-sulfonamide as a white solid.

LC-MS: (ES, m/z): [M+H]$^+$ 535

$^1$H-NMR: (300 MHz, DMSO-d$_6$, ppm): 8.59 (s, 1H), 7.88-7.80 (m, 1H), 7.70-7.68 (m, 2H), 7.59 (s, 1H), 7.43-7.38 (m, 1H), 3.81-3.70 (m, 1H), 3.37-3.29 (m, 2H), 1.86-1.79 (m, 4H).

Example 41

2,5-difluoro-4-[3-methoxy-5-(trifluoromethyl) phenoxy]-N-(3-methyl-1,2,4-thiadiazol-5-yl)benzene-1-sulfonamide

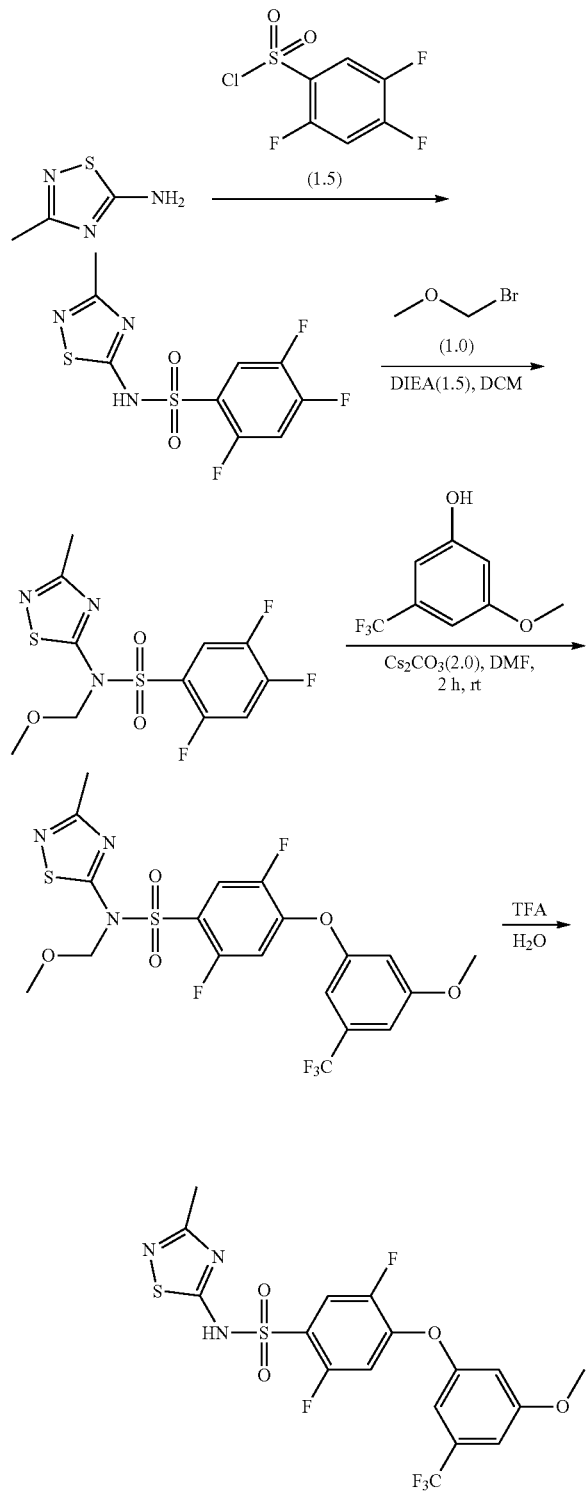

Step 1. Synthesis of 2,4,5-trifluoro-N-(3-methyl-1,2,4-thiadiazol-5-yl)benzene-1-sulfonamide

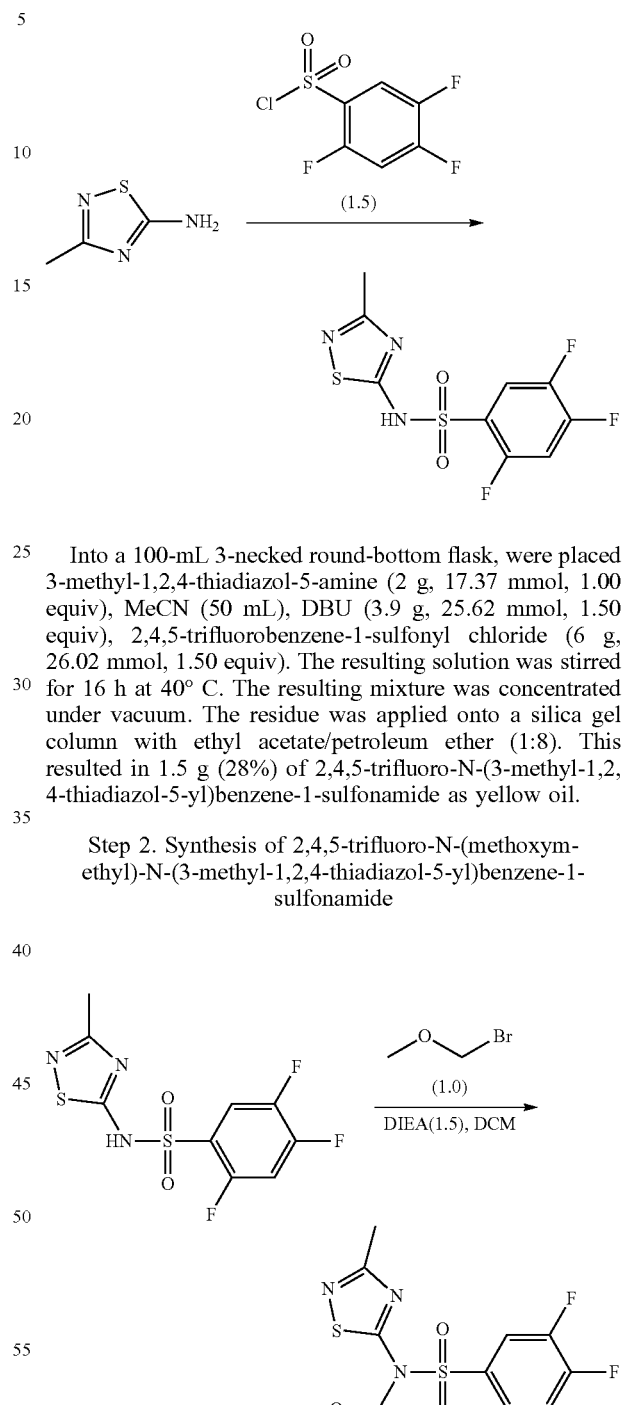

Into a 100-mL 3-necked round-bottom flask, were placed 3-methyl-1,2,4-thiadiazol-5-amine (2 g, 17.37 mmol, 1.00 equiv), MeCN (50 mL), DBU (3.9 g, 25.62 mmol, 1.50 equiv), 2,4,5-trifluorobenzene-1-sulfonyl chloride (6 g, 26.02 mmol, 1.50 equiv). The resulting solution was stirred for 16 h at 40° C. The resulting mixture was concentrated under vacuum. The residue was applied onto a silica gel column with ethyl acetate/petroleum ether (1:8). This resulted in 1.5 g (28%) of 2,4,5-trifluoro-N-(3-methyl-1,2,4-thiadiazol-5-yl)benzene-1-sulfonamide as yellow oil.

Step 2. Synthesis of 2,4,5-trifluoro-N-(methoxymethyl)-N-(3-methyl-1,2,4-thiadiazol-5-yl)benzene-1-sulfonamide Into a 50-mL round-bottom flask, were placed 2,4,5-trifluoro-N-(3-methyl-1,2,4-thiadiazol-5-yl)benzene-1-sulfonamide (310 mg, 1.00 mmol, 1.00 equiv), dichloromethane (5 mL), DIEA (155 mg, 1.20 mmol, 1.20 equiv), bromo(methoxy)methane (125 mg, 1.00 mmol, 1.00 equiv). The resulting solution was stirred for 5 min at room temperature. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 360 mg (crude) of 2,4,5-trifluoro-N-(methoxymethyl)-N-(3-methyl-1,2,4-thiadiazol-5-yl)benzene-1-sulfonamide as yellow oil.

Step 3. Synthesis of 2,5-difluoro-4-[3-methoxy-5-(trifluoromethyl)phenoxy]-N-(methoxymethyl)-N-(3-methyl-1,2,4-thiadiazol-5-yl)benzene-1-sulfonamide

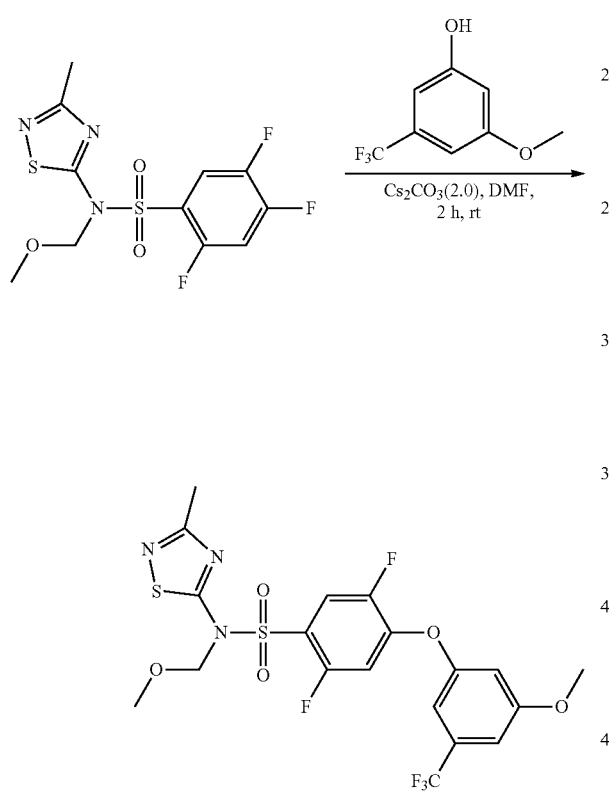

Into a 25-mL round-bottom flask, were placed 2,4,5-trifluoro-N-(methoxymethyl)-N-(3-methyl-1,2,4-thiadiazol-5-yl)benzene-1-sulfonamide (100 mg, 0.28 mmol, 1.00 equiv), N,N-dimethylformamide (5 mL), Cs$_2$CO$_3$ (185 mg, 0.57 mmol, 2.00 equiv), 3-methoxy-5-(trifluoromethyl)phenol (54.4 mg, 0.28 mmol, 1.00 equiv). The resulting solution was stirred for 2 h at room temperature. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 110 mg (74%) of 2,5-difluoro-4-[3-methoxy-5-(trifluoromethyl)phenoxy]-N-(methoxymethyl)-N-(3-methyl-1,2,4-thiadiazol-5-yl)benzene-1-sulfonamide as a yellow oil.

Step 4. Synthesis of 2,5-difluoro-4-[3-methoxy-5-(trifluoromethyl)phenoxy]-N-(3-methyl-1,2,4-thiadiazol-5-yl)benzene-1-sulfonamide

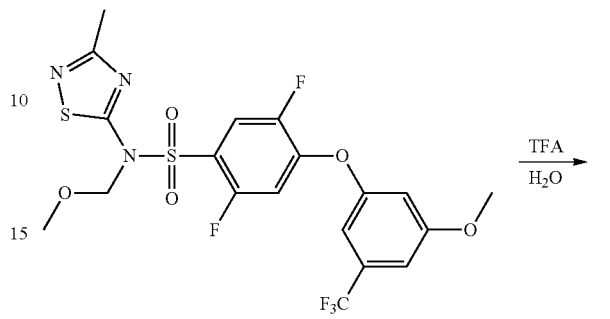

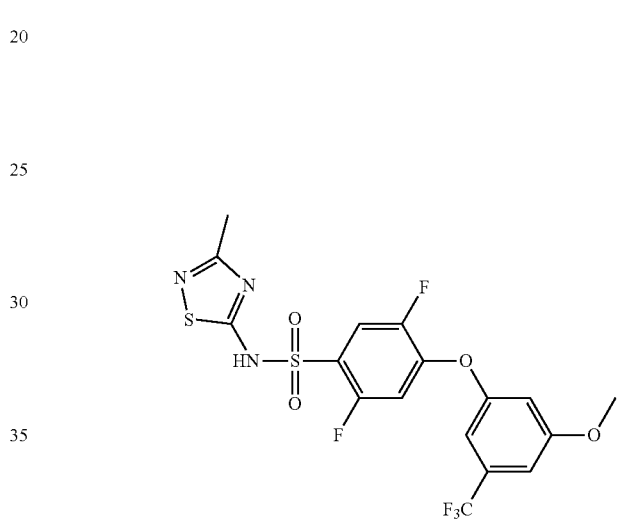

Into a 25-mL round-bottom flask, was placed 2,5-difluoro-4-[3-methoxy-5-(trifluoromethyl)phenoxy]-N-(methoxymethyl)-N-(3-methyl-1,2,4-thiadiazol-5-yl)benzene-1-sulfonamide (100 mg, 0.19 mmol, 1.00 equiv), water (3 mL), trifluoroacetic acid (2 mL). The resulting solution was stirred for 16 h at 80° C. The pH value of the solution was adjusted to 8 with sodium bicarbonate (1 mol/L). The resulting solution was extracted with ethyl acetate and the organic layers combined. The resulting mixture was washed with brine, dried and concentrated under vacuum. The crude product (80 mg) was purified by Prep-HPLC with the following conditions (1 #-Pre-HPLC-005(Waters)): Column, SunFire Prep C18; mobile phase, water with 0.05% TFA and CH$_3$CN (10.0% CH$_3$CN up to 90.0% in 7 min, up to 95.0% in 1 min, down to 10.0% in 1 min); Detector, UV 254 nm. This resulted in 50 mg (55%) of 2,5-difluoro-4-[3-methoxy-5-(trifluoromethyl)phenoxy]-N-(3-methyl-1,2,4-thiadiazol-5-yl)benzene-1-sulfonamide as a white solid.

LC-MS: (ES, m/z): [M+H]$^+$ 482

$^1$H-NMR: (400 MHz, DMSO-d$_6$, ppm): δ7.82-7.78 (m, 1H), 7.31-7.27 (m, 1H), 7.14 (s, 1H), 7.09-7.08 (m, 2H), 3.84 (s, 3H), 2.31 (s, 3H).

Example 42

N-(3-benzyl-1,2,4-thiadiazol-5-yl)-2,5-difluoro-4-[3-methoxy-5-(trifluoromethyl)phenoxy]benzene-1-sulfonamide

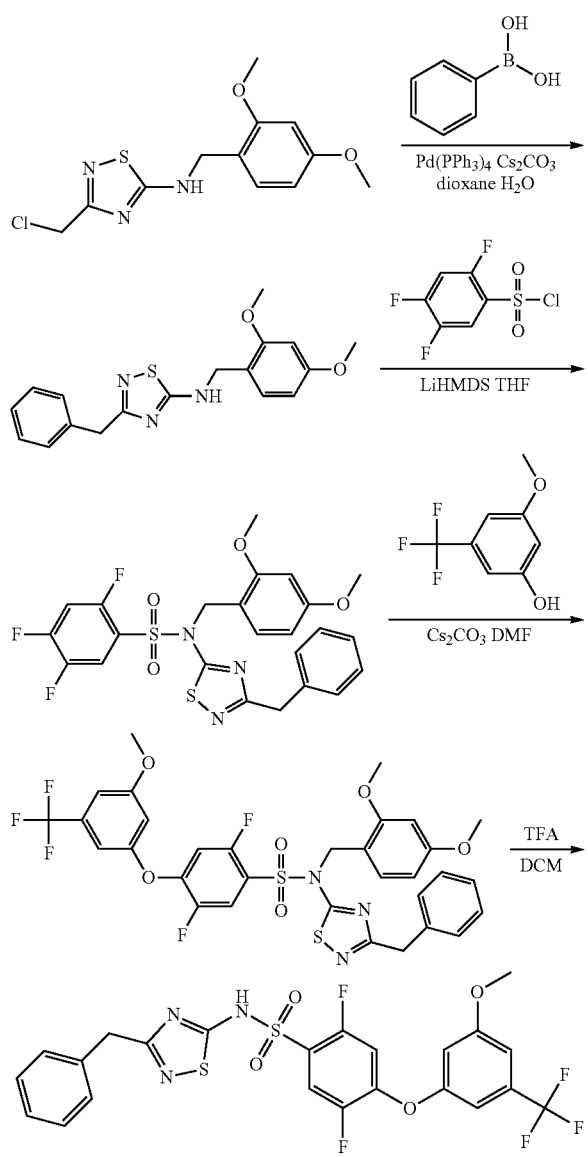

Step 1. Synthesis of 3-benzyl-N-[(2,4-dimethoxyphenyl)methyl]-1,2,4-thiadiazol-5-amine

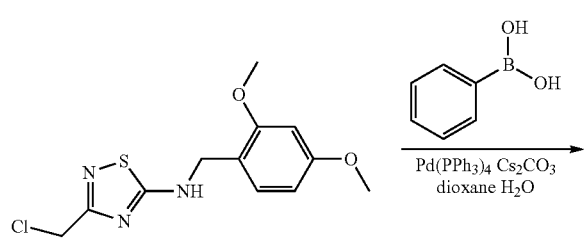

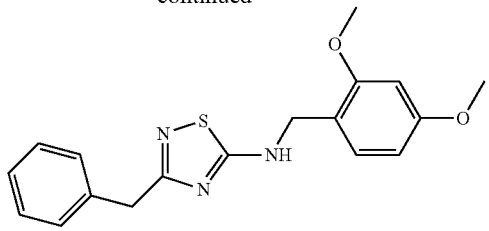

Into a 100-mL round-bottom flask purged and maintained with an inert atmosphere of nitrogen, was placed a solution of 3-(chloromethyl)-N-[(2,4-dimethoxyphenyl)methyl]-1,2,4-thiadiazol-5-amine (700 mg, 2.34 mmol, 1.00 equiv) in dioxane (16 mL). To the solution were added phenylboronic acid (337 mg, 2.76 mmol, 1.20 equiv), a solution of $Cs_2CO_3$ (1.5 g, 4.60 mmol, 2.00 equiv) in water (4 mL) and $Pd(PPh_3)_4$ (268 mg, 0.23 mmol, 0.10 equiv). The resulting solution was stirred for 16 h at 80° C. in an oil bath. The reaction was then quenched by the addition of 50 mL of water. The resulting solution was extracted with ethyl acetate (2×50 mL) and the organic layers combined. The resulting mixture was washed with brine (50 mL), dried over anhydrous sodium sulfate and concentrated under vacuum. The residue was applied onto a silica gel column with ethyl acetate/petroleum ether (1:4). This resulted in 300 mg (38%) of 3-benzyl-N-[(2,4-dimethoxyphenyl)methyl]-1,2,4-thiadiazol-5-amine as yellow oil.

Step 2. Synthesis of N-(3-benzyl-1,2,4-thiadiazol-5-yl)-N-[(2,4-dimethoxyphenyl)methyl]-2,4,5-trifluorobenzene-1-sulfonamide

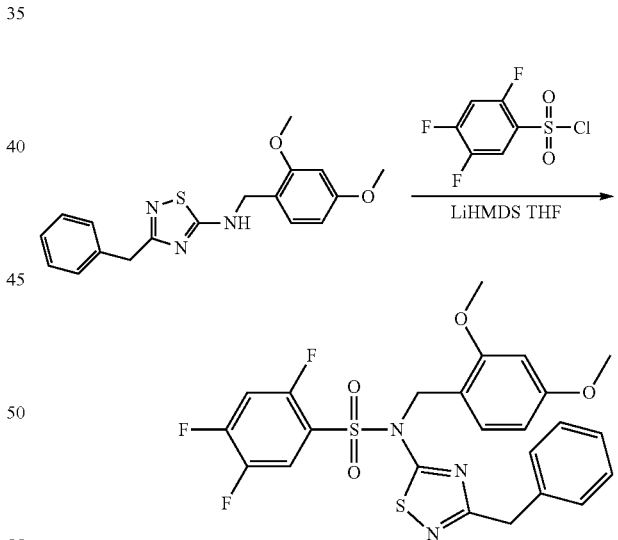

Into a 50-mL 3-necked round-bottom flask purged and maintained with an inert atmosphere of nitrogen, was placed a solution of 3-benzyl-N-[(2,4-dimethoxyphenyl)methyl]-1,2,4-thiadiazol-5-amine (155 mg, 0.45 mmol, 1.00 equiv) in tetrahydrofuran (10 mL). This was followed by the addition of LiHMDS (1.35 mL, 3.00 equiv) dropwise with stirring at −78° C. and then stirred for another two hours at this temperature. To this was added 2,4,5-trifluorobenzene-1-sulfonyl chloride (125 mg, 0.54 mmol, 1.10 equiv) at −78° C. The resulting solution was stirred for 2 h at room temperature. The reaction was then quenched by the addition of 50 mL of NH₄Cl aqueous. The resulting solution was extracted with ethyl acetate (2×100 mL) and the organic layers combined and concentrated under vacuum. The residue was applied onto a silica gel column with ethyl acetate/petroleum ether (1:10). This resulted in 170 mg (70%) of N-(3-benzyl-1,2,4-thiadiazol-5-yl)-N-[(2,4-dimethoxyphenyl)methyl]-2,4,5-trifluorobenzene-1-sulfonamide as yellow oil.

Step 3. Synthesis of N-(3-benzyl-1,2,4-thiadiazol-5-yl)-N-[(2,4-dimethoxyphenyl)methyl]-2,5-difluoro-4-[3-methoxy-5-(trifluoromethyl)phenoxy]benzene-1-sulfonamide

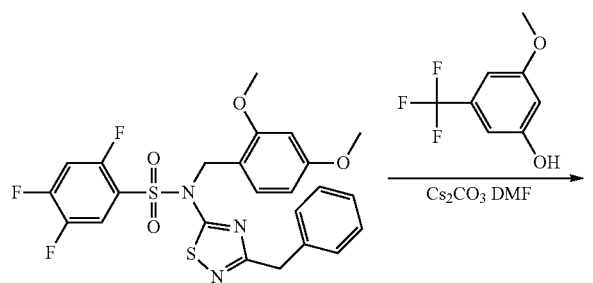

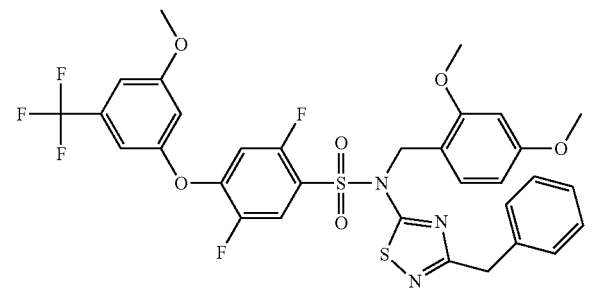

Into a 25-mL round-bottom flask purged and maintained with an inert atmosphere of nitrogen, was placed a solution of N-(3-benzyl-1,2,4-thiadiazol-5-yl)-N-[(2,4-dimethoxyphenyl)methyl]-2,4,5-trifluorobenzene-1-sulfonamide (100 mg, 0.19 mmol, 1.00 equiv) in N,N-dimethylformamide (10 mL). To the solution were added Cs₂CO₃ (121 mg, 0.37 mmol, 2.00 equiv) and 3-methoxy-5-(trifluoromethyl)phenol (35.8 mg, 0.19 mmol, 1.00 equiv). The resulting solution was stirred for 2 h at room temperature. The reaction was then quenched by the addition of 10 mL of brine. The resulting solution was extracted with ethyl acetate (2×20 mL) and the organic layers combined and concentrated under vacuum. This resulted in 100 mg (76%) of N-(3-benzyl-1,2,4-thiadiazol-5-yl)-N-[(2,4-dimethoxyphenyl)methyl]-2,5-difluoro-4-[3-methoxy-5-(trifluoromethyl)phenoxy]benzene-1-sulfonamide as yellow oil Step 4. Synthesis of N-(3-benzyl-1,2,4-thiadiazol-5-yl)-2,5-difluoro-4-[3-methoxy-5-(trifluoromethyl)phenoxy]benzene-1-sulfonamide

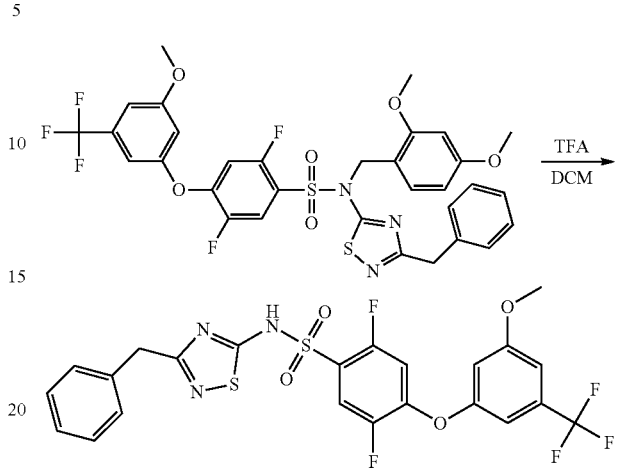

Into a 25-mL round-bottom flask, was placed a solution of N-(3-benzyl-1,2,4-thiadiazol-5-yl)-N-[(2,4-dimethoxyphenyl)methyl]-2,5-difluoro-4-[3-methoxy-5-(trifluoromethyl)phenoxy]benzene-1-sulfonamide (100 mg, 0.14 mmol, 1.00 equiv) in dichloromethane (10 mL). To the solution was added trifluoroacetic acid (5 mL). The resulting solution was stirred for 1 h at room temperature. The resulting mixture was concentrated under vacuum. The crude product (100 mg) was purified by Prep-HPLC with the following conditions (Waters): Column, X-Bridge; mobile phase, water (0.5% NH₄HCO₃)/ACN=35:65 increasing to water (0.5% NH₄HCO₃)/ACN=15:85 within 12 min; Detector, UV 254 nm. This resulted in 10.1 mg (13%) of N-(3-benzyl-1,2,4-thiadiazol-5-yl)-2,5-difluoro-4-[3-methoxy-5-(trifluoromethyl)phenoxy]benzene-1-sulfonamide as a white solid.

LC-MS: (ES, m/z): [M+H]⁺ 558

¹H-NMR: (400 MHz, DMSO-d₆, ppm): δ 7.76-7.72 (m, 1H), 7.36-7.20 (m, 6H), 7.12 (s, 1H), 7.07-7.06 (m, 2H), 3.94-3.89 (s, 2H), 3.83 (s, 3H).

Example 44

4-[3,5-bis(trifluoromethyl)phenoxy]-2-cyano-N-(1,3,4-thiadiazol-2-yl)benzene-1-sulfonamide

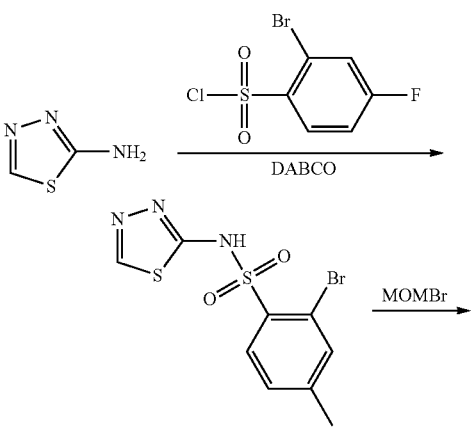

-continued

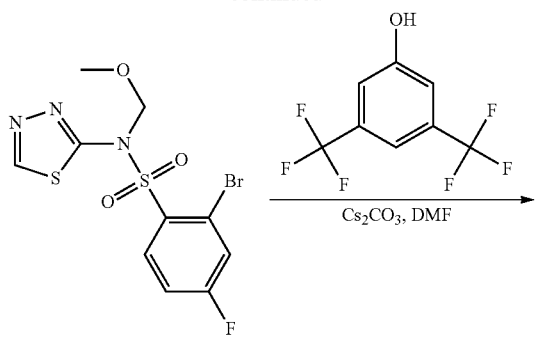

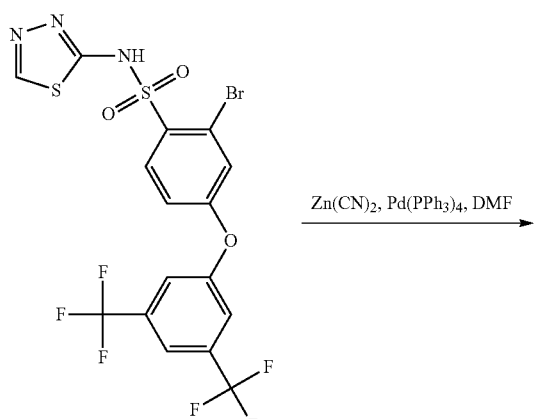

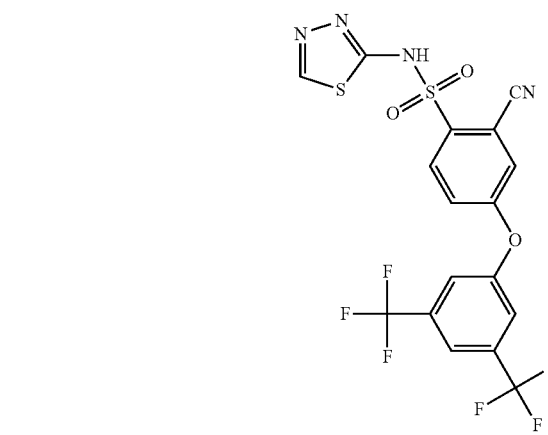

Step 1. Synthesis of 2-bromo-4-fluoro-N-(1,3,4-thiadiazol-2-yl)benzene-1-sulfonamide

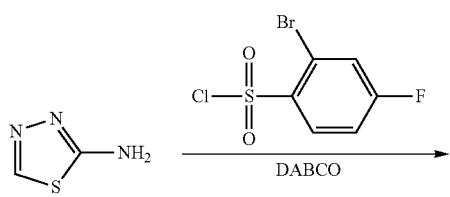

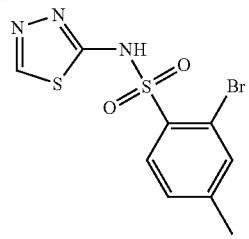

Into a 100-mL round-bottom flask, was placed a solution of 1,3,4-thiadiazol-2-amine (1 g, 9.89 mmol, 1.00 equiv) in pyridine (50 mL). To the solution was added 2-bromo-4-fluorobenzene-1-sulfonyl chloride (2.7 g, 9.87 mmol, 1.00 equiv). The resulting solution was stirred for 16 h at 120° C. in an oil bath.

The resulting mixture was concentrated under vacuum. The residue was applied onto a silica gel column with ethyl acetate/petroleum ether (1:1). This resulted in 800 mg (24%) of 2-bromo-4-fluoro-N-(1,3,4-thiadiazol-2-yl)benzene-1-sulfonamide as a white solid.

Step 2. Synthesis of 2-bromo-4-fluoro-N-(methoxymethyl)-N-(1,3,4-thiadiazol-2-yl)benzene-1-sulfonamide

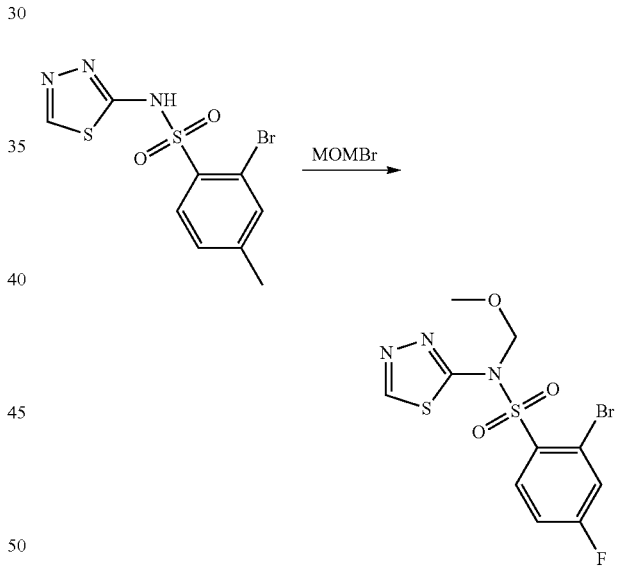

Into a 100-mL round-bottom flask, was placed a solution of 2-bromo-4-fluoro-N-(1,3,4-thiadiazol-2-yl)benzene-1-sulfonamide (800 mg, 2.37 mmol, 1.00 equiv) in dichloromethane (30 mL). To the solution was added MOMBr (293.5 mg, 2.37 mmol, 1.00 equiv) and DIEA (610.7 mg, 4.73 mmol, 2.00 equiv). The resulting solution was stirred for 3 h at room temperature. The resulting solution was extracted with dichloromethane (3×30 mL) and the organic layers combined and concentrated under vacuum. This resulted in 800 mg (88%) of 2-bromo-4-fluoro-N-(methoxymethyl)-N-(1,3,4-thiadiazol-2-yl)benzene-1-sulfonamide as a white solid.

Step 3. Synthesis of 4-[3,5-bis(trifluoromethyl)phenoxy]-2-bromo-N-(1,3,4-thiadiazol-2-yl)benzene-1-sulfonamide

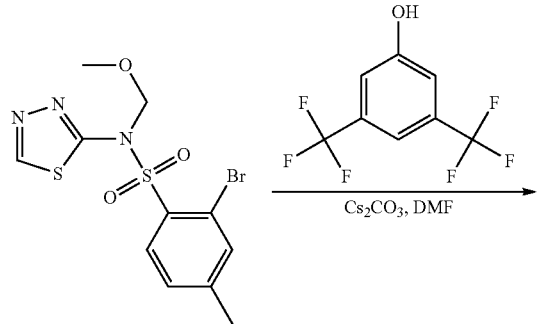

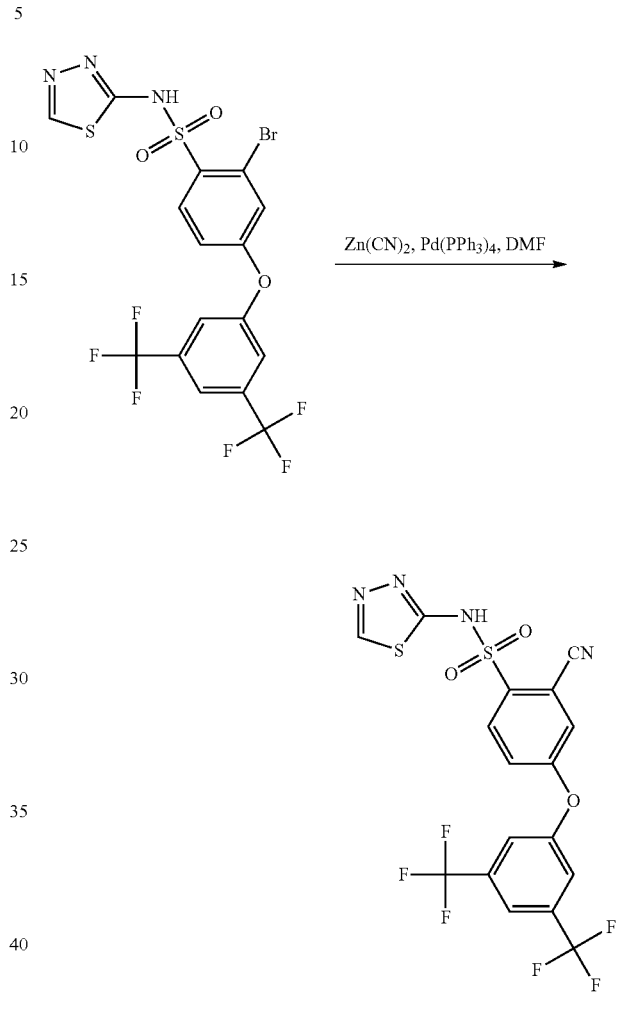

Step 4. Synthesis of 4-[3,5-bis(trifluoromethyl)phenoxy]-2-cyano-N-(1,3,4-thiadiazol-2-yl)benzene-1-sulfonamide Into a 100-mL round-bottom flask, was placed a solution of 2-bromo-4-fluoro-N-(methoxymethyl)-N-(1,3,4-thiadiazol-2-yl)benzene-1-sulfonamide (800 mg, 2.09 mmol, 1.00 equiv) in N,N-dimethylformamide (30 mL). To the solution were added 3-(1,1-difluoroethyl)-5-(trifluoromethyl)phenol (473.3 mg, 2.09 mmol, 1.00 equiv) and Cs$_2$CO$_3$ (1.37 g, 4.20 mmol, 2.00 equiv). The resulting solution was stirred for 16 h at 90° C. in an oil bath. The resulting solution was extracted with ethyl acetate (3×50 mL) and the organic layers combined and concentrated under vacuum. The residue was applied onto a silica gel column with ethyl acetate/petroleum ether (1:1). The collected fractions were combined and concentrated under vacuum. This resulted in 450 mg (39%) of 4-[3,5-bis(trifluoromethyl)phenoxy]-2-bromo-N-(1,3,4-thiadiazol-2-yl)benzene-1-sulfonamide as a white solid.

Into a 10-mL vial, was placed a solution of 4-[3,5-bis(trifluoromethyl)phenoxy]-2-bromo-N-(1,3,4-thiadiazol-2-yl)benzene-1-sulfonamide (450 mg, 0.82 mmol, 1.00 equiv) in N,N-dimethylformamide (5 mL). To the solution were added Zn(CN)$_2$ (142.9 mg, 1.23 mmol, 1.50 equiv) and Pd(PPh$_3$)$_4$ (94.9 mg, 0.08 mmol, 0.10 equiv). The resulting solution was stirred for 0.5 h at 150° C. The resulting solution was extracted with ethyl acetate (3×30 mL) and the organic layers combined and concentrated under vacuum. The crude product was purified by Pre p-HPLC with conditions: Column, XBridge Prep Shield RP18, 5 um, 19×150 mm; Mobile phase, H$_2$O (0.05% NH$_4$HCO$_3$)/CH$_3$CN (30%-80% in 10 min); Detector, 254 nm, 220 nm; RT=8.0 min. This resulted in 3.3 mg (1%) of 4-[3,5-bis(trifluoromethyl)phenoxy]-2-cyano-N-(1,3,4-thiadiazol-2-yl)benzene-1-sulfonamide as a white solid.

LC-MS: (ES, m/z): [M+H]$^+$ 495

$^1$H NMR (300 MHz, DMSO, ppm) δ 7.39-7.42 (m, 1H), 7.71-7.71 (m, 1H), 7.91-7.97 (m, 4H), 8.55 (s, 3H).

Example 45

2,5-difluoro-4-[3-methoxy-5-(trifluoromethyl)phenoxy]-N-[3-(methoxymethyl)-1,2,4-thiadiazol-5-yl]benzene-1-sulfonamide

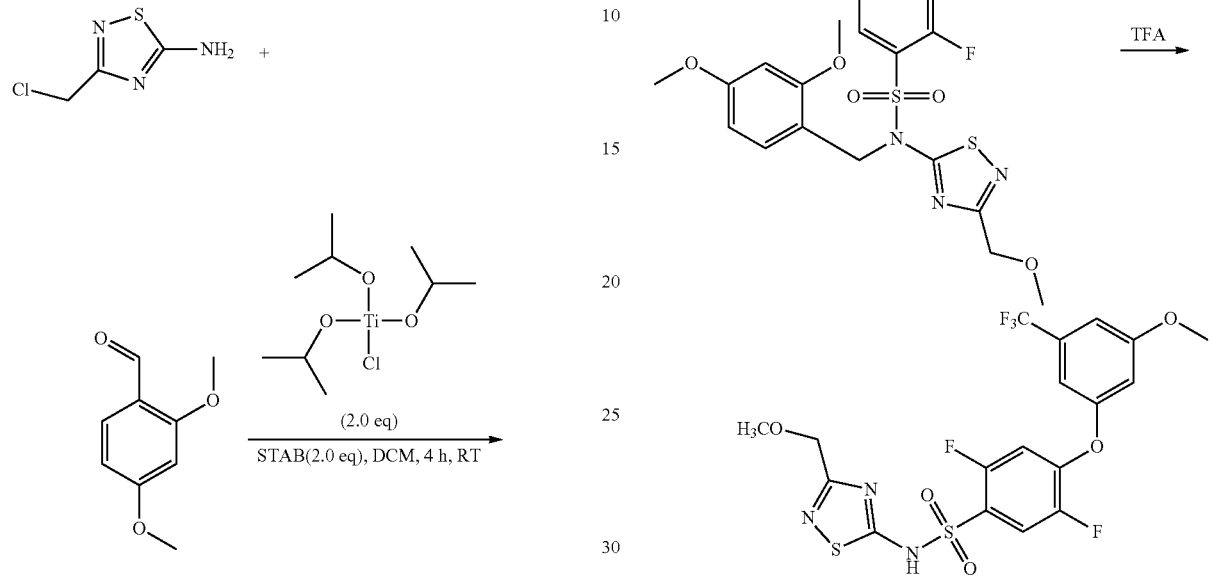

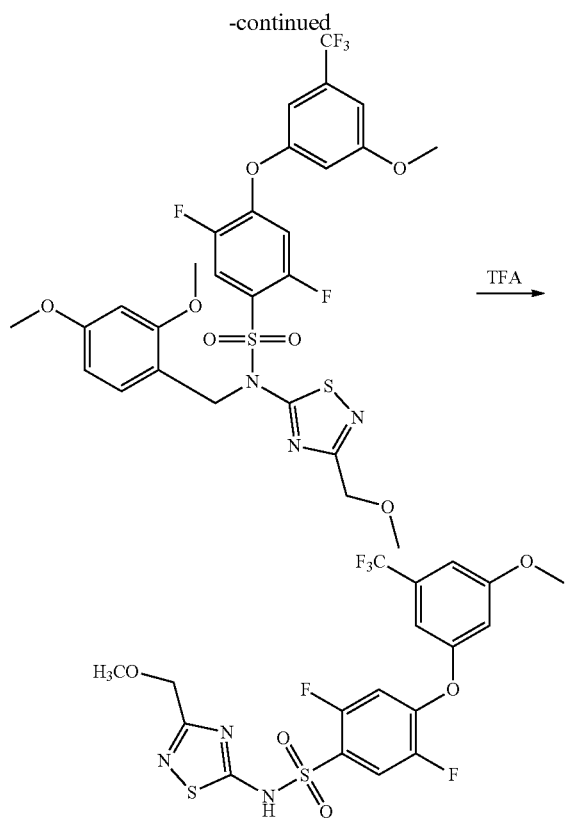

Step 1. Synthesis of 3-(chloromethyl)-N-[(2,4-dimethoxyphenyl)methyl]-1,2,4-thiadiazol-5-amine

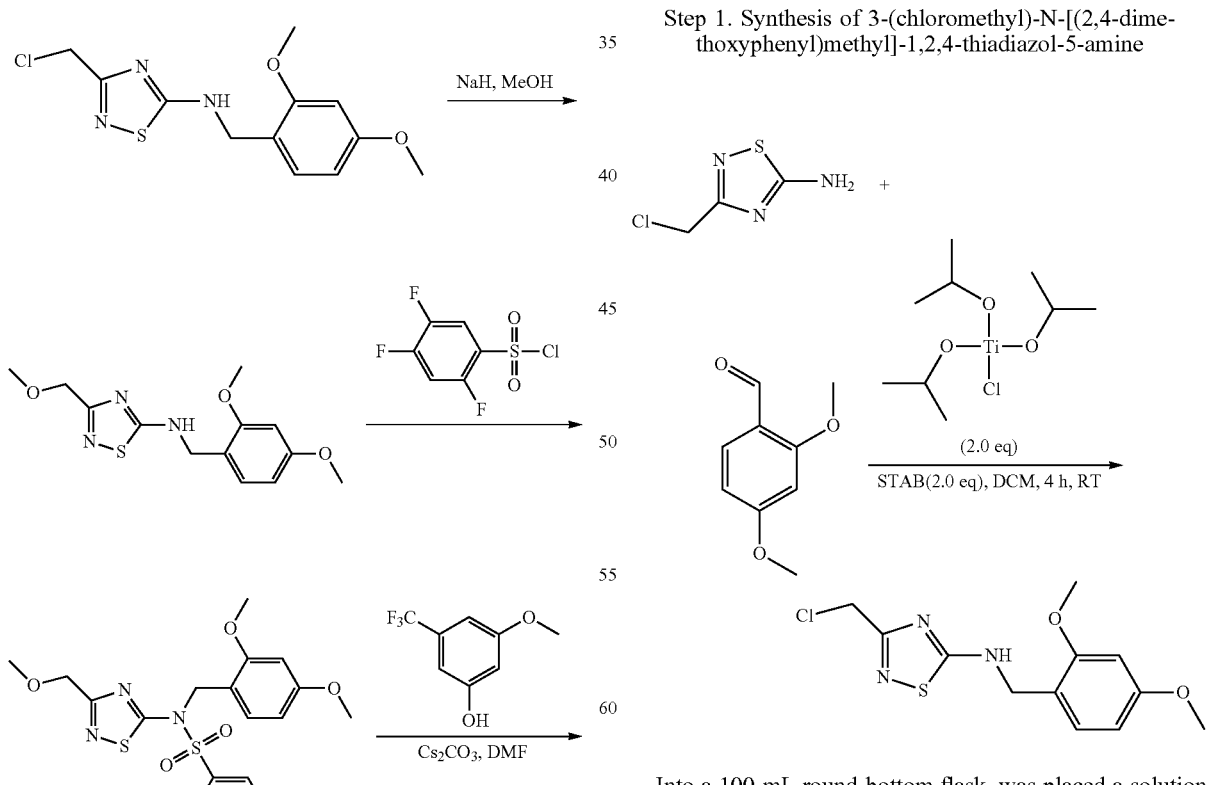

Into a 100-mL round-bottom flask, was placed a solution of 2,4-dimethoxybenzaldehyde (1.11 g, 6.68 mmol, 1.00 equiv) in dichloromethane (50 mL). To the solution were added 3-(chloromethyl)-1,2,4-thiadiazol-5-amine (1 g, 6.68 mmol, 1.00 equiv), triisopropoxytitanium(IV) chloride (3.49 g, 2.00 equiv, 260%) and STAB (2.85 g, 13.44 mmol, 2.00 equiv). The resulting solution was stirred for 16 h at room temperature. The reaction was then quenched by the addition of 20 mL of water. The pH value of the solution was adjusted to 10 with sodium hydroxide aqueous (10 mol/L). The resulting solution was extracted with dichloromethane (3×100 mL) and the organic layers combined and concentrated under vacuum. This resulted in 1.3 g (65%) of 3-(chloromethyl)-N-[(2,4-dimethoxyphenyl)methyl]-1,2,4-thiadiazol-5-amine as a white solid.

Step 2. Synthesis of N-[(2,4-dimethoxyphenyl)methyl]-3-(methoxymethyl)-1,2,4-thiadiazol-5-amine

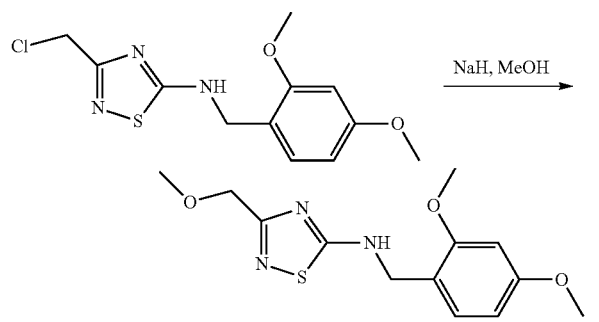

Into a 100-mL round-bottom flask, was placed a solution of 3-(chloromethyl)-N-[(2,4-dimethoxyphenyl)methyl]-1,2,4-thiadiazol-5-amine (1.3 g, 4.34 mmol, 1.00 equiv) in tetrahydrofuran (50 mL). To the solution were added sodium hydride (347 mg, 14.46 mmol, 2.00 equiv) and methanol (1.39 g, 43.38 mmol, 10.00 equiv). The resulting solution was stirred for 16 h at room temperature. The reaction was then quenched by the addition of 30 mL of NH₄Cl aqueous. The resulting solution was extracted with ethyl acetate (3×50 mL) and the organic layers combined and concentrated under vacuum. The residue was applied onto a silica gel column with ethyl acetate/petroleum ether (1:5). The collected fractions were combined and concentrated under vacuum. This resulted in 800 mg (62%) of N-[(2,4-dimethoxyphenyl)methyl]-3-(methoxymethyl)-1,2,4-thiadiazol-5-amine as a white solid.

Step 3. Synthesis of N-[(2,4-dimethoxyphenyl)methyl]-2,4,5-trifluoro-N-[3-(methoxymethyl)-1,2,4-thiadiazol-5-yl]benzene-1-sulfonamide

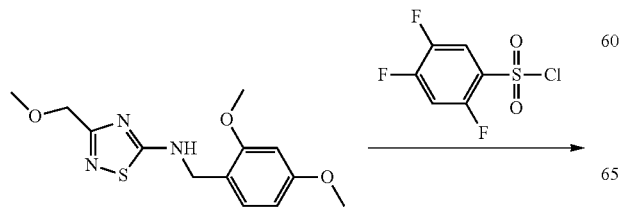

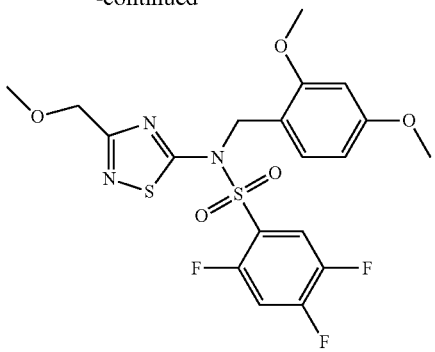

Into a 100-mL round-bottom flask, was placed a solution of N-[(2,4-dimethoxyphenyl)methyl]-3-(methoxymethyl)-1,2,4-thiadiazol-5-amine (300 mg, 1.02 mmol, 1.00 equiv) in N,N-dimethylformamide (30 mL). To the solution were added 2,4,5-trifluorobenzene-1-sulfonyl chloride (626.4 mg, 2.72 mmol, 1.00 equiv) and sodium hydride (162.7 mg, 6.78 mmol, 1.50 equiv). The resulting solution was stirred for 16 h at room temperature. The resulting solution was extracted with ethyl acetate (3×30 mL) and the organic layers combined and concentrated under vacuum. The residue was applied onto a silica gel column with ethyl acetate/petroleum ether (1:10). The collected fractions were combined and concentrated under vacuum. This resulted in 350 mg (70%) of N-[(2,4-dimethoxyphenyl)methyl]-2,4,5-trifluoro-N-[3-(methoxymethyl)-1,2,4-thiadiazol-5-yl]benzene-1-sulfonamide as a white solid.

Step 4. Synthesis of N-[(2,4-dimethoxyphenyl)methyl]-2,5-difluoro-4-[3-methoxy-5-(trifluoromethyl)phenoxy]-N-[3-(methoxymethyl)-1,2,4-thiadiazol-5-yl]benzene-1-sulfonamide

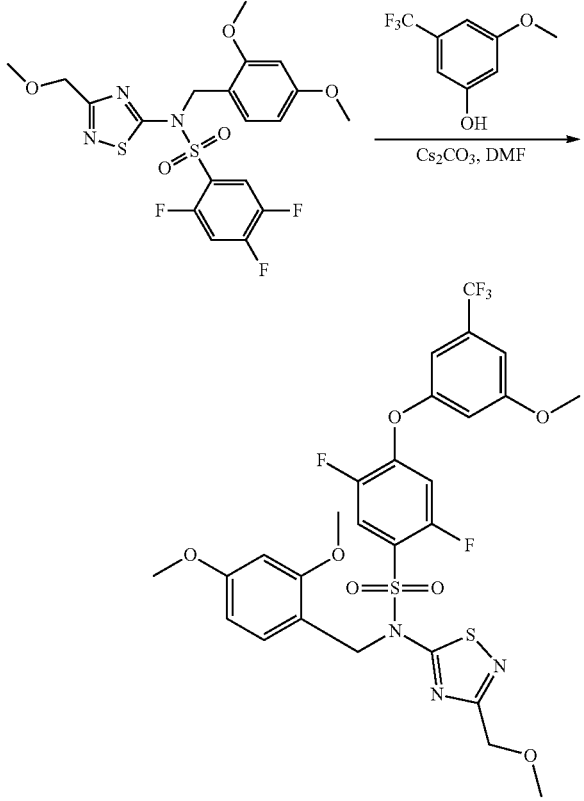

Into a 100-mL round-bottom flask, was placed a solution of N-[(2,4-dimethoxyphenyl)methyl]-2,4,5-trifluoro-N-[3-(methoxymethyl)-1,2,4-thiadiazol-5-yl]benzene-1-sulfonamide (350 mg, 0.72 mmol, 1.00 equiv) in N,N-dimethylformamide (30 mL). To the solution were added 3-methoxy-5-(trifluoromethyl)phenol (137 mg, 0.71 mmol, 1.00 equiv) and $Cs_2CO_3$ (466.7 mg, 1.43 mmol, 2.00 equiv). The resulting solution was stirred for 16 min at room temperature. The resulting solution was extracted with ethyl acetate (3×30 mL) and the organic layers combined and concentrated under vacuum. The residue was applied onto a silica gel column with ethyl acetate/petroleum ether (1:10). The collected fractions were combined and concentrated under vacuum. This resulted in 250 mg (53%) of N-[(2,4-dimethoxyphenyl)methyl]-2,5-difluoro-4-[3-methoxy-5-(trifluoromethyl)phenoxy]-N-[3-(methoxymethyl)-1,2,4-thiadiazol-5-yl]benzene-1-sulfonamide as a white solid.

Step 5. Synthesis of 2,5-difluoro-4-[3-methoxy-5-(trifluoromethyl)phenoxy]-N-[3-(methoxymethyl)-1,2,4-thiadiazol-5-yl]benzene-1-sulfonamide

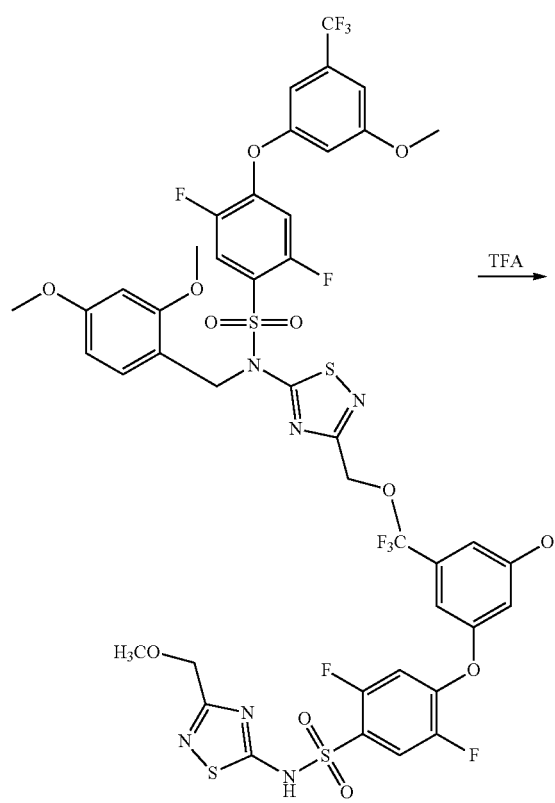

Into a 100-mL round-bottom flask, was placed a solution of N-[(2,4-dimethoxyphenyl)methyl]-2,5-difluoro-4-[3-methoxy-5-(trifluoromethyl)phenoxy]-N-[3-(methoxymethyl)-1,2,4-thiadiazol-5-yl]benzene-1-sulfonamide (250 mg, 0.38 mmol, 1.00 equiv) in dichloromethane (30 mL) and trifluoroacetic acid (3 mL). The resulting solution was stirred for 16 h at room temperature. The resulting mixture was concentrated under vacuum. The crude product was purified by Prep-HPLC with conditions: Column, XBridge Prep Shield RP18, 5 um, 19×150 mm; Mobile phase, $H_2O$ (0.05% TFA)/$CH_3CN$ (20%-80% in 10 min); Detector, 254 nm, 220 nm; RT=6.2 min. This resulted in 83.1 mg (43%) of 2,5-difluoro-4-[3-methoxy-5-(trifluoromethyl)phenoxy]-N-[3-(methoxymethyl)-1,2,4-thiadiazol-5-yl]benzene-1-sulfonamide as a white solid.

LC-MS: (ES, m/z): $[M+H]^+$ 512

$^1$H-NMR: $^1$H NMR (300 MHz, DMSO, ppm) δ 3.31 (s, 3H), 3.84 (s, 3H), 4.39 (s, 2H), 7.10-7.14 (m, 3H), 7.28-7.34 (m, 1H), 7.80-7.86 (m, 1H).

Example 46

2,5-difluoro-4-[3-methoxy-5-(trifluoromethyl)phenoxy]-N-[3-(morpholin-4-ylmethyl)-1,2,4-thiadiazol-5-yl]benzene-1-sulfonamide

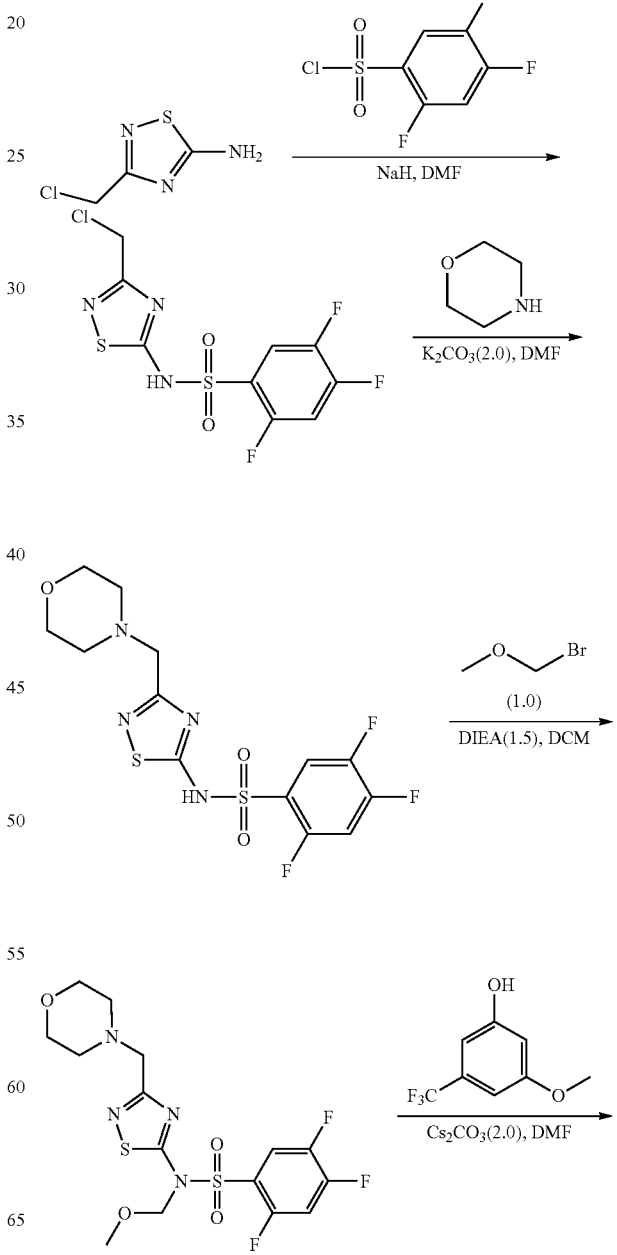

-continued

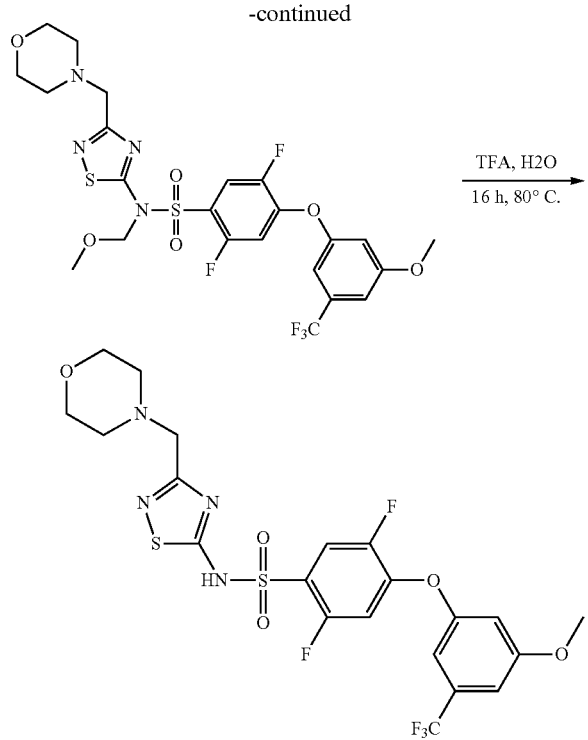

Step 1. Synthesis of N-[3-(chloromethyl)-1,2,4-thiadiazol-5-yl]-2,4,5-trifluorobenzene-1-sulfonamide

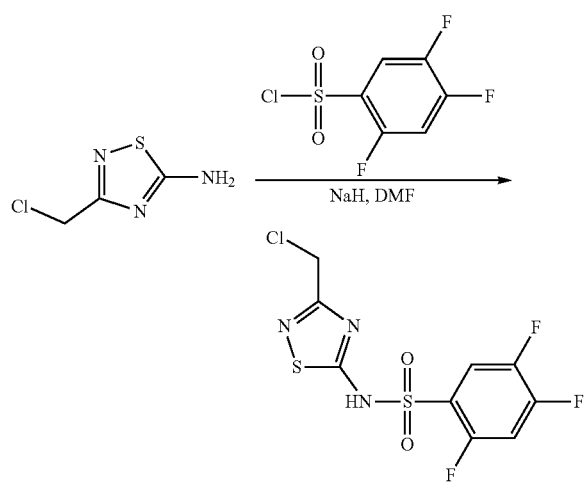

Into a 100-mL round-bottom flask, were placed 3-(chloromethyl)-1,2,4-thiadiazol-5-amine (1.00 g, 6.68 mmol, 1.00 equiv), N,N-dimethylformamide (30 mL), sodium hydride (242 mg, 10.08 mmol, 1.50 equiv), 2,4,5-trifluorobenzene-1-sulfonyl chloride (1.85 g, 8.02 mmol, 1.00 equiv). The resulting solution was stirred for 1.5 h at room temperature. The reaction was then quenched by the addition of water. The resulting solution was extracted with ethyl acetate and the organic layers combined. The resulting mixture was washed with brine, dried and concentrated under vacuum. The residue was applied onto a silica gel column with ethyl acetate/petroleum ether (1:6). This resulted in 700 mg (30%) of N-[3-(chloromethyl)-1,2,4-thiadiazol-5-yl]-2,4,5-trifluorobenzene-1-sulfonamide as a yellow solid.

Step 2. Synthesis of 2,4,5-trifluoro-N-[3-(morpholin-4-ylmethyl)-1,2,4-thiadiazol-5-yl]benzene-1-sulfonamide Into a 100-mL round-bottom flask, were placed N-[3-(chloromethyl)-1,2,4-thiadiazol-5-yl]-2,4,5-trifluorobenzene-1-sulfonamide (500 mg, 1.45 mmol, 1.00 equiv), N,N-dimethylformamide (10 mL), potassium carbonate (401 mg, 2.90 mmol, 2.00 equiv), morpholine (190 mg, 2.18 mmol, 1.50 equiv). The resulting solution was stirred for 16 h at room temperature. The reaction was then quenched by the addition of 10 mL of water. The resulting solution was extracted with 3×50 mL of ethyl acetate and the organic layers combined. The resulting mixture was washed with brine, dried and concentrated under vacuum. This resulted in 400 mg (70%) of 2,4,5-trifluoro-N-[3-(morpholin-4-ylmethyl)-1,2,4-thiadiazol-5-yl]benzene-1-sulfonamide as yellow oil.

Step 3. Synthesis of 2,4,5-trifluoro-N-(methoxymethyl)-N-[3-(morpholin-4-ylmethyl)-1,2,4-thiadiazol-5-yl]benzene-1-sulfonamide

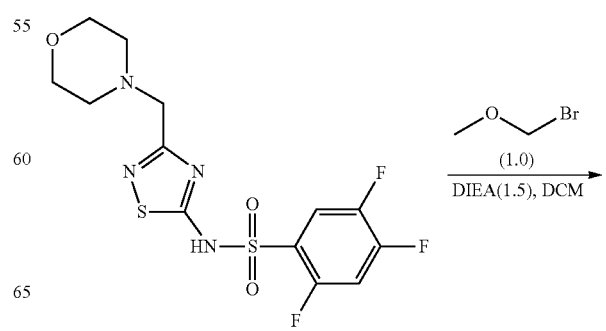

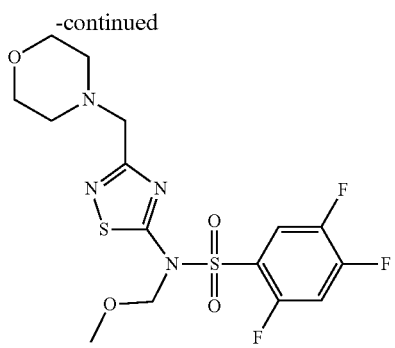

Into a 100-mL round-bottom flask, were placed 2,4,5-trifluoro-N-[3-(morpholin-4-ylmethyl)-1,2,4-thiadiazol-5-yl]benzene-1-sulfonamide (400 mg, 1.01 mmol, 1.00 equiv), dichloromethane (10 mL), DIEA (196 mg, 1.52 mmol, 1.50 equiv), bromo(methoxy)methane (127 mg, 1.02 mmol, 1.00 equiv). The resulting solution was stirred for 5 min at room temperature. The reaction was then quenched by the addition of water. The resulting solution was extracted with ethyl acetate and the organic layers combined. The resulting mixture was washed with brine. The mixture was dried over anhydrous sodium sulfate and concentrated under vacuum. The residue was applied onto a silica gel column with ethyl acetate/petroleum ether (1:1.5). This resulted in 180 mg (40%) of 2,4,5-trifluoro-N-(methoxymethyl)-N-[3-(morpholin-4-ylmethyl)-1,2,4-thiadiazol-5-yl]benzene-1-sulfonamide as colorless oil.

Step 4. Synthesis of 2,5-difluoro-4-[3-methoxy-5-(trifluoromethyl)phenoxy]-N-(methoxymethyl)-N-[3-(morpholin-4-ylmethyl)-1,2,4-thiadiazol-5-yl]benzene-1-sulfonamide

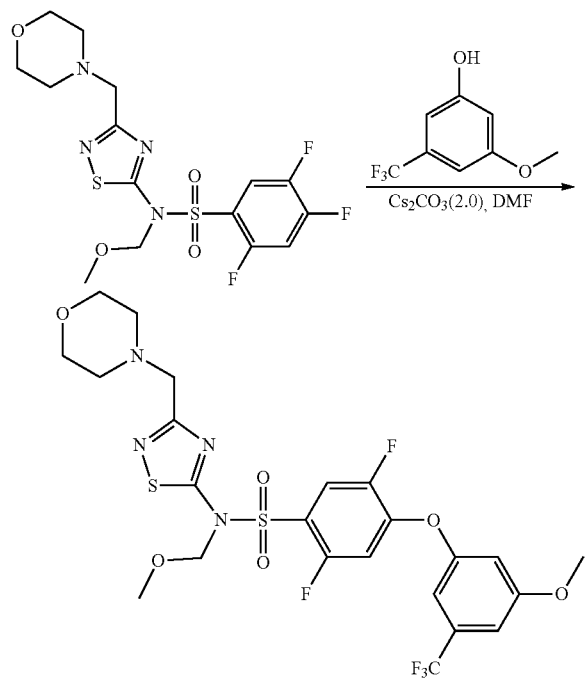

Into a 50-mL round-bottom flask, was placed 3-methoxy-5-(trifluoromethyl)phenol (80 mg, 0.42 mmol, 1.10 equiv), caesio methaneperoxoate caesium (247 mg, 0.76 mmol, 2.00 equiv), N,N-dimethylformamide (5 mL), 2,4,5-trifluoro-N-(methoxymethyl)-N-[3-(morpholin-4-ylmethyl)-1,2,4-thiadiazol-5-yl]benzene-1-sulfonamide (166 mg, 0.38 mmol, 1.00 equiv). The resulting solution was stirred for 6 h at room temperature. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 200 mg (87%) of 2,5-difluoro-4-[3-methoxy-5-(trifluoromethyl)phenoxy]-N-(methoxymethyl)-N-[3-(morpholin-4-ylmethyl)-1,2,4-thiadiazol-5-yl]benzene-1-sulfonamide as yellow oil.

Step 5. Synthesis of 2,5-difluoro-4-[3-methoxy-5-(trifluoromethyl)phenoxy]-N-[3-(morpholin-4-ylmethyl)-1,2,4-thiadiazol-5-yl]benzene-1-sulfonamide

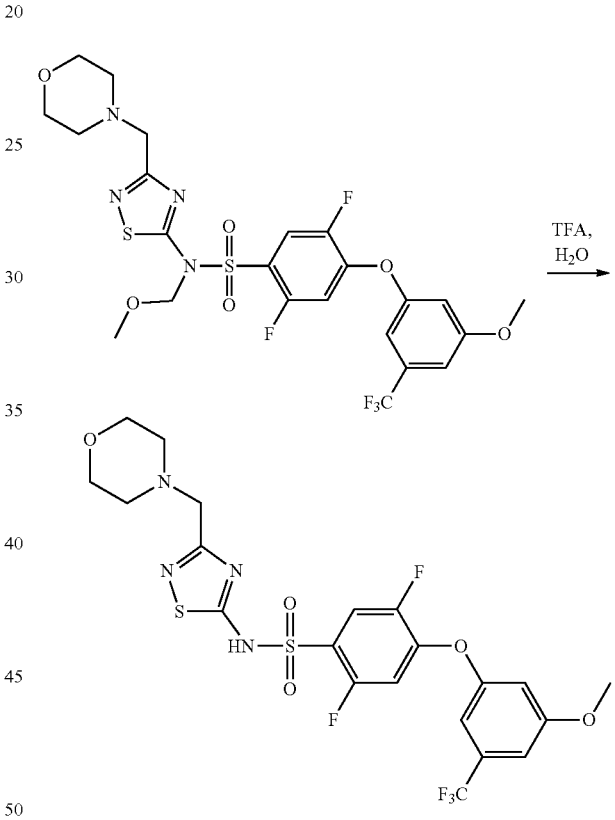

Into a 25-mL round-bottom flask, were placed 2,5-difluoro-4-[3-methoxy-5-(trifluoromethyl)phenoxy]-N-(methoxymethyl)-N-[3-(morpholin-4-ylmethyl)-1,2,4-thiadiazol-5-yl]benzene-1-sulfonamide (150 mg, 0.25 mmol, 1.00 equiv), water (4 mL), trifluoroacetic acid (3 mL). The resulting solution was stirred for 16 h at 80° C. The reaction was then quenched by water. The resulting solution was extracted with ethyl acetate and the organic layers combined. The resulting mixture was washed with brine, dried and concentrated under vacuum. The crude product (100 mg) was purified by Prep-HPLC with the following conditions (1 #-Pre-HPLC-005(Waters)): Column, SunFire Prep C18, 19*150 mm 5 um; mobile phase, water with 0.05% TFA and CH₃CN (10.0% CH₃CN up to 90.0% in 7 min, up to 95.0% in 1 min, down to 10.0% in 1 min); Detector, UV 254 nm. This resulted in 45 mg (32%) of 2,5-difluoro-4-[3- methoxy-5-(trifluoromethyl)phenoxy]-N-[3-(morpholin-4-ylmethyl)-1,2,4-thiadiazol-5-yl]benzene-1-sulfonamide as a white solid.

LC-MS: (ES, m/z): [M+H]⁺ 567

¹H-NMR: (400 MHz, DMSO-$d_6$, ppm): δ 7.70-7.66 (m, 1H), 7.24-7.20 (m, 1H), 7.12-7.09 (m, 1H), 7.03 (s, 2H), 4.10-4.01 (m, 2H), 3.83 (s, 3H), 3.78-3.76 (m, 4H), 3.06 (s, 4H).

Example 47

4-[3-(azetidin-1-yl)-5-(trifluoromethyl)phenoxy]-2,5-difluoro-N-(1,2,4-thiadiazol-5-yl)benzenesulfonamide

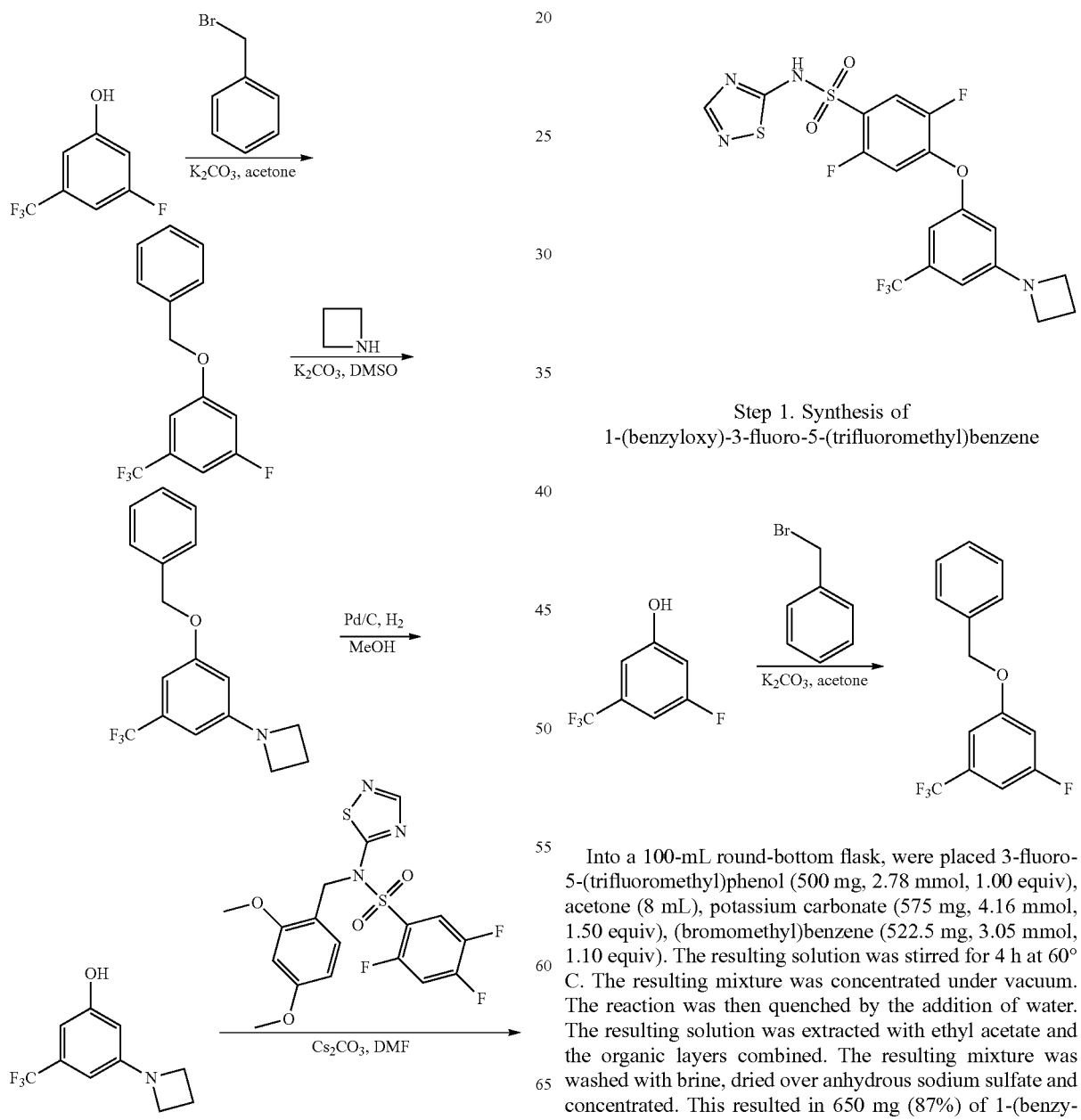

Step 1. Synthesis of 1-(benzyloxy)-3-fluoro-5-(trifluoromethyl)benzene

Into a 100-mL round-bottom flask, were placed 3-fluoro-5-(trifluoromethyl)phenol (500 mg, 2.78 mmol, 1.00 equiv), acetone (8 mL), potassium carbonate (575 mg, 4.16 mmol, 1.50 equiv), (bromomethyl)benzene (522.5 mg, 3.05 mmol, 1.10 equiv). The resulting solution was stirred for 4 h at 60° C. The resulting mixture was concentrated under vacuum. The reaction was then quenched by the addition of water. The resulting solution was extracted with ethyl acetate and the organic layers combined. The resulting mixture was washed with brine, dried over anhydrous sodium sulfate and concentrated. This resulted in 650 mg (87%) of 1-(benzyloxy)-3-fluoro-5-(trifluoromethyl)benzene as colorless oil.

Step 2. Synthesis of 1-[3-(benzyloxy)-5-(trifluoromethyl)phenyl]azetidine

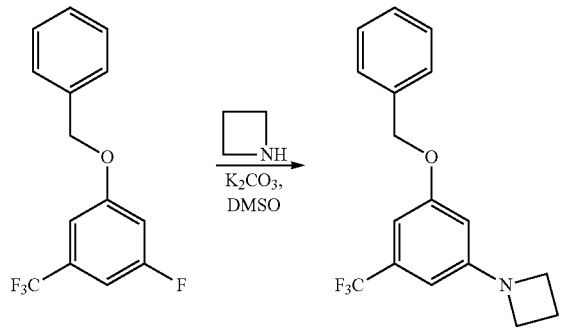

Into a 50-mL round-bottom flask, were placed 1-(benzyloxy)-3-fluoro-5-(trifluoromethyl)benzene (260 mg, 0.96 mmol, 1.00 equiv), potassium carbonate (266 mg, 1.92 mmol, 2.00 equiv), DMSO (3 mL), azetidine (220 mg, 3.85 mmol, 4.00 equiv). The resulting solution was stirred for 6 h at 100° C. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 270 mg (91%) of 1-[3-(benzyloxy)-5-(trifluoromethyl)phenyl]azetidine as a yellow solid.

Step 3. Synthesis of 3-(azetidin-1-yl)-5-(trifluoromethyl)phenol

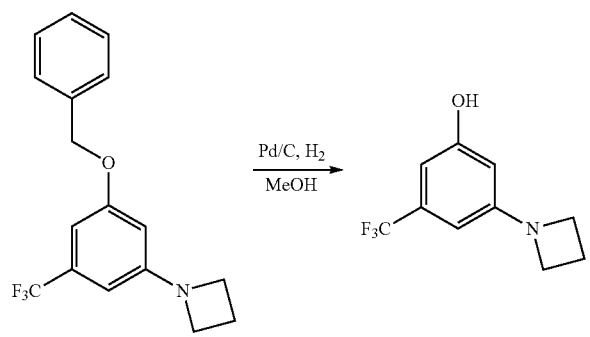 [SMILES: "MeOH" ; FC(F)(F)c1cc(OCc2ccccc2)cc(N2CCC2)c1 ; Oc1cc(N2CCC2)cc(C(F)(F)F)c1]

Into a 50-mL round-bottom flask purged and maintained with an inert atmosphere of $H_2$, were placed 1-[3-(benzyloxy)-5-(trifluoromethyl)phenyl]azetidine (260 mg, 0.85 mmol, 1.00 equiv), methanol (3 mL), Palladium carbon (30 mg, 0.10 equiv). To the above $H_2$ was introduced in. The resulting solution was stirred for 5 h at room temperature. The solids were filtered out and filtrated was concentrated under vacuum. The residue was applied onto a silica gel column with ethyl acetate/petroleum ether (1:10). This resulted in 150 mg (82%) of 3-(azetidin-1-yl)-5-(trifluoromethyl)phenol as a white solid.

Step 4. Synthesis of 4-[3-(azetidin-1-yl)-5-(trifluoromethyl)phenoxy]-N-[(2,4-dimethoxyphenyl)methyl]-2,5-difluoro-N-(1,2,4-thiadiazol-5-yl)benzene-1-sulfonamide

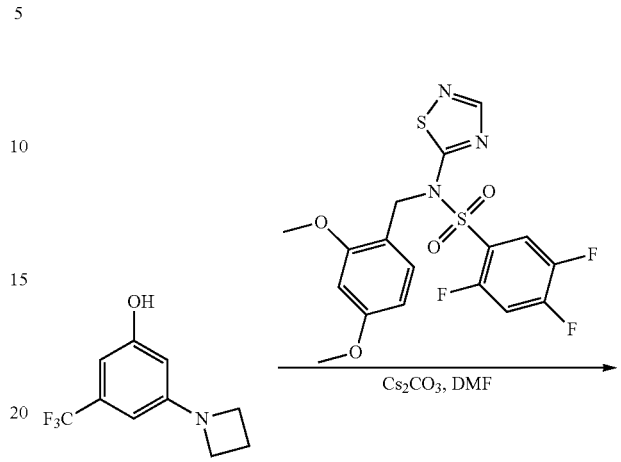

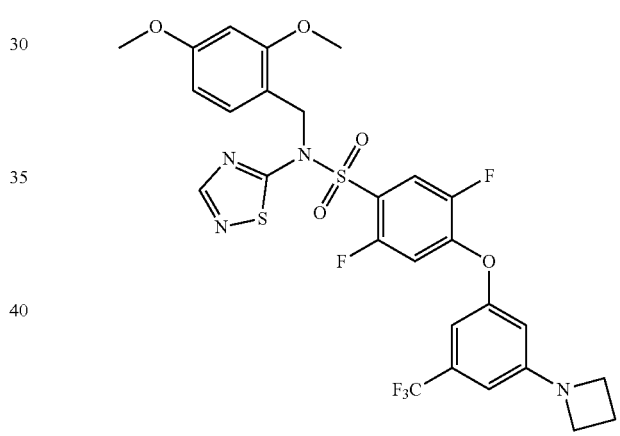

Into a 50-mL round-bottom flask, were placed N-[(2,4-dimethoxyphenyl)methyl]-2,4,5-trifluoro-N-(1,2,4-thiadiazol-5-yl)benzene-1-sulfonamide (82 mg, 0.18 mmol, 1.00 equiv), 3-(azetidin-1-yl)-5-(trifluoromethyl)phenol (40 mg, 0.18 mmol, 1.00 equiv), Cs2CO3 (120 mg, 0.37 mmol, 2.00 equiv), N,N-dimethylformamide (4 mL). The resulting solution was stirred for 2 h at room temperature. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 100 mg (85%) of 4-[3-(azetidin-1-yl)-5-(trifluoromethyl)phenoxy]-N-[(2,4-dimethoxyphenyl)methyl]-2,5-difluoro-N-(1,2,4-thiadiazol-5-yl)benzene-1-sulfonamide as yellow oil.

189

Step 5. Synthesis of 4-[3-(azetidin-1-yl)-5-(trifluoromethyl)phenoxy]-2,5-difluoro-N-(1,2,4-thiadiazol-5-yl)benzene-1-sulfonamide

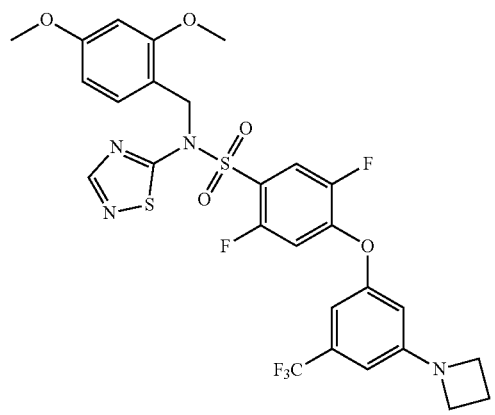

Into a 25-mL round-bottom flask, were placed 4-[3-(azetidin-1-yl)-5-(trifluoromethyl)phenoxy]-N-[(2,4-dimethoxyphenyl)methyl]-2,5-difluoro-N-(1,2,4-thiadiazol-5-yl)benzene-1-sulfonamide (100 mg, 0.16 mmol, 1.00 equiv), dichloromethane (3 mL), trifluoroacetic acid (1 mL). The resulting solution was stirred for 1 h at room temperature. The resulting mixture was concentrated under vacuum. The crude product (75 mg) was purified by Prep-HPLC with the following conditions (1 #-Pre-HPLC-005(Waters)): Column, C18, 19*150 mm 5 um; mobile phase, water with 0.05% TFA and CH3CN (10.0% CH3CN up to 90.0% in 7 min, up to 95.0% in 1 min, down to 10.0% in 1 min); Detector, UV 254 nm. This resulted in 48 mg (63%) of 4-[3-(azetidin-1-yl)-5-(trifluoromethyl)phenoxy]-2,5-difluoro-N-(1,2,4-thiadiazol-5-yl)benzene-1-sulfonamide as a white solid.

LC-MS: (ES, m/z): [M+H]$^+$=492

$^1$H-NMR: (300 MHz, DMSO-$d_6$, ppm): δ 8.47 (s, 1H), 7.86-7.77 (m, 1H), 7.21-7.16 (m, 1H), 6.68 (s, 1H), 6.49 (s, 1H), 6.42 (s, 1H), 3.90-3.85 (m, 4H), 2.36-2.27 (m, 2H).

190

Example 48

2,5-difluoro-4-[3-(3-hydroxyazetidin-1-yl)-5-(trifluoromethyl)phenoxy]-N-(1,2,4-thiadiazol-5-yl)benzenesulfonamide

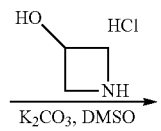
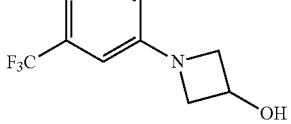
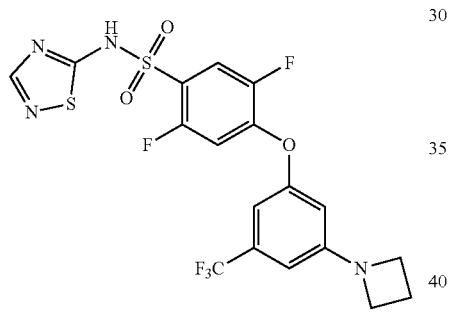
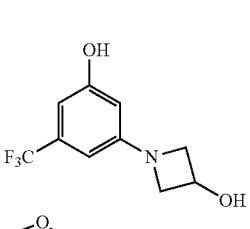
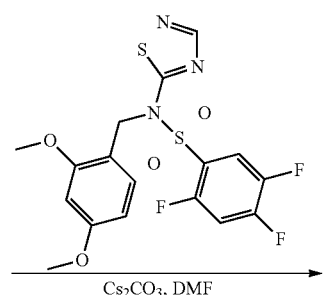
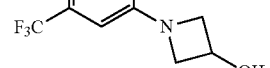

191

-continued

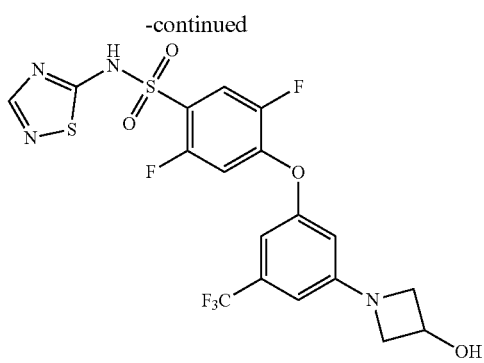

Step 1. Synthesis of 1-[3-(benzyloxy)-5-(trifluoromethyl)phenyl]azetidin-3-ol

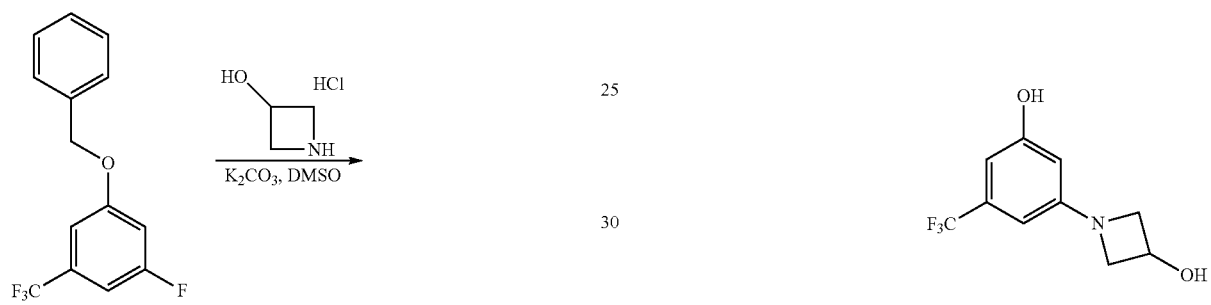

Into a 50-mL round-bottom flask, were placed 1-(benzyloxy)-3-fluoro-5-(trifluoromethyl)benzene (270 mg, 1.00 mmol, 1.00 equiv), DMSO (15 mL), potassium carbonate (1.1 g, 7.96 mmol, 8.00 equiv), 1-amino-3-chloropropan-2-ol (880 mg, 8.03 mmol, 8.00 equiv). The resulting solution was stirred for 2 days at 130° C. The reaction was then quenched by the addition of water. The resulting solution was extracted with ethyl acetate and the organic layers combined. The resulting mixture was washed with brine. The mixture was dried over anhydrous sodium sulfate and concentrated under vacuum. The residue was applied onto a silica gel column with ethyl acetate/petroleum ether (1:10). This resulted in 110 mg (34%) of 1-[3-(benzyloxy)-5-(trifluoromethyl)phenyl]azetidin-3-ol as a white solid.

192

Step 2. Synthesis of 1-[3-hydroxy-5-(trifluoromethyl)phenyl]azetidin-3-ol

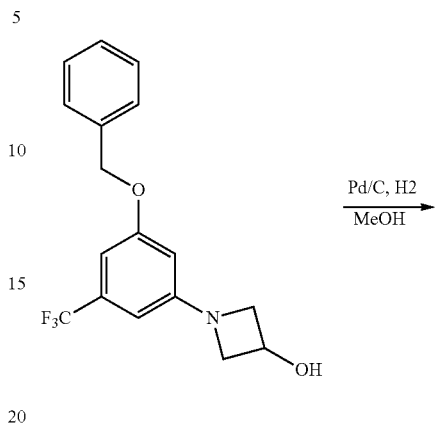

Into a 50-mL round-bottom flask purged and maintained with an inert atmosphere of $H_2$, were placed 1-[3-(benzyloxy)-5-(trifluoromethyl)phenyl]azetidin-3-ol (110 mg, 0.34 mmol, 1.00 equiv), methanol (5 mL), Palladium carbon (22 mg, 0.20 equiv). To the above $H_2$ (g) was introduced in. The resulting solution was stirred for 4 h at room temperature. The solids were filtered out. The resulting mixture was concentrated under vacuum. This resulted in 62 mg (78%) of 1-[3-hydroxy-5-(trifluoromethyl)phenyl]azetidin-3-ol as a white solid.

Step 3. Synthesis of N-[(2,4-dimethoxyphenyl)methyl]-2,5-difluoro-4-[3-(3-hydroxyazetidin-1-yl)-5-(trifluoromethyl)phenoxy]-N-(1,2,4-thiadiazol-5-yl)benzene-1-sulfonamide

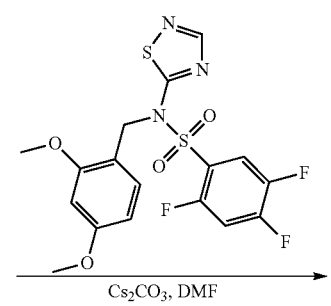

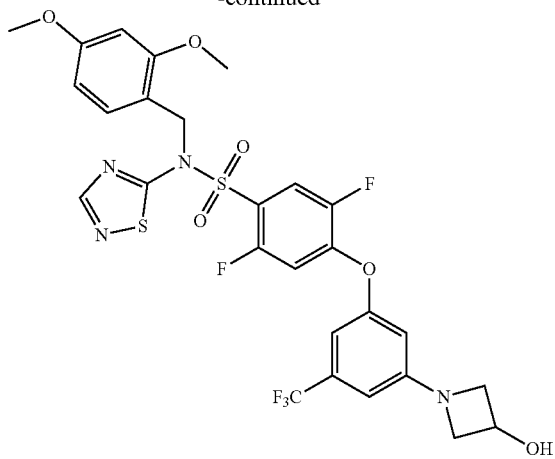

Into a 50-mL round-bottom flask, were placed N-[(2,4-dimethoxyphenyl)methyl]-2,4,5-trifluoro-N-(1,2,4-thiadiazol-5-yl)benzene-1-sulfonamide (115 mg, 0.26 mmol, 1.00 equiv), 1-[3-hydroxy-5-(trifluoromethyl)phenyl]azetidin-3-ol (60 mg, 0.26 mmol, 1.00 equiv), Cs2CO3 (168 mg, 0.52 mmol, 2.00 equiv), N,N-dimethylformamide (5 mL). The resulting solution was stirred for 1.5 h at room temperature. The reaction was then quenched by the addition of water. The resulting solution was extracted with ethyl acetate and the organic layers combined. The resulting mixture was washed with brine, dried over anhydrous sodium sulfate and concentrated under vacuum. This resulted in 120 mg (71%) of N-[(2,4-dimethoxyphenyl)methyl]-2,5-difluoro-4-[3-(3-hydroxyazetidin-1-yl)-5-(trifluoromethyl)phenoxy]-N-(1,2,4-thiadiazol-5-yl)benzene-1-sulfonamide as yellow oil.

Step 4. Synthesis of 2,5-difluoro-4-[3-(3-hydroxyazetidin-1-yl)-5-(trifluoromethyl)phenoxy]-N-(1,2,4-thiadiazol-5-yl)benzene-1-sulfonamide

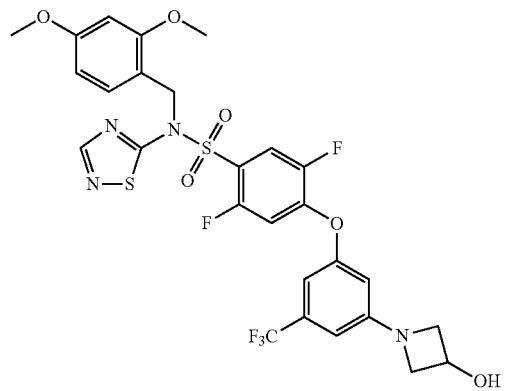

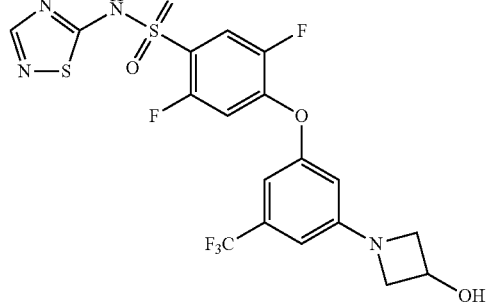

Into a 50-mL round-bottom flask, were placed N-[(2,4-dimethoxyphenyl)methyl]-2,5-difluoro-4-[3-(3-hydroxyazetidin-1-yl)-5-(trifluoromethyl)phenoxy]-N-(1,2,4-thiadiazol-5-yl)benzene-1-sulfonamide (100 mg, 0.15 mmol, 1.00 equiv), dichloromethane (3 mL), trifluoroacetic acid (1 mL). The resulting solution was stirred for 1 h at room temperature. The resulting mixture was concentrated under vacuum. The crude product (80 mg) was purified by Prep-HPLC with the following conditions (1 #-Pre-HPLC-005(Waters)): Column, SunFire Prep C18, 19*150 mm 5 um; mobile phase, water with 0.05% TFA and CH3CN (10.0% CH3CN up to 90.0% in 7 min, up to 95.0% in 1 min, down to 10.0% in 1 min); Detector, UV 254 nm. This resulted in 35 mg (45%) of 2,5-difluoro-4-[3-(3-hydroxyazetidin-1-yl)-5-(trifluoromethyl)phenoxy]-N-(1,2,4-thiadiazol-5-yl)benzene-1-sulfonamide as a white solid.

LC-MS: (ES, m/z): [M+H]$^+$=508

$^1$H-NMR: (300 MHz, DMSO-d$_6$, ppm): δ 8.29 (s, 1H), 7.77-7.72 (m, 1H), 7.18-7.12 (m, 1H), 6.66 (s, 1H), 6.58 (s, 1H), 6.52 (s, 1H), 5.71 (s, 1H), 4.56-4.55 (m, 1H), 4.14-4.09 (m, 2H), 3.61-3.57 (m, 2H).

Example 49

Synthesis of (2S,4S)—N-((3',5'-bis(trifluoromethyl)-[1,1'-biphenyl]-3-yl)methyl)-4-fluoropyrrolidine-2-carboxamide

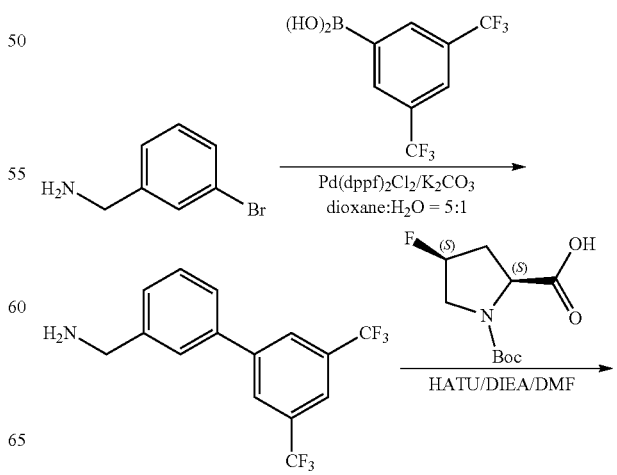

195
-continued

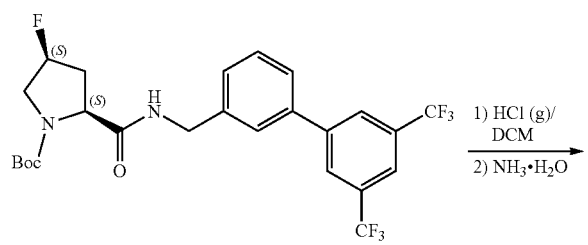

1) HCl (g)/DCM
2) NH₃•H₂O

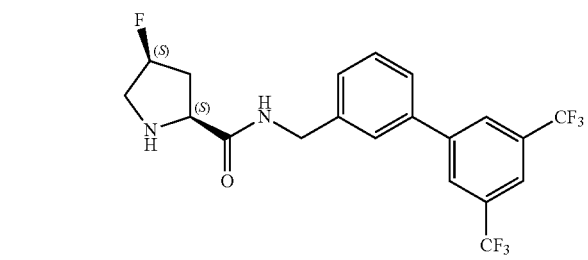

Step 1. Synthesis of [3-[3,5-bis(trifluoromethyl)phenyl]phenyl]methanamine

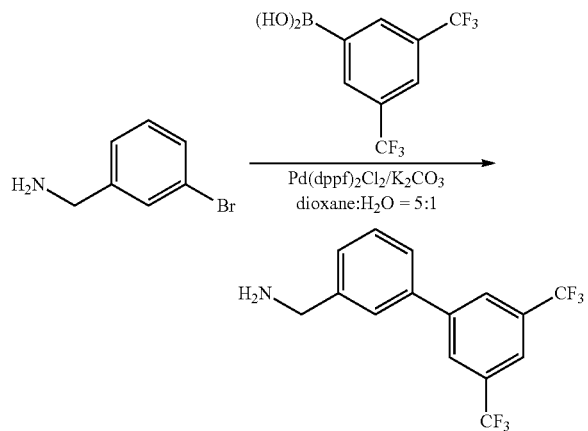

Into a 100-mL 3-necked round-bottom flask, purged and maintained with an inert atmosphere of nitrogen, was placed a solution of (3-bromophenyl)methanamine (400 mg, 2.15 mmol, 1.00 equiv) in dioxane/water=5:1 (12 mL). [3,5-Bis(trifluoromethyl)phenyl]boronic acid (558 mg, 2.16 mmol, 1.00 equiv), Pd(dppf)₂Cl₂ (158 mg, 0.10 equiv) and potassium carbonate (895 mg, 6.48 mmol, 3.00 equiv) were added. The resulting solution was stirred overnight at 90° C. After cooling to room temperature the solution was diluted with 50 mL of ethyl acetate, washed with brine (2×20 mL), dried over anhydrous sodium sulfate and concentrated under vacuum. The resulting residue was purified by prep-TLC (DCM:MeOH=15:1) to give 450 mg (62%) of [3-[3,5-bis(trifluoromethyl)phenyl]phenyl]methanamine as light yellow oil.

196

Step 2. Synthesis of tert-butyl (2S,4S)-2-[([3-[3,5-bis(trifluoromethyl)phenyl]phenyl]methyl)carbamoyl]4-fluoropyrrolidine-1-carboxylate

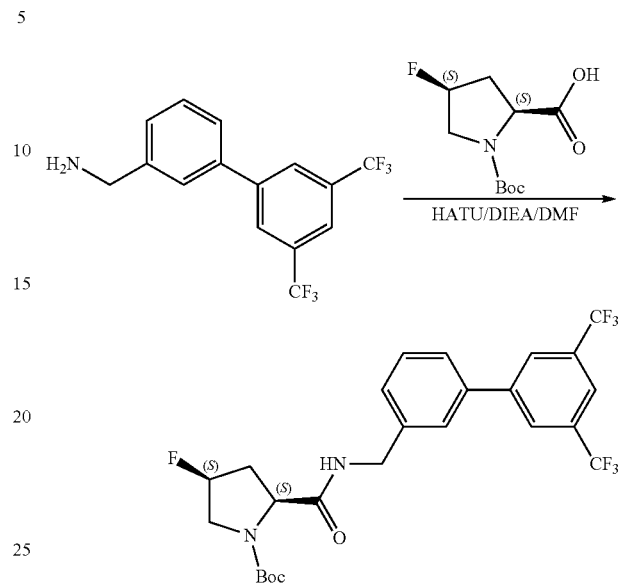

Into a 100-mL round-bottom flask was placed a solution of (2S,4S)-1-[(tert-butoxy)carbonyl]-4-fluoropyrrolidine-2-carboxylic acid (329 mg, 1.41 mmol, 1.00 equiv) in N,N-dimethylformamide (10 mL). [3-[3,5-Bis(trifluoromethyl)phenyl]phenyl]methanamine (450 mg, 1.41 mmol, 2.00 equiv), HATU (804 mg, 2.11 mmol, 1.50 equiv), and DIEA (364 mg, 2.82 mmol, 2.00 equiv) were added. After stirring for 1 hour at room temperature the solution was diluted with 40 mL of ethyl acetate, washed with brine (3×20 mL), dried over anhydrous sodium sulfate and concentrated under vacuum. The residue was purified by prep-TLC (DCM:MeOH=15:1) to give 600 mg (76%) of tert-butyl (2S,4S)-2-[([3-[3,5-bis(trifluoromethyl)phenyl]phenyl]methyl)carbamoyl]-4-fluoropyrrolidine-1-carboxylate as light yellow oil.

Step 3. Synthesis of (2S,4S)—N-([3-[3,5-bis(trifluoromethyl)phenyl]phenyl]methyl)-4-fluoropyrrolidine-2-carboxamide

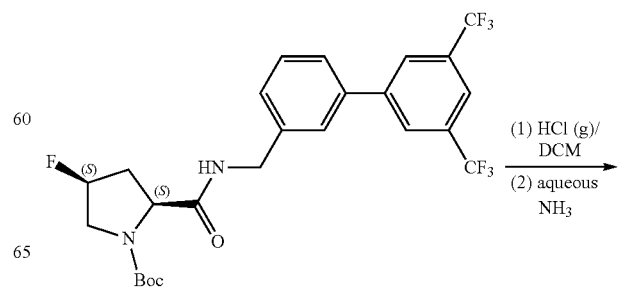

(1) HCl (g)/DCM
(2) aqueous NH₃

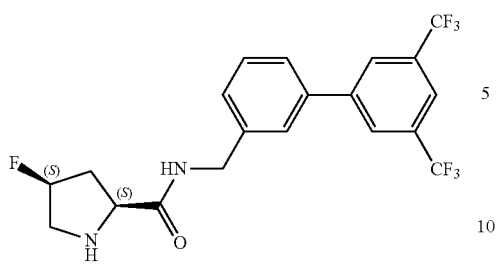
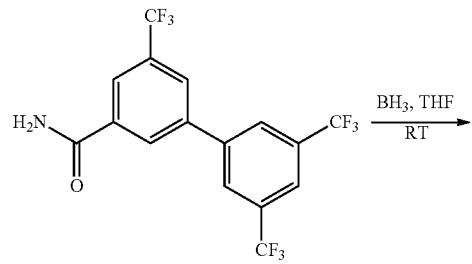

Into a 50-mL round-bottom flask was placed a solution of tert-butyl (2S,4S)-2-[([3-[3,5-bis(trifluoromethyl)phenyl]phenyl]methyl)carbamoyl]-4-fluoropyrrolidine-1-carboxylate (250 mg, 0.47 mmol, 1.00 equiv) in dichloromethane (10 mL). Hydrogen chloride gas was bubbled into this solution.

After stirring for 30 min at room temperature the resulting solids were collected by filtration and diluted with 10 mL of water. The pH value of the solution was adjusted to 9-10 with aqueous $NH_3$ (10%). The mixture was extracted with ethyl acetate (3×10 mL), the combined organic layers were dried over $Na_2SO_4$ and concentrated under vacuum. This resulted in 68.2 mg (33%) of (2S,4S)—N-([3-[3,5-bis(trifluoromethyl)phenyl]phenyl]methyl)-4-fluoropyrrolidine-2-carboxamide as a white solid.

LC-MS: (ES, m/z): [M+H]$^+$=435.

$^1$H-NMR: (300 MHz, DMSO-d$_6$, ppm): δ 8.61-8.58 (m, 1H), 8.30 (s, 2H), 8.12 (s, 1H), 7.79-7.70 (m, 2H), 7.50-7.47 (m, 1H), 7.38-7.36 (m, 1H), 5.29-5.15 (m, 1H), 4.54-4.48 (m, 1H), 4.35-4.30 (m, 1H), 3.71-3.69 (m, 1H), 3.20-3.03 (m, 3H), 2.35-2.12 (m, 2H).

Example 50

Synthesis of 1-amino-N-((3',5,5'-tris(trifluoromethyl)-[1,1'-biphenyl]-3-yl)methyl)cyclopentane-1-carboxamide

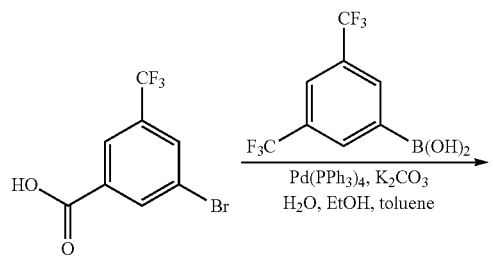

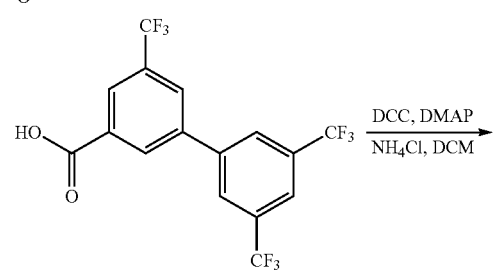

Step 1. Synthesis of 3-[3,5-bis(trifluoromethyl)phenyl]-5-(trifluoromethyl)benzoic acid

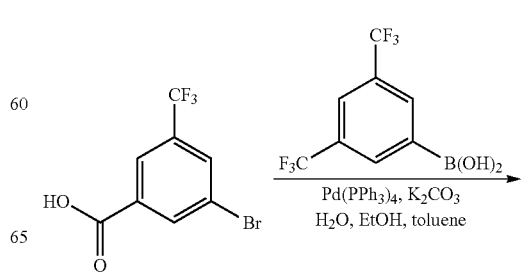

-continued

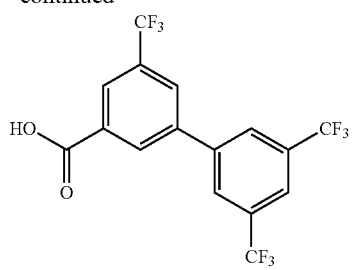

Into a 50-mL round-bottom flask was placed [3,5-bis(trifluoromethyl)phenyl]boronic acid (1 g, 3.88 mmol, 1.00 equiv), 3-bromo-5-(trifluoromethyl)benzoic acid (1.04 g, 3.87 mmol, 1.00 equiv), Pd(PPh₃)₄ (400 mg, 0.35 mmol, 0.09 equiv), potassium carbonate (1.06 g, 7.67 mmol, 1.98 equiv), toluene (8 mL), ethanol (4 mL), and water (2 mL). The resulting solution was heated to reflux overnight in an oil bath. The mixture was concentrated under vacuum and the residue was applied onto a silica gel column with dichloromethane/methanol (100:1). This resulted in 1.5 g (96%) of 3-[3,5-bis(trifluoromethyl)phenyl]-5-(trifluoromethyl)benzoic acid as a white solid.

Step 2. Synthesis of 3-[3,5-bis(trifluoromethyl)phenyl]-5-(trifluoromethyl)benzamide

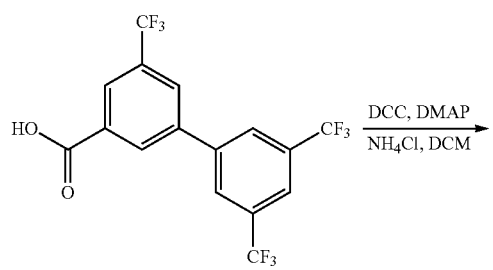

Into a 50-mL round-bottom flask was placed 3-[3,5-bis(trifluoromethyl)phenyl]-5-(trifluoromethyl)benzoic acid (1.5 g, 3.73 mmol, 1.00 equiv), NH₄Cl (400 mg, 7.48 mmol, 2.01 equiv), DCC (1.54 g, 7.46 mmol, 2.00 equiv), 4-dimethylaminopyridine (920 mg, 7.53 mmol, 2.02 equiv), and dichloromethane (30 g, 353.23 mmol, 94.72 equiv). The resulting solution was stirred overnight at 50° C. in an oil bath. The mixture was concentrated under vacuum and the residue was applied onto a silica gel column with dichloromethane/methanol (200:1). This resulted in 1 g (67%) of 3-[3,5-bis(trifluoromethyl)phenyl]-5-(trifluoromethyl)benzamide as a white solid.

Step 3. Synthesis of [3-[3,5-bis(trifluoromethyl)phenyl]-5-(trifluoromethyl)phenyl]methanamine

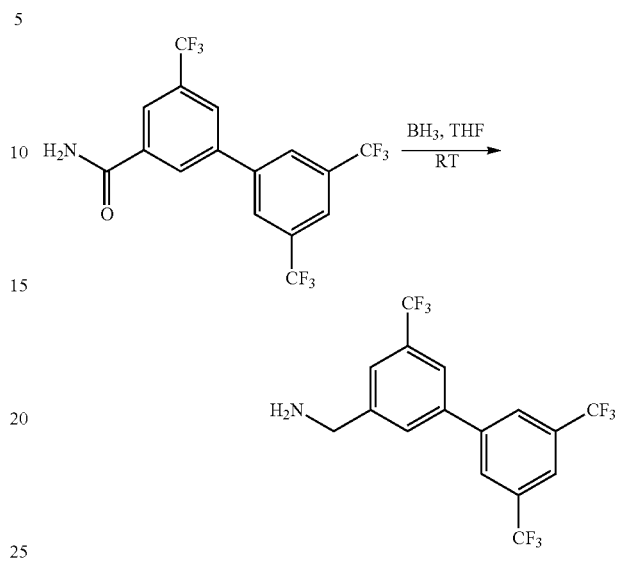

Into a 25-mL round-bottom flask was placed 3-[3,5-bis(trifluoromethyl)phenyl]-5-(trifluoromethyl)benzamide (1 g, 2.49 mmol, 1.00 equiv), tetrahydrofuran (10 mL), and BH₃·THF (5 ml, 1M). The resulting solution was stirred overnight at room temperature. The reaction was then quenched by the addition of 10 ml of NH₄Cl (aq.). The resulting solution was extracted with 2×30 ml of ethyl acetate, the organic layers were combined and concentrated under vacuum. The residue was applied onto a silica gel column with methanol/CH₂Cl₂ (1:20). This resulted in 200 mg (21%) of [3-[3,5-bis(trifluoromethyl)phenyl]-5-(trifluoromethyl)phenyl]methanamine as a white solid.

Step 4. Synthesis of tert-butyl N-[1-[([3-[3,5-bis(trifluoromethyl)phenyl]-5-(trifluoromethyl)phenyl]methyl)carbamoyl]cyclopentyl]carbamate

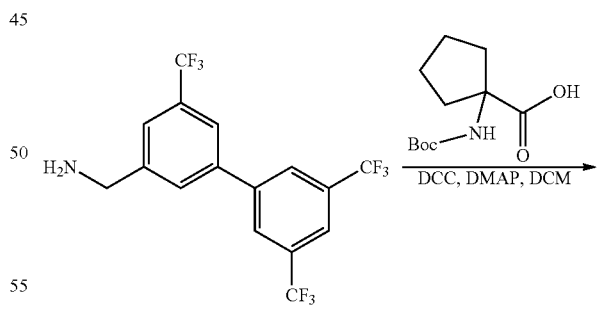

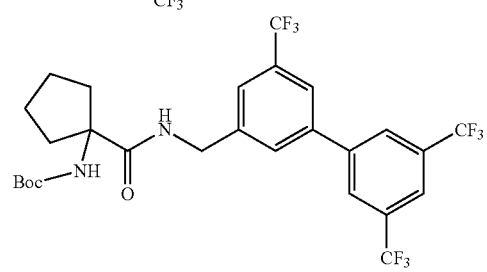

Into a 100-mL round-bottom flask was placed [3-[3,5-bis(trifluoromethyl)phenyl]-5-(trifluoromethyl)phenyl]methanamine (150 mg, 0.39 mmol, 1.00 equiv), dichloromethane (10 mL), DCC (159 mg, 0.77 mmol, 1.99 equiv), 4-dimethylaminopyridine (94 mg, 0.77 mmol, 1.99 equiv), and 1-[(tert-butoxy)carbonyl]aminocyclopentane-1-carboxylic acid (177 mg, 0.77 mmol, 1.99 equiv). The resulting solution was stirred overnight at 50° C. in an oil bath. The mixture was concentrated under vacuum and the residue was applied onto a silica gel column with dichloromethane/methanol (300:1). This resulted in 130 mg (56%) of tert-butyl N-[1-[([3-[3,5-bis(trifluoromethyl)phenyl]-5-(trifluoromethyl)phenyl]methyl)carbamoyl]cyclopentyl]carbamate as a white solid.

Step 5. Synthesis of 1-amino-N-([3-[3,5-bis(trifluoromethyl)phenyl]-5-(trifluoromethyl) phenyl]methyl)cyclopentane-1-carboxamide

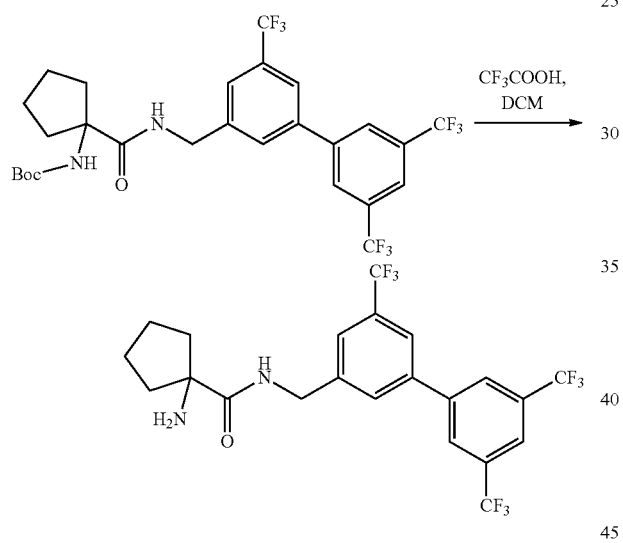

Into a 25-mL round-bottom flask was placed tert-butyl N-[1-[([3-[3,5-bis(trifluoromethyl)phenyl]-5-(trifluoromethyl)phenyl]methyl)carbamoyl]cyclopentyl]carbamate (130 mg, 0.22 mmol, 1.00 equiv), dichloromethane (5 mL), and CF$_3$COOH (1 mL). The resulting solution was stirred for 1 h at room temperature. The solution was diluted with 10 mL DCM and the pH value of the solution was adjusted to 8 with ammonia. The crude mixture was purified by preparative TLC (extending solvent: DCM:MeOH:ammonia=10:1:0.05). This resulted in 66.2 mg (61%) of 1-amino-N-([3-[3,5-bis(trifluoromethyl)phenyl]-5-(trifluoromethyl)phenyl]methyl)cyclopentane-1-carboxamide as a white solid.

LC-MS: [M+H]$^+$ 599, [M+CH$_3$CN]$^+$ 640.

$^1$H NMR (300 MHz, CDCl$_3$, ppm): δ 1.51-1.66 (m, 2H), 1.74-1.98 (m, 6H), 2.22-2.40 (m, 2H), 4.55 (d, 2H), 7.58 (s, 1H), 7.65-7.69 (d, 2H), 7.95 (s, 1H), 8.24 (s, 2H), 8.32 (brs, 1H).

Example 51

Synthesis (2S,4S)-4-fluoro-N-((3',5,5'-tris(trifluoromethyl)-[1,1'-biphenyl]-3-yl)methyl)pyrrolidine-2-carboxamide

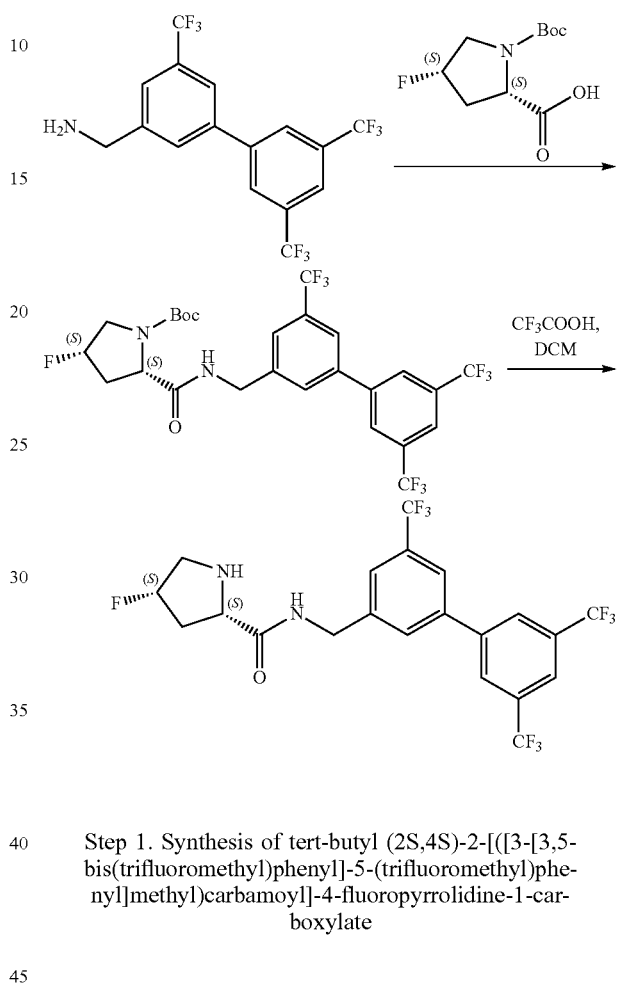

Step 1. Synthesis of tert-butyl (2S,4S)-2-[([3-[3,5-bis(trifluoromethyl)phenyl]-5-(trifluoromethyl)phenyl]methyl)carbamoyl]-4-fluoropyrrolidine-1-carboxylate

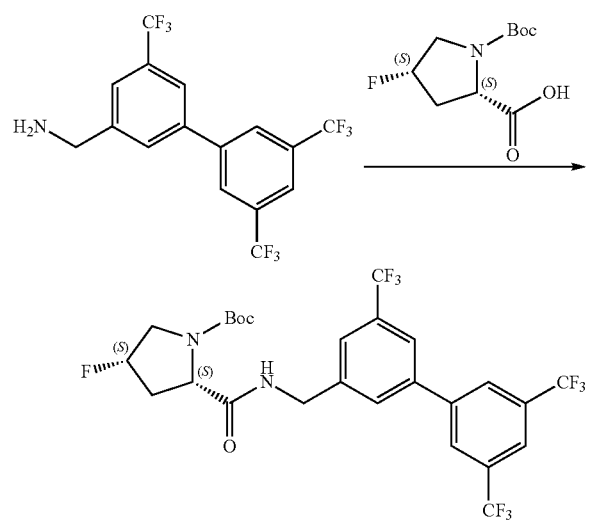

Into a 50-mL round-bottom flask was placed [3-[3,5-bis(trifluoromethyl)phenyl]-5-(trifluoromethyl)phenyl]methanamine (150 mg, 0.39 mmol, 1.00 equiv), 4-dimethylaminopyridine (95 mg, 0.78 mmol, 2.01 equiv), dichloromethane (10 mL), DCC (159 mg, 0.77 mmol, 1.99 equiv), and (2S,4S)-1-[(tert-butoxy)carbonyl]-4-fluoropyrrolidine-2-carboxylic acid (180 mg, 0.77 mmol, 1.99 equiv). The resulting solution was stirred overnight at room temperature. The mixture was concentrated under vacuum and the residue was applied onto a silica gel column with ethyl acetate/petroleum ether (1:5). This resulted in 120 mg (51%) of tert-butyl (2S,4S)-2-[([3-[3,5-bis(trifluoromethyl)phenyl]-5-(trifluoromethyl)phenyl]methyl)carbamoyl]-4-fluoropyrrolidine-1-carboxylate as a white solid.

Step 2. Synthesis of (2S,4S)—N-([3-[3,5-bis(trifluoromethyl)phenyl]-5-(trifluoromethyl)phenyl]methyl)-4-fluoropyrrolidine-2-carboxamide

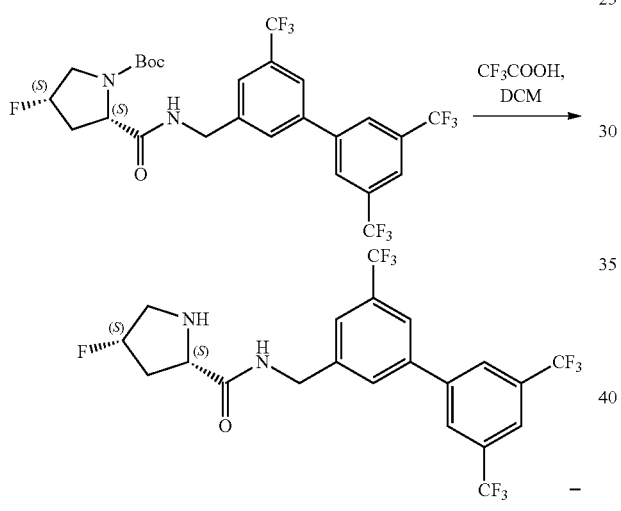

Into a 25-mL round-bottom flask was placed tert-butyl (2S,4S)-2-[([3-[3,5-bis(trifluoromethyl)phenyl]-5-(trifluoromethyl)phenyl]methyl)carbamoyl]-4-fluoropyrrolidine-1-carboxylate (120 mg, 0.20 mmol, 1.00 equiv), dichloromethane (5 mL), and trifluoroacetic acid (1 mL). The resulting solution was stirred for 2 h at room temperature. The solution was diluted with 10 mL DCM. The pH value of the solution was adjusted to 8 with ammonia. The crude mixture was purified by preparative TLC (extending solvent: DCM:MeOH:ammonia=10:1:0.05). This resulted in 55 mg (55%) of (2S,4S)—N-([3-[3,5-bis(trifluoromethyl)phenyl]-5-(trifluoromethyl)phenyl]methyl)-4-fluoropyrrolidine-2-carboxamide as a white solid.

LC-MS: [M+H]$^+$ 503, [M+CH$_3$CN]$^+$544.

$^1$H NMR (300 MHz, CD$_3$OD, ppm): δ 2.21-2.49 (m, 2H), 3.06-3.35 (m, 2H), 3.92 (d, 1H), 4.41 (d, 1H), 4.63 (d, 1H), 5.11-5.28 (d, 1H), 7.67 (s, 1H), 7.84 (s, 2H), 7.98 (s, 1H), 8.19 (s, 2H).

Example 52

Synthesis of (2R)—N-([3-[3,5-bis(trifluoromethyl)phenyl]-5-(trifluoromethyl)phenyl] methyl)pyrrolidine-2-carboxamide

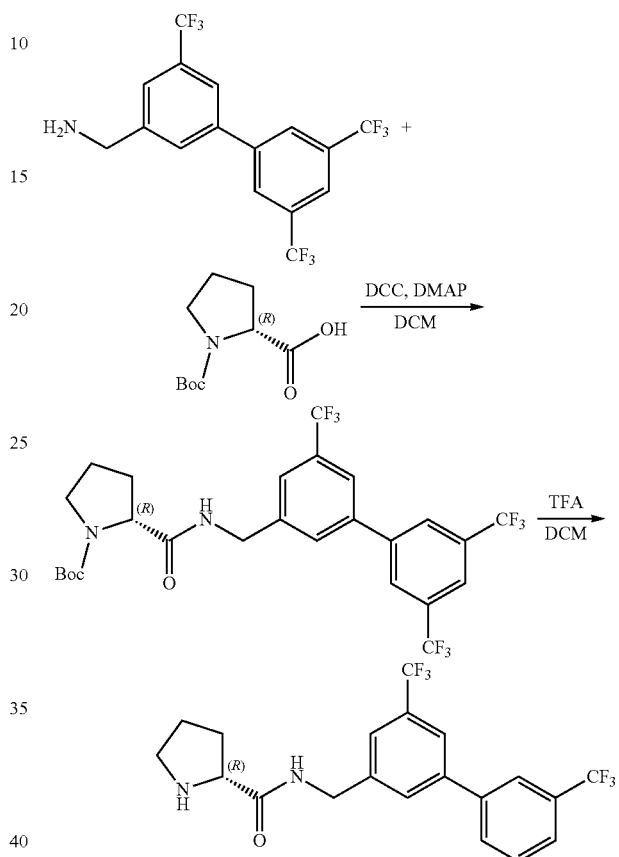

Step 1. Synthesis of tert-butyl (2R)-2-[([3-[3,5-bis(trifluoromethyl)phenyl]-5-(trifluoromethyl) phenyl]methyl)carbamoyl]pyrrolidine-1-carboxylate

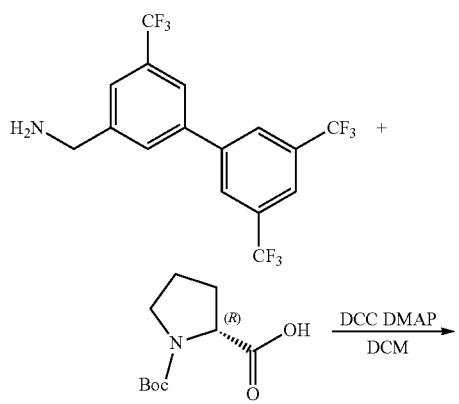

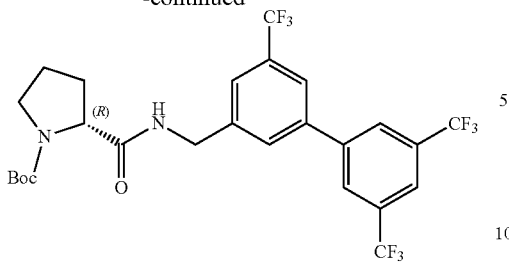

Into a 100-mL round-bottom flask was placed [3-[3,5-bis(trifluoromethyl)phenyl]-5-(trifluoromethyl)phenyl]methanamine (150 mg, 0.39 mmol, 1.00 equiv), dichloromethane (20 mL), (2R)-1-[(tert-butoxy)carbonyl]pyrrolidine-2-carboxylic acid (166.8 mg, 0.77 mmol, 2.00 equiv), 4-dimethylaminopyridine (94.672 mg, 0.77 mmol, 2.00 equiv), and DCC (159.856 mg, 5.91 mmol, 15.26 equiv). The resulting solution was stirred overnight at 50° C. in an oil bath. The mixture was concentrated under vacuum and the residue was applied onto a silica gel column with ethyl acetate/petroleum ether (1:5). This resulted in 120 mg (53%) of tert-butyl (2R)-2-[([3-[3,5-bis(trifluoromethyl)phenyl]-5-(trifluoromethyl)phenyl]methyl)carbamoyl]pyrrolidine-1-carboxylate as a white solid.

Step 2. Synthesis of (2R)—N-([3-[3,5-bis(trifluoromethyl)phenyl]-5-(trifluoromethyl)phenyl]methyl)pyrrolidine-2-carboxamide

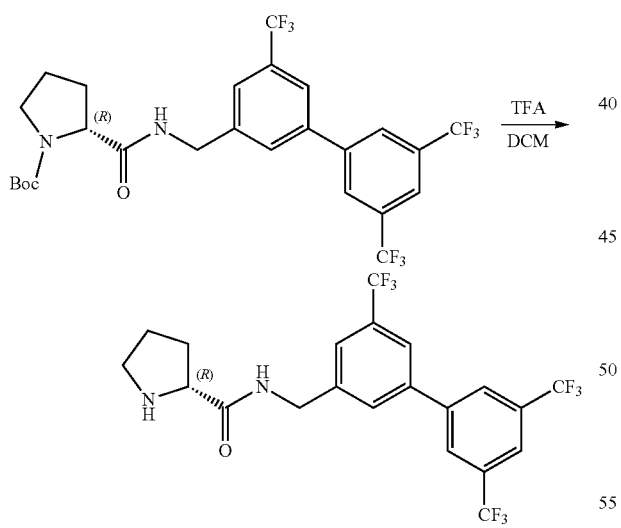

Into a 50-mL round-bottom flask was placed tert-butyl (2R)-2-[([3-[3,5-bis(trifluoromethyl)phenyl]-5-(trifluoromethyl)phenyl]methyl)carbamoyl]pyrrolidine-1-carboxylate (120 mg, 0.21 mmol, 1.00 equiv), dichloromethane (8 mL), and trifluoroacetic acid (2 mL). The solution was stirred for 3 h at room temperature and then concentrated under vacuum. The resulting solution was diluted with 10 mL DCM. The pH value of the solution was adjusted to 8 with ammonia. The crude mixture was purified by preparative TLC (extending solvent: DCM:MeOH:ammonia=10:1:

0.05). This resulted in 25.3 mg (25%) of (2R)—N-([3-[3,5-bis(trifluoromethyl)phenyl]-5-(trifluoromethyl)phenyl]methyl)pyrrolidine-2-carboxamide as off-white semi-solid.

LC-MS: (ES, m/z): [M+H]⁺=485.

¹H NMR (400 MHz, CD₃OD, ppm): δ 1.76-1.88 (m, 3H), 2.17-2.24 (m, 1H), 2.94-3.08 (m, 2H), 3.74-3.78 (m, 1H), 4.54-4.66 (m, 2H), 7.73 (s, 1H), 7.92-7.93 (d, 2H), 8.06 (s, 1H), 8.26 (s, 2H).

Example 53

N-([3-[3,5-bis(trifluoromethyl)phenyl]phenyl]methyl)cyclopentanecarboxamide

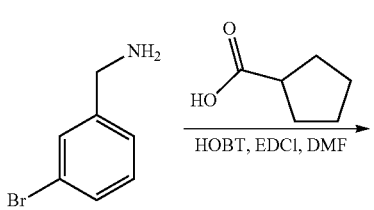

Step 1. Synthesis of N-[(3-bromophenyl)methyl]cyclopentanecarboxamide

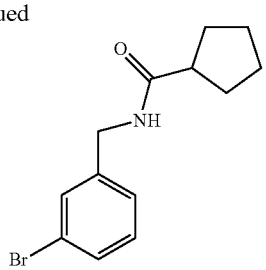

Cyclopentanecarboxylic acid (1.235 g, 10.82 mmol, 1.00 equiv), HOBT (1.46 g, 10.81 mmol, 1.00 equiv), EDCI (2.08 g, 10.85 mmol, 1.00 equiv), and (3-bromophenyl)methanamine (2.0 g, 10.75 mmol, 1.00 equiv) were dissolved in N, N-dimethylformamide (25 mL) at room temperature. The reaction was stirred for 2 h at 25° C. and then quenched by the addition of water. The resulting solution was extracted with ethyl acetate and the organic layers were combined, washed with brine, dried and concentrated in vacuo. This resulted in 3.0 g (crude) of N-[(3-bromophenyl)methyl] cyclopentanecarboxamide as white solid.

Step 2. Synthesis of N-([3-[3,5-bis(trifluoromethyl) phenyl]phenyl]methyl)cyclopentanecarboxamide

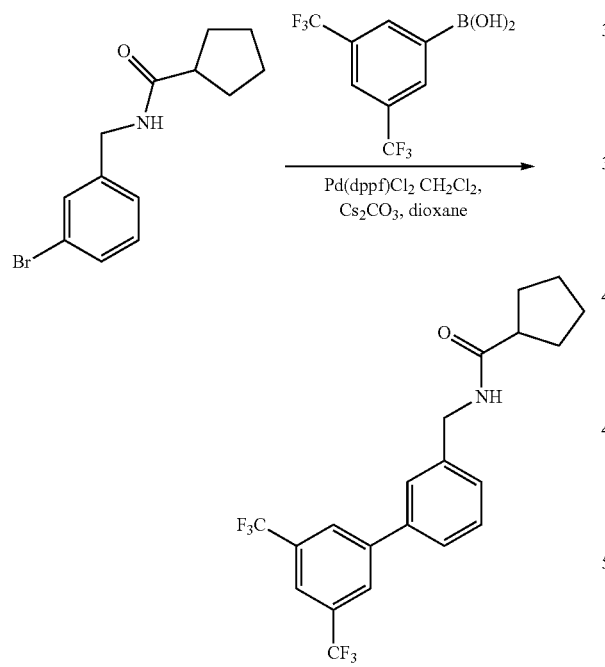

N-[(3-bromophenyl)methyl]cyclopentanecarboxamide (28.2 mg, 0.10 mmol, 1.00 equiv), [3,5-bis(trifluoromethyl) phenyl]boronic acid (25.8 mg, 0.10 mmol, 1.00 equiv), and Cs$_2$CO$_3$ (65.2 mg, 0.20 mmol, 2.00 equiv) were dissolved in dioxane (2 mL) under an inert nitrogen atmosphere. Then Pd(dppf)Cl$_2$.CH$_2$Cl$_2$ (8.17 mg, 0.10 equiv) was added. The resulting reaction was stirred for 16 h at 80° C. Then it was concentrated in vacuo. The residue was purified by silica gel column chromatography eluting with ethyl acetate/petroleum ether (1:10). This afforded 34 mg (82%) of N-([3-[3, 5-bis(trifluoromethyl)phenyl]phenyl]methyl)cyclopentanecarboxamide as white solid.

LC-MS: (ES, m/z): [M+H]$^+$ 416
$^1$H NMR (400 MHz, DMSO-d$_6$, ppm): δ 8.41-8.36 (m, 1H), 8.31 (s, 2H), 8.13 (s, 1H), 7.78-7.76 (d, 1H), 7.71 (s, 1H), 7.53-7.49 (t, 1H), 7.38-7.33 (m, 1H), 4.39-4.38 (d, 2H), 2.70-2.62 (m, 1H), 1.81-1.79 (m, 2H), 1.70-1.66 (m, 4H), 1.42-1.25 (m, 2H).

Example 54

Synthesis of (2S)—N-([3-[3,5-bis(trifluoromethyl) phenyl]phenyl]methyl)-1-methylpyrrolidine-2-carboxamide

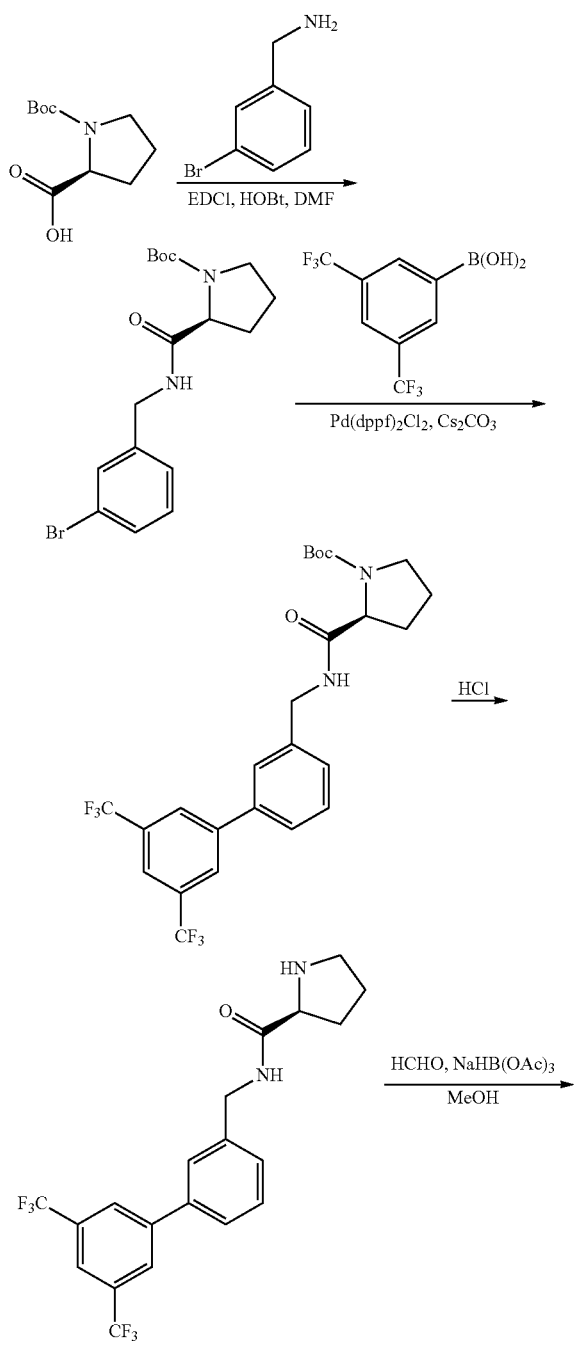

209
-continued

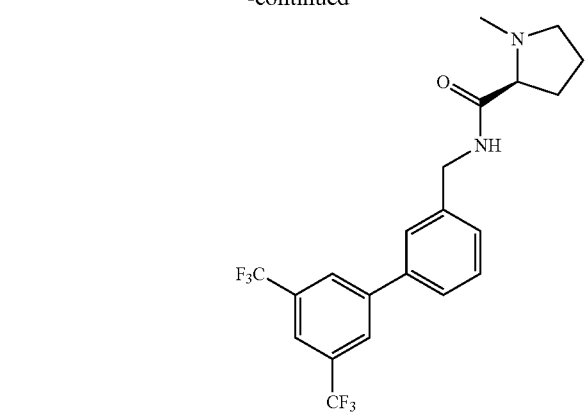

Step 1. Synthesis of tert-butyl (2S)-2-[[(3-bromophenyl)methyl]carbamoyl]pyrrolidine-1-carboxylate (2S)-1-[(tert-butoxy)carbonyl]pyrrolidine-2-carboxylic acid (6.45 g, 29.97 mmol, 1.00 equiv), HOBT (4.05 g, 29.97 mmol, 1.00 equiv), EDCI (5.76 g, 30.05 mmol, 1.00 equiv), and (3-bromophenyl)methanamine (5.55 g, 29.83 mmol, 1.00 equiv) were dissolved in N,N-dimethylformamide at room temperature. The reaction was stirred for 2 h. Then it was quenched by the addition of water. The resulting solution was extracted with ethyl acetate and the organic layers were combined and washed with 3×50 mL of saturated aqueous sodium bicarbonate, brine, and concentrated in vacuo. This resulted in 10 g (87%) of tert-butyl (2S)-2-[[(3-bromophenyl)methyl]carbamoyl]pyrrolidine-1-carboxylate as a white solid.

210

Step 2. Synthesis of tert-butyl (2S)-2-[([3-[3,5-bis(trifluoromethyl)phenyl]phenyl]methyl)carbamoyl]pyrrolidine-1-carboxylate

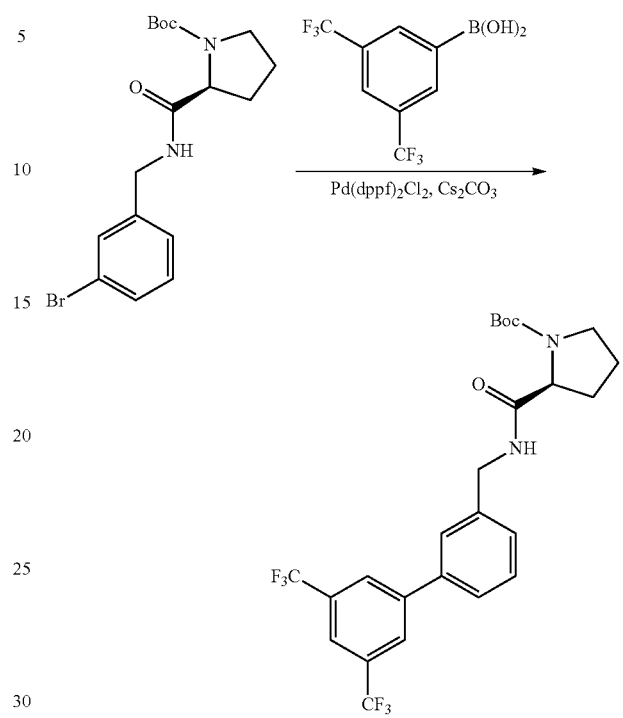

Tert-butyl (2S)-2-[[(3-bromophenyl)methyl]carbamoyl]pyrrolidine-1-carboxylate (3.8 g, 9.91 mmol, 1.00 equiv) was dissolved in dioxane (50 mL). Then [3,5-bis(trifluoromethyl)phenyl]boronic acid (2.6 g, 10.08 mmol, 1.02 equiv), Pd(dppf)$_2$Cl$_2$ (730 mg, 1.00 mmol, 0.10 equiv), and Cs$_2$CO$_3$ (6.52 g, 19.95 mmol, 2.01 equiv) were added. The reaction was stirred overnight at 80° C. in an oil bath then concentrated in vacuo. The residue was applied onto a silica gel column with ethyl acetate/petroleum ether (1:10). This resulted in 4 g (78%) of tert-butyl (2S)-2-[([3-[3,5-bis(trifluoromethyl)phenyl]phenyl]methyl)carbamoyl]pyrrolidine-1-carboxylate as a white solid.

Step 3. Synthesis of (2S)—N-([3-[3,5-bis(trifluoromethyl)phenyl]phenyl]methyl)pyrrolidine-2-carboxamide

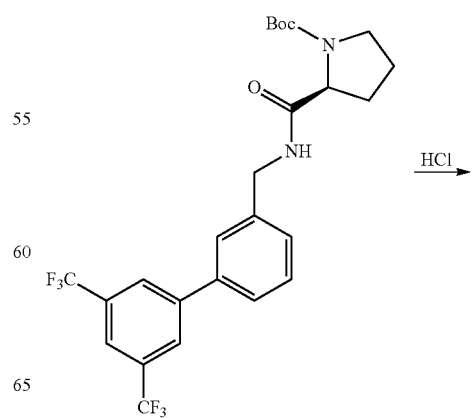

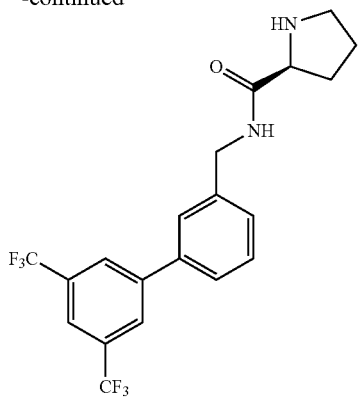

Tert-butyl (2S)-2-[([3-[3,5-bis(trifluoromethyl)phenyl]phenyl]methyl)carbamoyl]pyrrolidine-1-carboxylate (1 g, 1.94 mmol, 1.00 equiv) was dissolved in ethyl acetate (10 mL). Then a solution of hydrogen chloride (707 mg, 19.39 mmol, 10.00 equiv) in ethyl acetate (10 mL) was added. The reaction was stirred for 16 h at 25° C. The resulting mixture was concentrated in vacuo. The resulting mixture was washed with water, brine, and then concentrated in vacuo. This resulted in 800 mg (crude) of (2S)—N-([3-[3,5-bis(trifluoromethyl)phenyl]phenyl]methyl)pyrrolidine-2-carboxamide as a white solid.

Step 4. Synthesis of (2S)—N-([3-[3,5-bis(trifluoromethyl)phenyl]phenyl]methyl)-1-methylpyrrolidine-2-carboxamide (2S)—N-([3-[3,5-bis(trifluoromethyl)phenyl]phenyl]methyl)pyrrolidine-2-carboxamide (200 mg, 0.48 mmol, 1.00 equiv) was dissolved in methanol (8 mL). This was followed by the addition of HCHO (aq. 37%, 39 mg, 1.00 equiv.). The reaction was stirred for 30 min at room temperature. To this was added NaBH(OAc)₃ (203 mg, 0.96 mmol, 2.00 equiv). The resulting reaction was stirred for 3 h at 25° C., then quenched by the addition of water and extracted with ethyl acetate. The organic layers were combined washed with brine, dried over anhydrous sodium sulfate and concentrated in vacuo. The residue was purified by silica gel column chromatography eluting with ethyl acetate/petroleum ether (1:10). The collected fractions were combined and concentrated in vacuo. This resulted in 20 mg (10%) of (2S)—N-([3-[3,5-bis(trifluoromethyl)phenyl]phenyl]methyl)-1-methylpyrrolidine-2-carboxamide as an off-white solid.

LC-MS (ES, m/z): [M+H]⁺ 431.

¹H NMR (300 MHz, DMSO-d₆, ppm): δ 9.88-9.19 (m, 1H), 8.44-8.32 (m, 2H), 8.13 (s, 1H), 7.87-7.64 (m, 2H), 7.55-7.30 (m, 2H), 4.48 (s, 2H), 4.16-3.75 (m, 1H), 3.48 (s, 1H), 3.19-3.05 (m, 1H), 2.92-2.76 (m, 3H), 2.27 (s, 1H), 2.15-1.91 (m, 1H), 1.89-1.65 (m, 2H).

Example 55

(2S)—N-([3-[3,5-bis(trifluoromethyl)phenyl]phenyl]methyl)-N-methylpyrrolidine-2-carboxamide; trifluoroacetic acid

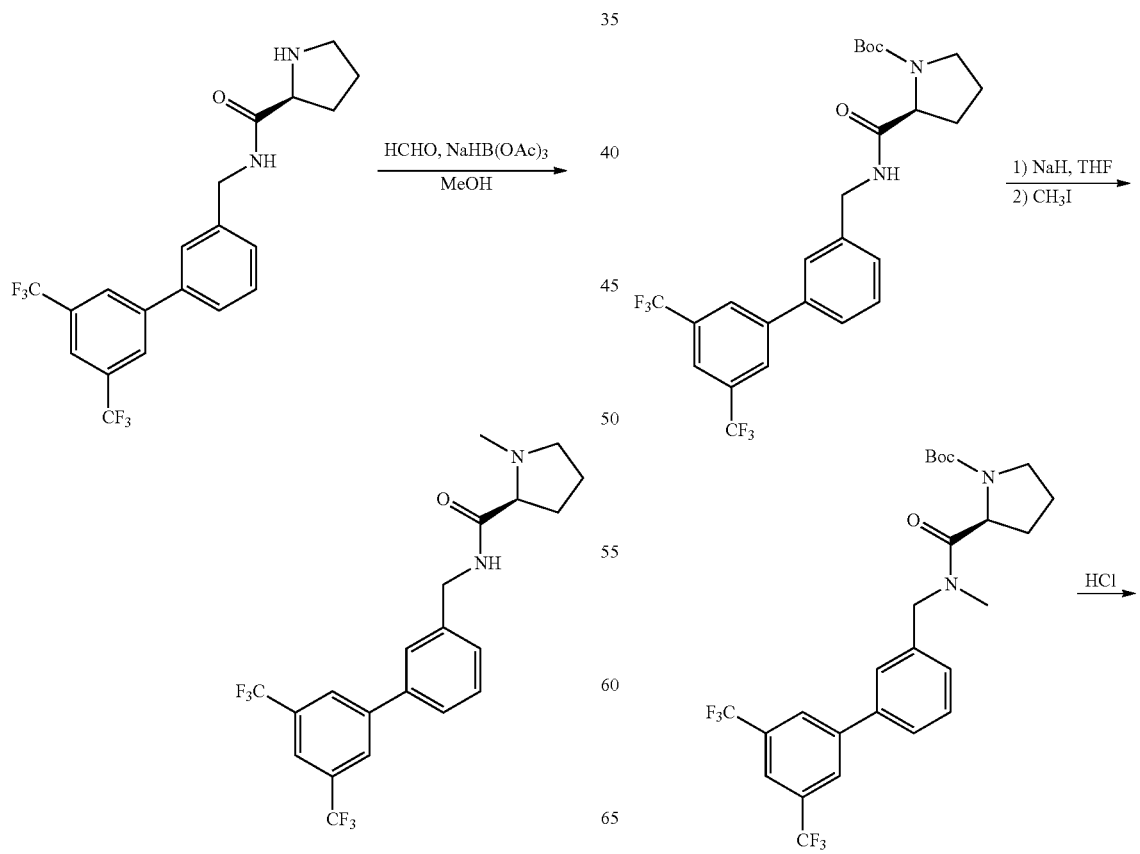

Step 1. Synthesis of tert-butyl (2S)-2-[([3-[3,5-bis(trifluoromethyl)phenyl]phenyl]methyl)(methyl)carbamoyl]pyrrolidine-1-carboxylate

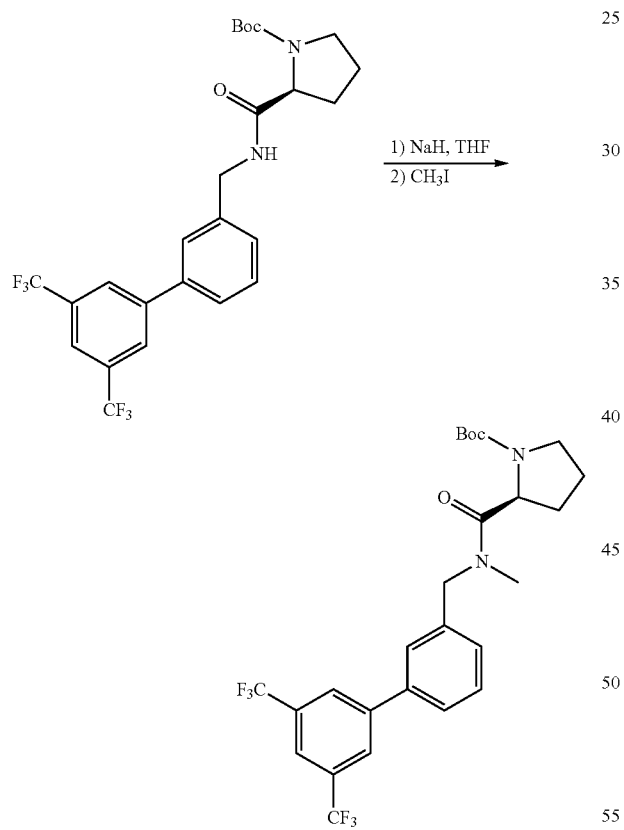

A solution of tert-butyl (2S)-2-[([3-[3,5-bis(trifluoromethyl)phenyl]phenyl]methyl)carbamoyl]pyrrolidine-1-carboxylate (516 mg, 1.00 mmol, 1.00 equiv) in tetrahydrofuran (10 mL) was placed into a 50-mL round-bottom flask. This was followed by the addition of sodium hydride (41 mg, 1.20 mmol, 1.20 equiv) in several batches at 0° C. The reaction was stirred for 30 min at 0° C., then iodomethane (156 mg, 1.10 mmol, 1.10 equiv) was added. The reaction was stirred for 3 h at 25° C. Then it was diluted with 20 mL of water, extracted with 2×20 mL of ethyl acetate, and the organic layers were combined and concentrated in vacuo. This resulted in 200 mg (38%) of tert-butyl (2S)-2-[([3-[3,5-bis(trifluoromethyl)phenyl]phenyl]methyl)(methyl)carbamoyl]pyrrolidine-1-carboxylate as a white solid.

Step 2. Synthesis of (2S)—N-([3-[3,5-bis(trifluoromethyl)phenyl]phenyl]methyl)-N-methylpyrrolidine-2-carboxamide; trifluoroacetic acid

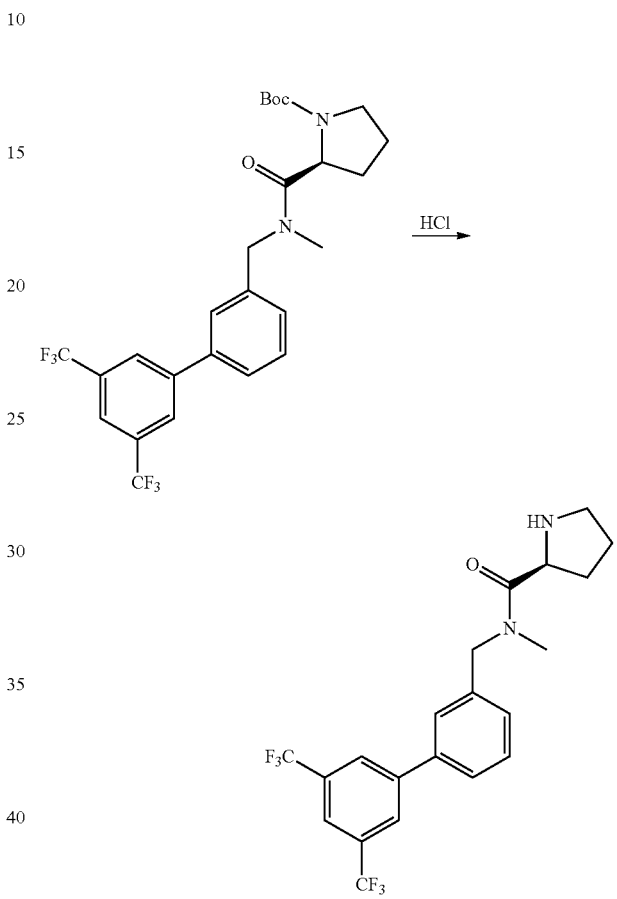

Tert-butyl (2S)-2-[([3-[3,5-bis(trifluoromethyl)phenyl]phenyl]methyl)(methyl)carbamoyl]pyrrolidine-1-carboxylate (100 mg, 0.19 mmol, 1.00 equiv) was dissolved in a solution of hydrogen chloride (68 mg, 10.00 equiv) in ethyl acetate (10 mL). The reaction was stirred for 16 h at 25° C. Then it was concentrated in vacuo. The crude product (85 mg) was purified by Prep-HPLC under the following conditions (HPrepC-007): Column, Xbridge Prep C18 5 um, 19*150 mm; mobile phase, water with 0.05% TFA and CH$_3$CN (10.0% CH$_3$CN up to 80.0% in 10 min, up to 100.0% in 2 min, down to 10.0% in 1 min); Detector, UV 220/254 nm. This afforded 71.1 mg (69%) of (2S)—N-([3-[3,5-bis(trifluoromethyl)phenyl]phenyl]methyl)-N-methylpyrrolidine-2-carboxamide; trifluoroacetic acid as a white solid.

LC-MS (ES, m/z): [M−THF+H]$^+$431.

$^1$H NMR (300 MHz, DMSO-d$_6$, ppm): δ 9.450 (s, 1H), 8.59 (s, 1H), 8.38-8.32 (d, 2H), 8.14 (s, 1H), 7.85-7.72 (m, 2H), 7.61-7.51 (m, 1H), 7.36-7.34 (m, 1H), 4.840-4.60 (m, 3H), 3.30-3.29 (m, 1H), 3.21-3.19 (m, 1H), 3.03-2.88 (m, 3H), 2.36-2.50 (m, 1H), 1.97-1.84 (m, 3H).

Example 56

Synthesis of (2S)—N-([3-[3,5-bis(trifluoromethyl)phenyl]phenyl]methyl)-1-(phenylsulfamoyl)pyrrolidine-2-carboxamide

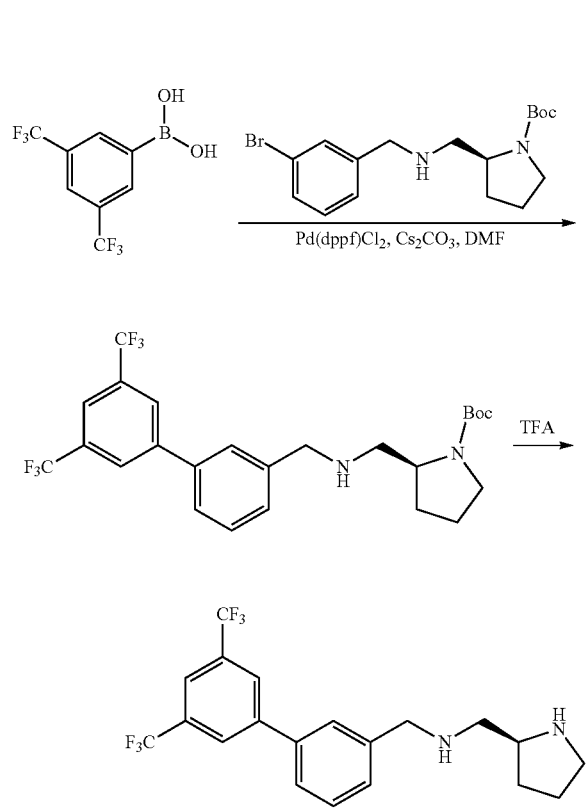

Step 1. Synthesis of tert-butyl (2S)-2-[([3-[3,5-bis(trifluoromethyl)phenyl]phenyl]methyl)carbamoyl]pyrrolidine-1-carboxylate

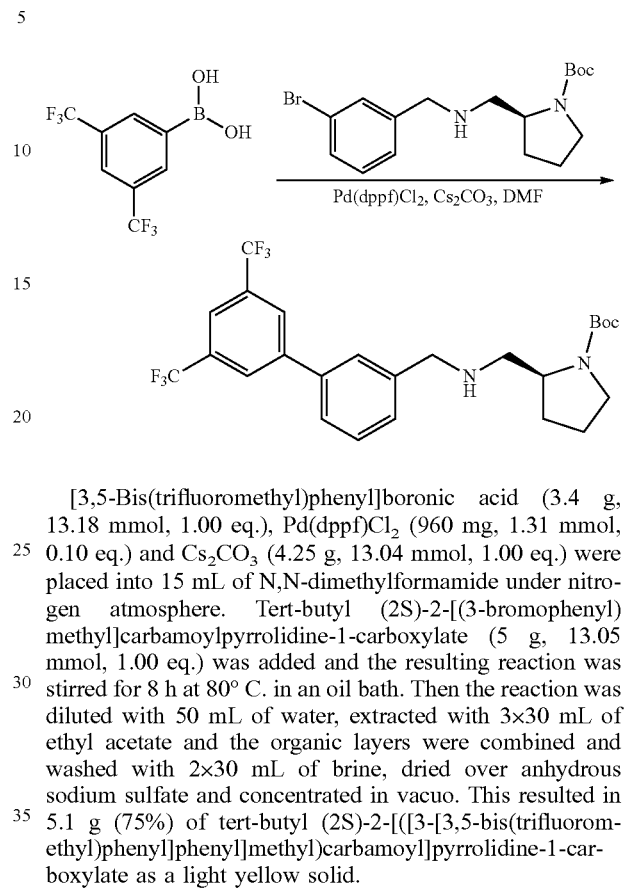

[3,5-Bis(trifluoromethyl)phenyl]boronic acid (3.4 g, 13.18 mmol, 1.00 eq.), Pd(dppf)Cl$_2$ (960 mg, 1.31 mmol, 0.10 eq.) and Cs$_2$CO$_3$ (4.25 g, 13.04 mmol, 1.00 eq.) were placed into 15 mL of N,N-dimethylformamide under nitrogen atmosphere. Tert-butyl (2S)-2-[(3-bromophenyl)methyl]carbamoylpyrrolidine-1-carboxylate (5 g, 13.05 mmol, 1.00 eq.) was added and the resulting reaction was stirred for 8 h at 80° C. in an oil bath. Then the reaction was diluted with 50 mL of water, extracted with 3×30 mL of ethyl acetate and the organic layers were combined and washed with 2×30 mL of brine, dried over anhydrous sodium sulfate and concentrated in vacuo. This resulted in 5.1 g (75%) of tert-butyl (2S)-2-[([3-[3,5-bis(trifluoromethyl)phenyl]phenyl]methyl)carbamoyl]pyrrolidine-1-carboxylate as a light yellow solid.

Step 2. Synthesis of (2S)—N-([3-[3,5-bis(trifluoromethyl)phenyl]phenyl]methyl)pyrrolidine-2-carboxamide

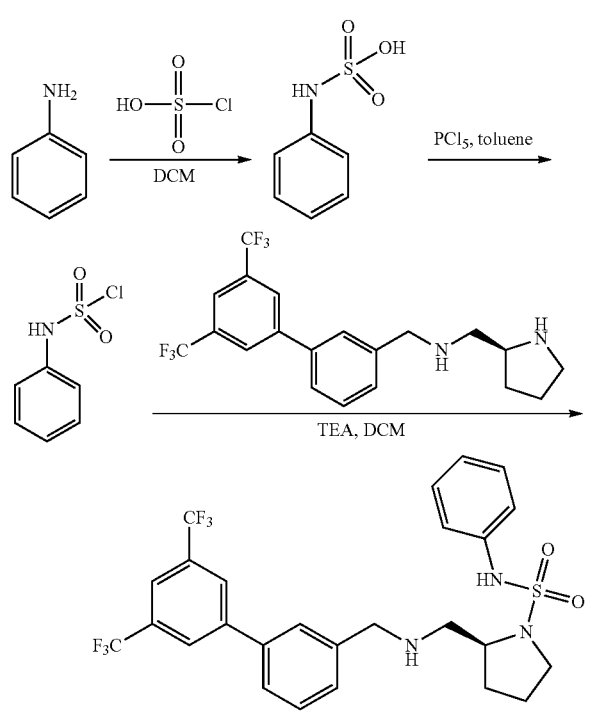

Tert-butyl (2S)-2-[([3-[3,5-bis(trifluoromethyl)phenyl]phenyl]methyl)carbamoyl]pyrrolidine-1-carboxylate (5 g, 9.68 mmol, 1.00 equiv) was dissolved in trifluoroacetic acid (20 mL). The reaction was stirred for 3 h at room temperature, and concentrated in vacuo. The residue was purified by silica gel column chromatography with EA/PE (1:4). This resulted in 4.0 g (99%) of (2S)—N-([3-[3,5-bis(trifluoromethyl)phenyl]phenyl]methyl)pyrrolidine-2-carboxamide as a light yellow solid.

Step 3. Synthesis of N-phenylsulfamic acid

Into a 100-mL 3-necked round-bottom flask, was placed aniline (3.2 g, 34.36 mmol, 2.00 equiv), dichloromethane (30 mL), and chloro sulfuric acid (2 g, 17.16 mmol, 1.00 equiv). The reaction was stirred for 2 h at 0° C. in a water/ice bath then diluted with 30 mL of water, extracted with 3×20 mL of dichloromethane and the organic layers were combined. The organic layers were washed with 2×30 mL of brine, dried over anhydrous sodium sulfate and concentrated in vacuo. This resulted in 2.8 g (94%) of N-phenylsulfamic acid as a white solid.

Step 4. Synthesis of N-phenylsulfamoyl chloride

N-phenylsulfamic acid (500 mg, 2.89 mmol, 1.00 equiv) and $PCl_5$ (1202 mg, 5.77 mmol, 2.00 equiv) were dissolved in toluene (20 mL). The reaction was stirred for 6 h at 80° C. in an oil bath and then concentrated in vacuo, diluted with 10 mL of water, and extracted with 3×10 mL of dichloromethane. The organic layers were washed with 2×10 mL of brine, dried over anhydrous sodium sulfate and concentrated in vacuo. This resulted in 500 mg (90%) of N-phenylsulfamoyl chloride as a light yellow oil.

Step 5. Synthesis of (2S)—N-([3-[3,5-bis(trifluoromethyl)phenyl]phenyl]methyl)-1-(phenylsulfamoyl)pyrrolidine-2-carboxamide

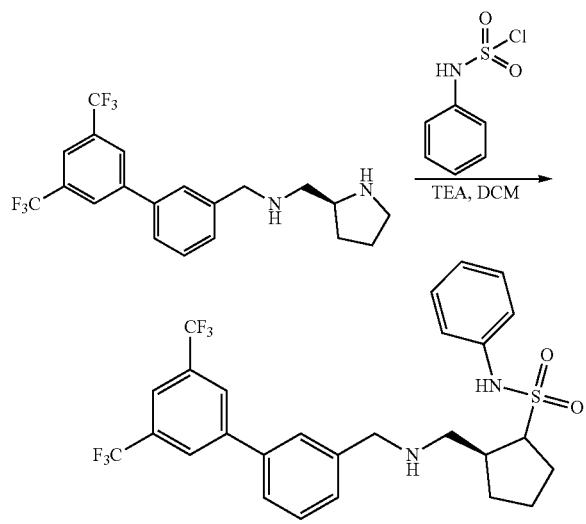

(2S)—N-(3-[3,5-bis(trifluoromethyl)phenyl]phenylmethyl)pyrrolidine-2-carboxamide (104 mg, 0.25 mmol, 1.00 equiv) and TEA (32 mg, 0.32 mmol, 1.20 equiv) were dissolved in dichloromethane (20 mL). Then N-phenylsulfamoyl chloride (50 mg, 0.26 mmol, 1.00 equiv) was added at 0° C. The reaction was stirred for 3 h at 0° C., then diluted with 30 mL of water, and extracted with 3×20 mL of dichloromethane. The organic layers were combined and washed with 2×30 mL of brine, dried over anhydrous sodium sulfate and concentrated in vacuo. The residue was purified by silica gel column chromatography with ethyl acetate/petroleum ether (1:3). This resulted in 23.6 mg (16%) of (2S)—N-([3-[3,5-bis(trifluoromethyl)phenyl]phenyl]methyl)-1-(phenylsulfamoyl)pyrrolidine-2-carboxamide as a white solid.

LC-MS (ES, m/z): $[M+H]^+$ 572.1.

$^1$H NMR (400 MHz, DMSO-$d_6$, ppm): δ 9.91 (brs, 1H), 8.43-8.40 (t, 1H), 8.32 (s, 2H), 8.10 (s, 1H), 7.76-7.74 (d, 2H), 7.50-7.47 (t, 1H), 7.38-7.36 (d, 1H), 7.28-7.27 (m, 4H), 4.42-4.32 (m, 2H), 4.18-4.16 (m, 1H), 3.41-3.39 (m, 1H), 3.33-3.27 (m, 2H), 1.91-1.77 (m, 3H), 1.69-1.67 (m, 1H).

Example 57

Synthesis of N-([3-[3,5-bis(trifluoromethyl)phenyl] phenyl] methyl)cyclohexanecarboxamide

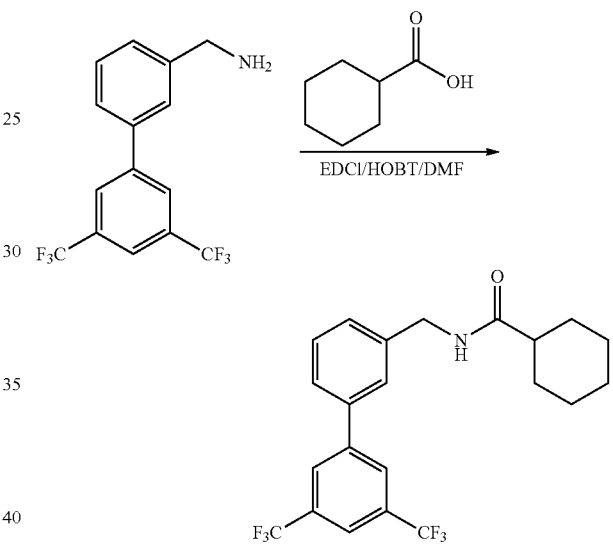

Cyclohexanecarboxylic acid (80 mg, 0.62 mmol, 1.00 equiv) was dissolved in 5 mL of DMF. Then (3-dimethylaminopropyl)ethyl-carbodiimid monohydrochloride (120 mg, 0.63 mmol, 1.00 equiv), 1-hydroxybenzotriazole (85 mg, 0.63 mmol, 1.00 equiv) and [3-[3,5-bis(trifluoromethyl)phenyl]phenyl]methanamine (200 mg, 0.63 mmol, 1.00 equiv) were added. The resulting reaction was stirred for 3 h at room temperature. Then the reaction was quenched by the addition of 50 mL of water, extracted with 100 mL×3 of ethyl acetate, washed with 100 mL×2 of brine, dried over anhydrous sodium sulfate, and concentrated in vacuo. The crude product was purified by Prep-HPLC under the following conditions: Column, Xbridge RP18, 19×150 mm; mobile phase: Water (0.05% $NH_3.H_2O$) and acetonitrile (50% acetonitrile up to 95% in 10 min, hold 100% for 3 min, down to 50% in 1 min); Detector, UV 254 nm. This resulted in 56.1 mg (21%) of N-([3-[3,5-bis(trifluoromethyl)phenyl] phenyl]methyl)cyclohexanecarboxamide as a white solid.

LC-MS (ES, m/z): 430.4 $(M+1)^+$; 471.5 $(M+1)^+$.

$^1$H NMR (400 MHz, CDCl$_3$): δ 1.20-1.36 (m, 3H), 1.48-1.57 (m, 2H), 1.67-1.72 (m, 1H), 1.84 (d, J=12.0 Hz, 2H), 1.94 (d, J=12.8 Hz, 2H), 2.12-2.22 (m, 1H), 4.57 (d, J=5.6 Hz, 2H), 5.85 (s, 1H), 7.39 (d, J=7.6 Hz, 1H), 7.48-7.55 (m, 3H), 7.89 (s, 1H), 8.02 (s, 2H).

Example 58

Synthesis of N-([3-[3,5-bis(trifluoromethyl)phenyl]phenyl]methyl)oxolane-2-carboxamide

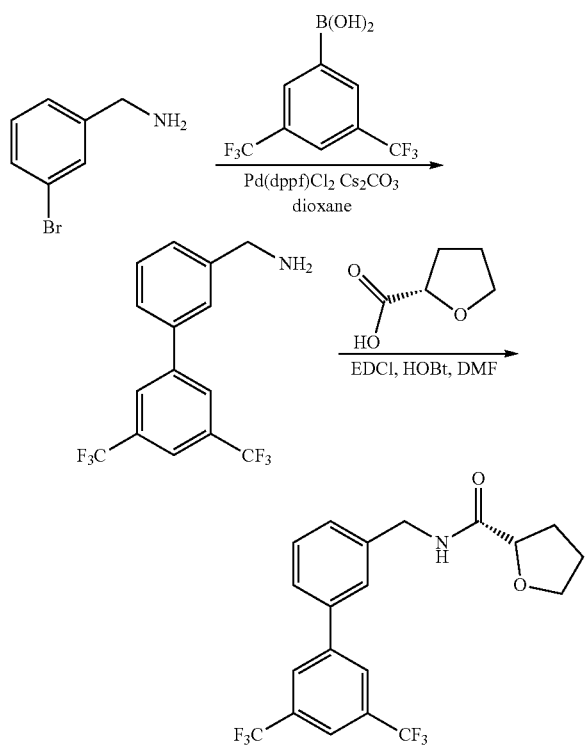

Step 1. Synthesis of [3-[3,5-bis(trifluoromethyl)phenyl]phenyl]methanamine

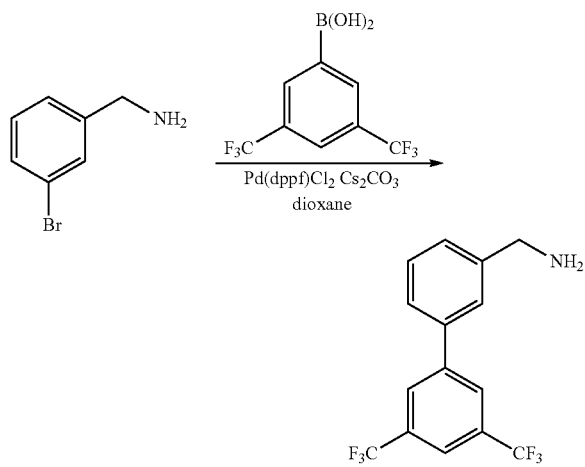

A mixture of [3,5-bis(trifluoromethyl)phenyl]boronic acid (2.58 g, 10.00 mmol, 1.00 equiv), (3-bromophenyl)methanamine (1.85 g, 9.94 mmol, 1.00 equiv), $Cs_2CO_3$ (6.52 g, 2.00 equiv), and $Pd_2(dppf)Cl_2$ (731 mg, 1.00 mmol, 0.10 equiv) were dissolved in dioxane (25 mL) under an inert atmosphere of nitrogen. The resulting reaction was stirred for 16 h at 80° C. and then concentrated in vacuo. The residue was purified by silica gel column chromatography with ethyl acetate/petroleum ether (1:20). This resulted in 3.0 g (94%) of [3-[3,5-bis(trifluoromethyl)phenyl]phenyl]methanamine as a brown oil.

Step 2. Synthesis of (S)—N-((3',5'-bis(trifluoromethyl)-[1,1'-biphenyl]-3-yl)methyl)tetrahydrofuran-2-carboxamide

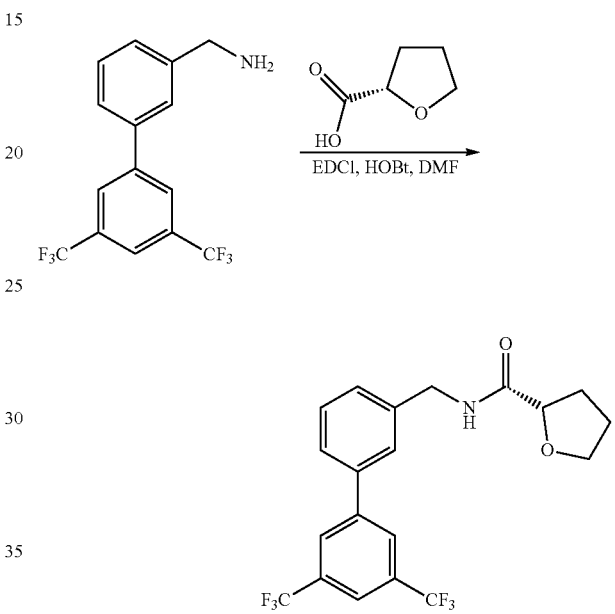

(S)-tetrahydrofuran-2-carboxylic acid (11 mg, 0.09 mmol, 1.01 equiv), EDCI (18 mg, 0.09 mmol, 1.00 equiv), HOBt (13 mg, 0.10 mmol, 1.02 equiv), and [3-[3,5-bis(trifluoromethyl)phenyl]phenyl]methanamine (30 mg, 0.09 mmol, 1.00 equiv) were dissolved in 2 mL of DMF. The resulting reaction was stirred for 2 h at room temperature. Then the reaction was quenched by the addition of 50 mL of water. The resulting solution was extracted with 3×30 mL of ethyl acetate and the organic layers were combined. The residue was purified by silica gel column chromatography with ethyl acetate/petroleum ether (1:1). The crude product was purified by Prep-HPLC with conditions: Column, XBridge Prep Shield RP18, 5 μm, 19×150 mm; mobile phase, $CH_3CN$/$H_2O$ (0.05% $NH_4HCO_3$)=30% increasing to $CH_3CN$/$H_2O$ (0.05% $NH_4HCO_3$)=70% within 10 min; Detector, UV 254 nm. This resulted in 16.1 mg (41%) of (S)—N-((3',5'-bis(trifluoromethyl)-[1,1'-biphenyl]-3-yl)methyl)tetrahydrofuran-2-carboxamide as an off-white solid.

LC-MS: (ES, m/z): $[M+H]^+$=418

$^1$H NMR (400 MHz, DMSO, ppm): δ 8.46 (t, 1H), 8.30 (s, 2H), 8.11 (s, 1H), 7.76-7.72 (m, 2H), 7.50 (t, 1H), 7.37 (d, 1H), 4.47-4.28 (m, 3H), 3.98-3.92 (m, 1H), 63.83-3.77 (m, 1H), 2.19-2.09 (m, 1H), 1.95-1.78 (m, 3H).

Example 59

Synthesis of (2S,4S)—N-([3-[3,5-bis(trifluoromethyl)phenyl]phenyl]methyl)-4-fluoro-1-methylpyrrolidine-2-carboxamide

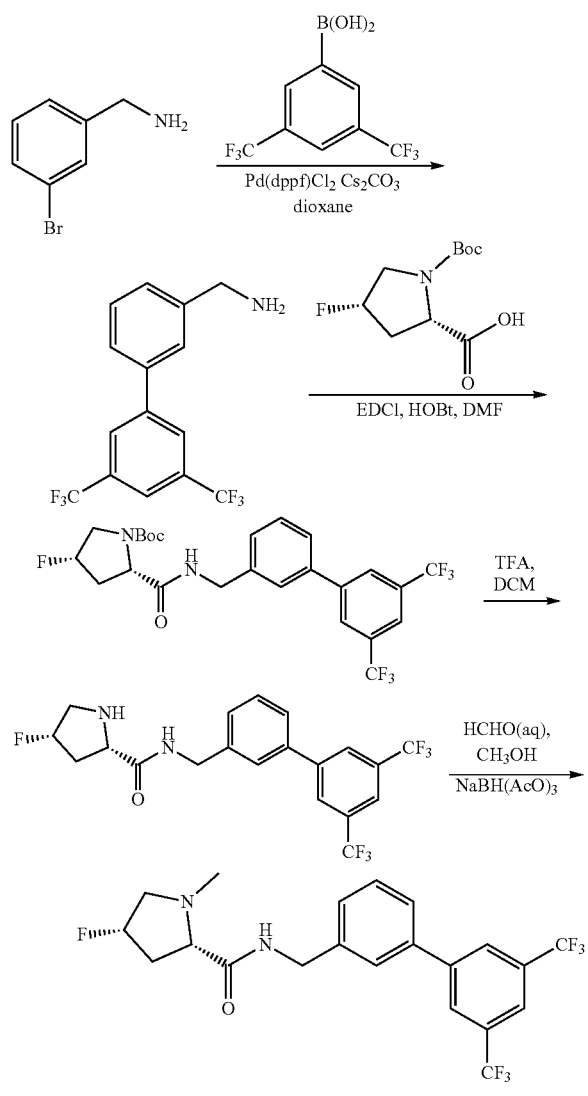

Step 1. Synthesis of [3-[3,5-bis(trifluoromethyl)phenyl]phenyl]methanamine

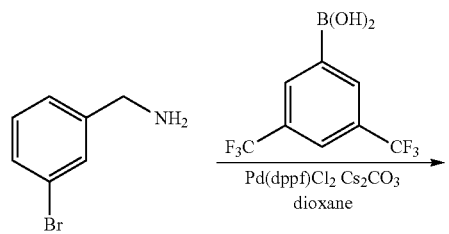

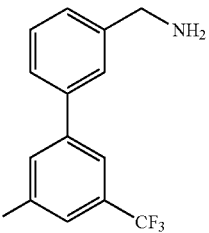

[3,5-Bis(trifluoromethyl)phenyl]boronic acid (2.58 g, 10.00 mmol, 1.00 equiv), (3-bromophenyl)methanamine (1.85 g, 9.94 mmol, 1.00 equiv), and Cs$_2$CO$_3$ (6.52 g, 2.00 equiv) were dissolved in 35 mL of dioxane under a nitrogen atmosphere. Then Pd(dppf)Cl$_2$ (731 mg, 1.00 mmol, 0.10 equiv) was added while maintaining the inert atmosphere. The resulting reaction was stirred for 16 h at 80° C. Then it was concentrated in vacuo. The residue was purified by silica gel column chromatography with ethyl acetate/petroleum ether (1:20). This resulted in 3.0 g (94%) of [3-[3,5-bis(trifluoromethyl)phenyl]phenyl]methanamine as a brown oil.

Step 2. Synthesis of (2S,4S)—N-([3-[3,5-bis(trifluoromethyl)phenyl]phenyl]methyl)-4-fluoropyrrolidine-2-carboxamide

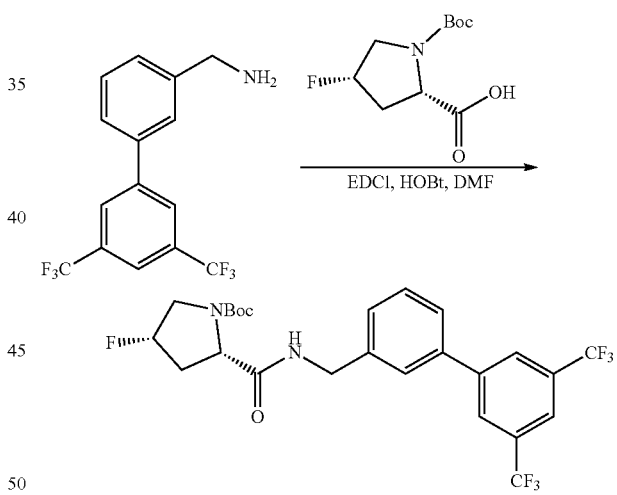

[3-[3,5-Bis(trifluoromethyl)phenyl]phenyl]methanamine (400 mg, 1.25 mmol, 1.00 equiv), (2S,4S)-1-[(tert-butoxy)carbonyl]-4-fluoropyrrolidine-2-carboxylic acid (292 mg, 1.25 mmol, 1.00 equiv), N,N-dimethylformamide (10 mL), HOBT (169 mg, 1.25 mmol, 1.00 equiv), EDCI (240 mg, 1.25 mmol, 1.00 equiv). The resulting solution was stirred for 2 h at room temperature. The reaction was then quenched by the addition of 100 mL of Na$_2$CO$_3$ (aq). The resulting solution was extracted with 3×50 mL of ethyl acetate and the organic layers combined and concentrated in vacuo. The residue was applied onto a silica gel column with ethyl acetate/petroleum ether (1:2). This resulted in 600 mg (90%) of tert-butyl (2S,4S)-2-[([3-[3,5-bis(trifluoromethyl)phenyl]phenyl]methyl)carbamoyl]-4-fluoropyrrolidine-1-carboxylate as a white solid.

Step 3. Synthesis of tert-butyl (2S,4S)-2-[([3-[3,5-bis(trifluoromethyl)phenyl]phenyl]methyl)carbamoyl]-4-fluoropyrrolidine-1-carboxylate

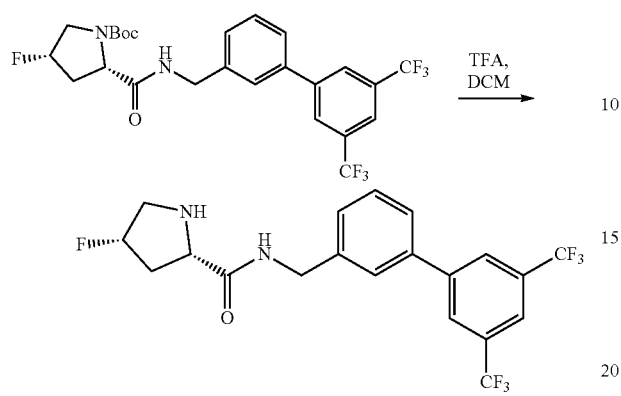

(5S,7S)—N-([3-[3,5-bis(trifluoromethyl)phenyl]phenyl]methyl)-1-tert-butyl-5-fluoro-2-oxo-1 [3],3-oxazepane-7-carboxamide (600 mg, 1.12 mmol, 1.00 equiv) and trifluoroacetic acid (5 mL) were dissolved in dichloromethane (15 mL). The reaction was stirred for 2 h at room temperature, concentrated in vacuo, diluted with 100 mL of H₂O, and the pH value of the solution was adjusted to pH 10 with sodium carbonate (sat.). Then it was extracted with 3×80 mL of ethyl acetate and the organic layers were combined and concentrated in vacuo. This resulted in 550 mg (crude) of (2S,4S)—N-([3-[3,5-bis(trifluoromethyl)phenyl]phenyl]methyl)-4-fluoropyrrolidine-2-carboxamide as a white solid.

Step 4. Synthesis of (2S,4S)—N-([3-[3,5-bis(trifluoromethyl)phenyl]phenyl]methyl)-4-fluoro-1-methylpyrrolidine-2-carboxamide

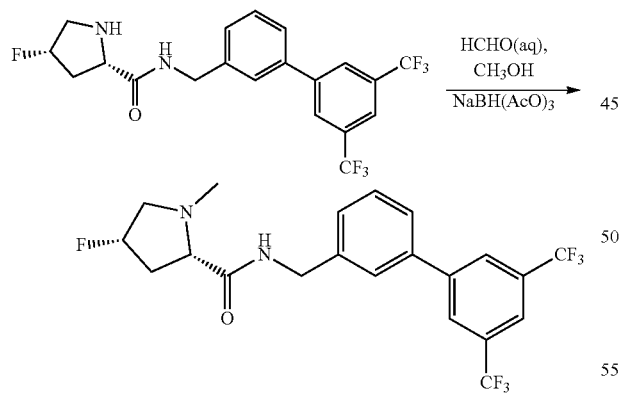

(2S,4S)—N-([3-[3,5-Bis(trifluoromethyl)phenyl]phenyl]methyl)-4-fluoropyrrolidine-2-carboxamide (550 mg, 1.27 mmol, 1.00 equiv) followed by HCHO (aq., 382 mg, 12.73 mmol, 10.06 equiv) and 1-(sodioboranyl)ethan-1-one acetyl acetate dihydrate (806 mg, 3.73 mmol, 2.95 equiv) were dissolved into in methanol (10 mL). The resulting reaction was stirred overnight at room temperature. Then the reaction was quenched by the addition of 30 mL of sodium bicarbonate (sat.) and extracted with 3×50 mL of ethyl acetate. The organic layers were combined and concentrated in vacuo. The product was precipitated by the addition of hexane. The solids were collected by filtration. This resulted in 144 mg (25%) of (2S,4S)—N-([3-[3,5-bis(trifluoromethyl)phenyl]phenyl]methyl)-4-fluoro-1-methylpyrrolidine-2-carboxamide as an off-white solid.

LC-MS (ES, m/z): [M+H]⁺=449.

¹H NMR (400 MHz, DMSO, ppm): δ 8.54 (s, 1H), δ8.30 (s, 2H), 8.14 (d, 1H), 7.77-7.71 (m, 1H), 7.50 (t, 1H), 7.38 (d, 1H), 6.43 (d, 1H), 5.21 (d, 1H), 4.53-4.47 (m, 1H), 4.40-4.35 (m, 1H), 3.40-3.15 (m, 1H), δ2.94 (s, 1H), 2.72-2.52 (m, 2H), 2.39 (s, 3H), 2.02-1.94 (m, 1H).

Examples 60 and 61

Synthesis of N-([3-[3,5-bis(trifluoromethyl)phenyl]phenyl]methyl)-3-hydroxycyclopentane-1-carboxamide (cis and trans isomers) (Isomer A=Example 60; Isomer B=Example 61)

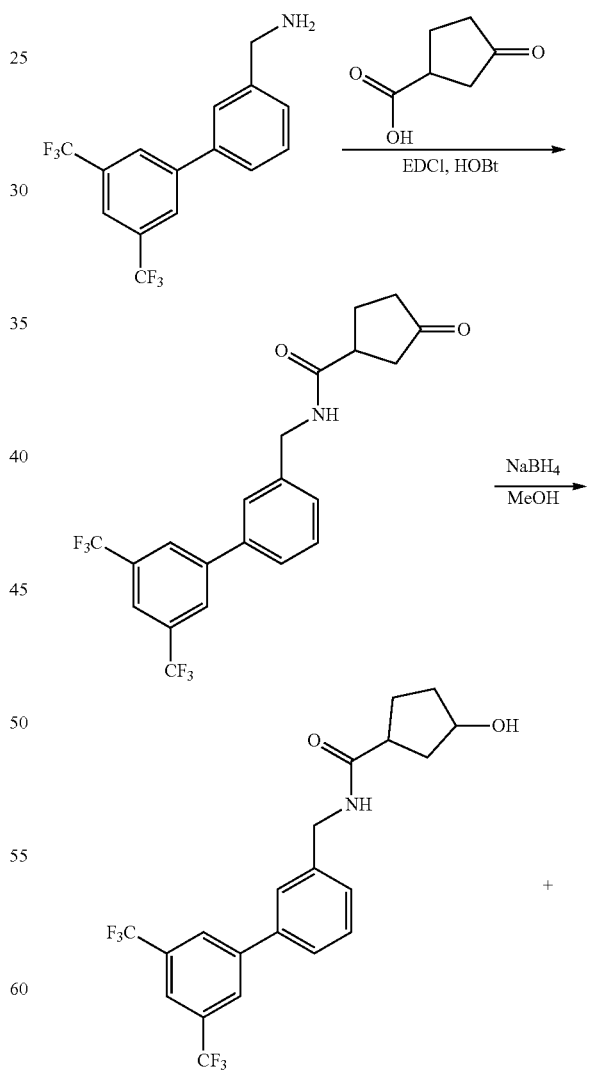

cis-unconfirmed

Isomer A

225

-continued

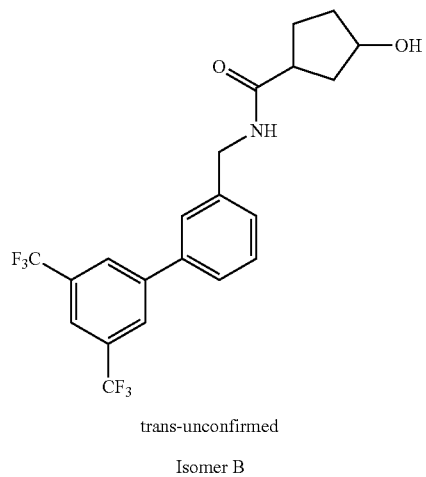

trans-unconfirmed

Isomer B

Step 1. Synthesis of N-([3-[3,5-bis(trifluoromethyl) phenyl]phenyl]methyl)-3-oxocyclopentane-1-carboxamide

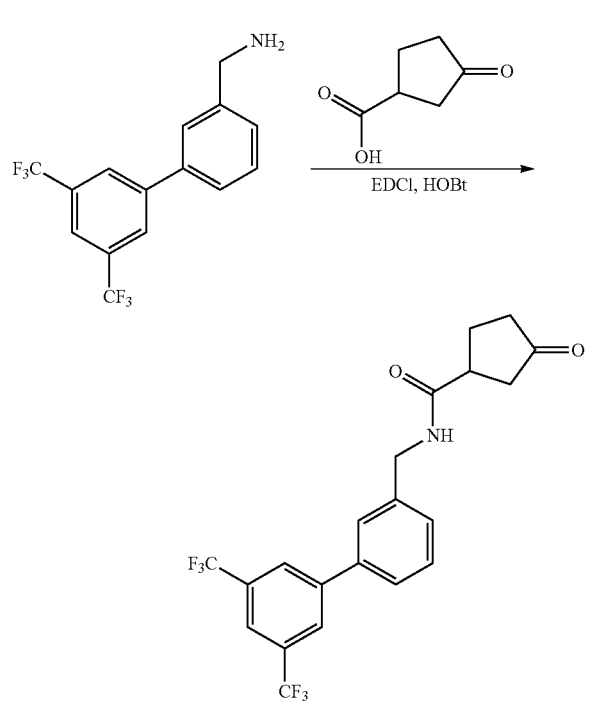

Into a 25-mL round-bottom flask, was placed [3-[3,5-bis(trifluoromethyl)phenyl]phenyl]methanamine (500 mg, 1.57 mmol, 1.00 equiv), EDCI (300 mg, 1.56 mmol, 1.00 equiv), HOBt (212 mg, 1.57 mmol, 1.00 equiv), 3-oxocyclopentane-1-carboxylic acid (201 mg, 1.57 mmol, 1.00 equiv) and 5 mL of DMF. The reaction was stirred for 6 h at room temperature. Then it was diluted with 20 mL of water, extracted with 3×20 mL of ethyl acetate and the organic layers were combined, washed with 2×20 mL of saturated aqueous solution of sodium chloride, dried over anhydrous sodium sulfate and concentrated in vacuo. This resulted in 280 mg (39%) of N-([3-[3,5-bis(trifluoromethyl)phenyl]phenyl]methyl)-3-oxocyclopentane-1-carboxamide as a light yellow solid.

Step 2. Synthesis of N-([3-[3,5-bis(trifluoromethyl) phenyl]phenyl]methyl)-3-hydroxycyclopentane-1-carboxamide (cis and trans isomers) (Isomer A=Example 60; Isomer B=Example 61)

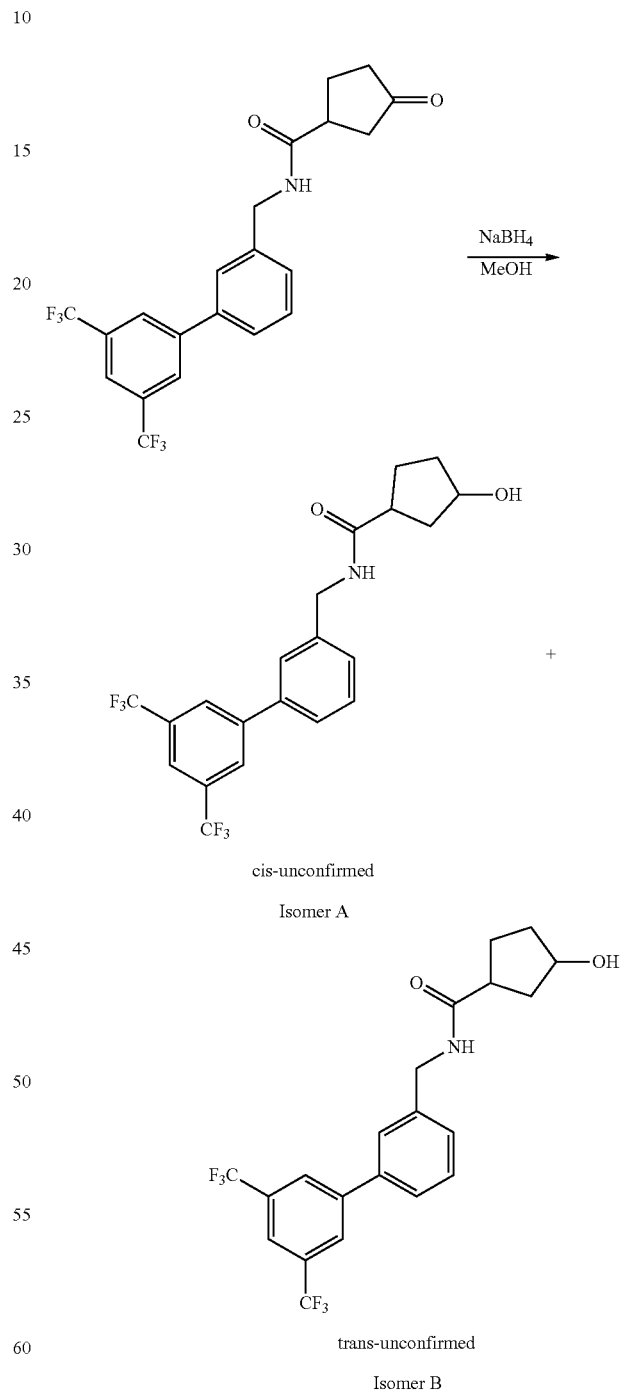

N-([3-[3,5-bis(trifluoromethyl)phenyl]phenyl]methyl)-3-oxocyclopentane-1-carboxamide (280 mg, 0.65 mmol, 1.00 equiv), was dissolved in 8 mL of methanol and sodium borohydride (48 mg, 1.30 mmol, 2.00 equiv) was added. The reaction was stirred for 2 h at 0° C. in an ice/water bath. Then the reaction was quenched by the addition of 10 mL of 10% aqueous hydrogen chloride, extracted with 3×10 mL of ethyl acetate. The organic layers were combined, washed with 2×10 mL of saturated aqueous sodium chloride, dried over anhydrous sodium sulfate and concentrated in vacuo. The crude product was purified by Prep-HPLC under the following conditions: Column, Xbridge RP18, 19×150 mm; mobile phase, Water (0.05% NH$_4$HCO$_3$) and acetonitrile (35% acetonitrile up to 70% in 10 min, hold 95% for 2 min, down to 35% in 1 min); Detector, UV 220 and 254 nm. This resulted in 30 mg (11%) of N-([3-[3,5-bis(trifluoromethyl)phenyl]phenyl]methyl)-3-hydroxycyclopentane-1-carboxamide (Isomer A) as a white solid. And 80 mg (28%) of N-([3-[3,5-bis(trifluoromethyl)phenyl]phenyl]methyl)-3-hydroxycyclopentane-1-carboxamide (Isomer B) as a white solid.

Isomer A:

LC-MS (ES, m/z): [M+H]$^+$=432.

$^1$H NMR (300 MHz, DMSO-d$_6$, ppm): δ 8.41-8.37 (m, 1H), 8.29 (s, 2H), 8.12 (s, 1H), 7.76-7.70 (m, 2H), 7.52-7.47 (m, 1H), 7.36-7.33 (m, 1H), 4.47-4.46 (d, 1H), 4.37-4.35 (m, 2H), 4.20-4.19 (d, 1H), 2.89-2.87 (m, 1H), 1.91-1.50 (m, 6H).

Isomer B:

LC-MS: (ES, m/z): [M+H]$^+$=432.

$^1$H NMR (300 MHz, DMSO-d$_6$, ppm): δ 8.41-8.37 (m, 1H), 8.30 (s, 2H), 8.11 (s, 1H), 7.78-7.72 (m, 2H), 7.52-7.47 (m, 1H), 7.36-7.33 (m, 1H), 4.72-4.70 (d, 1H), 4.39-4.37 (m, 2H), 4.12-4.08 (d, 1H), 2.71-2.65 (m, 1H), 2.01-1.50 (m, 6H).

Example 62

(3R)—N-({3-[3,5-bis(trifluoromethyl)phenyl]phenyl}methyl)-3-fluorocyclopentane-1-carboxamide

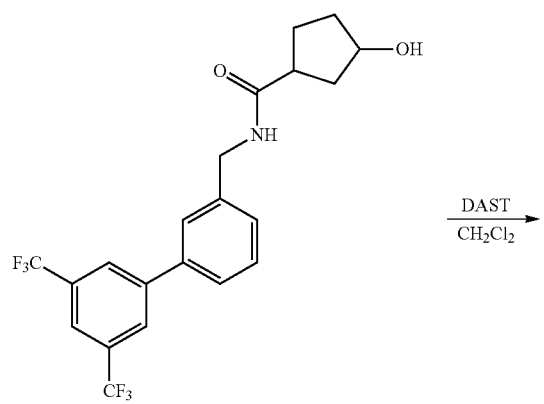

Step 1. Synthesis of (3S)—N-([3-[3,5-bis(trifluoromethyl)phenyl]phenyl]methyl)-3-fluorocyclopentane-1-carboxamide

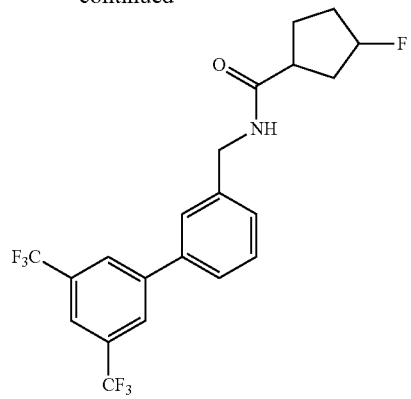

Into a 10-mL round-bottom flask, was placed (3R)—N-([3-[3,5-bis(trifluoromethyl)phenyl]phenyl]methyl)-3-hydroxycyclopentane-1-carboxamide (60 mg, 0.14 mmol, 1.00 equiv), dichloromethane (4 mL), Diethylaminosulfur trifluoride (34 mg, 0.21 mmol, 1.50 equiv). The resulting solution was stirred for 2 h at −70° C. in a liquid nitrogen bath. The reaction was then quenched by the addition of 10 mL of water. The resulting solution was extracted with 3×10 mL of dichloromethane and the organic layers combined. The resulting mixture was washed with 2×10 mL of saturated aqueous solution of sodium chloride. The mixture was dried over anhydrous sodium sulfate and concentrated under vacuum. The residue was applied onto a silica gel column with ethyl acetate/petroleum ether (1:1). This resulted in 24 mg (40%) of (3S)—N-([3-[3,5-bis(trifluoromethyl)phenyl]phenyl]methyl)-3-fluorocyclopentane-1-carboxamide as a off-white solid.

LC-MS: (ES, m/z): [M+H]$^+$=434

$^1$H-NMR: (400 MHz, DMSO-d$_6$, ppm): δ 8.48 (s, 1H), 8.30 (s, 2H), 8.11 (s, 1H), 7.71 (m, 2H), 7.50 (m, 1H), 7.37 (m, 1H), 5.28-5.15 (d, 1H), 4.40-4.38 (m, 2H), 2.95 (m, 1H), 2.08-1.74 (m, 6H).

Example 63

Ion Channel Activity Assays

The compounds described herein were assayed for their ability to block ion channels, such as the Nav1.7 channel (see Table 2, infra). These compounds can also be assayed for modulation of, e.g., voltage gated sodium channels (e.g., other Na$^+$ channel isoforms or Ca$^{2+}$ channels such as Ca$_v$3.2 T-type channels). Exemplary methods are described herein, but additional methods are known in the art.

Cell Generation and Maintenance

The generation of HEK 293F cell lines stably expressing human Nav1.7 (h Nav1.7), human Nav1.5 (hNav1.5) and rat Nav1.2 (r Nav1.2) was achieved by subcloning SCN9A, SCN5A, and SCN2A genes into inducible expression vectors followed by transfection into target cells using standard techniques. In the case of h Nav1.7, an expression vector encoding the human Navβ1 auxiliary subunit gene, SCN1B, was co-transfected with the expression vector bearing the SCN9A gene. Clones were selected using appropriate selection agents (0.3 mg/mL Zeocin and 0.8 mg/mL Geneticin) and maintained in Dulbecco's Modified Eagle medium, 10% fetal bovine serum, 1% non-essential amino acids to ~80% confluence at 37° C. in a humidified incubator with 95% atmosphere and 5% $CO_2$.

Nav1.5 Assay

Inhibition of the TTX-resistant Nav1.5 sodium channel, a key cardiac ion channel, can have profound effects on the duration and amplitude of the cardiac action potential and can result in arrhythmias and other heart malfunctions. To assess the potential cardiac liability of compounds at an early stage in the drug discovery process, a Nav1.5 sodium channel screening assay can be performed on Molecular Device's PatchXpress™ automated electrophysiology platform. Under voltage-clamp conditions, Nav1.5 currents can be recorded from HEK cells expressing the human Nav1.5 channel in the absence and presence of increasing concentrations of the test compound to obtain an $IC_{50}$ value. The external recording solution can contain (in mM): 90 TEACl, 50 NaCl, 1.8 CaCl, 1 $MgCl_2$, 10 HEPES, 10 glucose, adjusted to pH 7.4 with TEA-OH and to 300 mOsm with sucrose (if necessary), while the internal patch pipette solution contained (in mM): 129 CsF, 2 $MgCl_2$, 11 EGTA, 10 HEPES, 3 $Na_2$ATP adjusted to pH 7.2 with CsOH and to 290 mOsm with sucrose (if necessary). Nav1.5 channel currents can be evoked using a cardiac action potential waveform at 1 Hz, digitized at 31.25 kHz and low-pass filtered at 12 kHz.

Nav Ion Channel Potency Assessment of Compounds

On the day of each experiment, cells that were grown to 80% confluence in a T75 flask were harvested for use on PatchXpress (Molecular Devices, CA, USA). Following a recovery period at 37° C. in a humidified incubator with 95% atmosphere and 5% $CO_2$ in Dulbecco's Modified Eagle Medium, the media was replaced with an external recording solution containing (in mM): 90 TEACl, 50 NaCl, 1.8 $CaCl_2$, 1 $MgCl_2$, 10 HEPES, 10 glucose, adjusted to pH 7.4 with TEAOH and 300 mOsm with sucrose. The internal recording solution contained (in mM): 129 CsF, 2 $MgCl_2$, 11 EGTA, 10 HEPES, 6 NaCl, 3 $Na_2$ATP adjusted to pH 7.2 with CsOH and 280 mOsm with sucrose. The automated liquid handling facility of PatchXpress dispensed cells and added compound. Modulation of Nav1.7 channels by compounds was assessed by promoting the channels into the inactivated state using a conditioning voltage pulse of variable amplitude, followed by a brief hyperpolarizing pulse with a subsequent depolarized voltage step to measure the current amplitude in the presence and absence of compound.

In some cases, the potency of compounds was measured using either the Patchliner automated patch clamp platform (Nanion) or manual patch clamp techniques. Both approaches allowed the compounds to be characterized based upon the ability of a compound to modulate use- and/or state-dependence across human Nav1.7 (hNav1.7), human Nav1.5 (hNav1.5) and rat Nav1.2 (rNav1.2). The potency data is tabulated in Table 2 and is represented by six data fields. Three of the six fields represent potency data measured with the Patchliner automated platform under varying use- and state-dependent electrophysiology protocols similar to the PatchXpress protocols detailed above. For example, the second data column describes the potency of compounds in their ability to block 50% of Nav1.7 channels when the channel is repetitively activated by depolarizing voltage potentials to induce slow inactivation in approximately 50% of channels (Table 2: h Nav1.7: IC50 Slow Inactivation Block, Automated Patchclamp). The next three data fields describe the data generated from manual patchclamp electrophysiology measurements using similar methods to those employed for automated patchclamp studies. For example, the first data column demonstrates the potency at which 50% of channel activity was inhibited when repetitively activated with depolarizing voltage potentials to induce slow inactivation in approximately 50% of channels (Table 2: hNav1.7: IC50 Slow Inactivation Block, Manual patchclamp).

TABLE 2

| Compound No. | hNav1.7 IC50 Slow Inactivation Block (nM) (Manual Patchclamp) | hNav1.7 IC50 Slow Inactivation Block (nM) (Automated Patchclamp) | rNav1.2 IC50 Slow Inactivation Block (nM) (Manual Patchclamp) | rNav1.2 IC50 Slow Inactivation Block (nM) (Automated Patchclamp) | hNav1.5 IC50 Slow Inactivation Block (nM) (Manual Patchclamp) | hNav1.5 IC50 Slow Inactivation Block (nM) (Automated Patchclamp) |
|---|---|---|---|---|---|---|
| 1 | 294 | | | | | <1000 |
| 2 | 484 | | | | | >3200 |
| 3 | 1340 | 5780 | 1890 | | | |
| 4 | 217 | 977 | 146 | 1870 | 116 | |
| 5 | 393 | 7250 | 19400 | 32000 | 16600 | |
| 6 | ~39000 | | >10000 | | | |
| 7 | | >32000 | | | | |
| 8 | | >32000 | | | | |
| 9 | | ~29500 | | | | |
| 10 | >10000 | >32000 | >10000 | | | |
| 11 | >3200 | >32000 | >10000 | | | |
| 12 | ~5590 | >32000 | >3200 | | | |
| 13 | ~10300 | 19200 | >10000 | | | |
| 14 | 4940 | ~49000 | >10000 | >32000 | | |
| 15 | 4960 | >32000 | 4320 | | | |
| 16 | Incomplete block | 21100 | >10000 | >32000 | | |
| 17 | 470 | 8430 | 479 | 18700 | ~2500 | |
| 18 | ~9760 | >32000 | | >32000 | | |
| 19 | 1380 | ~10200 | ~1250 | 5660 | | |
| 20 | ~1260 | 5780 | ~1320 | 4260 | | |
| 21 | ~383 | | ~389 | | 550 | |
| 22 | >3200 | >32000 | | >32000 | | |
| 23 | >10000 | >32000 | >10000 | >32000 | | |
| 24 | 3890 | 23600 | >10000 | >32000 | | |
| 25 | ~19200 | ~41800 | | >32000 | | |

TABLE 2-continued

| Compound No. | hNav1.7 IC50 Slow Inactivation Block (nM) (Manual Patchclamp) | hNav1.7 IC50 Slow Inactivation Block (nM) (Automated Patchclamp) | rNav1.2 IC50 Slow Inactivation Block (nM) (Manual Patchclamp) | rNav1.2 IC50 Slow Inactivation Block (nM) (Automated Patchclamp) | hNav1.5 IC50 Slow Inactivation Block (nM) (Manual Patchclamp) | hNav1.5 IC50 Slow Inactivation Block (nM) (Automated Patchclamp) |
|---|---|---|---|---|---|---|
| 26 | 2130 | ~37200 | >10000 | >32000 | | |
| 27 | 2170 | 18000 | ~32000 | ~32000 | | |
| 28 | ~3960 | ~37900 | >10000 | >32000 | | |
| 29 | 678 | 14600 | >32000 | >32000 | ~7570 | |
| 30 | 4840 | ~36000 | 11400 | ~25200 | | |
| 31 | 286 | 750 | 387 | ~1220 | ~1460 | |
| 32 | 942 | ~21100 | >10000 | >32000 | | |
| 33 | 118 | ~10000 | ~4910 | | ~4010 | |
| 34 | 186 | ~6250 | ~2740 | | 1600 | |
| 35 | ~16200 | >32000 | | | | |
| 36 | 256 | ~11900 | >10000 | | ~4960 | |
| 37 | ~413 | ~17600 | >10000 | | 7210 | |
| 38 | 1600 | ~17100 | | | >32000 | |
| 39 | ~6930 | ~21700 | | | | |
| 40 | >3200 | >32000 | | | | >32000 |
| 41 | >3200 | >32000 | | | | >32000 |
| 42 | | | | | | |
| 43 | >10000 | >32000 | | | | >32000 |
| 44 | >10000 | >32000 | | | | |
| 45 | >10000 | >32000 | | | | >32000 |
| 46 | | | | | | |
| 47 | | | | | | |
| 48 | 142 | ~3060 | | | ~650 | ~6660 |
| 49 | 404 | ~7680 | | | 1600 | ~17200 |
| 50 | | | | | | |
| 51 | | | | | | |
| 52 | 466 | 4440 | 928 | 5540 | 1040 | 4050 |
| 53 | 225 | 1880 | 120 | 1090 | | |
| 54 | 741 | 5130 | 744 | | | |
| 55 | 162 | 3610 | 156 | 2580 | | |
| 56 | 173 | 712 | 219 | 5850 | 462 | |
| 57 | 160 | 5620 | 176 | 12300 | | |
| 58 | 777 | 2470 | 733 | 2750 | | |
| 59 | 153 | 8690 | 166 | 8730 | | |
| 60 | 136 | | 124 | | | |
| 61 | 1720 | | 2850 | | | |
| 62 | 557 | | 584 | | | |
| 63 | 2680 | | 2370 | | | |
| 64 | 1570 | | 961 | | | |
| 65 | 477 | | 351 | | | |

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety. This application incorporates by reference U.S. Ser. No. 61/945,309, filed on Feb. 27, 2014, in its entirety.

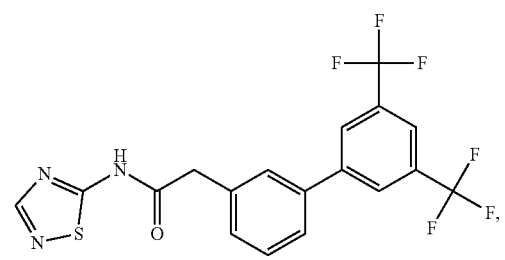
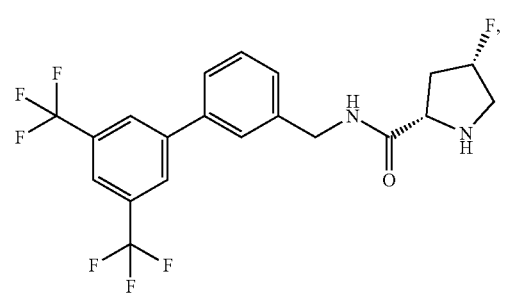
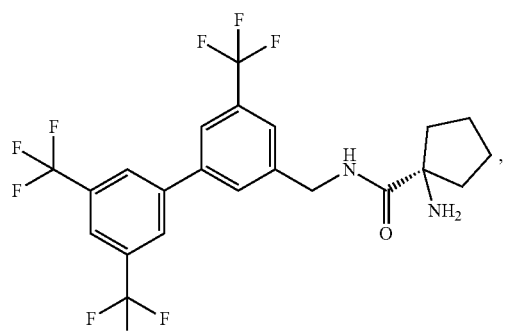
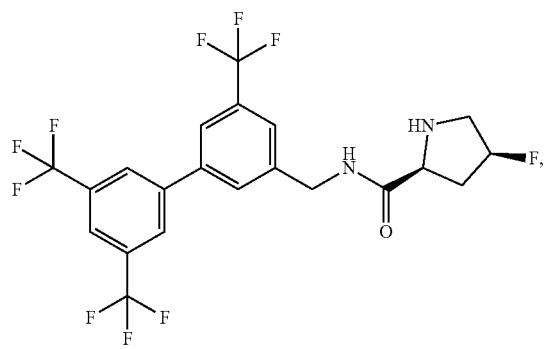
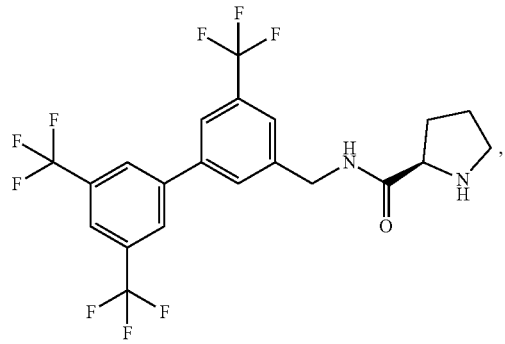
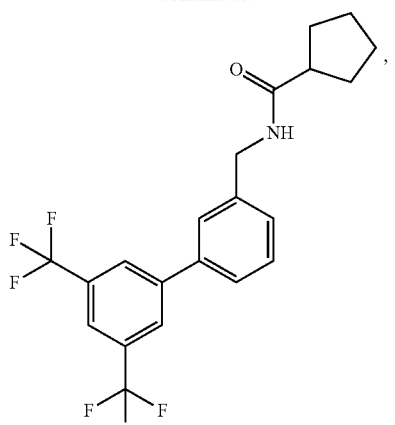
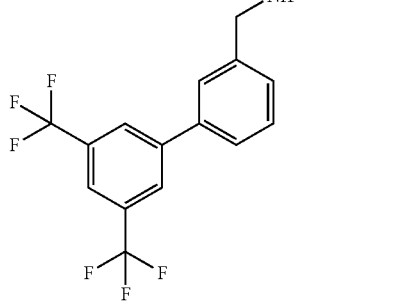
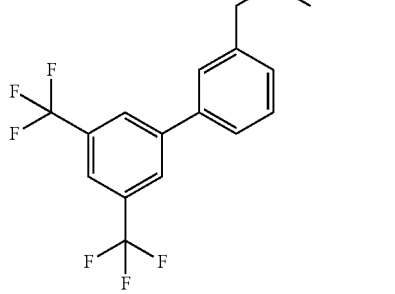

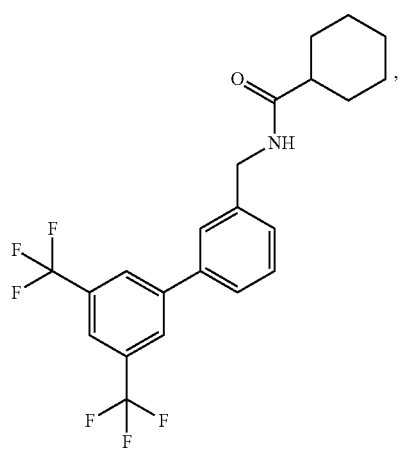
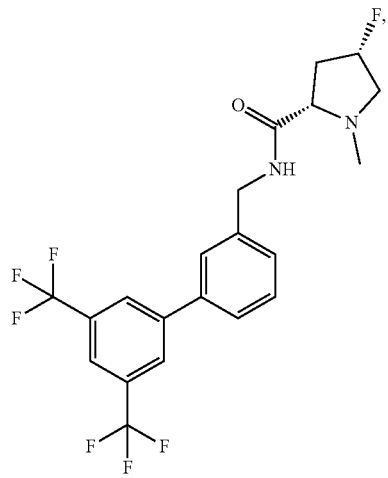

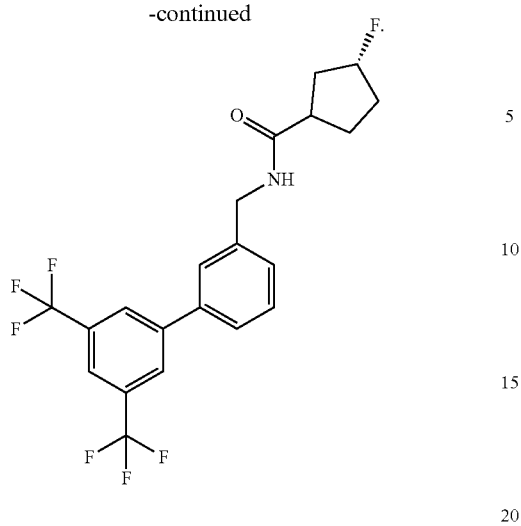

What is claimed is:

1. A compound having a structure according to the following formula,

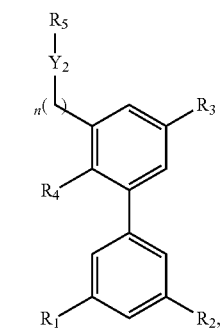

(III)

or a stereoisomer thereof; or a pharmaceutically acceptable salt thereof, wherein
$R_1$ and $R_2$ are $CF_3$;
$R_3$ and $R_4$ are independently H, a halogen, or a nitrile;
$R_5$ is a monocyclic ring substituted with at least two substituents selected from the group consisting H, a halogen, —$NH_2$, —$SO_2NHPh$, methyl, or hydroxyl; and $Y_2$ is —NHCO; n is 1.

2. The compound of claim 1, wherein the structure is selected from any one of: